US012599592B2

(12) United States Patent
Chan et al.

(10) Patent No.: US 12,599,592 B2
(45) Date of Patent: Apr. 14, 2026

(54) THERAPEUTIC SMALL MOLECULES FOR TREATMENT OF PULMONARY HYPERTENSION

(71) Applicants: UNIVERSITY OF PITTSBURGH—OF THE COMMONWEALTH SYSTEM OF HIGHER EDUCATION, Pittsburgh, PA (US); THE TEXAS A&M UNIVERSITY SYSTEM, College Station, TX (US)

(72) Inventors: Stephen Yu-Wah Chan, Pittsburgh, PA (US); Seungchan Kim, Cypress, TX (US)

(73) Assignees: UNIVERSITY OF PITTSBURGH-OF THE COMMONWEALTH SYSTEM OF HIGHER EDUCATION, Pittsburgh, PA (US); THE TEXAS A&M UNIVERSITY SYSTEM, College Station, TX (US)

(*) Notice: Subject to any disclaimer, the term of this patent is extended or adjusted under 35 U.S.C. 154(b) by 510 days.

(21) Appl. No.: 18/036,735

(22) PCT Filed: Nov. 9, 2021

(86) PCT No.: PCT/US2021/058511
§ 371 (c)(1),
(2) Date: May 12, 2023

(87) PCT Pub. No.: WO2022/103706
PCT Pub. Date: May 19, 2022

(65) Prior Publication Data

US 2023/0414590 A1 Dec. 28, 2023

Related U.S. Application Data

(60) Provisional application No. 63/112,994, filed on Nov. 12, 2020.

(51) Int. Cl.

| | |
|---|---|
| ***A61K 31/4412*** | (2006.01) |
| ***A61K 45/06*** | (2006.01) |
| ***C12Q 1/48*** | (2006.01) |
| ***G01N 33/573*** | (2006.01) |

(52) U.S. Cl.
CPC .......... *A61K 31/4412* (2013.01); *A61K 45/06* (2013.01); *C12Q 1/48* (2013.01); *G01N 33/573* (2013.01); *G01N 2333/91177* (2013.01); *G01N 2800/321* (2013.01)

(58) Field of Classification Search
CPC ...... A61K 31/4412; A61K 45/06; C12Q 1/48; G01N 33/573; G01N 2333/91177; G01N 2800/321; G01N 2800/52; C07D 211/22
See application file for complete search history.

(56) References Cited

U.S. PATENT DOCUMENTS

2018/0133157 A1 5/2018 Desai et al.
2018/0369223 A1 12/2018 Zheng et al.

OTHER PUBLICATIONS

Adams, et. al., Synthesis, cellular evaluation, and mechanismof action of piperlongumine analogs, PNAS | Sep. 18, 2012 | vol. 109 | No. 38 | 15115-15120 (Year: 2012).*
International Search Report in PCT/US2021/058511. mailed Feb. 24, 2022. 5 pages.
Written Opinion in PCT/US2021/058511. mailed Feb. 24, 2022. 6 pages.
Adams et al. "Synthesis, cellular evaluation, and mechanism of action of piperlongumine analogs" PNAS. 1 B Sep. 2012.
Negi et al. "Computational repurposing oftherapeutic small molecules from cancer to pulmonary hypertension" Science Advances. Oct. 20, 2021.
Ye et al. "Piperlongumine attenuates vascular remodeling in hypoxic pulmonary hypertension by regulating autophagy" Journal of Cardiology, Sep. 10, 2021.
Barman SA et al. Galectin-3 Promotes Vascular Remodeling and Contributes to Pulmonary Hypertension. Am J Respir Crit Care Med. 2018; 197:1488-1492.
Barretina J et al. The Cancer Cell Line Encyclopedia enables predictive modelling of anticancer drug sensitivity. Nature. 2012;483:603-7.
Bauer PM et al. Activated CD47 promotes pulmonary arterial hypertension through targeting caveolin-1. Cardiovascular rescarch. 2012;93:682-93.
Belkina AC et al. BET protein function is required for inflammation: Brd2 genetic disruption and BET inhibitor JQ1 impair mouse macrophage inflammatory responses. J Immunol. 2013;190:3670-8.
Bertero, T.; Cottrill, K.; Krauszman, A.; Lu, Y.; Annis, S.; Hale, A.; Bhat, B.; Waxman, A.B.; Chau, B.N.; Kuebler, W.M.; et al. The microRNA-130/301 family controls vasoconstriction in pulmonary hypertension. *J. Biol. Chem.* 2014, 290, 2069-2085.
Bertero T et al. Systems-level regulation of microRNA networks by miR-130/301 promotes pulmonary hypertension. J Clin Invest. 2014;124:3514-28.

(Continued)

*Primary Examiner* — Jeffrey S Lundgren
*Assistant Examiner* — Paul Randall Gauger
(74) *Attorney, Agent, or Firm* — Meunier Carlin & Curfman LLC

(57) ABSTRACT

Disclosed are pathogenic mechanisms in pulmonary hypertension and molecular inhibitors of the same. Particularly, GSTP1 (glutathione S-transferase P1) have been demonstrated as having a role in regulating the endothelial ISCU function in pulmonary hypertension. Accordingly, methods for treating pulmonary hypertension in a subject in need thereof comprising administering a therapeutically effective amount of a pharmaceutical composition that inhibits glutathione S-transferase P (GSTP1) and/or increasing ISCU expression are disclosed. The GSTP1 inhibitor can comprise a piperlongumine analog, such as BRD-K34222889, or a derivative thereof.

11 Claims, 66 Drawing Sheets

Specification includes a Sequence Listing.

(56) References Cited

OTHER PUBLICATIONS

Bertero T et al. Vascular stiffness mechanoactivates YAP/TAZ-dependent glutaminolysis to drive pulmonary hypertension. J Clin Invest. 2016;126:3313-35.
Bezerra DP et al. In vitro and in vivo antitumor effect of 5-FU combined with piplartine and piperine. J Appl Toxicol. 2008, 28, 156-163.
Boucherat O et al. The cancer theory of pulmonary arterial hypertension. Pulm Circ. 2017;7:285-299.
Brown JD et al. NF-kB Directs Dynamic Super Enhancer Formation in Inflammation and Atherogenesis. Mol Cell. 2014, 56, 219-231.
Budhiraja R et al. Endothelial dysfunction in pulmonary hypertension. Circulation. 2004;109:159-65.
Calvier L et al. Galectin-3 and aldosterone as potential tandem biomarkers in pulmonary arterial hypertension. Heart. 2016;102:390-6.
Cattanco V et al. Galcctin-8 elicits pro-inflammatory activities in the endothelium. Glycobiology. 2014;24:966-73.
Chabert C et al. Inhibition of BET Proteins Reduces Right Ventricle Hypertrophy and Pulmonary Hypertension Resulting from Combined Hypoxia and Pulmonary Inflammation. International journal of molecular sciences. 2018;19, 2224.
Chaidos A et al. Potent antimyeloma activity of the novel bromodomain inhibitors I-BET151 and I-BET762. Blood. 2014; 123:697-705.
Chan SY et al. MicroRNA-210 controls mitochondrial metabolism during hypoxia by repressing the iron-sulfur cluster assembly proteins ISCU1/2. Cell Metab. 2009;10:273-84.
Cheng, Feixiong, et al. Network-based approach to prediction and population-based validation of in silico drug repurposing. Nature communications 9.1 (2018): 2691.
Crnkovic S et al. Disconnect between Fibrotic Response and Right Ventricular Dysfunction. Am J Respir Crit Care Med. 2018, 199, 1550-1560.
Dai J et al. Smooth muscle cell-specific FoxM1 controls hypoxia-induced pulmonary hypertension. Cellular signalling. 2018;51:119-129.
Dudley, Andrew C. Tumor endothelial cells. Cold Spring Harbor perspectives in medicine 2.3 (2012), a006536.
Evans, Colin E., et al. “Endothelial cells in the pathogenesis of pulmonary arterial hypertension.” European Respiratory Journal 58.3 (2021), 2003957.
Fernandez MM et al. Glycosylation-dependent binding of galectin-8 to activated leukocyte cell adhesion molecule (ALCAM/CD166) promotes its surface segregation on breast cancer cells. Biochim Biophys Acta. 2016;1860:2255-68.
Galletti M et al. Dissecting histone deacetylase role in pulmonary arterial smooth muscle cell proliferation and migration. Biochemical pharmacology. 2014;91:181- 90.
Godinas L et al. Tyrosine kinase inhibitors in pulmonary arterial hypertension: a double-edge sword? Semin Respir Crit Care Med. 2013;34:714-24.
Goldthorpe, Heather, et al. Occlusive lung arterial lesions in endothelial-targeted, fas-induced apoptosis transgenic mice. American journal of respiratory cell and molecular biology 53.5 (2015): 712-718.
Goncharova EA. mTOR and vascular remodeling in lung diseases: current challenges and therapeutic prospects. FASEB J. 2013;27:1796-807.
Gramatica R et al. Graph theory enables drug repurposing—how a mathematical model can drive the discovery of hidden mechanisms of action. PLoS One. 2014;9:e84912.
Hadari YR et al. Galectin-8 binding to integrins inhibits cell adhesion and induces apoptosis. J Cell Sci. 2000;113 ( Pt 13):2385-97.
Hara Y et al. Inhibition of MRP4 prevents and reverses pulmonary hypertension in mice. J Clin Invest. 2011;121:2888-97.
Harshbarger W et al. Structural and Biochemical Analyses Reveal the Mechanism of Glutathione S-Transferase Pi 1 Inhibition by the Anti-cancer Compound Piperlongumine. J Biol Chem. 2017;292:112-120.
Huang M et al. BET Bromodomain Suppression Inhibits VEGF-induced Angiogenesis and Vascular Permeability by Blocking VEGFR2-mediated Activation of PAK1 and eNOS. Scientific reports. 2016;6:23770.
Hussong M et al. The bromodomain protein BRD4 regulates splicing during heat shock. Nucleic Acids Res. 2017;45:382-394.
Jung S et al. EDDY: a novel statistical gene set test method to detect differential genetic dependencies. Nucleic Acids Res. 2014;42:e60.
Jurasz P et al. Role of apoptosis in pulmonary hypertension: from experimental models to clinical trials. Pharmacol Ther. 2010;126:1-8.
Kitagawa MG et al. Hemodynamic and Pathologic Characterization of the TASK-1(−/−) Mouse Does Not Demonstrate Pulmonary Hypertension. Frontiers in medicinc. 2017;4:177.
Levy Y et al. Sustained induction of ERK, protein kinase B, and p70 S6 kinase regulates cell spreading and formation of F-actin microspikes upon ligation of integrins by galectin-8, a mammalian lectin. J Biol Chem. 2003;278:14533-42.
Luo H et al. Galectin-3 mediates pulmonary vascular remodeling in hypoxia-induced pulmonary arterial hypertension. Journal of the American Society of Hypertension : JASH. 2017;11:673-683 e3.
Mazurek JA et al. Galectin-3 Levels Are Elevated and Predictive of Mortality in Pulmonary Hypertension. Heart, lung & circulation. 2017;26:1208-1215.
Meloche J et al. Bromodomain-Containing Protein 4: The Epigenetic Origin of Pulmonary Arterial Hypertension. Circ Res. 2015;117:525-35.
Michelakis ED et al. Inhibition of pyruvate dehydrogenase kinase improves pulmonary arterial hypertension in genetically susceptible patients. Sci Transl Med. 2017;9.
Michelakis ED. Spatio-temporal diversity of apoptosis within the vascular wall in pulmonary arterial hypertension: heterogeneous BMP signaling may have therapeutic implications. Circ Res. 2006;98:172-5.
Mirguet O et al. Discovery of epigenetic regulator I-BET762: lead optimization to afford a clinical candidate inhibitor of the BET bromodomains. J Med Chem. 2013;56:7501-15.
Mumby S et al. Bromodomain and extra-terminal protein mimic JQ1 decreases inflammation in human vascular endothelial cells: Implications for pulmonary arterial hypertension. Respirology. 2017;22:157-164.
Nicodeme E et al. Suppression of inflammation by a synthetic histone mimic. Nature. 2010;468:1119-23.
Piska K et al. Piperlongumine (piplartine) as a lead compound for anticancer agents—Synthesis and properties of analogues: A mini-review. Eur J Med Chem. 2018; 156:13-20.
Potoka KP et al. Vasculopathy and pulmonary hypertension in sickle cell disease. American Journal of Physiology—Lung Cellular and Molecular Physiology. 2015;308:L314-L324.
Price LC et al. Inflammation in pulmonary arterial hypertension. Chest. 2012;141:210-21.
Prins KW et al. Repurposing Medications for Treatment of Pulmonary Arterial Hypertension: What’s Old Is New Again. Journal of the American Heart Association. 2019;8:e011343.
Pullamsetti SS et al. Lung cancer-associated pulmonary hypertension: Role of microenvironmental inflammation based on tumor cell-immune cell cross-talk. Sci Transl Med. 2017;9.
Pullamsetti SS et al. Translational Advances in the Field of Pulmonary Hypertension. From Cancer Biology to New Pulmonary Arterial Hypertension Therapeutics. Targeting Cell Growth and Proliferation Signaling Hubs. Am J Respir Crit Care Med. 2017;195:425-437.
Rabinovich GA et al. Unlocking the secrets of galectins: a challenge at the frontier of glyco-immunology. J Leukoc Biol. 2002;71:741-52.
Rabinovitch M et al. Inflammation and immunity in the pathogenesis of pulmonary arterial hypertension. Circ Res. 2014;115:165-75.
Ranchoux B et al. Endothelial dysfunction in pulmonary arterial hypertension: an evolving landscape (2017 Grover Conference Series). Pulm Circ. 2018;8:2045893217752912.
Rees MG et al. Correlating chemical sensitivity and basal gene expression reveals mechanism of action. Nat Chem Biol. 2016;12:109-16.

(56) References Cited

OTHER PUBLICATIONS

Reid G et al. The human multidrug resistance protein MRP4 functions as a prostaglandin efflux transporter and is inhibited by nonsteroidal antiinflammatory drugs. Proc Natl Acad Sci U S A. 2003;100:9244-9.
Rogers NM et al. TSP1-CD47 signaling is upregulated in clinical pulmonary hypertension and contributes to pulmonary arterial vasculopathy and dysfunction. Cardiovascular research. 2017;113:15-29.
Ryan JJ et al. Emerging concepts in the molecular basis of pulmonary arterial hypertension: part I: metabolic plasticity and mitochondrial dynamics in the pulmonary circulation and right ventricle in pulmonary arterial hypertension. Circulation. 2015;131:1691-702.
Seashore-Ludlow B et al. Harnessing Connectivity in a Large-Scale Small-Molecule Sensitivity Dataset. Cancer Discov. 2015;5:1210-23.
Shameer K et al. A Network-Biology Informed Computational Drug Repositioning Strategy to Target Disease Risk Trajectories and Comorbidities of Peripheral Artery Disease. AMIA Jt Summits Transl Sci Proc. 2018;2017:108-117.
Sironi JJ et al. STAT1-induced apoptosis is mediated by caspases 2, 3, and 7. J Biol Chem. 2004;279:4066-74.
Speyer G et al. Differential Pathway Dependency Discovery Associated with Drug Response across Cancer Cell Lines. Pac Symp Biocomput. 2017;22:497-508.
Stearman RS et al. Systems Analysis of the Human Pulmonary Arterial Hypertension Lung Transcriptome. Am J Respir Cell Mol Biol. 2018, 60, 637-649.
Steiner MK et al. Interleukin-6 overexpression induces pulmonary hypertension. Circ Res. 2009;104:236-44, 28p following 244.
Tang X et al. BET bromodomain proteins mediate downstream signaling events following growth factor stimulation in human lung fibroblasts and are involved in bleomycin-induced pulmonary fibrosis. Molecular pharmacology. 2013;83:283-93.
Tang X et al. Mitochondria, endothelial cell function, and vascular diseases. Frontiers in physiology. 2014;5:175.
Tew KD et al. Regulatory functions of glutathione S-transferase P1-1 unrelated to detoxification. Drug Metab Rev. 2011;43:179-93.
Thurston TL et al. Galectin 8 targets damaged vesicles for autophagy to defend cells against bacterial invasion. Nature. 2012;482:414-8.
Troncoso MF et al. Galectin-8: a matricellular lectin with key roles in angiogenesis. Glycobiology. 2014;24:907-14.
Tyner JW et al. CYT387, a novel JAK2 inhibitor, induces hematologic responses and normalizes inflammatory cytokines in murine myeloproliferative neoplasms. Blood. 2010;115:5232-40.
Uppal S et al. The Bromodomain Protein 4 Contributes to the Regulation of Alternative Splicing. Cell Rep. 2019;29:2450-2460 e5.
Van der Feen DE et al. Multicenter Preclinical Validation of BET Inhibition for the Treatment of Pulmonary Arterial Hypertension. Am J Respir Crit Care Med. 2019;200:910-920.
Weise-Cross L et al. Redox Regulation of Ion Channels and Receptors in Pulmonary Hypertension. Antioxid Redox Signal. 2019;31:898-915.
White K et al. Genetic and hypoxic alterations of the microRNA-210-ISCU1/2 axis promote iron-sulfur deficiency and pulmonary hypertension. EMBO Mol Med. 2015;7:695-713.
Wyce A et al. Inhibition of BET bromodomain proteins as a therapeutic approach in prostate cancer. Oncotarget. 2013;4:2419-29.
Yamamura A et al. Tadalafil induces antiproliferation, apoptosis, and phosphodiesterase type 5 downregulation in idiopathic pulmonary arterial hypertension in vitro. Eur J Pharmacol. 2017;810:44-50.
Yu Q et al. Mitochondrial and Metabolic Drivers of Pulmonary Vascular Endothelial Dysfunction in Pulmonary Hypertension. Adv Exp Med Biol. 2017;967:373-383.
Zhang L et al. Galectin-3-Mediated Transdifferentiation of Pulmonary Artery Endothelial Cells Contributes to Hypoxic Pulmonary Vascular Remodeling. Cellular physiology and biochemistry : international journal of experimental cellular physiology, biochemistry, and pharmacology. 2018;51:763-777.
Zhao J et al. Long Range Endocrine Delivery of Circulating miR-210 to Endothelium Promotes Pulmonary Hypertension. Circ Res. 2020, 127, 677-692.

* cited by examiner

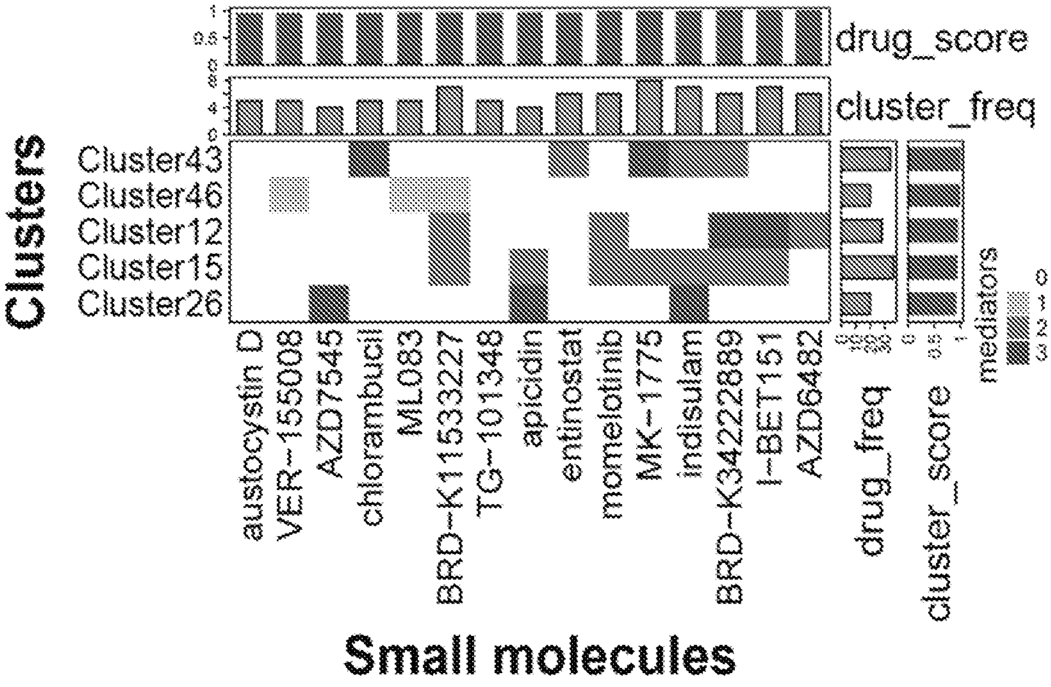

*Figure 1C*

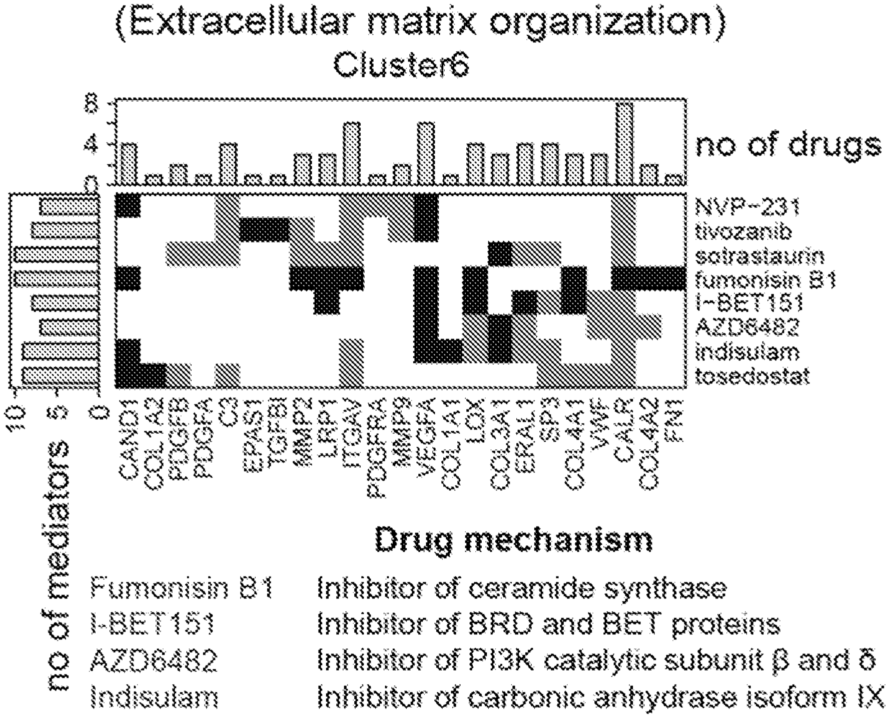

Drug mechanism

| | |
|---|---|
| Fumonisin B1 | Inhibitor of ceramide synthase |
| I-BET151 | Inhibitor of BRD and BET proteins |
| AZD6482 | Inhibitor of PI3K catalytic subunit β and δ |
| Indisulam | Inhibitor of carbonic anhydrase isoform IX |
| Sotrastaurin | Inhibitor of protein kinase C beta |
| Tosedostat | Inhibitor of leucine aminopeptidase 3 |
| NVP-231 | Inhibitor of ceramide kinase |
| Tivozanib | Inhibitor of VEGFRs |

*Figure 1D*

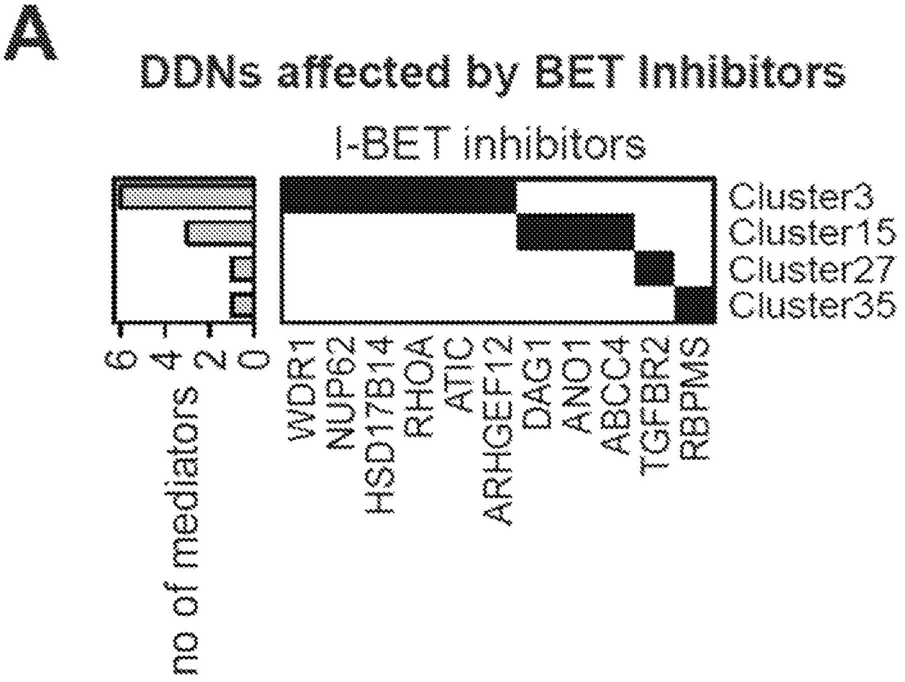
*Figure 2A*
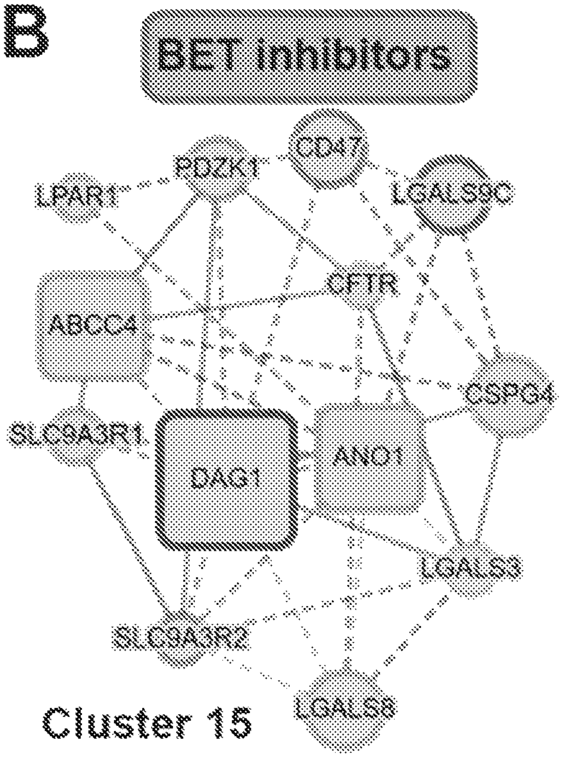
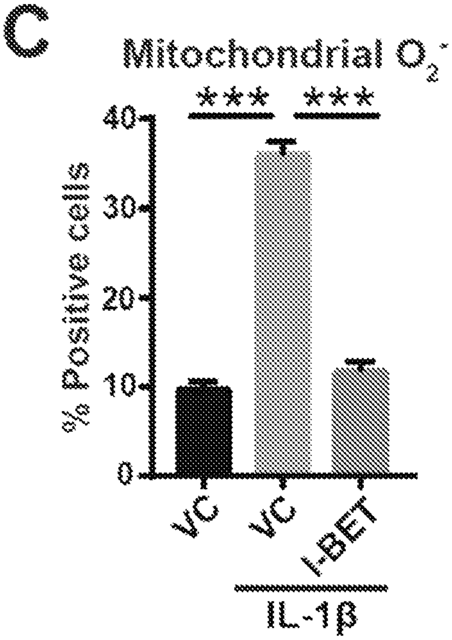
*Figure 2B* *Figure 2C*

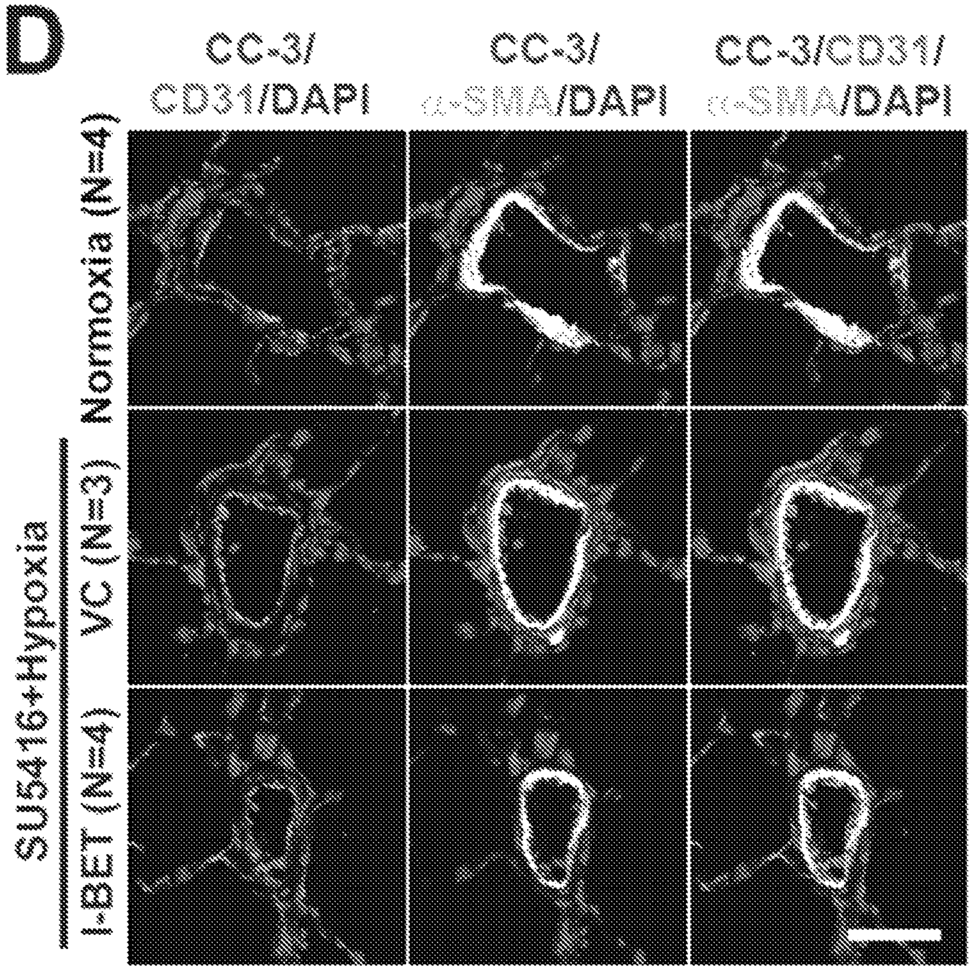
*Figure 4D*
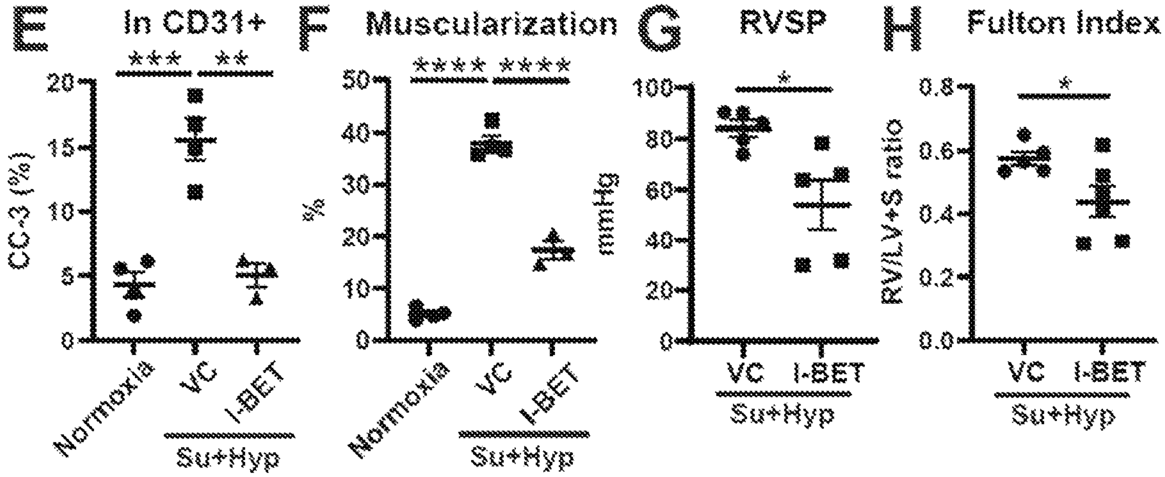
*Figure 4E* *Figure 4F* *Figure 4G* *Figure 4H*

I

I-BET762 (30mg/kg i.p., daily)

Day 0             Day 12       Day 26

MCT (60mg/kg i.p.)

Echo, hemodynamics, tissue harvest

J

LGALS8/ CD31/DAPI     LGALS8/ α-SMA/DAPI     LGALS8/CD31/ α-SMA/DAPI

VC (N=4)

Monocrotaline   VC (N=3)

I-BET (N=4)

BRD2889 structure

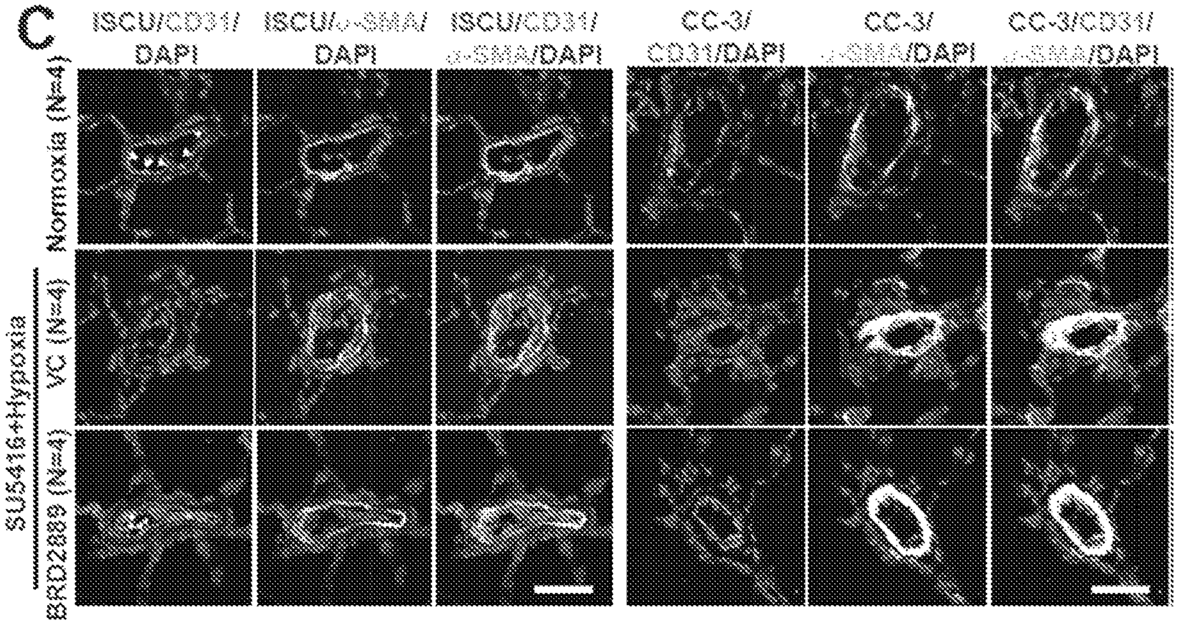
*Figure 9C*
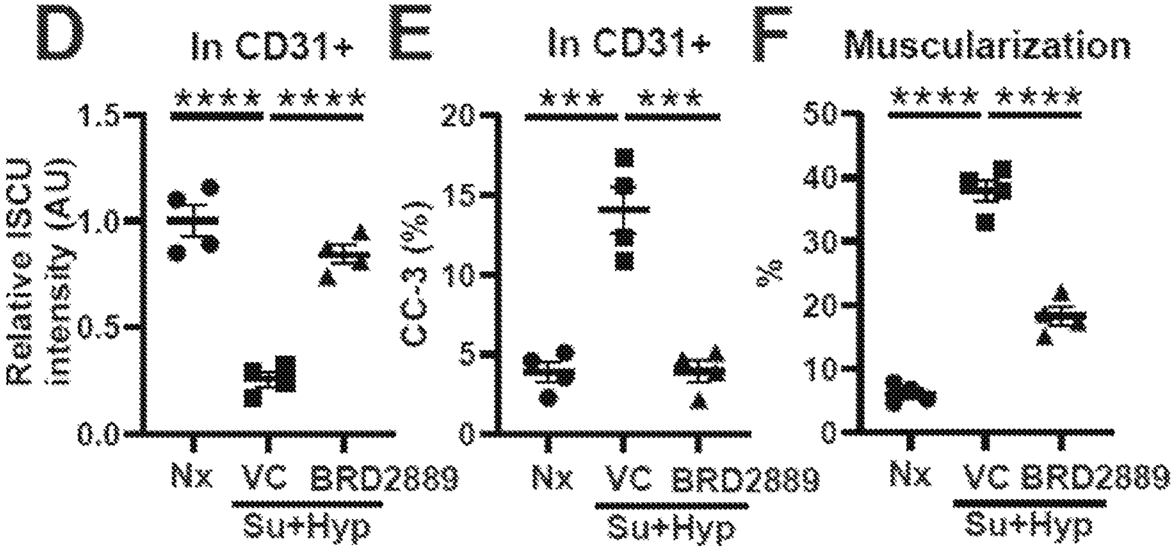
*Figure 9D* *Figure 9E* *Figure 9F*

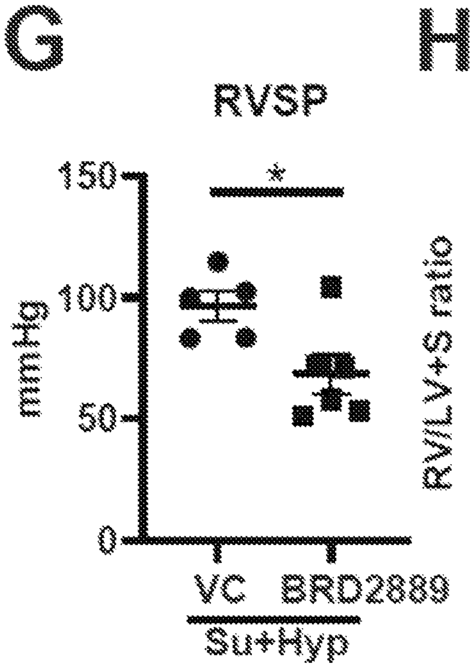
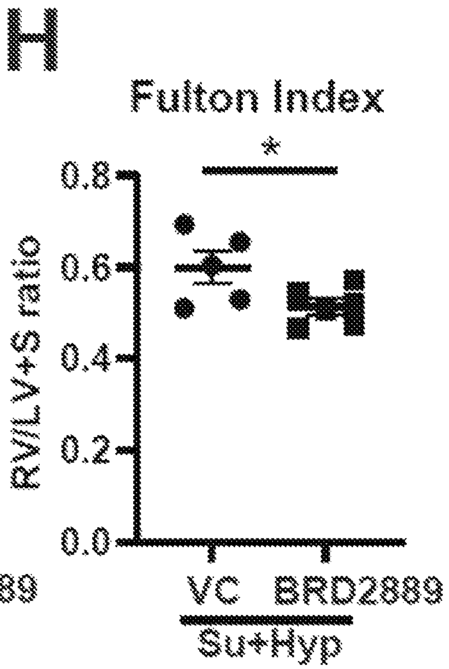
*Figure 9G* *Figure 9H*
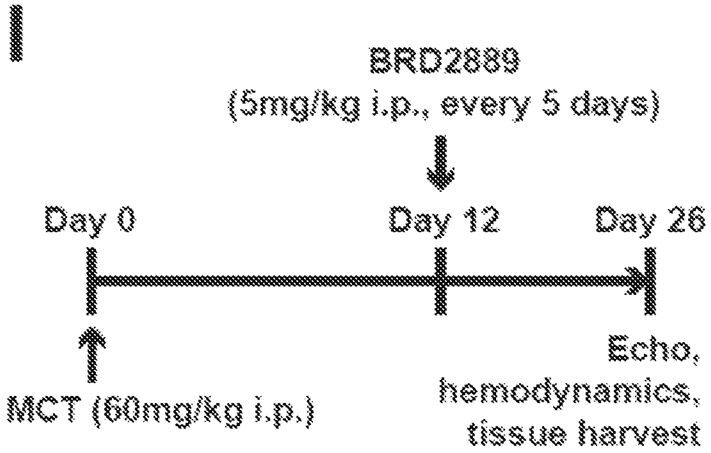
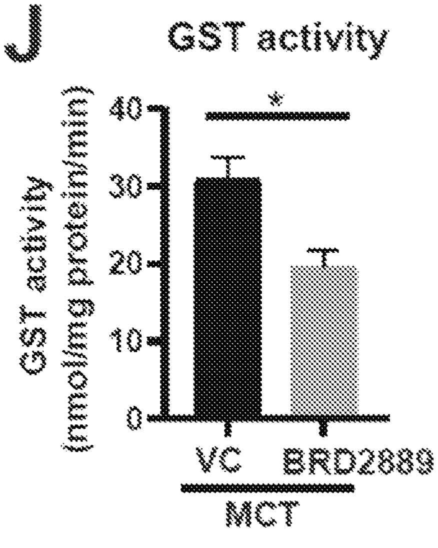
*Figure 9I* *Figure 9J*

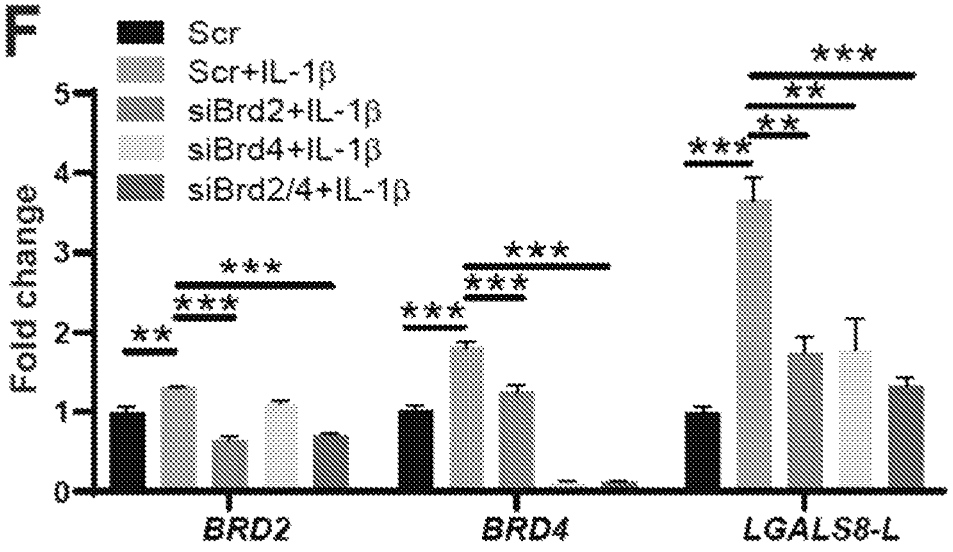
*Figure 11F*
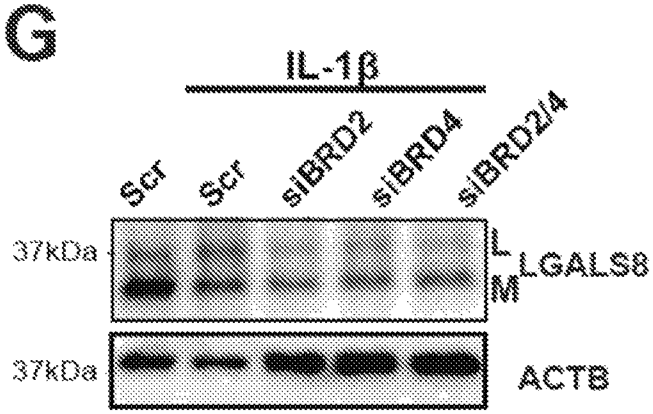
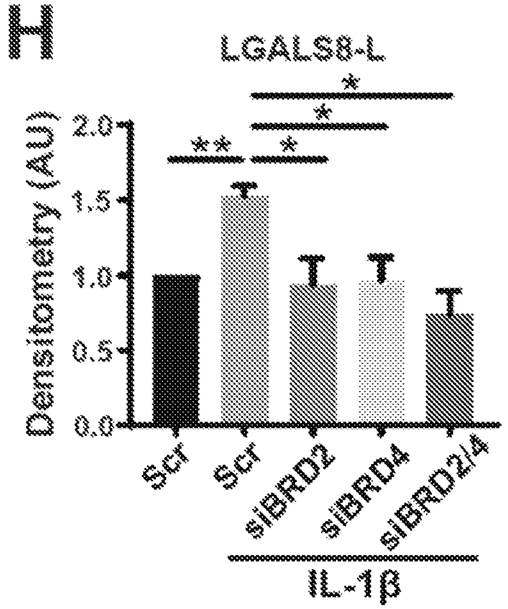
*Figure 11G* *Figure 11H*

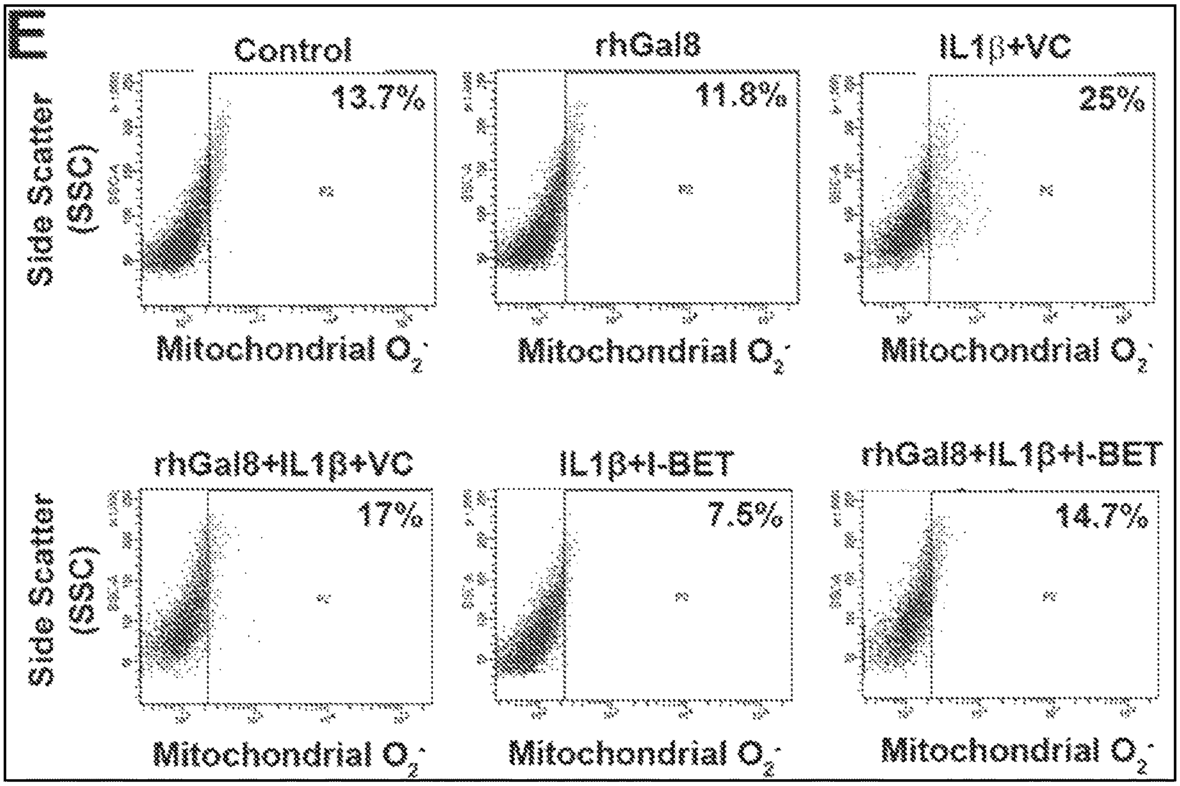
*Figure 13E*
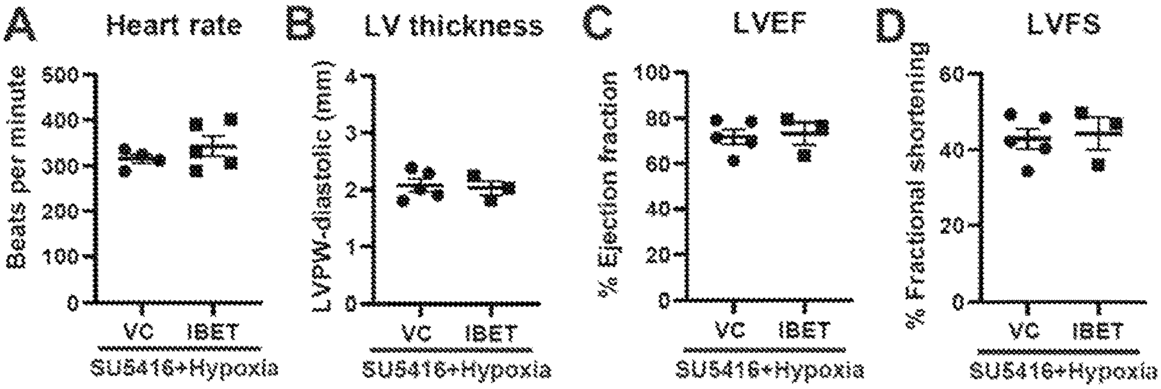
*Figure 14A* *Figure 14B* *Figure 14C* *Figure 14D*

THERAPEUTIC SMALL MOLECULES FOR TREATMENT OF PULMONARY HYPERTENSION

CROSS-REFERENCE TO RELATED APPLICATIONS

This application is a U.S. National Stage application filed under 35 U.S.C. § 371 of PCT/US2021/058511 filed Nov. 9, 2021, which claims the benefit of priority to U.S. Provisional Application 63/112,994 filed Nov. 12, 2020, each of which is hereby incorporated herein by reference in its entirety.

STATEMENT REGARDING FEDERALLY SPONSORED RESEARCH

This invention was made with government support under grant number TR002073 awarded by the National Institutes of Health. The government has certain rights in the invention.

BACKGROUND

Pulmonary hypertension (PH) is an often fatal vascular disease, characterized by dysfunction of pulmonary vascular and inflammatory cell types, among others. Current medications used for pulmonary hypertension primarily promote pulmonary vasodilation and are not curative. Thus, there is an unmet need for new drug discovery. The advancing appreciation of broad molecular parallels between pulmonary hypertension and cancer pathogenesis in general as well as the link between developing pulmonary hypertension in the setting of lung cancer specifically has increased enthusiasm for repurposing existing small molecules inhibitors. However, the traditional methods of manual drug screening have been labor-intensive, expensive, and slow to progress. The increasing availability of large-scale-omics profiling for cancer has offered promise for discerning the landscape of relevant molecular targets and pathways. Prior work with such molecular data sets has primarily utilized analyses of differential gene expression. However, such analytic platforms alone underestimate the systems-level pathways inherently represented by such data and can be inadequate for more complex predictions regarding the functional overlap of drugs and target pathways across various human diseases. There is a need for methods of screening and defining compounds and composition for treating pulmonary hypertension. The methods, compounds, and compositions disclosed herein address these and other needs.

SUMMARY

By leveraging the molecular parallels between cancer and pulmonary hypertension (PH), new pathogenic mechanisms in pulmonary hypertension have been described herein and molecular inhibitors of pulmonary hypertension are disclosed. Particularly, it has been demonstrated that GSTP1 (glutathione S-transferase P1) have important roles in regulating the endothelial ISCU function in pulmonary hypertension. Accordingly, modulators of the GSTP1-ISCU axis in pulmonary hypertension are disclosed herein as a new target pathway for therapeutic development. Piperlongumine analogs and derivatives thereof are shown as being selectively sensitive to a "hot-spot" gene cluster that is dependent upon the iron-sulfur biogenesis gene ISCU, where deficiency drives pulmonary hypertension. In vitro and in vivo models of PAH show the piperlongumine analog BRD-K34222889 inhibit glutathione S-transferase P (GSTP1), which increased ISCU protein stability via preventing glutathionylation and thereby increased oxidative metabolism and decreased PAEC apoptosis.

Disclosed herein are methods for treating pulmonary hypertension in a subject in need thereof. The methods disclosed include treating pulmonary arterial hypertension. Also disclosed herein are methods of treating a disorder associated with ISCU protein instability or deficiency in a subject in need thereof. In some aspects of the disclosed methods of treating pulmonary hypertension or disorder associated with ISCU protein instability, the methods can comprise administering a therapeutically effective amount of a pharmaceutical composition that inhibits glutathione S-transferase P (GSTP1). In some aspects of the disclosed methods of treating pulmonary hypertension, the methods can comprise administering a therapeutically effective amount of a pharmaceutical composition that increases iron-sulfur cluster assembly (ISCU) protein stability, increases ISCU expression, or a combination thereof. For example, the methods can include administering a therapeutically effective amount of a piperlongumine analog. In some instances, the GSTP1 inhibitor inhibits or reduces pulmonary arterial endothelial cell (PAEC) apoptosis in the subject. In some instances, the GSTP1 inhibitor increases iron-sulfur cluster assembly (ISCU) protein stability, increases ISCU protein expression, or a combination thereof, in the subject. In some instances, the GSTP1 inhibitor increases oxidative metabolism and/or decreases pulmonary arterial endothelial cell (PAEC) apoptosis in the subject.

As described herein, the GSTP1 inhibitor can comprise a piperlongumine analog, such as BRD-K34222889, or a derivative thereof. The piperlongumine analog or derivative thereof can have a structure according to Formula I:

Formula I

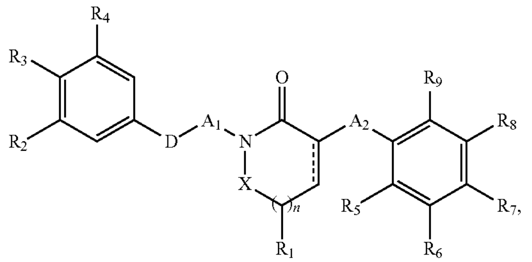

wherein $A_1$ is C(O) or $S(O)_2$;

$A_2$ is selected from —C≡C— or —C(R')=C(R")—, wherein R' and R" are independently selected from hydrogen, $C_1$-$C_6$ alkyl, $C_1$-$C_6$ alkoxy, halogen, or $C_1$-$C_6$ haloalkyl;

X is selected from CH(R'"), C(O), SO, $SO_2$, or NR'", wherein R'" is selected from hydrogen, halogen, $C_1$-$C_6$ alkyl, $C_2$-$C_6$ alkenyl, $C_1$-$C_6$ alkoxy, or $C_1$-$C_6$ haloalkyl;

D is selected from —C≡C— or —C(R')=C(R")—, wherein R' and R" are independently selected from hydrogen, $C_1$-$C_6$ alkyl, $C_1$-$C_6$ alkoxy, halogen, or $C_1$-$C_6$ haloalkyl;

$R_1$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, or nitro, and wherein $R_1$ is optionally substituted with one or more groups;

$R_2$, $R_3$, and $R_4$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

$R_5$, $R_6$, $R_7$, $R_8$, and $R_9$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

n is 1 or 2; and

------- represents a bond that is present of absent;

or a pharmaceutically acceptable salt, ester, or prodrug thereof.

One or more additional agents effective to treat pulmonary hypertension can be administered to the subject in addition to the compounds and compositions disclosed herein. For example, one or more of phosphodiesterase inhibitors, calcium channel blockers, endothelin receptor antagonists, inotropic agents, prostacyclin pathway agonists, anti-coagulants, guanylate cyclase stimulators, PDE-5 inhibitors, or a combination thereof, conventionally used for treating pulmonary hypertension can be administered to the subject.

Methods for diagnosing pulmonary hypertension in a subject in need thereof are also disclosed. The method can include detecting an expression level of glutathione S-transferase P (GSTP1) in a sample obtained from the subject; comparing the level of expression of GSTP1 in the sample compared to a control sample; diagnosing the subject as having pulmonary hypertension when the level of expression of GSTP1 in the sample is higher than the level of expression in the control sample; and treating the subject for pulmonary hypertension when the quantity of GSTP1 in the sample indicates elevated levels of GSTP1 compared to the control sample. Detecting the level of expression in the sample (a) and the control sample (b) can comprises: assaying the sample or control sample using a GSTP1 antibody or isolating GSTP1 from the sample and subjecting the isolated GSTP1 to quantitative spectrometry. The GSTP1 antibody or GSTP1 can be conjugated to a fluorescent moiety or a radioactive moiety in the diagnostic methods.

Methods of assaying the efficacy of a compound for treating pulmonary hypertension are also disclosed. The method can include expressing glutathione S-transferase P (GSTP1) in a sample obtained from a subject; contacting the sample with the compound; and testing whether GSTP1 is inhibited in the sample. In some embodiments, the compound can include a piperlongumine analog or a derivative thereof.

BRIEF DESCRIPTION OF THE FIGURES

FIG. 1A-FIG. 1D. EDDY-CTRP-PH provides in silico predictions of small molecules that depend upon rewired pulmonary hypertension-specific differential dependency networks for activity. (FIG. 1A) In silico workflow: EDDY-CTRP-PH identifies relationships between nodes (genes) in differential dependency networks (DDNs) where each characteristic line indicates the identified relationship: drug-sensitive (red), drug-resistant (blue), and both (gray) as well as known interactions (solid) and previously unknown statistical dependencies (dashed). Size and shape of the nodes indicated the role of a given gene in the structural network integrity of the differential dependency network—large nodes reflected the degree of betweenness centrality, and square nodes represented essentiality or specificity mediators of the differential dependency network. (FIG. 1B) EDDY-CTRP-PH data landscape: Clusters and small molecules were sorted according to their score and represented as a heatmap, where increasing red intensity denotes the number of mediators involved in a particular cluster-drug interaction. Green bar graphs along x- and y-axes: score of each small molecule and cluster, respectively; Gray bar graphs: frequency of significantly rewired clusters for a given small molecule and frequency of small molecules linked to rewiring of a given cluster. Top axis (right to left): cluster 43, cluster 46, cluster 12, cluster 15, cluster 26, cluster 16, cluster 42, cluster 48, cluster 25, cluster 28, cluster 36, cluster 11, cluster 23, cluster 17, cluster 49, cluster 29, cluster 24, cluster 47, cluster 31, cluster 41, cluster 27, cluster 52, cluster 14, cluster 34, cluster 38, cluster 13, cluster 32, cluster 6, cluster 35, cluster 37, cluster 33, cluster 21, cluster 30, cluster 20, cluster 50, cluster 19, cluster 40, cluster 39, cluster 51, cluster 18, cluster 44, cluster 10, and cluster 45. Left axis (drug name; top to bottom): VAF-347, TG-100-115, BRD-K48477130, BRD-K79669418, vandetanib, BCL-LZH-4, A-804598, GSK1059615, azacytidine, trametinib, BRD-K29313308, BRD-K03911514, linsitinib, dexamethasone, ciclosporin, nelarabine, Compound 1541A, BEC, Mdivi-1, alisertib, BRD-K14844214, CIL55, BRD-A02303741, ISOX, U0155056, arinopyrrole A, simvastatin, BRD-K99006945, sildenafil, BRD-K16147474, EX-527, BRD-09587429, saracatinib, BRD-A71883111, O-6-benzylguanine, BRD-K88742110, BIX-01294, yricetin, lenvatinib, NVP-BEZ235, SB-525334, BRD-K33199242, BRD-K50799972, MK-0752, RD-K92856060, COL-3, carboplatin, panda-costat, spautin-1, CIL41, CCT036477, pitstop2, PF-84, BRD-K07442505, Ki8751, istradefylline, thalidomide, nintedanib, tanespimycin, AZD8055, kepinone-L, PF-543BIRB-796, gefitinib, cabozantinib, fluorouracil, pifithrin-mu, dasatinib, emagacestat, AC55649, CBB-1007, ETP-46464, tigecycline, MI-2, decitabine, neratinib, BMS-70394, MLN2480, pyrazolanthrone, RG-108, BRD-K55473186, AZD4547, BRD-K71781559, RD-K66532283, BMS-536924, BRD8899, nilotinib, bardoxolone methyl, BRD-K24690302, RD-K17060750, serdemetan, avrainvillamide, nutlin-3, BMS-195614, AZD1480, SJ-172550, ingolimod, epigallocatechin-3-monogallate, BRD9647, itraconazole, SB-431542, TPCA-1, RITA, Repligen 136, AT7867, ML258, BRD6340, IC-87114, sunitinib, tipifarnib-P1, compound B, Platin, JW-74, UNC0638, SU11274, BIBR-1532, Compound 7d-cis, PRL-3 inhibitor I, AY10576, lapatinib, masitinib, BRD-K28456706, CHIR-99021, foretinib, piperlongumine, RD-94377914, BRD-K99584050, tamatinib, BRD-K90370028, PF-4800567 hydrochloride, osutinib, RD-K13999467, KH-CB19, afatinib, OSI-027, ML203, BRD-K51490254, tacrolimus, BRD-37390332, LE-135, BRD-K61166597, PD 153035, axitinib, cytochalasin B, Ko-143, YL54, tomoxir, vorinostat, temozolomide, GSK2636771, BRD-K27188169, GDC-0879, MGCD-265, F-750, HLI 373, JQ-1, NSC19630, WP1130, CD-437, IU1, ciclopirox, ruxolitinib, KW-2449, luripotin, tubastatin A, tacedinaline, ML031, SRT-1720, ML029, STF-31, valdecoxib, MK-2206, exarotene, PRIMA-1-Met, PF-573228, tretinoin, OSI-930, BRD-K26531177, tamoxifen, anertinib, purmorphamine, GSK4112, elocalcitol, vorapaxar, R04929097, ML311, belinostat, rismodegib, BRD-K02492147, NVP-231, BYL-719, PYR-41, GSK-3 inhibitor IX, ibrutinib, matinib, ABT-737, quizartinib, BRD-K03536150, UNC0321, ML239, BRD-K80183349, SGX-23, sotrastaurin, barasertib, CAY10594, PHA-793887, BRD1812, tipifarnib-P2, PLX-4720, KU 060648, PL-DI, teniposide, isoevodiamine, tosedostat, B02, PIK-93, necrostatin-7, PDMP, BRD-63431240, necrostatin-1, mitomycin, WAY-362450, XL765, hyperforin, NSC30930, evonedistat, dabrafenib, tivozanib, ABT-199, brivanib, AA-COCF3, Ch-55, crizotinib, 16-beta-romoandrosterone, cytarabine hydrochloride, NSC95397, fumonisin B1, austocystin D, VER-55008, AZD7545, chlorambucil, BRD-K11533227, ML083, TG-101348, apicidin, entinostat, omelotinib, MK-1775, indisulam, BRD-K34222889, I-BET151, and AZD6482. (FIG. 1C) High-activity hot-spot linking small molecules with pulmonary hypertension clusters: Visualization representing the bottom right portion (blue box) of heat map in (FIG. 1B) containing top 5 clusters and 15 small molecules. (FIG. 1D) Predictions of small molecules affecting Cluster 6: Visualization of Cluster 6, enriched in extracellular matrix (ECM) genes, indicates convergence of eight small molecules with known and previously unknown (e.g., for fumonosin B1 and indisulam) associations with ECM biology. Black cells: predicted gene (column)-drug (row) interaction; Red cells: literature support of interaction. Bar plots on x- and y-axes: frequency of drugs and mediators, respectively. Listed below the figure are the drug mechanisms. Information on pulmonary hypertension clusters, drugs, and cluster scores are provided in Table 1-Table 3.

FIG. 2A-FIG. 2J. I-BET protects against apoptosis and alters C15 gene expression in cultured pulmonary endothelial cells (PAECs). (FIG. 2A) Schematic representation of clusters and relevant mediator genes demonstrated rewiring across four pulmonary hypertension differential dependency networks (Clusters 3, 15, 27 and 35) by all three bromodomain and extra-terminal motif (BET) inhibitor drugs represented in CTRP (I-BET151, I-BET762, and JQ-1). Black cells: the cluster to which each mediator belongs. Bar graph on y-axis: number of BET inhibitor-associated mediators for each cluster. (FIG. 2B) differential dependency network of Cluster 15 representing rewiring associated with the collective actions of all three BET inhibitors; red: drug-sensitive interactions; blue: drug resistant; gray: both. Solid lines: known interactions; dotted lines: new statistically determined dependencies; square boxes: critical mediators. (FIG. 2C-FIG. 2E) In PAECs+/−IL-1β exposure, I-BET762 (I-BET), when compared with vehicle control (VC), reversed the IL-1β-induced increases of (FIG. 2C) mitochondrial superoxide ($O_2^-$) levels as determined by flow cytometry of MitoSOX Red staining (n=5/grp), (FIG. 2D) apoptosis as assessed by caspase-3/7 activity (n=6/grp), and (FIG. 2E) expression of Cluster 15 (C15) gene galectin-8 (LGALS8) as determined by RT-qPCR (n=3/grp). (FIG. 2F-FIG. 2H) By representative immunoblot (FIG. 2F) and densitometry of LGALS8-L (FIG. 2G) and LGALS8-M (FIG. 2H) in PAECs (n=3/grp), I-BET reversed the IL-1β-induced increase of the L isoform, but not the M isoform, of LGALS8, as compared with VC. (FIG. 2I-FIG. 2J) Using immunofluorescence staining (FIG. 2I) and respective quantification, expression of LGALS8 was increased in CD31+ pulmonary arteriolar endothelium (FIG. 2J) of human patients with World Symposium on Pulmonary Hypertension (WSPH) Group 1 (n=8) and Group 3 (n=8) pulmonary hypertension as compared to non-pulmonary hypertension controls (n=6). Data from (FIG. 2C-FIG. 2H) are represented as fold change with respect to Un and plotted as mean±SEM. Statistical significance is indicated using one-way ANOVA with Bonferroni's multiple comparisons testing (*p<0.05, ***<0.001).

(FIG. 3A-FIG. 3B) Interaction of LGALS8 and the α3 subunit of integrin 301 was demonstrated by proximity ligation assay (PLA) in PAECs. Positive interaction was depicted by Texas Red signal; blue, DAPI. Controls include deletion of either antibody or both (n=3/grp); scale bar, 200 μm. (FIG. 3C-FIG. 3E) In PAECs, representative immunoblot (FIG. 3C) and densitometry demonstrated increased STAT1 (FIG. 3D) and pSTAT1 (FIG. 3E) levels with IL-1β exposure (1 h); these levels were attenuated by knockdown of integrin α3 (siITGα3), integrin β1 (siITGβ1) or both (n=3/grp). (FIG. 3F-FIG. 3H) By representative immunoblots (FIG. 3F) and densitometry of total STAT1 (FIG. 3G) and phosphorylated STAT1 (pSTAT1, FIG. 3H) in PAECs, knockdown of LGALS8 (siLGALS8) attenuated the IL-1β (1 h)-induced increase of pSTAT1 (n=3/grp). (FIG. 3I-FIG. 3J) Similarly, siLGALS8 reduced the IL-1β (48 h)-dependent increases of mitochondrial 02 as assessed by MitoSOX staining and flow cytometry (FIG. 3I) and apoptosis as assessed by caspase-3/7 activity (FIG. 3J) (n=6/grp). (FIG. 3K-FIG. 3L) In IL-1β-exposed (48 h) PAECs treated with I-BET and recombinant galectin-8 (rhGal8; 24 h), rhGal8 reversed the I-BET-induced attenuation of mitochondrial 02 (FIG. 3K) and caspase 3/7 activity (FIG. 3L) (n=3-6/grp). Data plotted as mean±SEM. Statistical significance is indicated using one-way ANOVA with Bonferroni's multiple comparisons testing (*p<0.05, <0.01, *<0.001, ****<0.0001).

FIG. 4A-FIG. 4P. I-BET762 reduces LGALS8, endothelial apoptosis, and improves existing pulmonary arterial hypertension in multiple pulmonary arterial hypertension rat models. (FIG. 4A) Sprague-Dawley rats were administered SU5416 i.p. (20 mg/kg) followed by hypoxia for 21 days to promote pulmonary arterial hypertension (PAH). Rats were then treated with I-BET762 vs. vehicle control by daily i.p. injection (30 mg/kg) at Days 21-35 in normoxia (n=3-6/grp). (FIG. 4B-FIG. 4E) By immunofluorescence staining and quantification of LGALS8 (FIG. 4B-FIG. 4E) and cleaved caspase-3 (CC-3) expression (FIG. 4D-FIG. 4E) in pulmonary arterioles, I-BET decreased LGALS8 and apoptotic CC-3, notably in CD31+ endothelium. (FIG. 4F-FIG. 4H) I-BET reduced arteriolar muscularization (FIG. 4F), right ventricularly systolic pressure (RVSP) (FIG. 4G), and Fulton index (right ventricle [RV]/left ventricle+septum [LV+S] mass ratio, FIG. 4H). (FIG. 4J-FIG. 4M) By immunofluorescence staining and quantification of LGALS8 (FIG. 4J-FIG. 4K) and cleaved caspase-3 (CC-3) expression (FIG. 4L-FIG. 4M) in pulmonary arterioles, I-BET decreased LGALS8 and apoptotic CC-3, notably in CD31+ endothelium. (FIG. 4N-FIG. 4P) I-BET reduced arteriolar muscularization (FIG. 4N), RVSP (FIG. 4O), and Fulton index (RV/LV+S; FIG. 4P). Data are plotted as mean±SEM. Scale bar, 50 μm. Statistical significance is indicated using one-way ANOVA with Bonferroni's multiple comparisons testing (*p<0.05, <0.01, *<0.001, ****<0.0001).

(FIG. 5A-FIG. 5I) Wildtype mice were exposed to 1 week or 3 weeks of hypoxia and treated with daily I-BET vs. vehicle control (VC). VC-treated normoxic mice were used as comparators (n=3-6/grp). With the exception of Fulton Index, I-BET reversed the 3 week hypoxia-dependent increases of these indices: muscularization as indicated by α-SMA+ staining (FIG. 5A-FIG. 5B); right ventricular systolic pressure (RVSP) (FIG. 5C); Fulton index (RV/[LV+S] mass ratio) (FIG. 5D); LGALS8 expression (FIG. 5E) in CD31+ endothelial cells (FIG. 5F), whole arterioles (FIG. 5G), or α-SMA+smooth muscle cells (FIG. 5H); and cleaved caspase-3 (CC-3, FIG. 5I). Consistent with the fact that endothelial apoptosis in pulmonary hypertension is more readily observed early in disease (Bertero T et al. J Cin Invest. 2016, 126, 3313-3335), the reduction of endothelial CC-3 by I-BET was more prominent at the earlier 1 week hypoxia time point. (FIG. 5O) Cartoon representing effect of I-BET on Lgals8 expression, controlling downstream STAT signaling pathway, endothelial apoptosis, and pulmonary hypertension. Data are plotted as mean±SEM. Statistical significance is indicated using one-way ANOVA with Bonferroni's multiple comparisons testing for (FIG. 5A-FIG. 5I) and Student's t-test for (FIG. 5J-FIG. 5N) (*p<0.05, <0.01, *<0.001, ****<0.0001). Scale bar, 50 μm.

(FIG. 6A) differential dependency network for Cluster 43 specific for BRD2889 predicted ISCU as a BRD2889-sensitive mediator. differential dependency network annotations by colors, edges, and boxes are defined in FIG. 1A. (FIG. 6L-FIG. 6Q) Compared with control (Scr) in hypoxic PAECs, GSTP1 knockdown (siGSTP1) phenocopied BRD2889 and reversed hypoxic changes in GST activity (FIG. 6L), GSTP1/ISCU protein (FIG. 6M, FIG. 6N), Complex I activity (FIG. 6O), caspase 3/7 activity (FIG. 6P), and BrdU incorporation (FIG. 6Q) (n=3/grp). Data are plotted as mean±SEM. Statistical significance is indicated using one-way ANOVA with Bonferroni's multiple comparisons testing (*p<0.05, <0.01, *<0.001, ****<0.0001).

(FIG. 7A-FIG. 7B) PAECs treated with siGSTP1 or siRNA control (Scr) were subjected to immunoprecipitation (IP) for IgG control, GSTP1 (FIG. 7A), or glutathione (α-GSH) (FIG. 7B) and immunoblotted for ISCU and GSTP1. Pulldown of ISCU with GSTP1 as well as pulldown of ISCU and GSTP1 with GSH were observed. Such pulldown was inhibited by siGSTP1. Input for both (FIG. 7A-FIG. 7B) is shown at the bottom; GAPDH=negative control. (FIG. 7C) Similarly treated PAECs were subjected to immunoprecipitation for IgG or ISCU followed by immunoblots of total ISCU, GSTP1, and glutathionylated ISCU (18 kDa). Pulldown of GSTP1 resulted with glutathionylated ISCU, but GSTP1 knockdown abrogated ISCU glutathionylation and this interaction. (FIG. 7D) PAECs were exposed to vehicle vs. BRD2889 in normoxia or hypoxia; immunoprecipitation and immunoblotting were performed as in (FIG. 7C). Hypoxia reduced total ISCU but increased relative levels of glutathionylated ISCU; BRD2889 reversed these findings. (FIG. 7E) Amino acid sequences of wildtype (WT) and mutant forms of ISCU at Cys-69. (FIG. 7F) In HEK293 cells transfected with expression plasmids encoding WT and mutant ISCU, immunoblots revealed that mutant ISCU isoforms displayed less glutathionylation. Correspondingly, hypoxia reduced WT ISCU but not C69A or C69S ISCU. (FIG. 7G-FIG. 7I) PAECs were treated with BRD2889 in hypoxia, along with siISCU vs. Scr control siRNA. The actions of BRD2889 to reverse hypoxic changes of mitochondrial Complex I activity (FIG. 7G), proliferation by BrdU incorporation (FIG. 7H), and apoptotic caspase 3/7 activity (FIG. 7I) were abolished by siISCU (n=4/grp). In (FIG. 7A-FIG. 7F), blots are representative for n=3/grp. Data are plotted as mean±SEM. Statistical significance is indicated using one-way ANOVA with Bonferroni's multiple comparisons testing (*p<0.05, <0.01, *<0.001, ****<0.0001).

(FIG. 8A) Transgenic interleukin-6 (IL-6 Tg) mice were exposed to chronic hypoxia for 14 days, and BRD2889 or vehicle control (VC) was administered (5 mg/kg, low and 10 mg/kg, high) every three days by IP from day 0 (n=3-8/grp). (FIG. 8B) BRD2889 decreased lung GST activity in a dose-dependent manner. (FIG. 8C-FIG. 8H) By immunofluorescence staining and quantification of ISCU (FIG. 8C-FIG. 8E) and cleaved caspase-3 (CC-3) expression (FIG. 8F-FIG. 8H) in whole vessels, BRD2889 increased ISCU and decreased CC-3, particularly in CD31+ endothelium (white arrowheads) (FIG. 8C). (FIG. 8I-FIG. 8K) BRD2889 reduced arteriolar muscularization (FIG. 8I), RVSP (FIG. 8J), and Fulton index (RV/LV+S; FIG. 8K). Data are plotted as mean±SEM. Scale bar, 50 μm. Statistical significance is indicated using one-way ANOVA with Bonferroni's multiple comparisons testing (*p<0.05, <0.01, *<0.001, ****<0.0001).

(FIG. 9A) Sprague-Dawley rats were administered SU5416 i.p. (20 mg/kg) followed by hypoxia for 21 days to promote pulmonary arterial hypertension. Rats were then treated with BRD2889 vs. vehicle control by i.p. injection (5 mg/kg) every 5 days for the next 2 weeks in normoxia (n=4-6/grp). (FIG. 9C-FIG. 9E) By immunofluorescence staining and quantification of ISCU (FIG. 9C-FIG. 9D) and cleaved caspase-3 (CC-3) expression (FIG. 9C & FIG. 9E) in CD31+ endothelium, BRD2889 increased ISCU and decreased apoptotic CC-3, notably in CD31+ endothelium (white arrowheads). (FIG. 9F-FIG. 9H) BRD2889 reduced arteriolar muscularization (FIG. 9F), right ventricular systolic pressure (RVSP) (FIG. 9G), and Fulton index (RV/LV+S; FIG. 9H). (FIG. 9I) Sprague-Dawley rats were administered monocrotaline (MCT) i.p. (60 mg/kg) to promote pulmonary arterial hypertension within 26 days. Rats were treated with BRD2889 vs. vehicle control by i.p. injection (5 mg/kg) every 5 days at Days 12-26 post-MCT injection (n=3-7/grp). (FIG. 9J) BRD2889 decreased lung GST activity. (FIG. 9N-FIG. 9P) BRD2889 reduced arteriolar muscularization (FIG. 9N), RVSP (FIG. 9O), and Fulton index (RV/LV+S; FIG. 9P). Data are plotted as mean±SEM. Scale bar, 50 μm. Statistical significance is indicated using Student's t-test for (FIG. 9B, FIG. 9J) and one-way ANOVA with Bonferroni's multiple comparisons testing in remaining panels (*p<0.05, <0.01, *<0.001, **<0.0001). (FIG. 9**Q) Cartoon summarizing model of actions of BRD2889 on GSTP1, ISCU glutathionylation (S-SG) and expression, endothelial apoptosis, and pulmonary hypertension.

FIG. 11A-FIG. 11H. I-BET alters C15 and protects from endothelial dysfunction by directly regulating LGALS8. (FIG. 11A) By RT-qPCR, IL-1β-induced expression changes in Cluster 15 members (SLC9A3R1, LGALS3) are shown with respect to vehicle control (VC); these effects were reversed by both I-BET151 and I-BET762 (n=3/grp). (FIG. 11B) By global transcriptomic microarray analysis, a heatmap (left) displays average gene expression (n=3/grp) across 524 genes that were found to have significant expression alterations with respect to IL-1β vs. vehicle control (VC) and that were reversed by I-BET762 (IL-1β+BRD2889) as compared to IL-1β with vehicle control (IL-1β+VC). Gene set enrichment analysis (GSEA) of these differentially expressed genes revealed enrichment of pathways relevant to cell death, cell metabolism, and endothelial function. The heatmap (right) depicts gene membership in these Gene Ontology (GO) biologic processes of interest. (FIG. 11C) Representative scatter plot of MitoSOX Red staining followed by flow cytometry data (summarized in FIG. 2C) showed IL-1β-driven upregulation of mitochondrial superoxide ($O_2^-$) levels reversed by I-BET762 (n=5/grp). (FIG. 11D) RT-qPCR analysis of C15 genes showed that the IL-1β-induced increase of CD47 and decrease of ABCC4 and DAG1 were all rescued by I-BET762 (n=3/grp). The two isoforms of LGALS8, LGALS8-L and LGALS8-M, were increased and decreased by IL-1β, respectively; I-BET762 reversed the alterations of LGALS8-L expression but not LGALS8-M (n=3/grp). (FIG. 11E) By RT-qPCR, the expression of cluster 15 (C15) genes in IL-1β-exposed pulmonary artery smooth muscle cells (PASMCs) vs. vehicle control (VC) was assessed (n=3/grp). (FIG. 11F) RT-qPCR demonstrated siRNA specific to BRD2 (siBRD2) led to a ~40% reduction in BRD2 transcript with no effect on BRD4, while siRNA specific to BRD4 (siBRD4) led to a ~90% reduction in BRD4 transcript with no effect on BRD2 and LGALS8-L was reduced by both siRNA alone and together—all compared to scrambled control (Scr; n=3/grp). (FIG. 11G-FIG. 11H) The IL-1β-induced expression of LGALS8-L was reversed by both Brd2 and 4 siRNA as confirmed by immunoblot at the protein level (n=3/grp). The data, except in (FIG. 11B) are plotted as mean±SEM. Statistical significance is indicated using one-way ANOVA with Bonferroni's multiple comparisons testing (*p<0.05, <0.01, *<0.001).

(FIG. 12A) By ELISA, the plasma level of LGALS8 expression was found to be unchanged among patients with Group 1 and 3 pulmonary hypertension compared to non-pulmonary hypertension controls (n=3-20/grp). FIG. 12B-FIG. 12C) and monocrotaline (MCT)-induced rat model of pulmonary hypertension (n=4; FIG. 12D-FIG. 12E) as compared to control (n=4). FIG. 12F, FIG. 12H) and monocrotaline (MCT; n=4-5/grp; FIG. 12G, FIG. 12I) rat models of pulmonary hypertension. (FIG. 12L-FIG. 12S) Using immunofluorescence staining (FIG. 12L) and quantification, IL-1β expression was increased in lung CD31+ endothelial cells (FIG. 12M) of human patients with Group 1 and Group 3 pulmonary hypertension compared to controls with non-pulmonary hypertension (n=6-8/grp), rats with SU5416-hypoxia (Su-Hyp) (n=4-5/grp; FIG. 12N-FIG. 12O), rats with monocrotaline (MCT)-induced pulmonary hypertension (n=4/grp; FIG. 12P-FIG. 12Q), and mice with hypoxia-induced pulmonary hypertension (n=6/grp; FIG. 12R-FIG. 12S). Data are plotted as mean±SEM. Statistical significance is indicated using one-way ANOVA with Bonferroni's multiple comparisons testing for (FIG. 12A, FIG. 12M) and Student's t-test for (FIG. 12C-FIG. 12K) and (FIG. 12N-FIG. 12S) (*p<0.05, p<0.01, *<0.001). Scale bar, 50 μm. See also Table 4.

FIG. 13A-FIG. 13E. LGALS8 regulates endothelial apoptosis and function. (FIG. 13A-FIG. 13B) Densitometry of immunoblots for integrin α3 (ITGA3) (FIG. 13A) and integrin β1 (ITGB1) (FIG. 13B) revealed increased expression of ITGA3 with IL-1β and no difference in expression of ITGB1, with 90% knockdown efficiency by their respective siRNAs. (FIG. 13C) siRNA knockdown of LGALS8 as determined by RT-qPCR (n=3/grp) showed 90% efficiency. (FIG. 13D) Representative scatter plot of MitoSOX Red staining followed by flow cytometry demonstrated that IL-1β-dependent upregulation of mitochondrial superoxide ($O_2^-$) was reversed by siRNA knockdown of LGALS8 (siLGALS8; n=5/grp); data summarized in FIG. 3I. (FIG. 13E) Representative scatter plot after flow cytometry showed that I-BET762-dependent reduction of IL-1β-induced mitochondrial superoxide ($O_2^-$) was attenuated by the presence of exogenous recombinant galectin-8 (rhGal8);

Figure 3A:
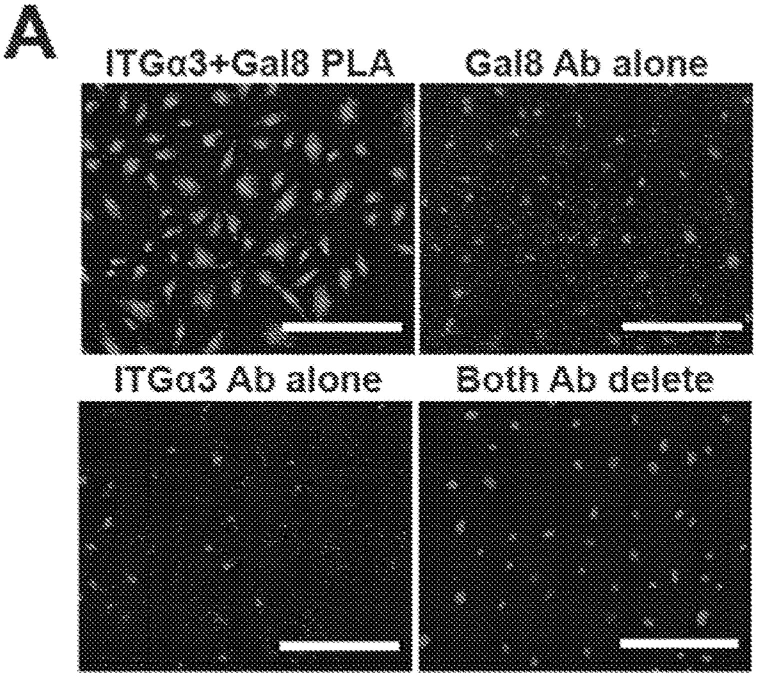
FIG. 3A-FIG. 3L. LGALS8 is a major effector of C15 controlling endothelial cell apoptosis via STAT1 signaling.
Figure 3B:
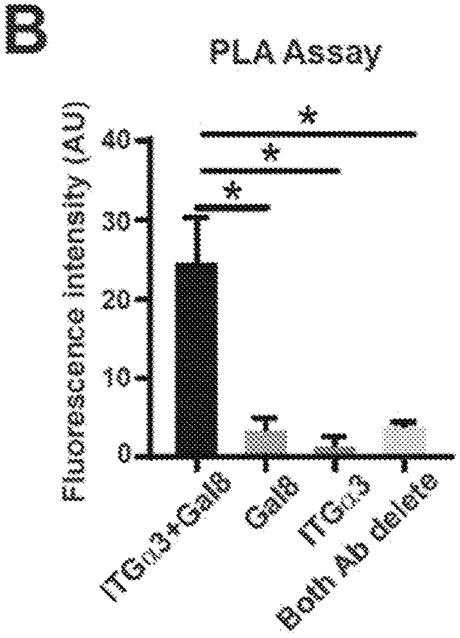
Figure 3C:
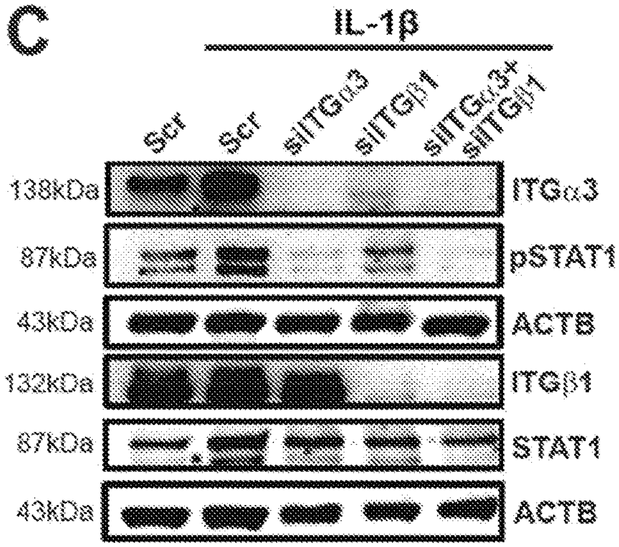
Figure 3D:
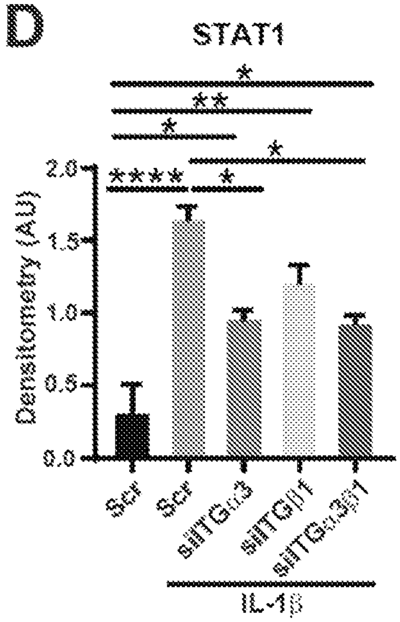
Figure 3E:
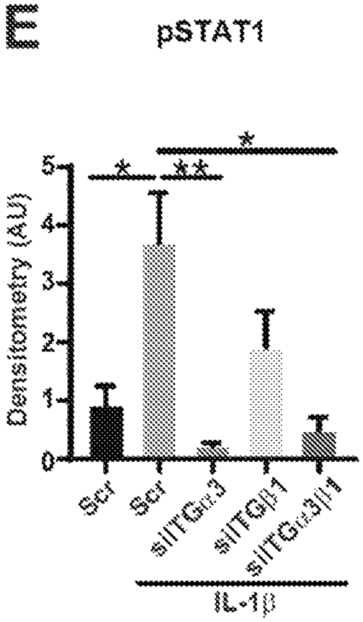
Figure 3F:
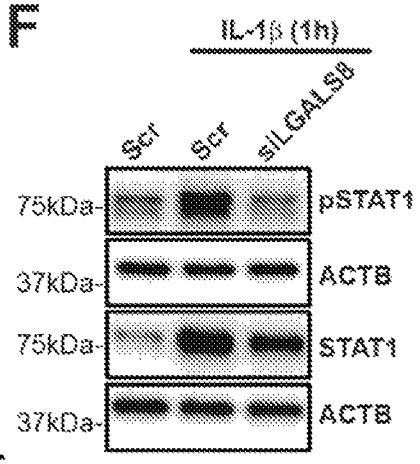
Figure 3G:
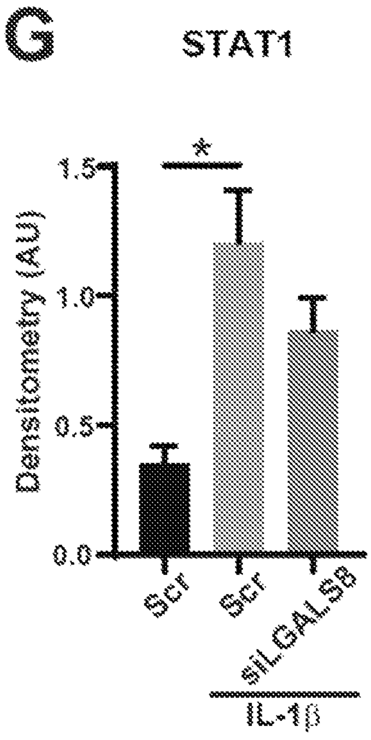
Figure 3H:
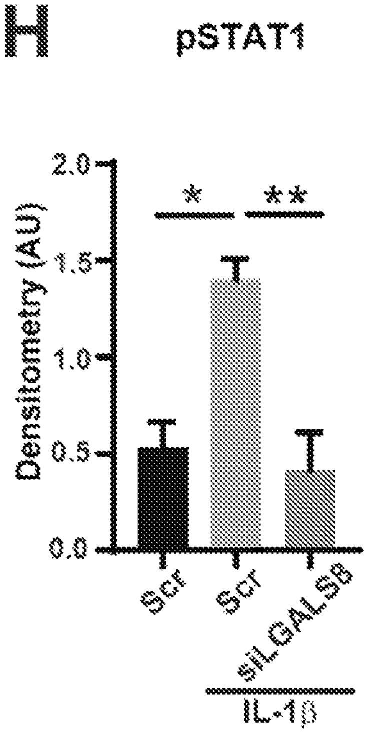
Figure 3I:
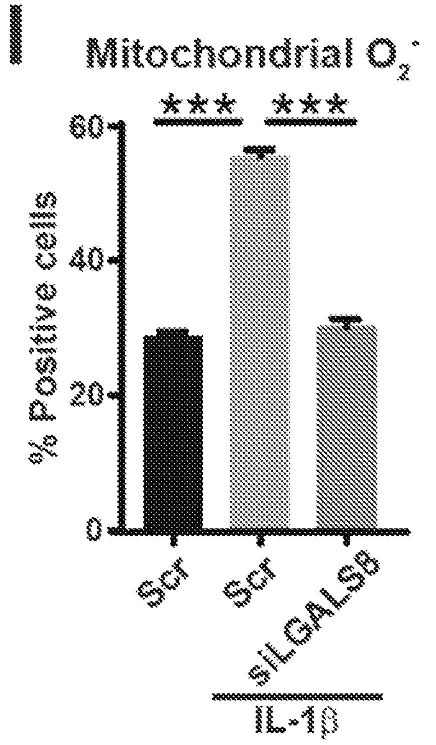
Figure 3J:
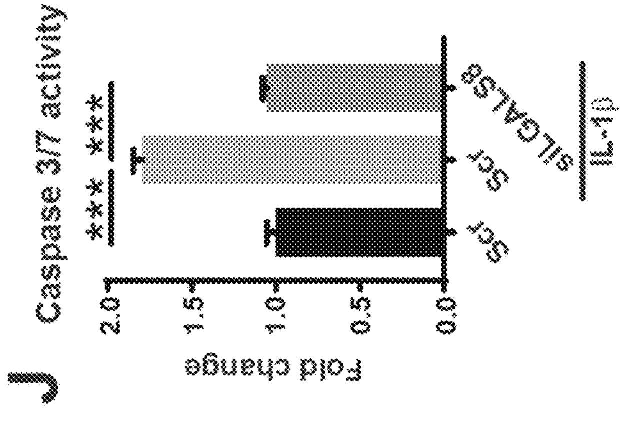
Figure 3K:
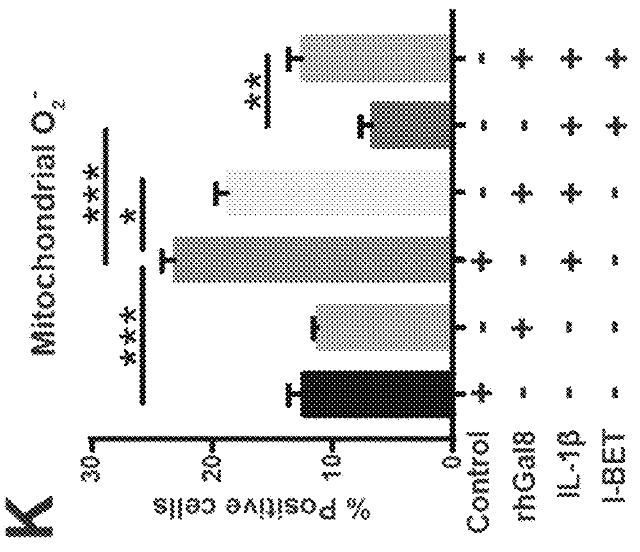

data summarized in FIG. 3K (n=3/grp). Statistical significance is indicated using one-way ANOVA with Bonferroni's multiple comparisons testing (*p<0.05, p<0.01, *p<0.001).

Figure 14E:
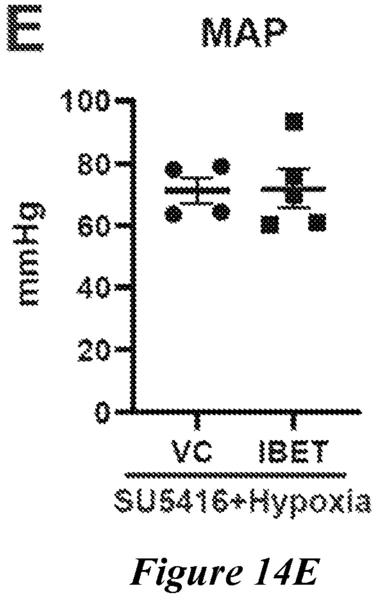
Figure 14F:
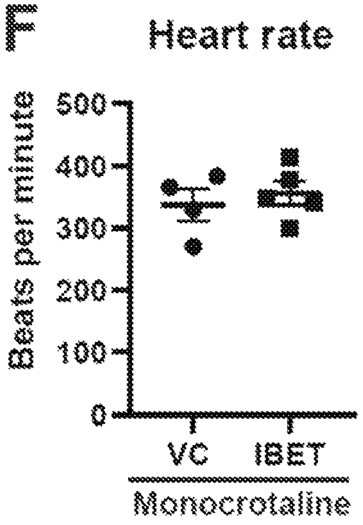
Figure 14G:
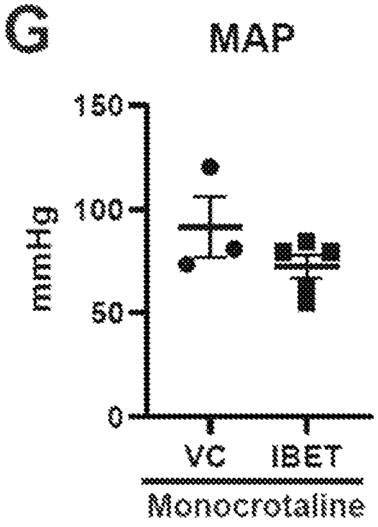

FIG. 14A-FIG. 14G. Parameters of cardiovascular function in pulmonary arterial hypertension rat models administered I-BET762. (FIG. 14A) Heart rate of SU5416-hypoxic pulmonary arterial hypertension rats administrated I-BET762 was not altered, as compared with vehicle control (VC) (n=4-5/grp). (FIG. 14B-FIG. 14D) SU5416-hypoxic rats administered I-BET762 did not exhibit altered left ventricular function compared to VC, as measured by left ventricle posterior wall (LVPW) thickness (FIG. 14B), ejection fraction (LVEF; FIG. 14C), and fractional shortening (LVFS; FIG. 14D) via transthoracic echocardiography (n=3-5/grp). (FIG. 14E) Aortic blood pressure (mean arterial pressure, MAP) of SU5416-hypoxic pulmonary arterial hypertension rats administered I-BET762 was not altered, as compared with vehicle control (VC) (n=4-5/grp). (FIG. 14F) Heart rate of monocrotaline-exposed pulmonary arterial hypertension rats administered I-BET762 was not altered, as compared with vehicle control (VC) (n=4-5/grp). (FIG. 14G) Aortic blood pressure (mean arterial pressure, MAP) of monocrotaline-exposed pulmonary arterial hypertension rats administered I-BET762 was not altered, as compared with vehicle control (VC) (n=3-5/grp). The data are plotted as mean±SEM. Statistical significance is indicated using Student's t-test (p>0.05 for all comparisons).

Figure 15A:
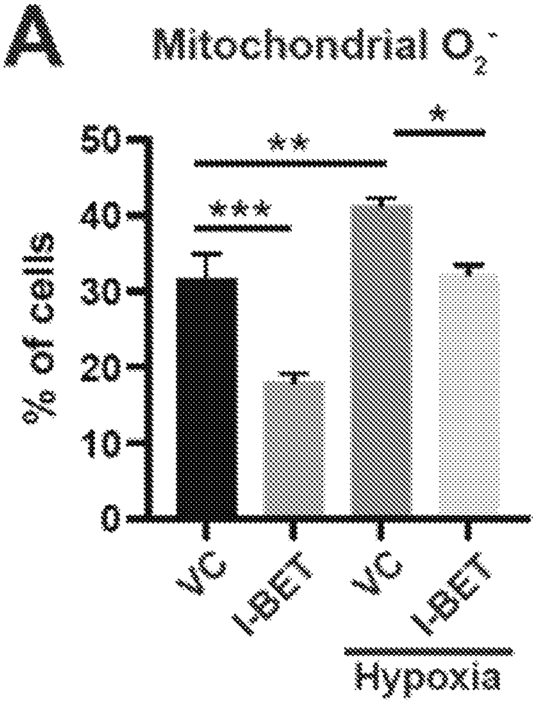
Figure 15B:
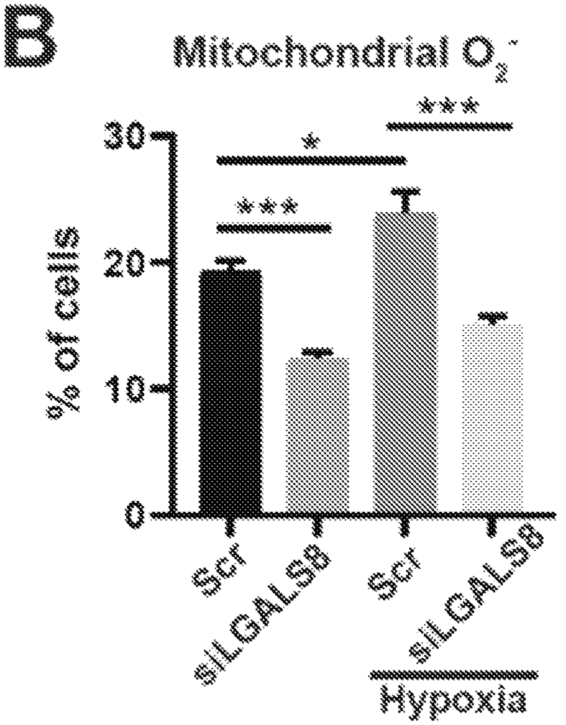
Figure 15C:
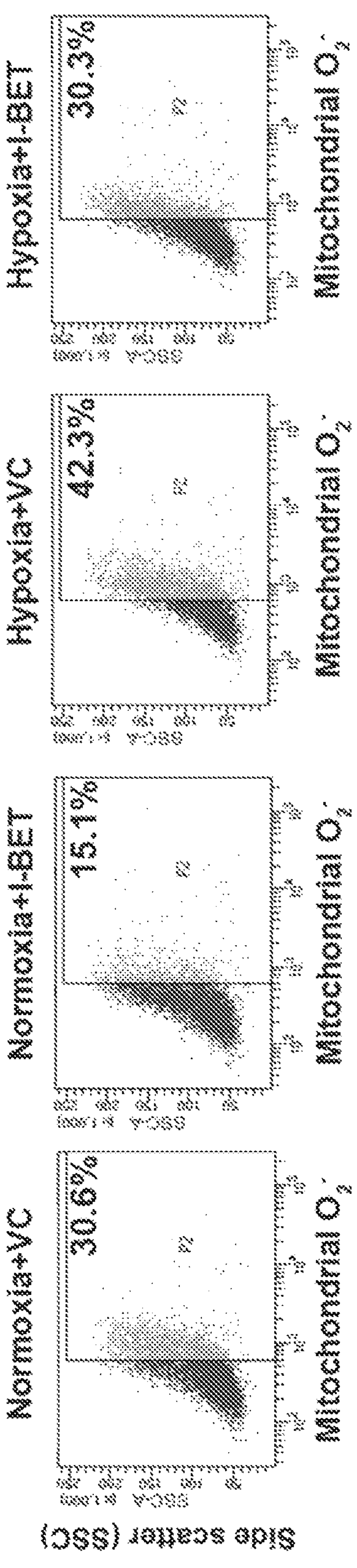
Figure 15D:
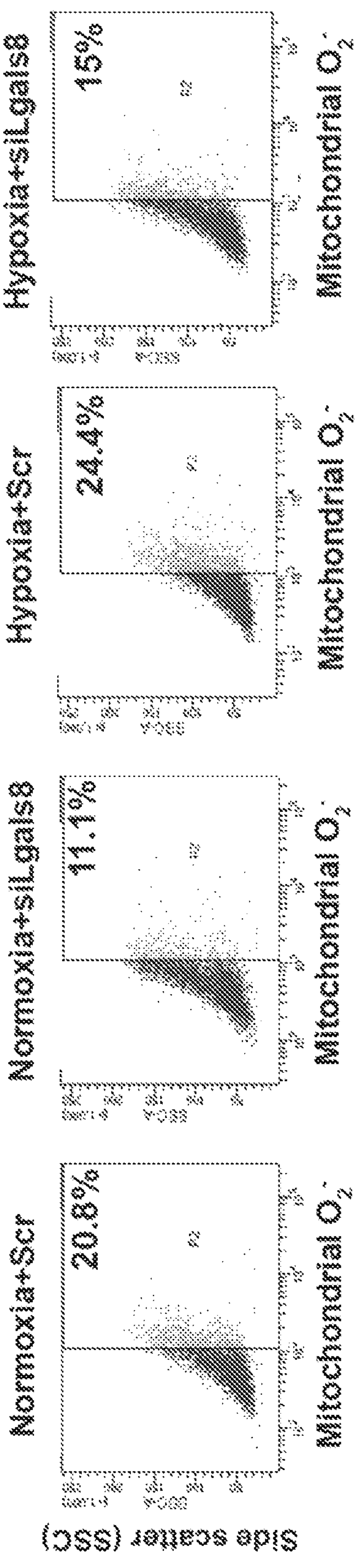
Figure 15E:
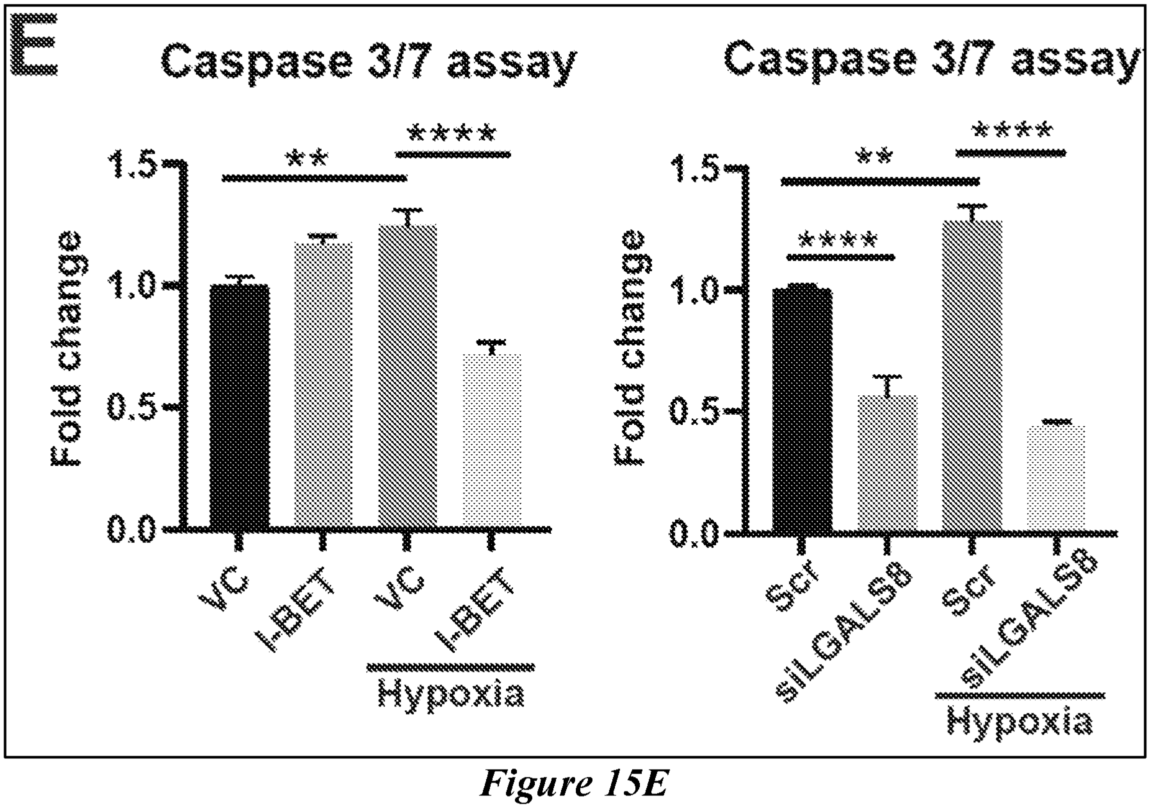

FIG. 15A-FIG. 15E. IBET-762 and LGALS8 control oxidant and apoptotic endothelial pathways driven by hypoxia. (FIG. 15A) In PAECs+/−hypoxic exposure, I-BET vs. vehicle controls (VC) reversed the hypoxia-induced increases of mitochondrial superoxide (02) levels as determined by flow cytometry of MitoSOX Red staining (n=5/grp). (FIG. 15B) In PAECs+/−hypoxic exposure, siLGALS8 compared with siRNA control (Scr) reversed the hypoxia-induced increases of mitochondrial superoxide ($O_2^-$) (n=5/grp). (FIG. 15C-FIG. 15D) Representative scatter plots of MitoSOX Red staining followed by flow cytometry for experiments in (FIG. 15A-FIG. 15B). (FIG. 15E) In PAECs+/−hypoxic exposure, I-BET vs. VC (left graph) and siLGALS8 vs. Scr (right graph) reversed the hypoxia-induced increases of apoptosis, as assessed by caspase-3/7 activity (n=4-6/grp). The data are plotted as mean±SEM. Statistical significance is indicated using two-way ANOVA with Bonferroni's multiple comparisons (*p<0.05, <0.01, *<0.001, ****<0.0001).

Figure 16A:
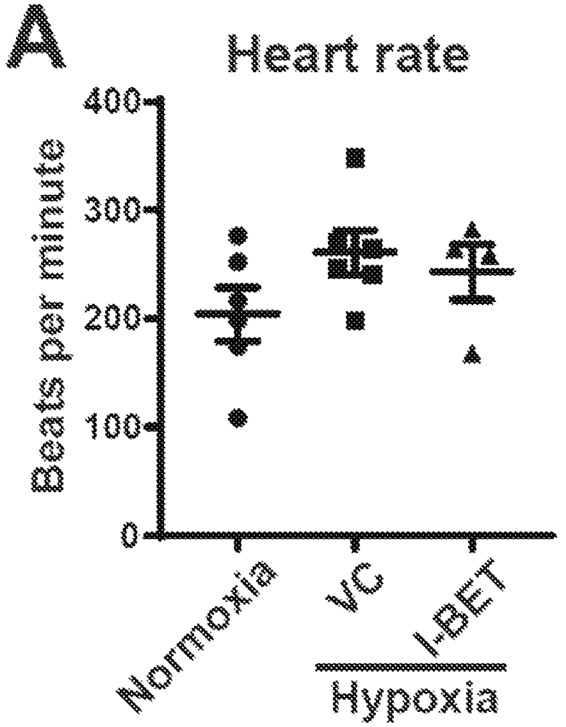
Figure 16B:
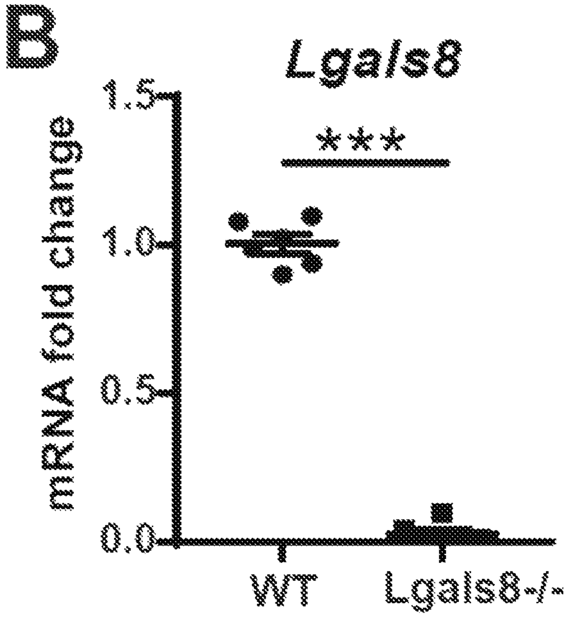
Figure 16C:
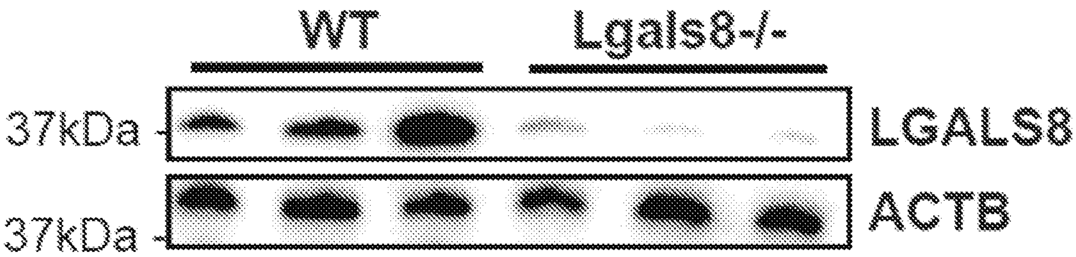
Figure 16D:
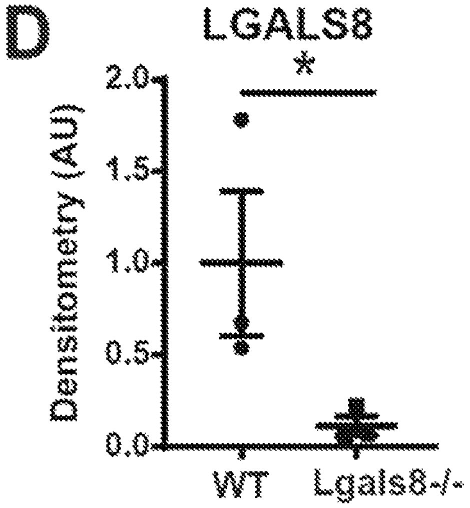
Figure 16E:
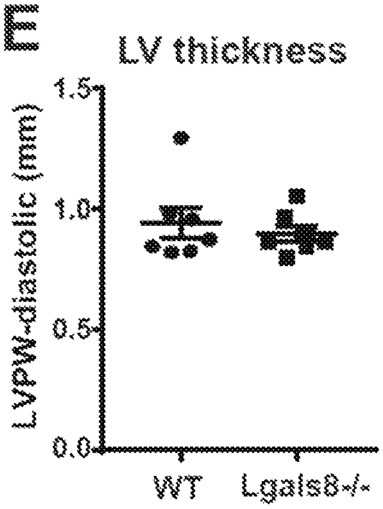
Figure 16F:
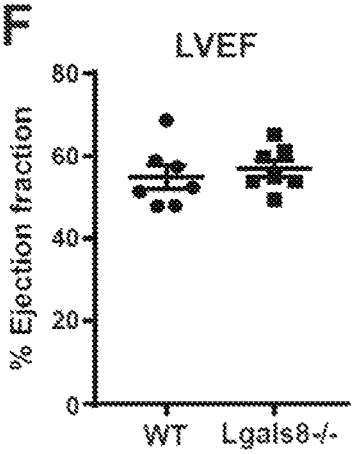
Figure 16G:
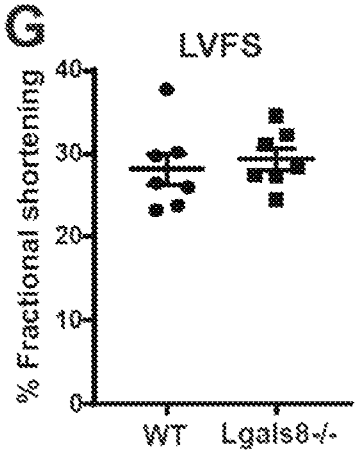
Figure 16H:
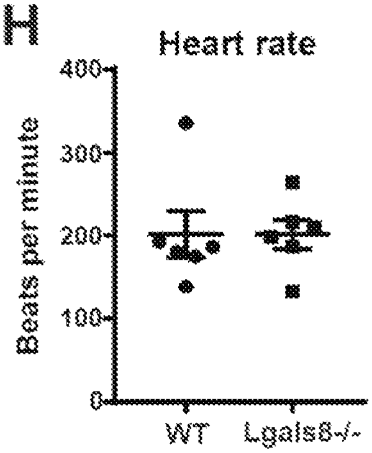
Figure 16I:
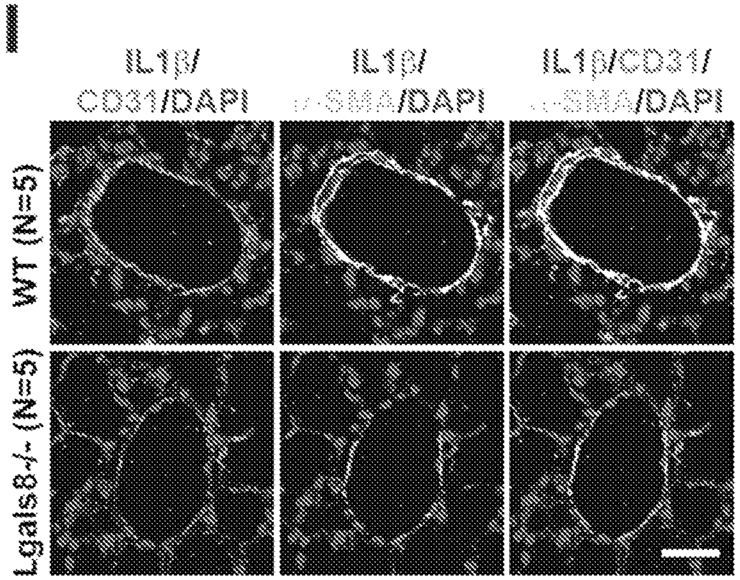
Figure 16J:
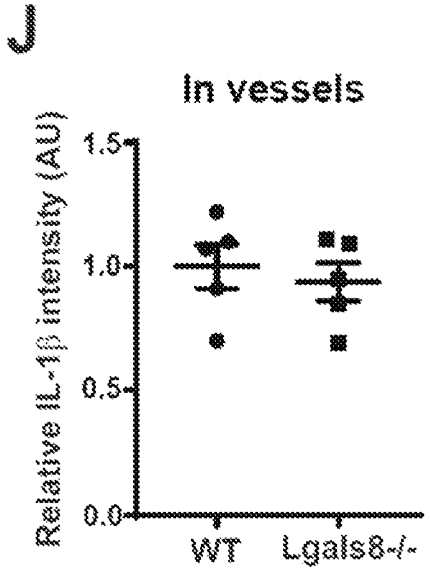
Figure 16K:
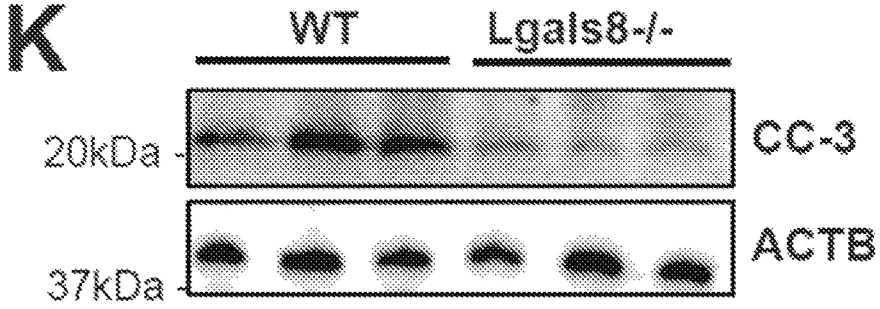
Figure 16L:
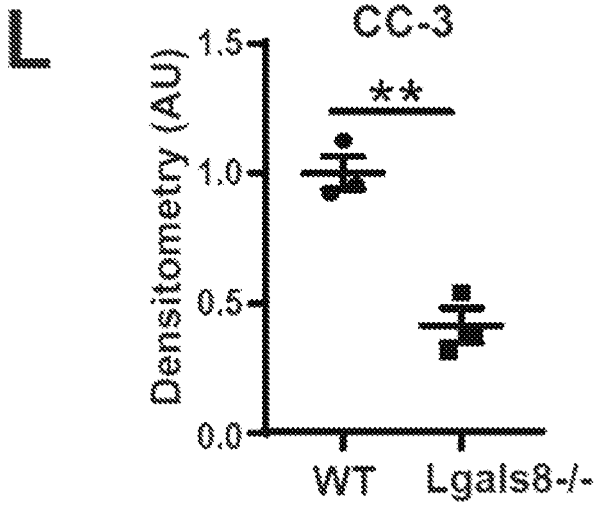

FIG. 16A-FIG. 16L. Parameters of cardiovascular and pulmonary vascular expression and function in hypoxia-induced pulmonary hypertension mice administered I-BET762 and in hypoxic Lgals8−/− mice. (FIG. 16A) Heart rate of hypoxic mice administered I-BET762 was not altered compared with vehicle control (VC) (n=4-6/grp). (FIG. 16B-FIG. 16D) The knockout efficiency of Lgals8−/− mice was determined at the mRNA (FIG. 16B) and protein (FIG. 16C-FIG. 16D) level in whole lung lysate measured by RT-qPCR (n=6/grp) and immunoblot/densitometry (n=3/grp), respectively. (FIG. 16E-FIG. 16G) Lgals8−/− mice did not exhibit altered left ventricular function compared to their littermate controls (WT) as measured by left ventricle thickness (FIG. 16E), ejection fraction (LVEF; FIG. 16E), and fractional shortening (LVFS; FIG. 16G) via transthoracic echocardiography (n=7/grp). (FIG. 16H) Heart rate was also unchanged between Lgals8−/− mice and their littermate controls (WT) (n=6/grp). (FIG. 16I-FIG. 16L) To determine the effect of Lgals8 knockout on pulmonary hypertension, Lgals8−/− mice were exposed to chronic hypoxia for 3 weeks. By immunofluorescence staining, IL-1β expression in the pulmonary vessels was not significantly altered in Lgals8−/− mice compared to WT mice (FIG. 16I-FIG. 16J, n=5/grp). Decreased apoptosis in whole lung homogenate was observed in Lgals8−/− mice as determined by immunoblot (FIG. 16K) and respective densitometry (FIG. 16L) of cleaved caspase 3 (n=3/grp). The data are plotted as mean±SEM. Statistical significance is indicated using one-way ANOVA with Bonferroni's multiple comparisons testing for (FIG. 16A) and Student's t-test for (FIG. 16B-FIG. 16L) (*p<0.05, ***p<0.001). Scale bar, 50 μm.

Figure 5A:
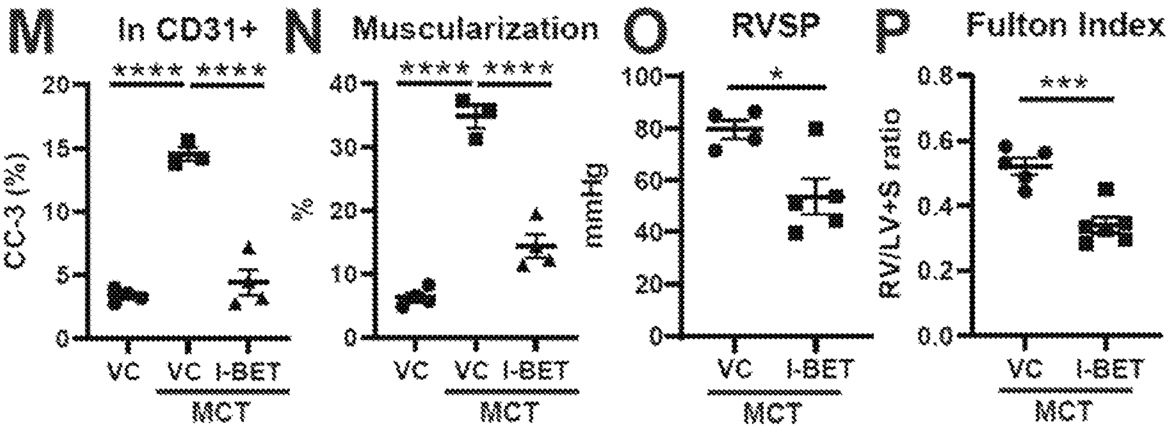
FIG. 5A-FIG. 5O. I-BET and genetic deficiency of LGALS8 independently protect against hypoxia-induced pulmonary hypertension in mice.
Figure 5A:
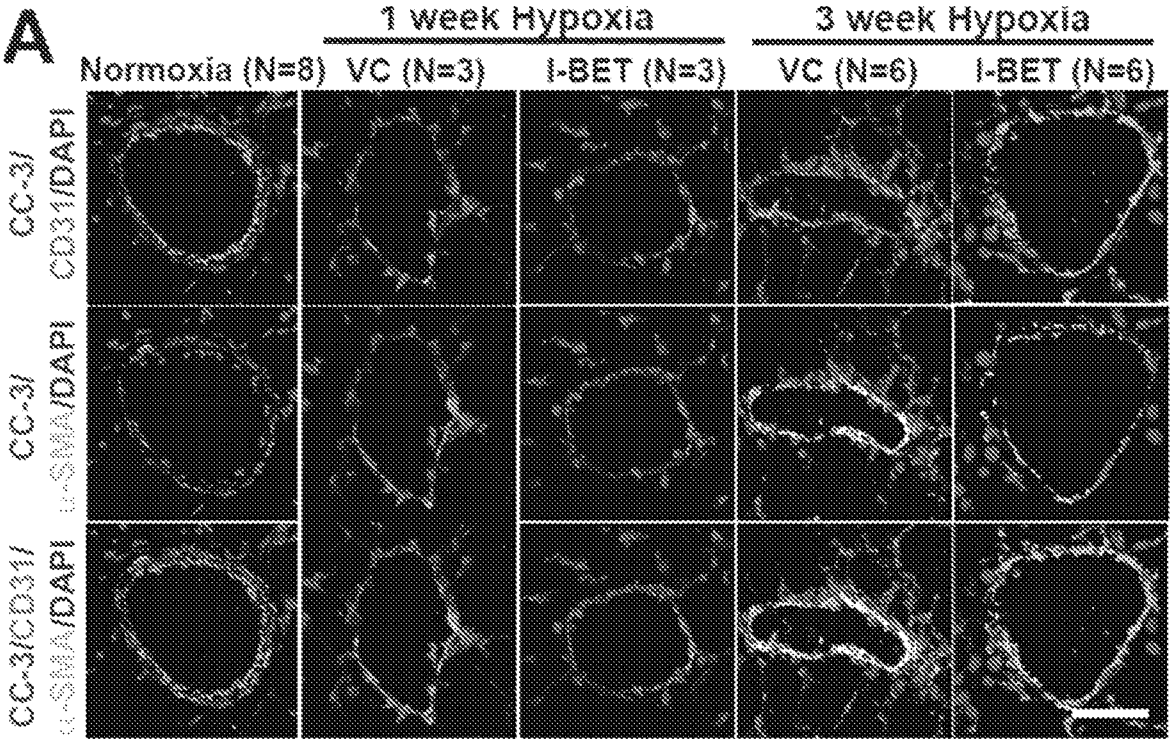
Figure 5E:
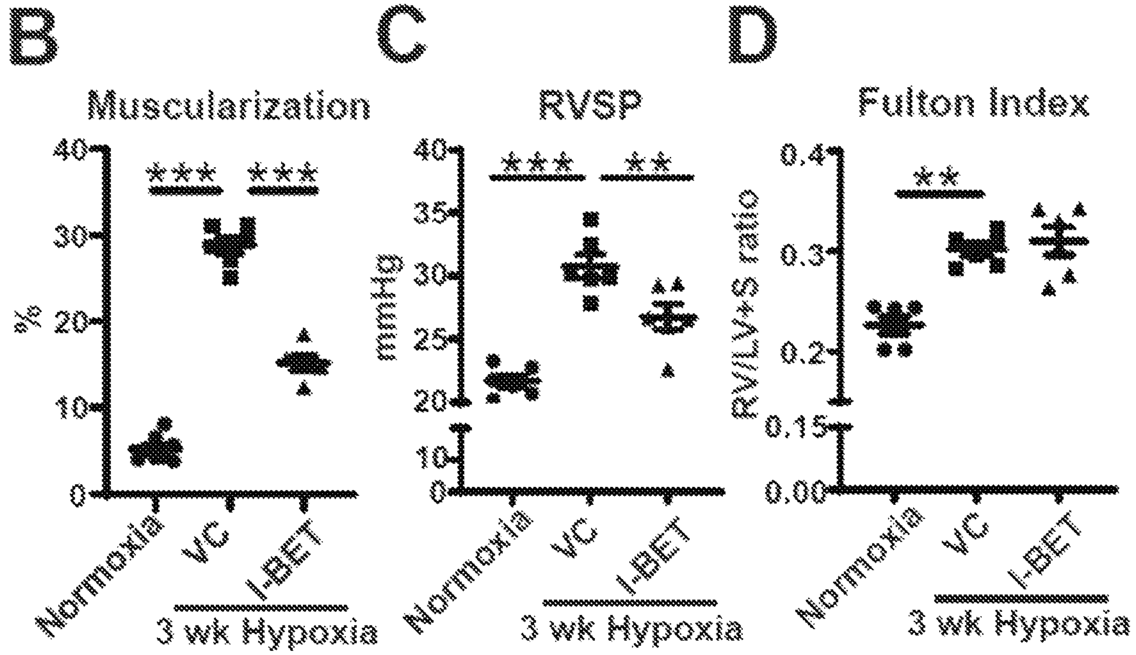
Figure 5E:
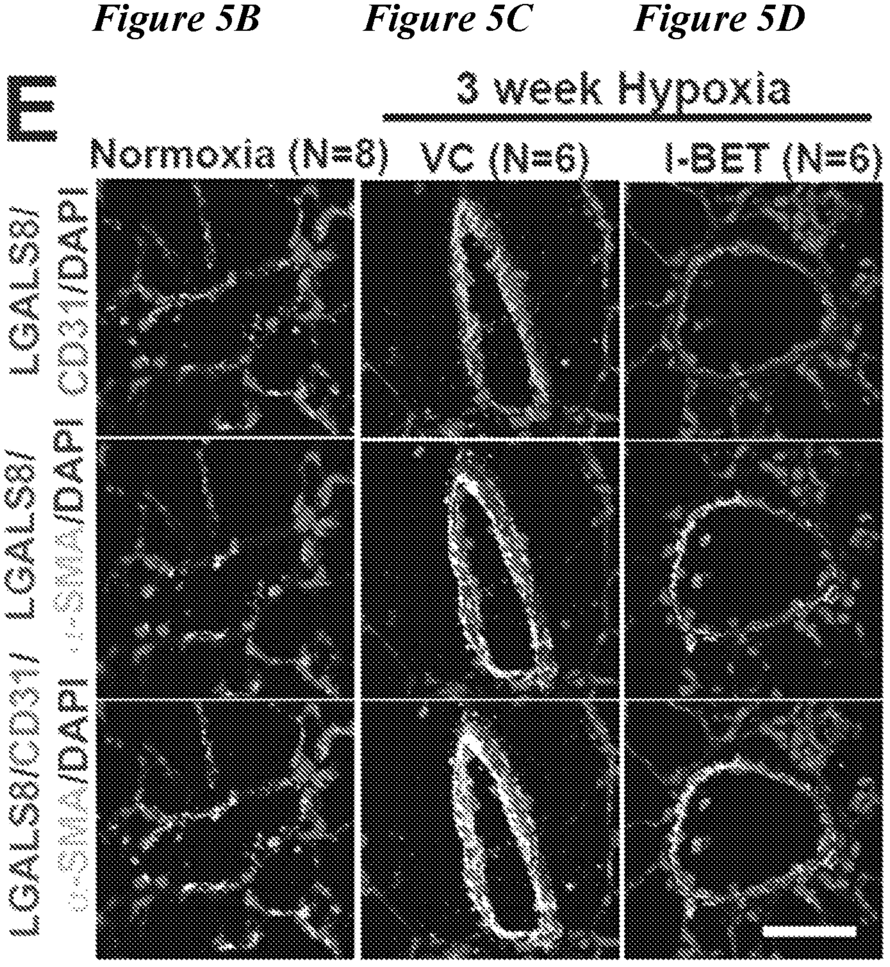
Figure 17A:
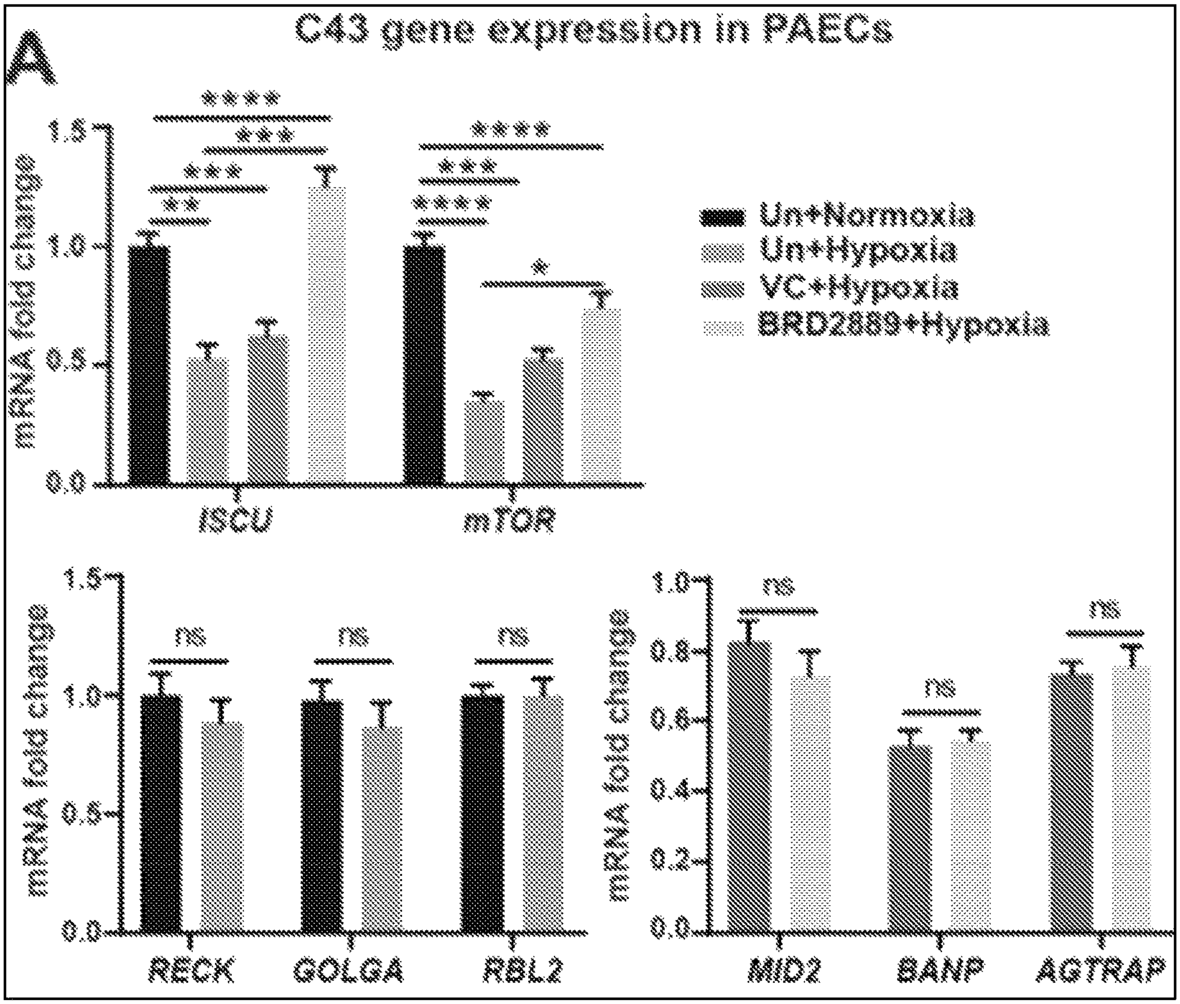
Figures 17B, 17C, 17D:
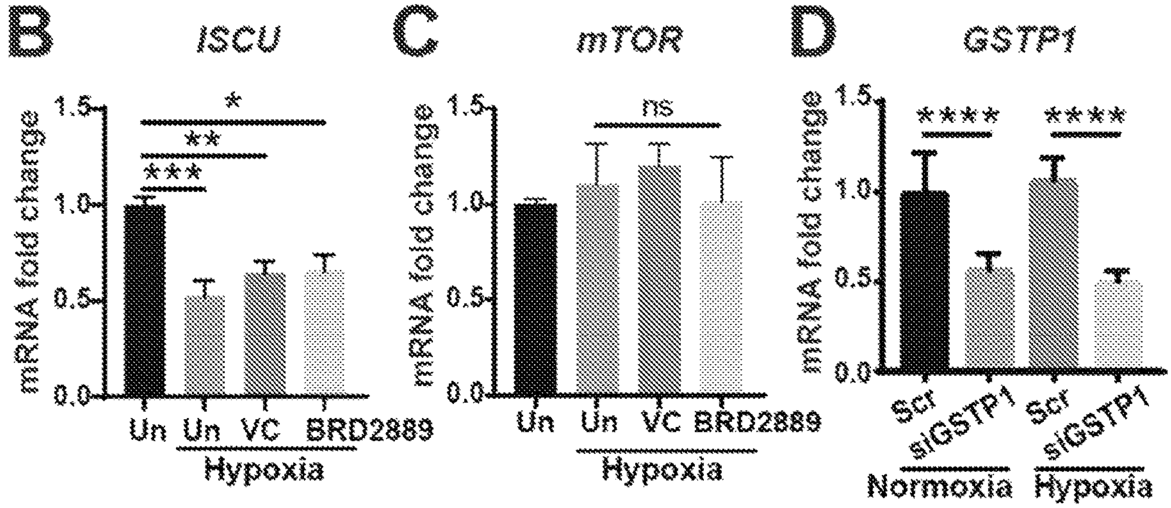
Figure 17E:
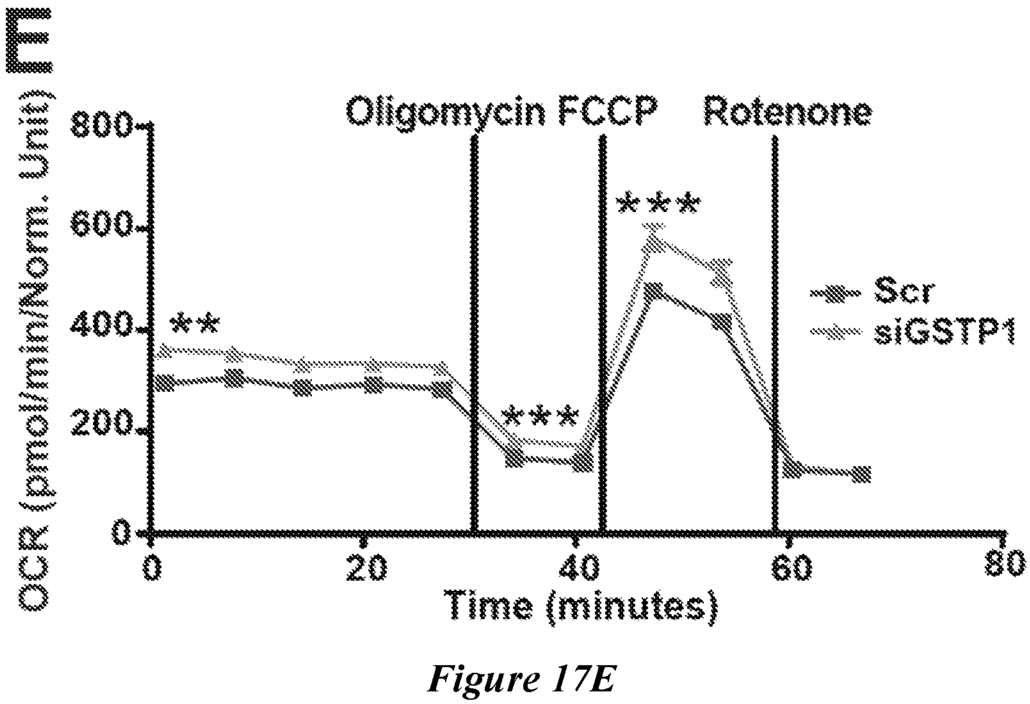
Figure 17F:
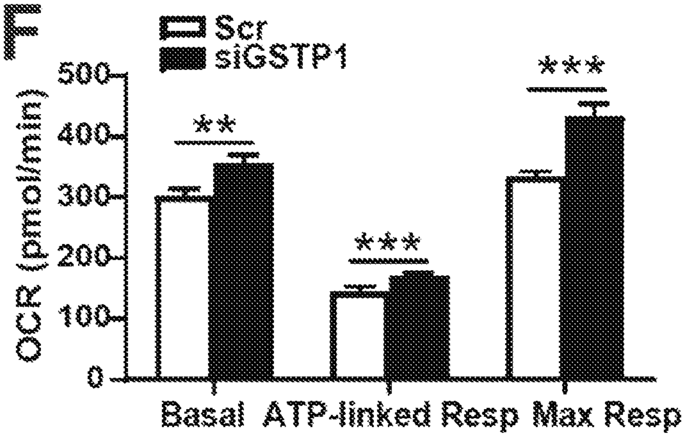
Figure 17G:
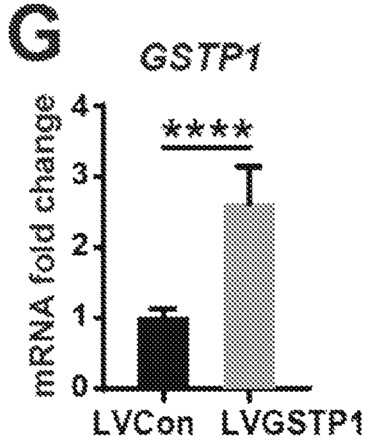
Figure 17H:
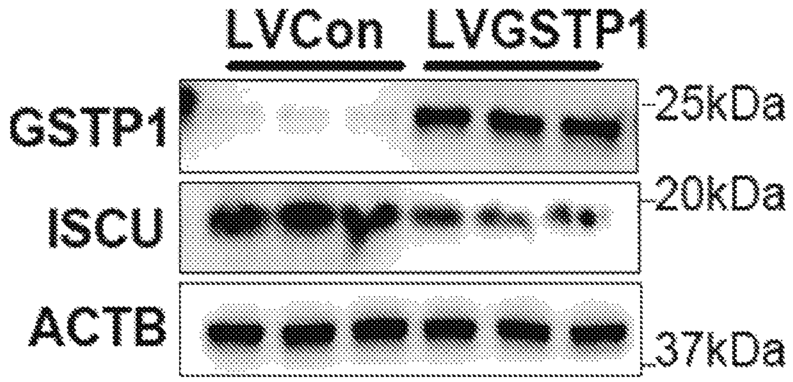
Figure 17I:
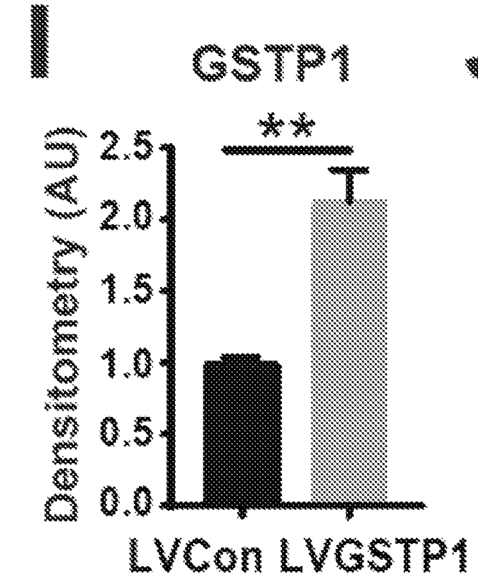
Figure 17J:
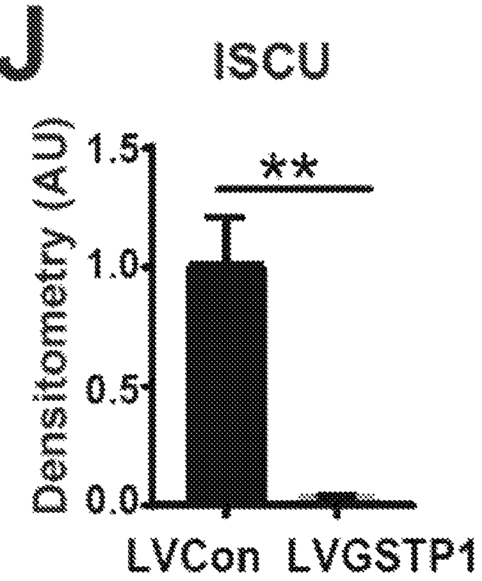
Figure 17K:
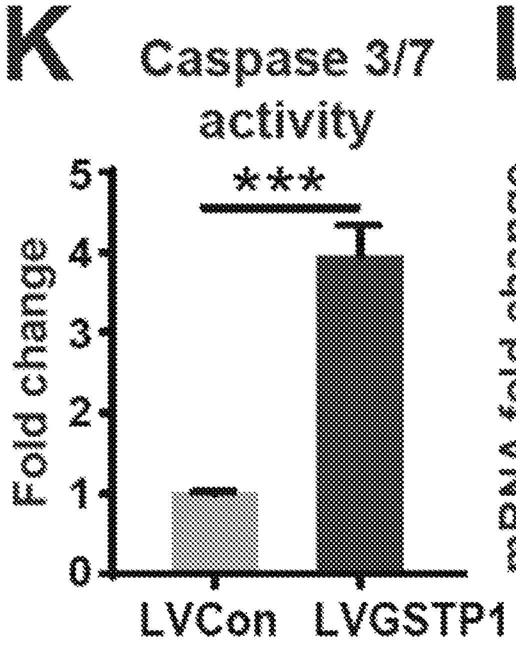
Figure 17L:
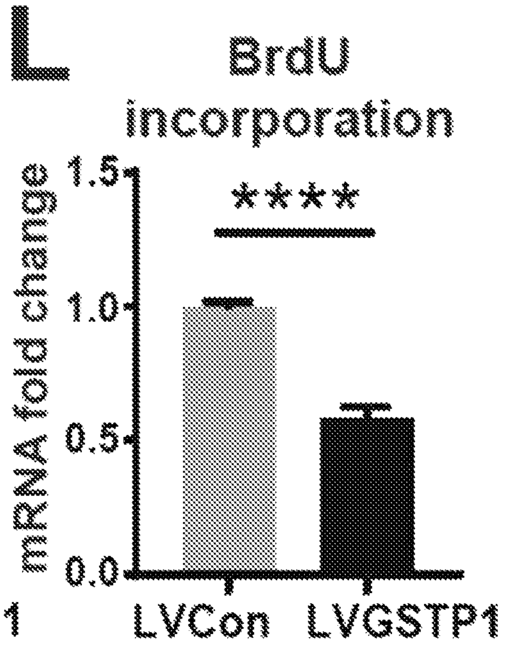
Figure 17M:
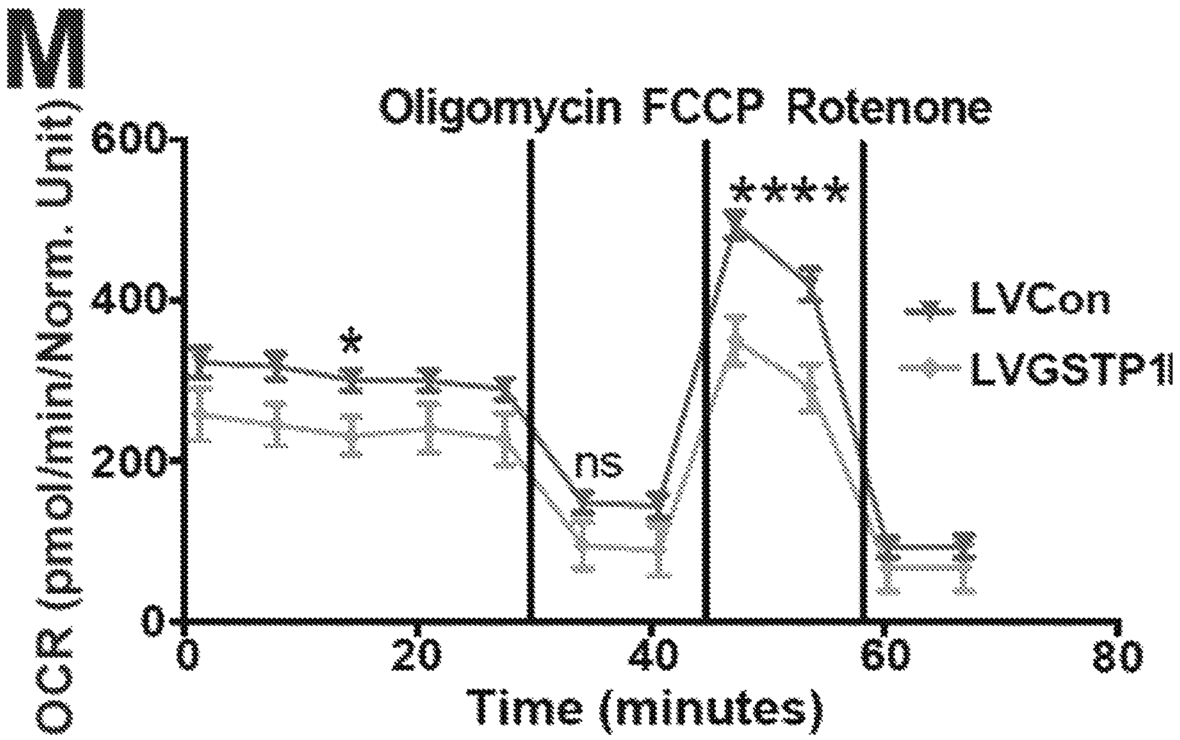
Figure 17N:
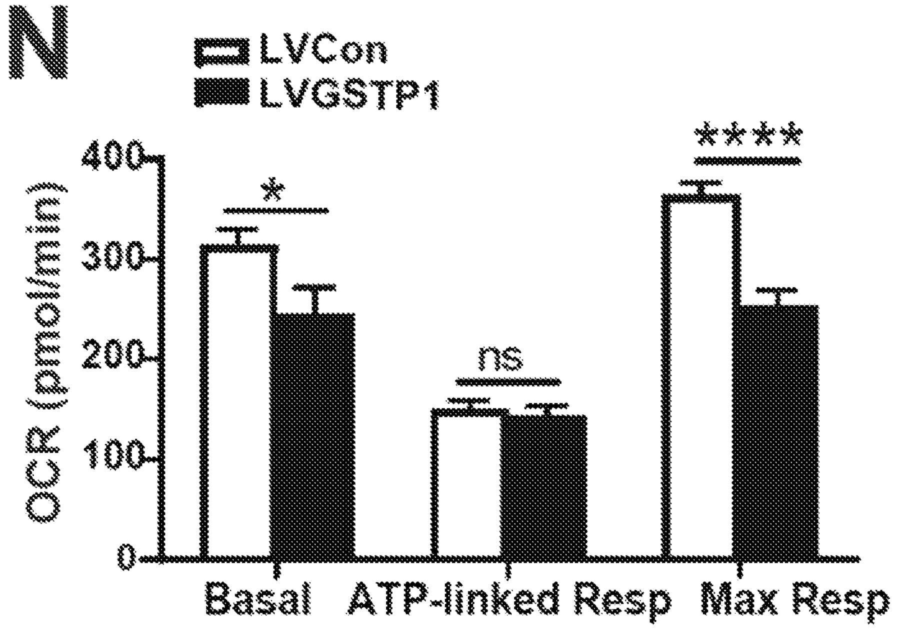
Figure 17O:
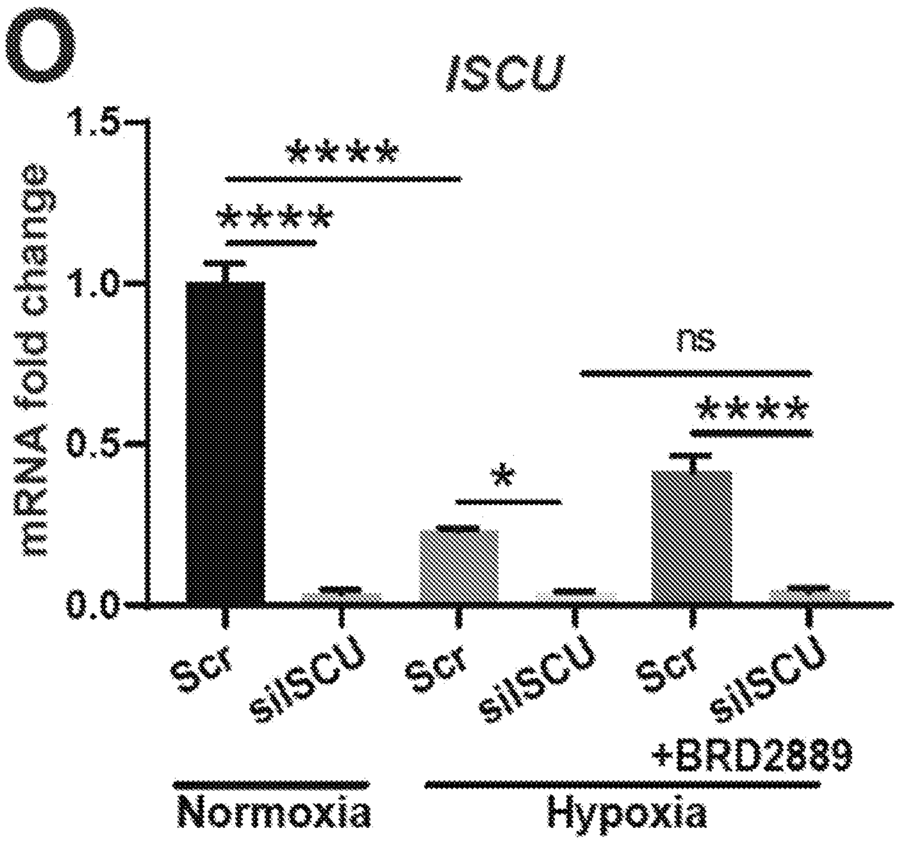
Figure 17P:
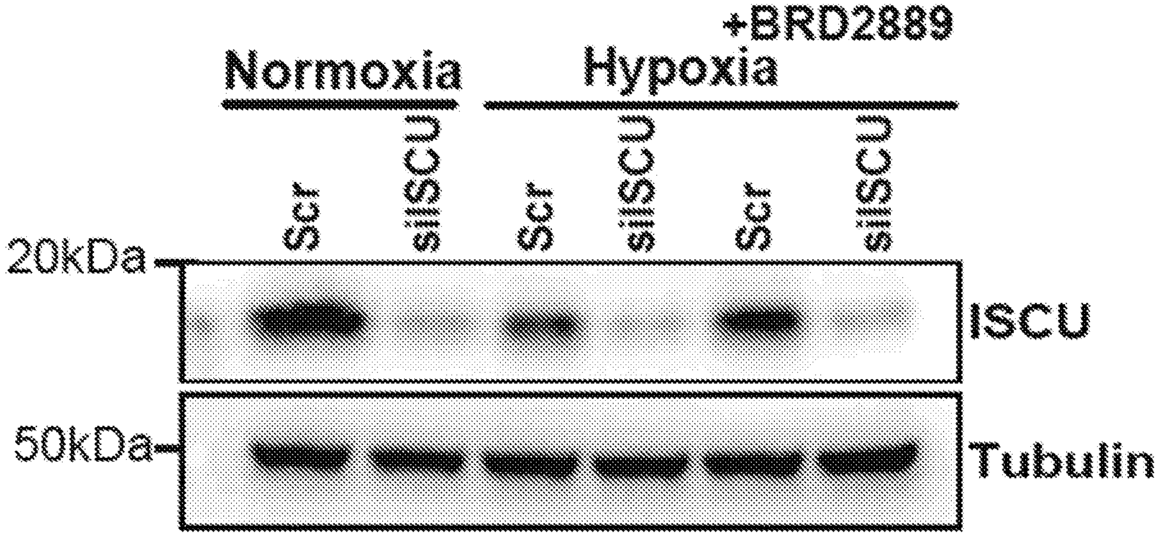
Figure 17Q:
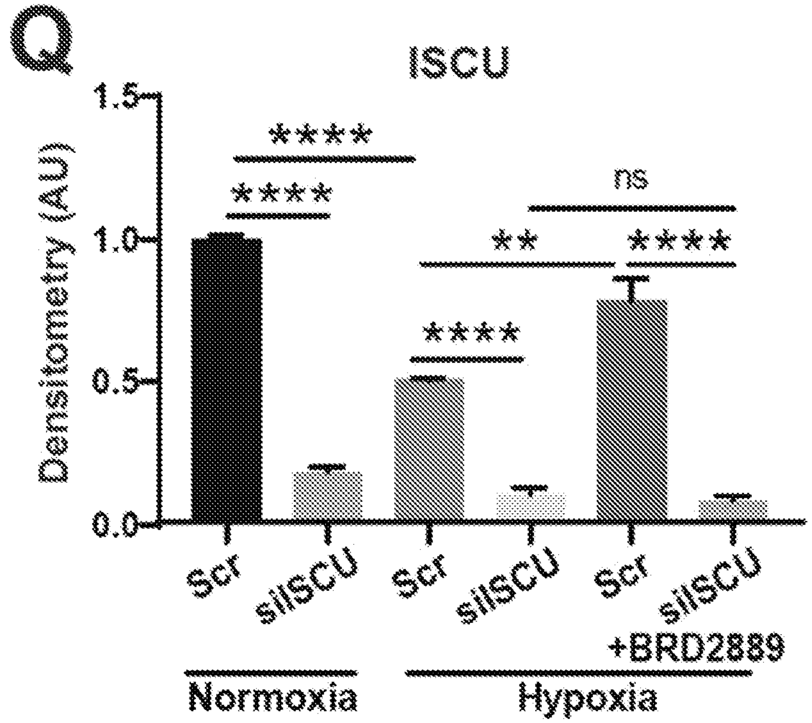

FIG. 17A-FIG. 17Q. BRD2889 controls C43 gene expression and improves mitochondrial function by targeting GSTP1. (FIG. 17A) By RT-qPCR, in PAECs, expression of C43 genes ISCU and mTOR were decreased by hypoxia (48 hrs) and rescued by BRD2889 (5 uM) vs. vehicle control (VC) (left graph). Other C43 genes were either unaffected by hypoxia (RECK, GOLGA, and RBL2, middle graph) or unaffected in hypoxia by BRD2889 (MID2, BANP, AGTRAP, right graph); Un, non-vehicle exposed cells (n=4/grp). Of note, remaining C43 genes KRT40 and MT1G were not assessed, given their disconnection from the BRD2889-specific differential dependency network (FIG. 5A). (FIG. 17B, FIG. 17C) In PASMCs, by RT-qPCR, hypoxic expression of C43 genes ISCU and mTOR was unaffected by BRD2889 (5 uM) (n=5/grp). (FIG. 17D) In PAECs, siRNA efficiency of GSTP1 was confirmed by RT-qPCR (n=4/grp). (FIG. 17E) In PAECs subjected to GSTP1 siRNA knockdown vs. scrambled siRNA control (Scr), a tracing was generated of oxygen consumption rate (OCR) using a Seahorse XFe96 flux analyzer recorded at baseline and following treatment with 1 mM oligomycin, 0.5 mM FCCP, and a 1 mM rotenone and antimycin mixture (n=3/grp). (FIG. 17F) GSTP1 knockdown vs. Scr control resulted in an increase in basal, ATP-linked, and maximal respiration compared to Scr (n=3/grp). (FIG. 17G-FIG. 17L) After lentiviral forced expression of GSTP1 (LVGSTP1), GSTP1 transcript (by RT-qPCR, G, n=3/grp) and protein (by immunoblot, FIG. 17H and densitometry quantification, FIG. 17I, n=3/grp) were increased compared with vector control (LVCon). Forced GSTP1 expression downregulated ISCU protein (FIG. 17J, n=3/grp), increased apoptosis (by caspase 3,7 activity, FIG. 17K, n=4/grp), and decreased proliferation (by BrdU incorporation, FIG. 17L, n=4/grp). (FIG. 17M-FIG. 17N) Forced GSTP1 expression also decreased basal and mitochondrial OCR (n=3/grp). (FIG. 17O-FIG. 17Q) In hypoxic PAECs treated with BRD2889, siRNA knockdown of ISCU vs. Scr control siRNA was performed in normoxia or hypoxia; siRNA efficiency was confirmed by RT-qPCR (FIG. 17O) and immunoblot/densitometry (FIG. 17P, FIG. 17Q) (n=3/grp). These data are plotted as mean±SEM. Statistical significance is indicated for multiple comparisons using one-way ANOVA with Bonferroni's multiple comparisons testing and for binary comparisons using Student's t-test (*p<0.05, <0.01, *<0.001, ****<0.0001).

Figure 18A:
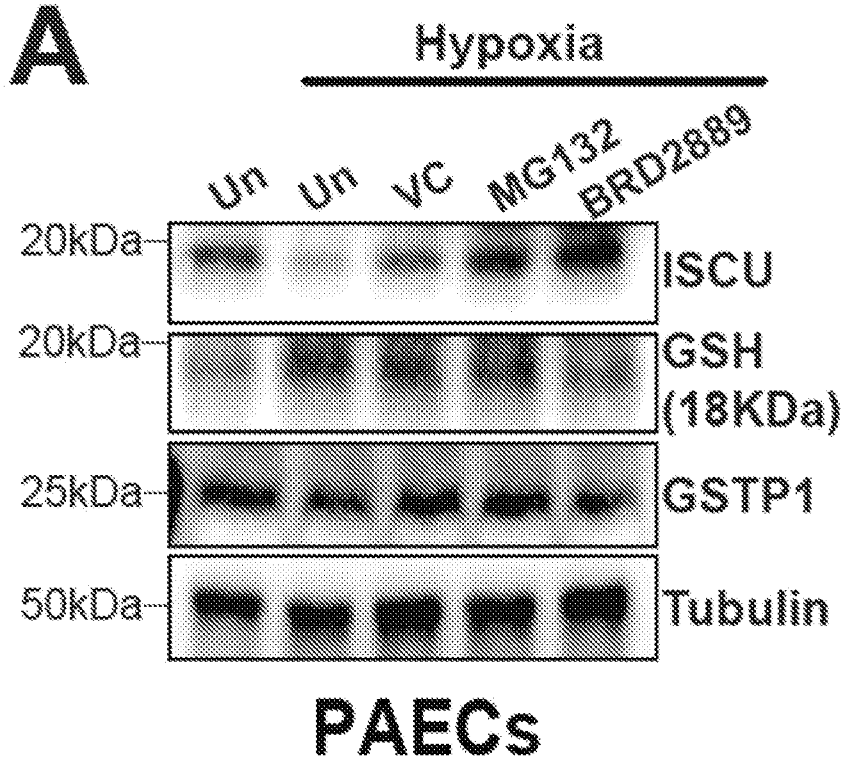
Figure 18B:
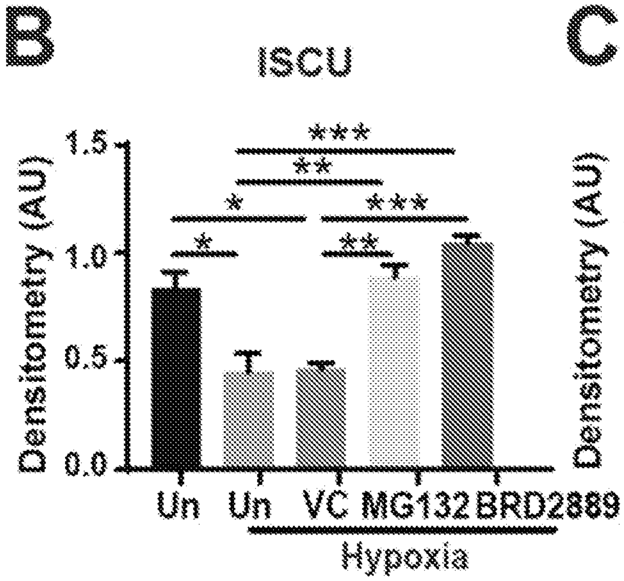
Figure 18C:
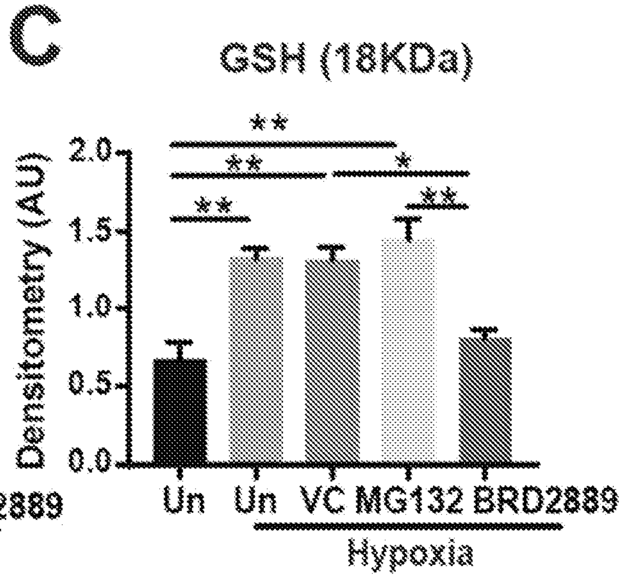
Figure 18D:
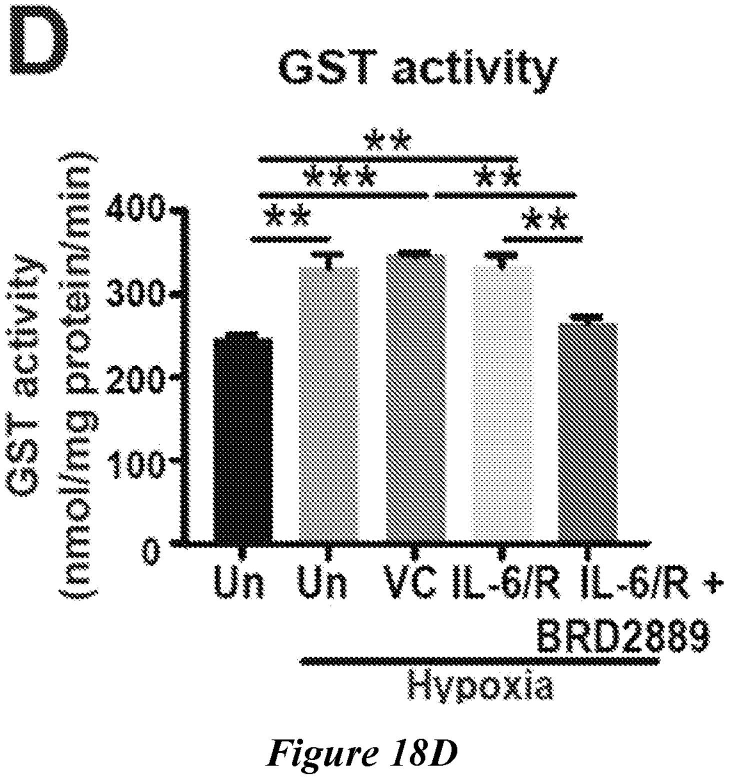
Figure 18E:
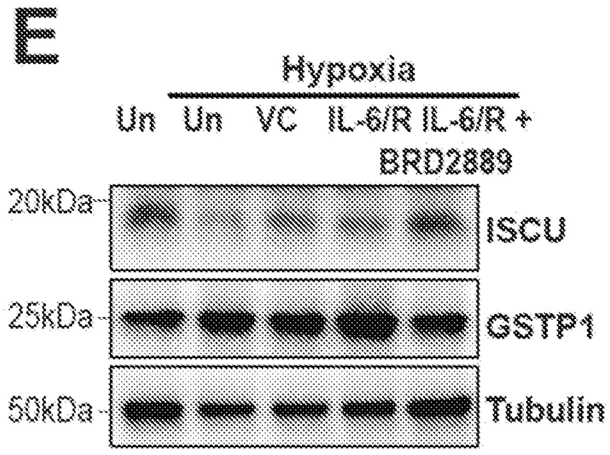
Figure 18F:
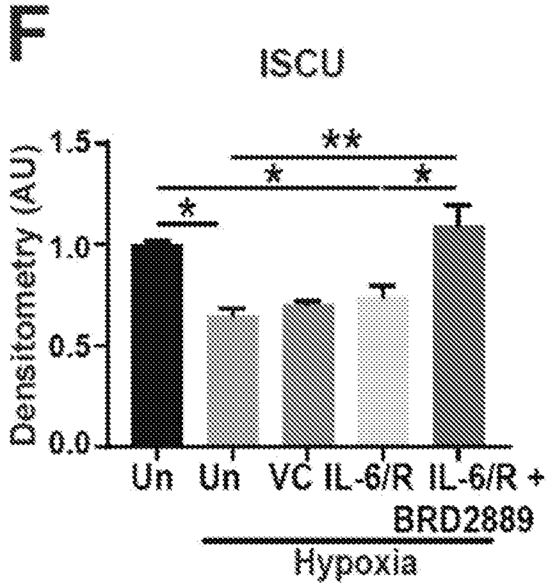
Figure 18G:
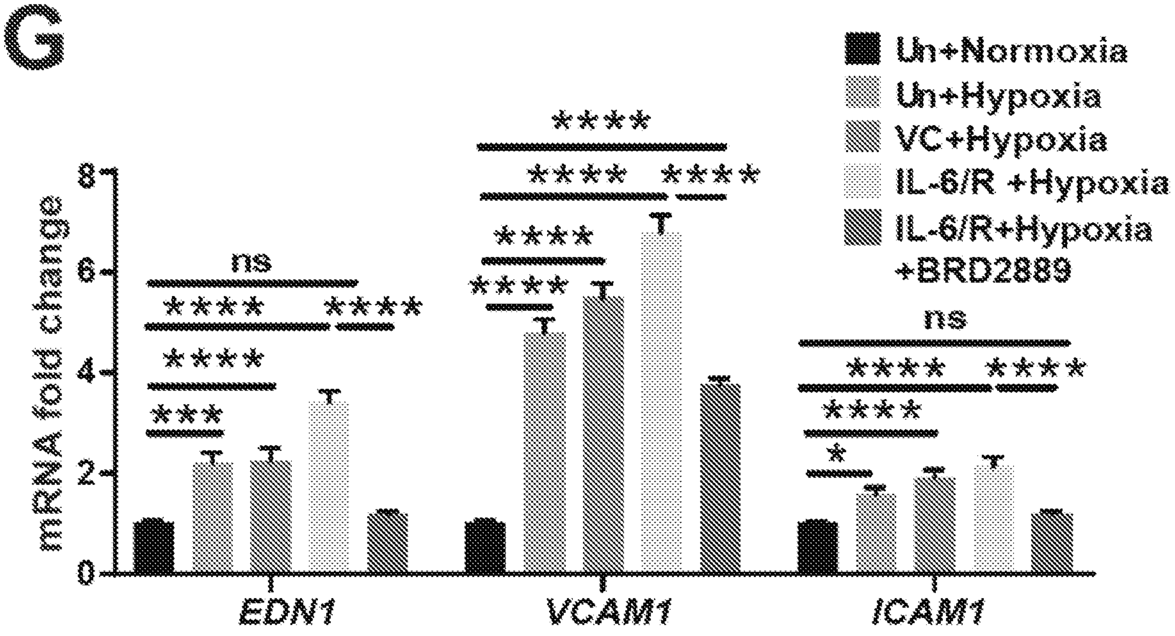
Figure 18H:
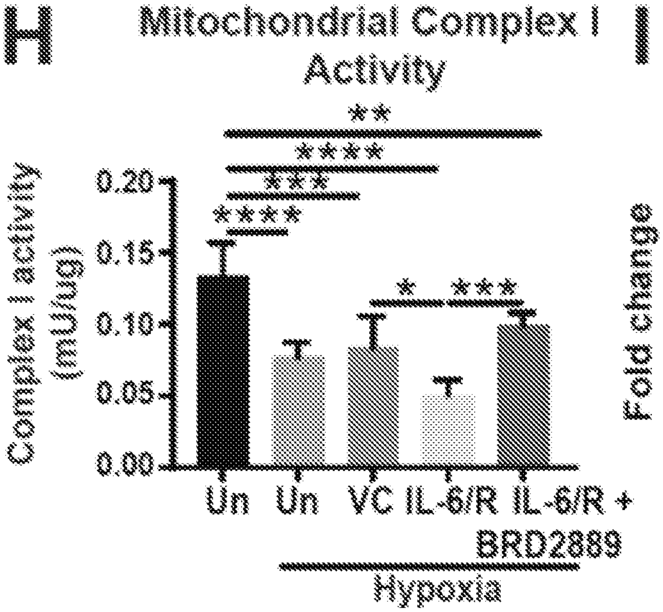
Figure 18I:
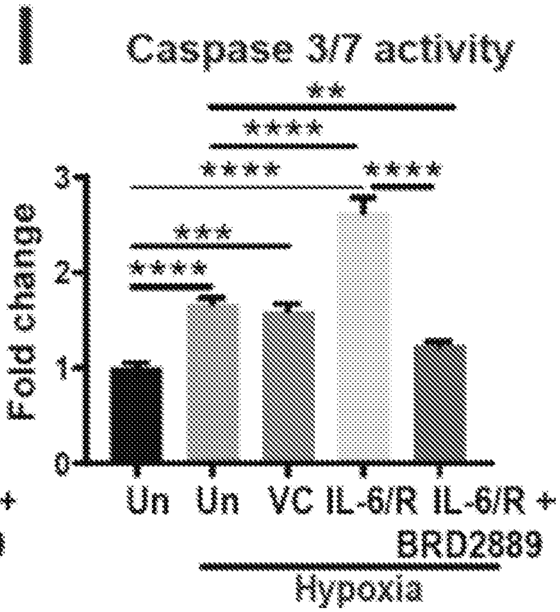
Figure 18J:
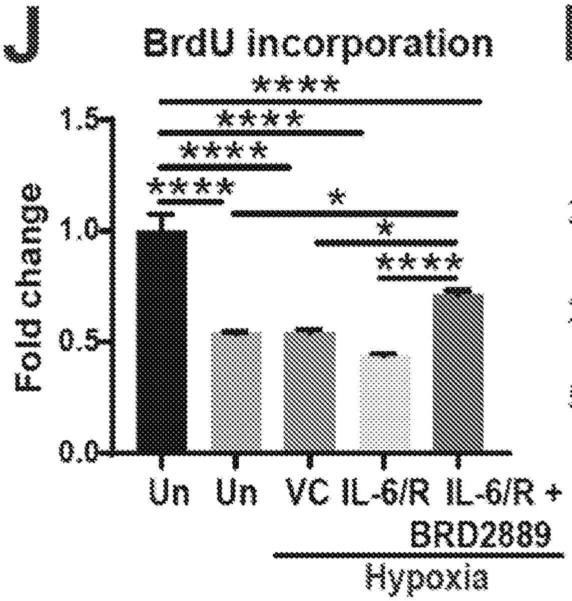
Figure 18K:
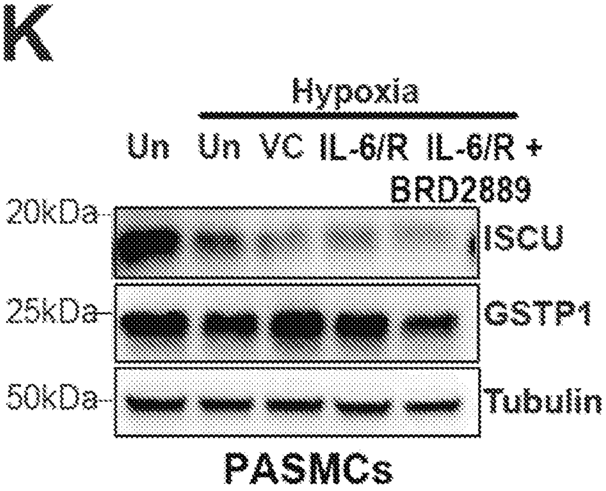
Figure 18L:
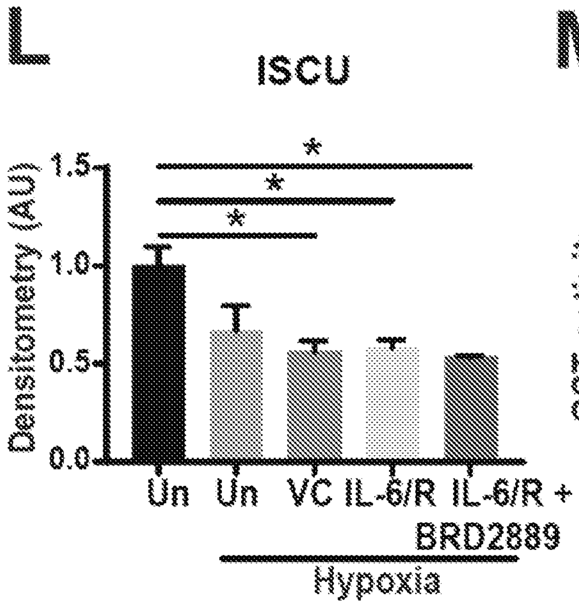
Figure 18M:
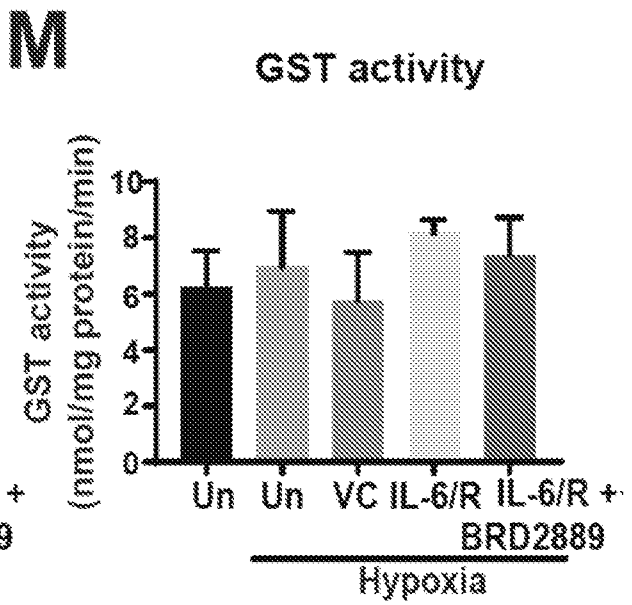
Figure 18N:
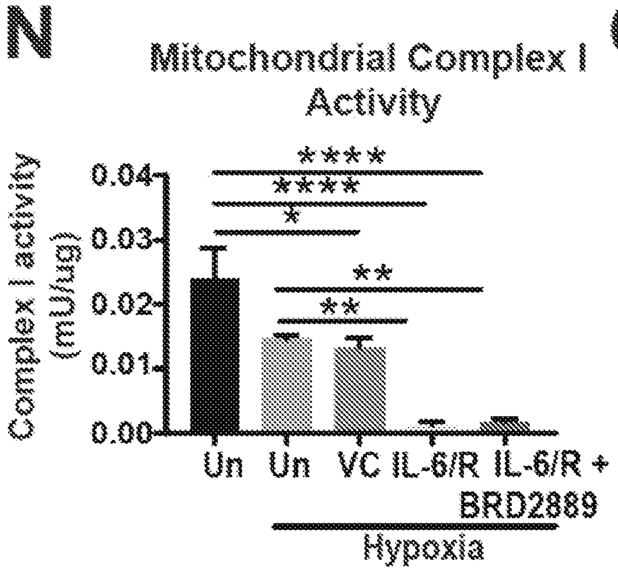
Figure 18O:
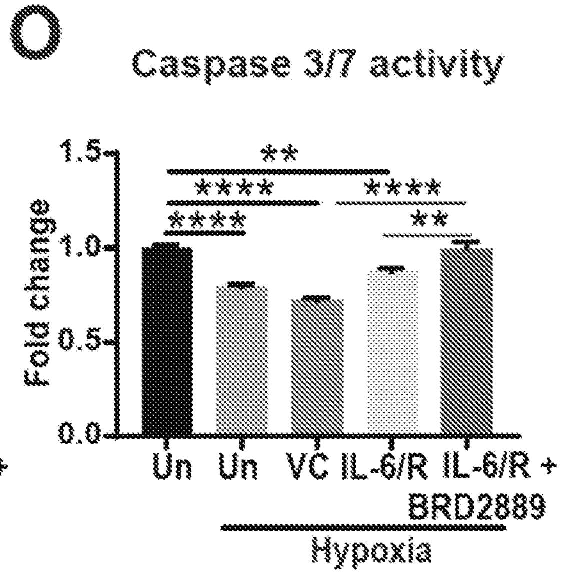
Figure 18P:
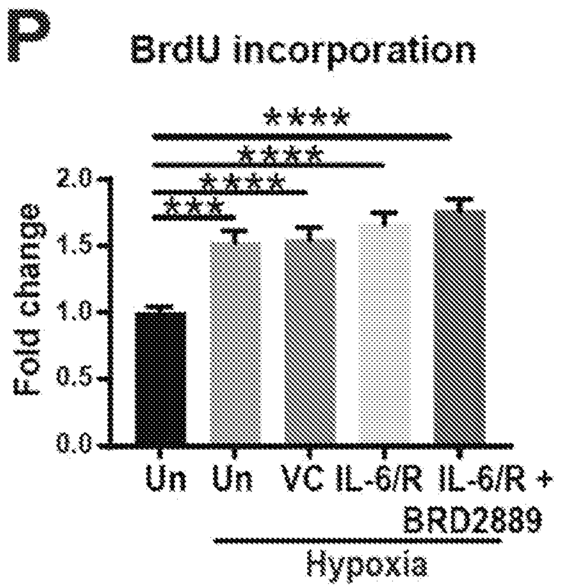
Figure 18Q:
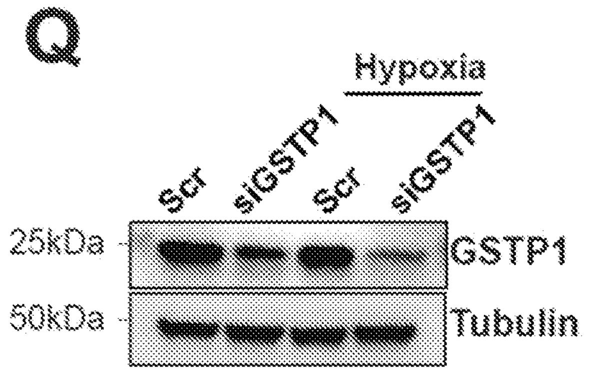
Figure 18R:
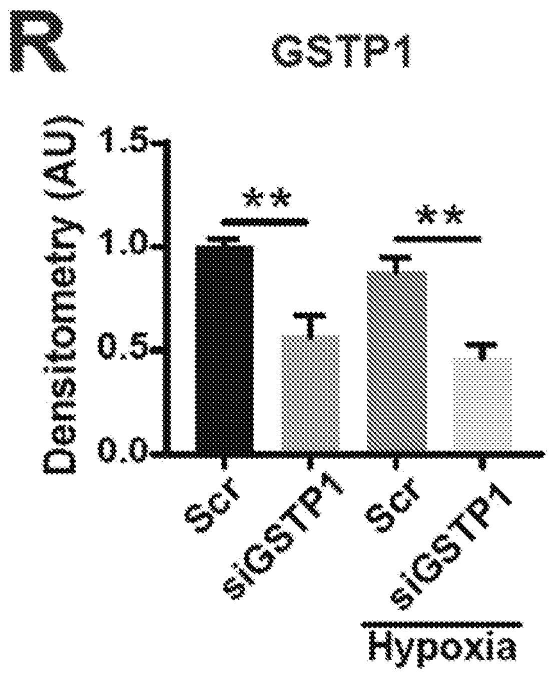
Figure 18S:
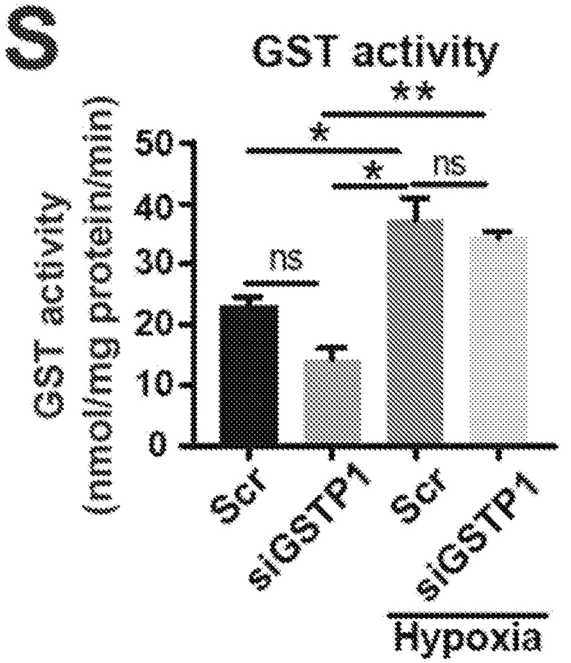

FIG. 18A-FIG. 18S. BRD2889 protects against endothelial-specific dysfunction induced by IL-6/soluble IL-6R+hypoxia. (FIG. 18A-FIG. 18C) In hypoxic PAECs, proteasome inhibitor MG132 (5 mM, 2 h), BRD2889 (1 mM, 24 h), vehicle (VC), or no treatment (Un) were added, followed by (FIG. 18A) immunoblot and densitometry of protein levels of ISCU (FIG. 18B) and GSH (glutathionylated-ISCU; FIG. 18C) (n=3/grp). MG132 reversed the hypoxia-induced reduction of ISCU without affecting GSTP1 or glutathionylation. BRD2889 also reversed the hypoxia-induced reduction of ISCU, but this was accompanied by a reversal of the hypoxic induction of ISCU glutathionylation.

(FIG. 18D-FIG. 18F) In PAECs, BRD2889 reversed the IL-6/R+hypoxia-mediated increase of GST activity (FIG. 18D) without altering GSTP1 expression (FIG. 18E) (n=3/grp). In doing so, BRD2889 reversed the IL-6/R+hypoxic decrease of ISCU, as determined by immunoblot (FIG. 18E) and respective densitometry (FIG. 18F). (FIG. 18G) In PAECs, expression of proinflammatory genes in response to IL-6/soluble IL-6 receptor (IL-6/R) and chronic hypoxia in cultured PAECs. Expression of EDN1, VCAM1, and ICAM1 transcripts were analyzed by RT-qPCR. IL-6/sIL-6R+hypoxia treatment induced these inflammatory gene transcripts, but BRD2889 normalized this upregulation (n=3/grp). (FIG. 18H-FIG. 18J) BRD2889 improved endothelial function by reversing the IL-6/R+hypoxia-mediated decrease in mitochondrial Complex I activity (FIG. 18H), the increase in apoptotic caspase 3/7 activity (FIG. 18I), and the decrease in BrdU incorporation as a measure of proliferation (FIG. 18J) (n=6/grp). (FIG. 18K-FIG. 18M) PASMCs were exposed similarly to IL-6/R+hypoxia. Representative immunoblot (FIG. 18K) and densitometry (FIG. 18L) demonstrated hypoxic IL-6/R+hypoxia-induced ISCU reduction that was not rescued by BRD2889 (1 uM). In addition, BRD2889 did not affect GSTP1 protein expression (FIG. 18K) or GST activity (FIG. 18M) (n=3/grp). (FIG. 18N-FIG. 18P) In PASMCs treated as in (FIG. 18K), BRD2889 did not affect the IL-6/sIL-6R+hypoxia-induced alterations of mitochondrial Complex I activity (FIG. 18N) and proliferation (FIG. 18P); and the modest alterations of apoptosis were only subtly changed by BRD2889 (FIG. 18O) (n=3/grp). (FIG. 18Q-FIG. 18S) siRNA knockdown of GSTP1 (siGSTP1) vs scrambled siRNA control (Scr) in PASMCs under normoxia or hypoxia. Despite knockdown of GSTP1 expression (by immunoblot and densitometry, FIG. 18Q-FIG. 18R), GST activity was not altered by siGSTP1 (S) (n=3/grp). These data are plotted as mean±SEM. Statistical significance is indicated using one-way ANOVA with Bonferroni's multiple comparisons testing (*p<0.05, <0.01, *<0.001, ****<0.0001).

Figure 19A:
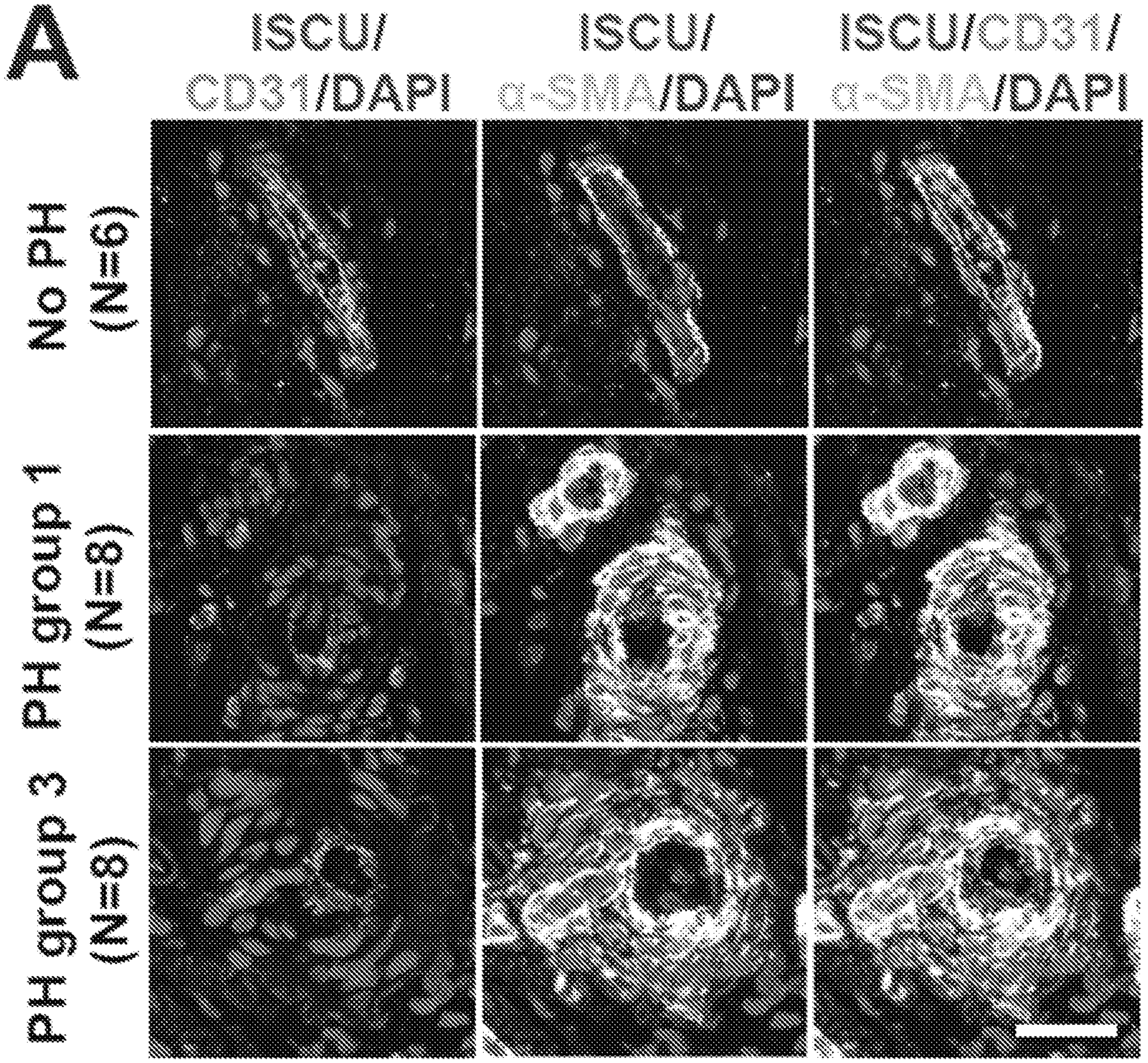
Figure 19B:
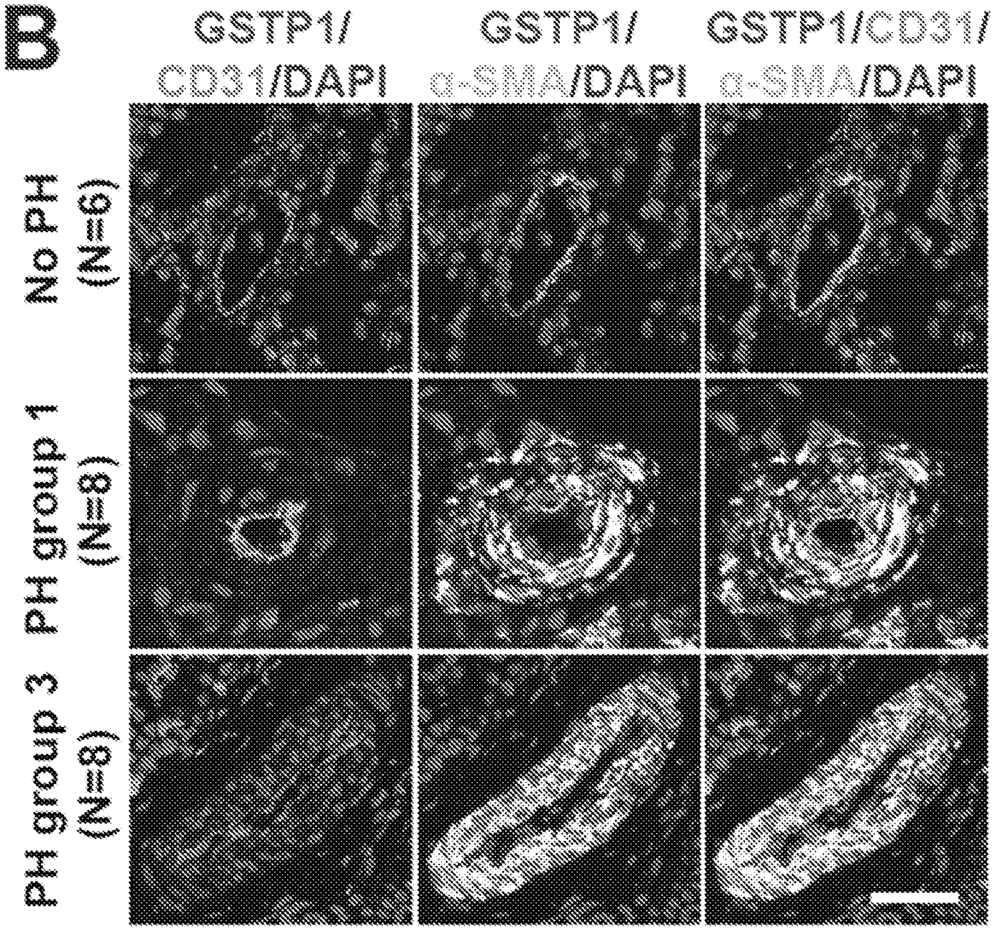
Figure 19C:
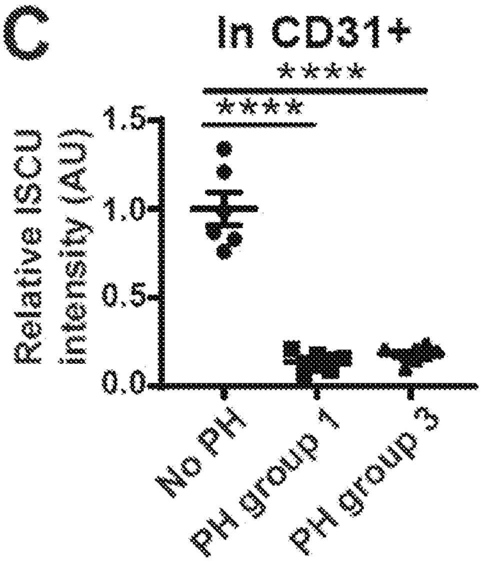
Figure 19D:
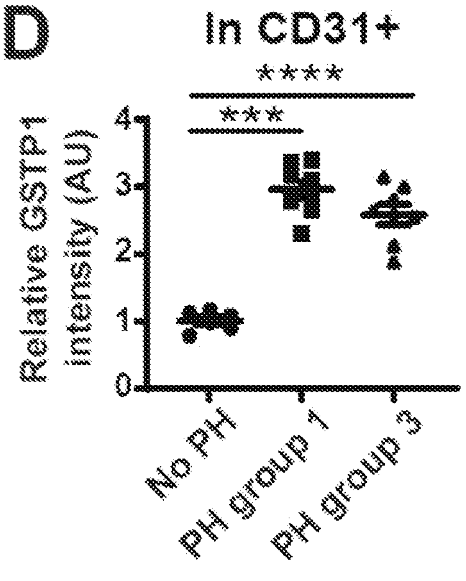
Figure 19E:
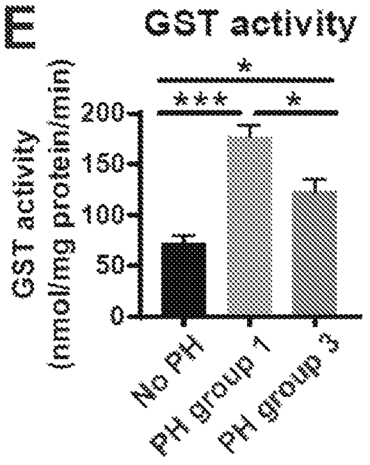

FIG. 19A-FIG. 19J. Expression of ISCU and GSTP1 in human pulmonary hypertension and parameters of cardiovascular function in hypoxic IL-6 Tg mice administered BRD2889. (FIG. 19A-FIG. 19E) Using immunofluorescence staining and respective quantification, expression of ISCU was decreased (FIG. 19A) and GSTP1 (FIG. 19B) was increased in CD31+(FIG. 19C-FIG. 19D) endothelium of lung sections from human patients with Group 1 (n=8) and Group 3 (n=8) pulmonary hypertension as compared to non-pulmonary hypertension controls (n=6). In addition, GST activity was increased in lung tissue of both Group 1 and Group 3 patients compared with non-pulmonary hypertension controls (n=4/grp) (FIG. 19E). (FIG. 19F) Lung GST activity was also increased in hypoxic IL-6 Tg pulmonary arterial hypertension mice vs. normoxic wildtype (WT) mice (n=4/grp). (FIG. 19G-FIG. 19J) No significant differences were observed in fractional shortening (FIG. 19G), ejection fraction (FIG. 19H), posterior wall (PW) thickness (FIG. 19I), and heart rate (FIG. 19J) of hypoxic IL-6 Tg mice following 10 days of treatment with either vehicle (n=3/grp) vs. BRD2889 (10 mg/kg, n=4/grp). Statistical significance is indicated using Student's t test comparing vehicle-treated and BRD2889 treatment groups in mice. Statistical significance is indicated using one-way ANOVA with Bonferroni's multiple comparisons testing for comparing human samples (*p<0.05, <0.01, *<0.001, ****<0.0001). See also Table 4.

Figure 20A:
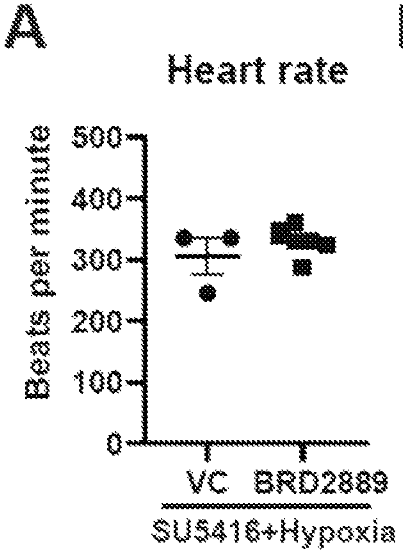
Figure 20B:
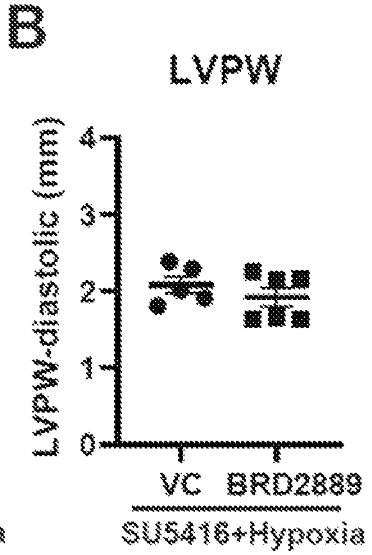
Figure 20C:
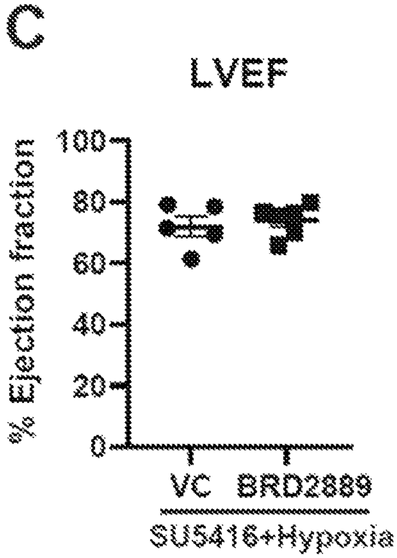
Figure 20D:
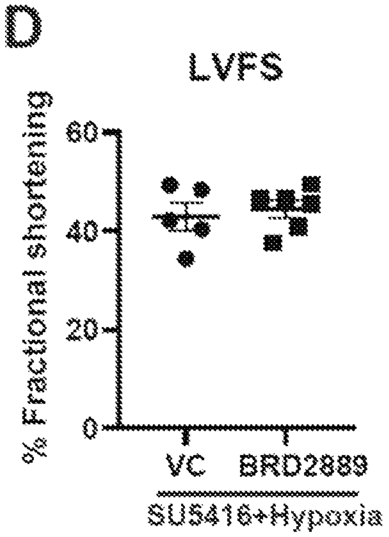
Figure 20E:
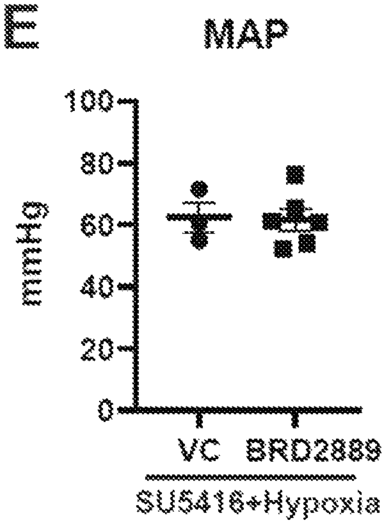
Figure 20F:
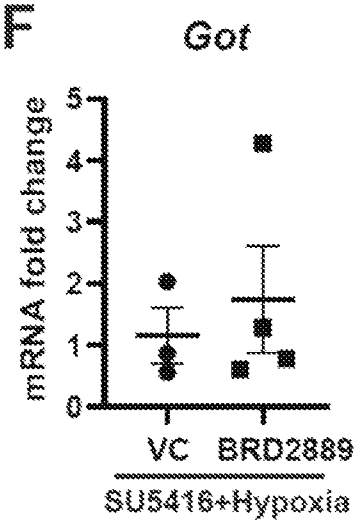
Figure 20G:
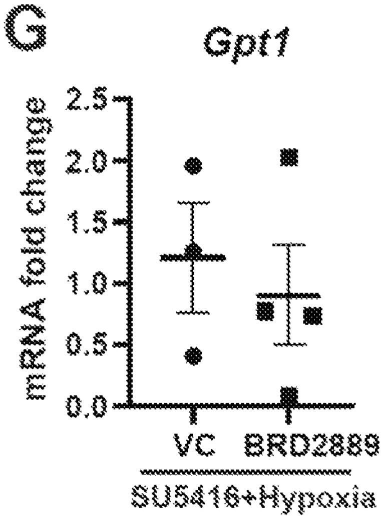
Figure 20H:
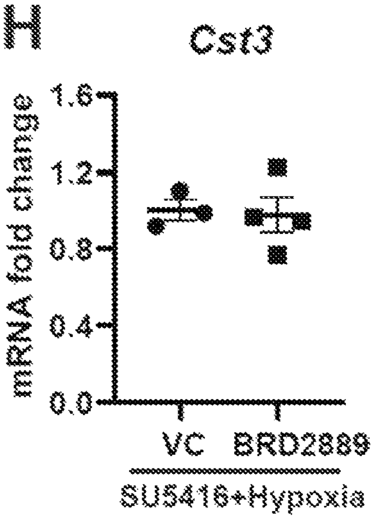
Figure 20I:
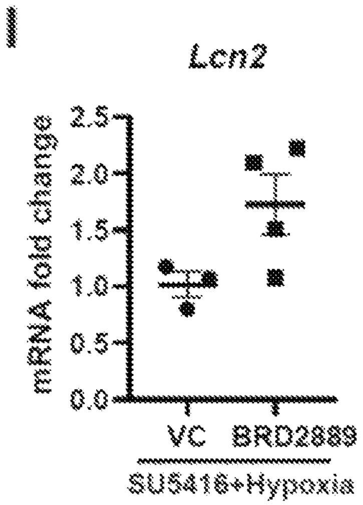
Figure 20J:
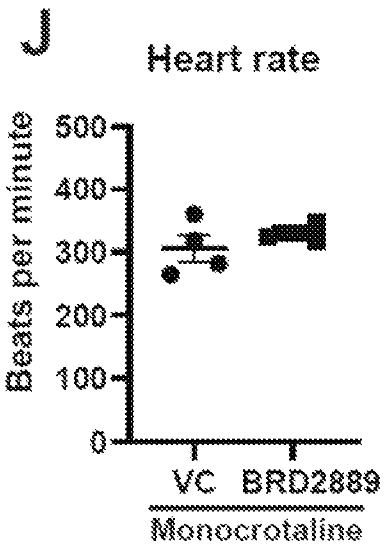
Figure 20K:
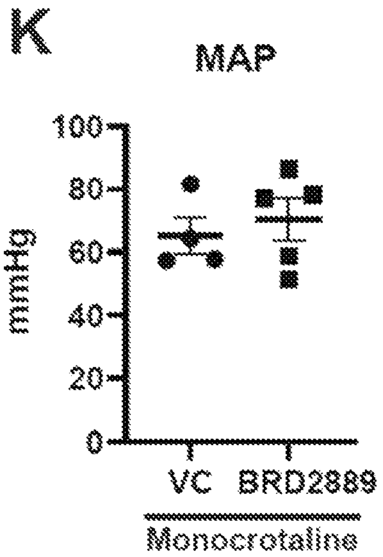
Figure 20L:
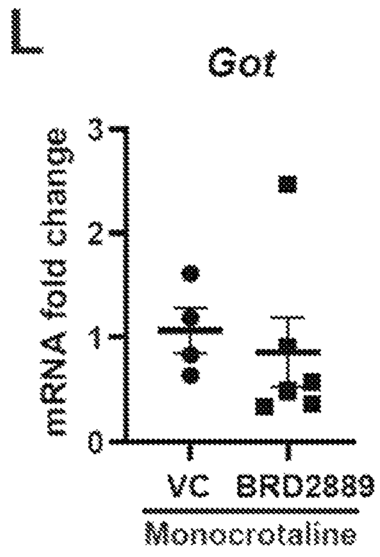
Figure 20M:
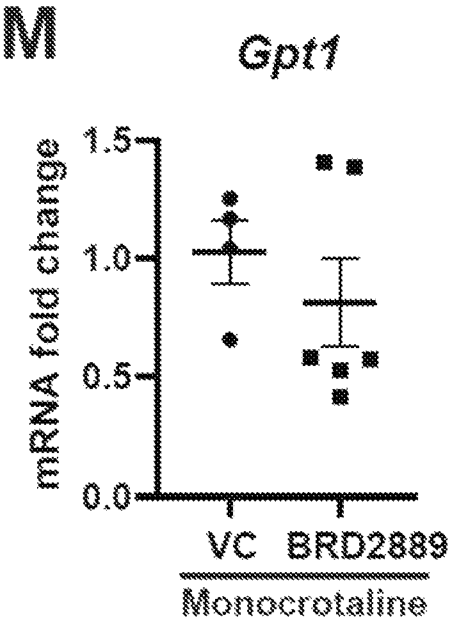
Figure 20N:
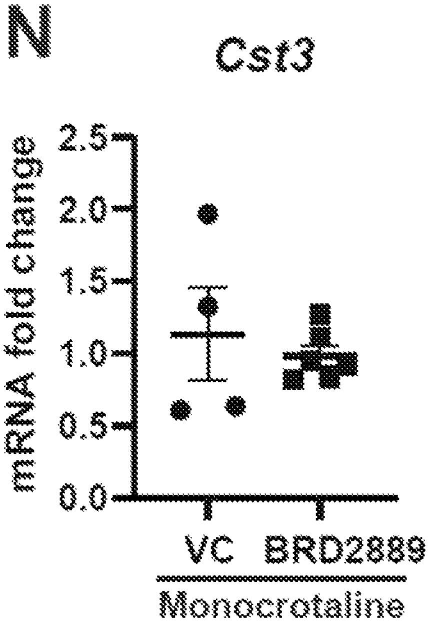
Figure 20O:
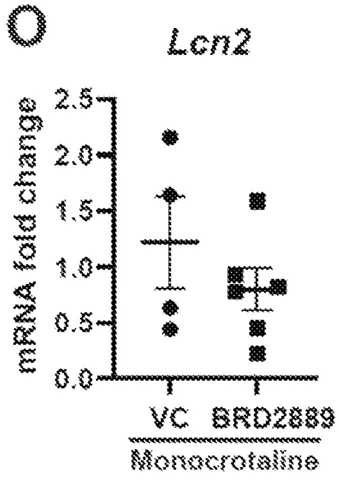
Figure 20P:
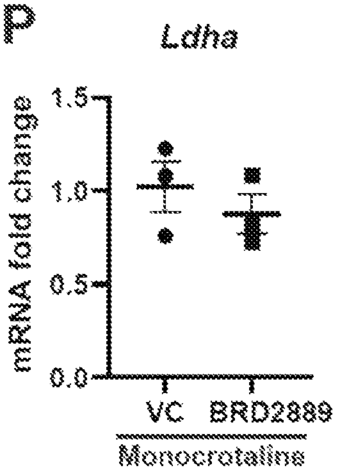

FIG. 20A-FIG. 20P. Parameters of cardiovascular function in pulmonary arterial hypertension rat models administered BRD2889. (FIG. 20A) Heart rate of SU5416-hypoxic pulmonary arterial hypertension rats administered BRD2889 was not altered, as compared with vehicle control (VC) (n=3-6/grp). (FIG. 20B-FIG. 20D) SU5416-hypoxic rats administered BRD2889 did not exhibit altered left ventricular function compared to VC, as measured by left ventricle posterior wall (LVPW) thickness (FIG. 20B), ejection fraction (LVEF; FIG. 20C), and fractional shortening (LVFS; FIG. 20D) via transthoracic echocardiography (n=5-6/grp). (FIG. 20E) Aortic blood pressure (mean arterial pressure, MAP) of SU5416-hypoxic pulmonary arterial hypertension rats administered BRD2889 was not altered, as compared with vehicle control (VC) (n=3-6/grp). (FIG. 20F-FIG. 20I) By RT-qPCR, transcript levels of injury markers of the liver (Got, FIG. 20F; Gpt1, FIG. 20G) or kidney (Cst3, FIG. 20H; Lcn2, FIG. 20I) were not altered by BRD2889 vs. VC in SU5416-hypoxic pulmonary arterial hypertension rats (n=4-6/grp). (FIG. 20J) Heart rate of monocrotaline-exposed pulmonary arterial hypertension rats administered BRD2889 was not altered, as compared with vehicle control (VC) (n=4-6/grp). (FIG. 20K) Aortic blood pressure (mean arterial pressure, MAP) of monocrotaline-exposed pulmonary arterial hypertension rats administered BRD2889 was not altered, as compared with vehicle control (VC) (n=4-5/grp). (FIG. 20L-FIG. 20P) By RT-qPCR, transcript levels of injury markers of the liver (Got, FIG. 20L; Gpt1, FIG. 20M), kidney (Cst3, FIG. 20N; Lcn2, FIG. 20O), or intestines (Ldha, FIG. 20P) were not altered by BRD2889 vs. VC in monocrotaline-exposed pulmonary arterial hypertension rats (n=3-4/grp). The data are plotted as mean±SEM. Statistical significance is indicated using Student's t-test (p>0.05 for all comparisons).

Figure 21:
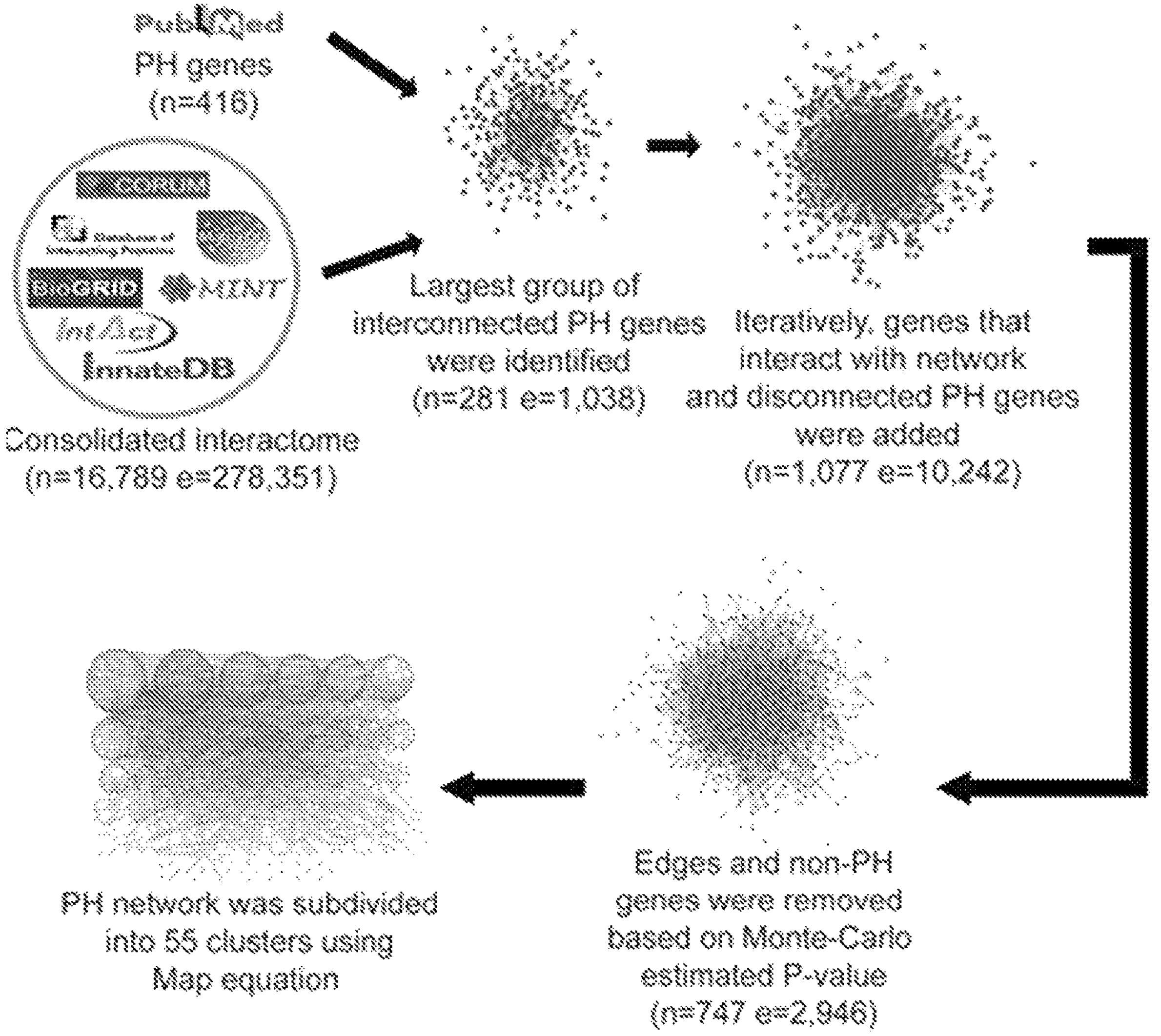

FIG. 21 is a schematic workflow for generation of a PH-extended network and DDN. A PH extended gene network was generated from 416 seed genes with known mechanistic importance for PH pathogenesis as curated from the scientific literature. Interconnections among these seed genes and their first degree interactors were mapped from a consolidated interactome representing a comprehensive catalog of functional interactions among human genes and as derived from various online databases and described herein. The largest connected component of the PH-extended network was generated and sub-divided into 55 clusters using a spectral partitioning algorithm (Map equation) that determined specifically connected gene clusters within the network. The n represented the number of genes present in the network, and e represents the number of interactions among those genes.

DETAILED DESCRIPTION

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an analog" includes mixtures of two or more such analogs, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., apoptosis). It is understood that this is typically in relation to some standard or expected value, in other words it is relative, but that it is not always necessary for the standard or relative value to be referred to. For example, "reduces apoptosis" means decreasing apoptosis relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. For purposes of this disclosure, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the occurrence of the disease, delay or slowing the progression of the disease, ameliorating the disease state, decreasing the dose of one or more other medications required to treat the disease, increasing the quality of life, and/or prolonging survival. In some variations, the composition reduces the severity of one or more symptoms associated with pulmonary hypertension by at least about any of 10%, 20%, 30%, 40%, 50%, 60%, 70%, 80%, 90%, 95%, or 100% compared to the corresponding symptom in the same subject prior to treatment or compared to the corresponding symptom in other subjects not receiving the composition. Also encompassed by "treatment" is a reduction of pathological consequence of pulmonary hypertension. The methods of the disclosure contemplate any one or more of these aspects of treatment.

As used herein, "delaying" the development of pulmonary hypertension refers to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of pulmonary hypertension is a method that reduces probability of disease development in a given time frame and/or reduces the extent of the disease in a given time frame, when compared to not using the method. Such comparisons are typically based on clinical studies, using a statistically significant number of subjects. Pulmonary hypertension development can be detectable using standard methods, such as routine physical exams, x-ray, electrocardiogram, and echocardiogram. Development may also refer to disease progression that may be initially undetectable and includes occurrence and onset.

As used herein, an "at risk" individual is an individual who is at risk of developing pulmonary hypertension. An individual "at risk" may or may not have detectable disease, and may or may not have displayed detectable disease prior to the treatment methods described herein. "At risk" denotes that an individual has one or more so-called risk factors, which are measurable parameters that correlate with development of pulmonary hypertension, which are described herein. An individual having one or more of these risk factors has a higher probability of developing pulmonary hypertension than an individual without these risk factor(s).

The term "patient" preferably refers to a human in need of treatment with an anti-hypertensive agent or treatment for any purpose, and more preferably a human in need of such a treatment to treat pulmonary hypertension, or a disorder associated with ISCU protein stability or deficiency. However, the term "patient" can also refer to non-human animals, preferably mammals such as dogs, cats, horses, cows, pigs, sheep and non-human primates, among others, that are in need of treatment for pulmonary hypertension.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula $—C(O)O^-$.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "cyano" as used herein is represented by the formula —CN The term "azido" as used herein is represented by the formula $—N_3$.

The term "sulfonyl" is used herein to refer to the sulfo-oxo group represented by the formula $—S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modem methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to pulmonary hypertension, an effective amount comprises an amount that increases iron-sulfur cluster assembly (ISCU) protein stability, increases ISCU protein expression, increases oxidative metabolism and/or decreases pulmonary arterial endothelial cell (PAEC) apoptosis, or a combination thereof. In some embodiments, an effective amount is an amount sufficient to delay development. In some embodiments, an effective amount is an amount sufficient to prevent or delay occurrence and/or recurrence. An effective amount can be administered in one or more doses.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

The term "derivative" refers to a structurally similar compound that retains sufficient functional attributes of the identified analog. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry textbooks, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Pharmaceutically acceptable derivative" or "pharmaceutically acceptable salt" refers to a prodrug or salt that is pharmaceutically acceptable and has the desired pharmacological properties. Such derivatives or salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Examples of prodrugs that can be used include esters, optionally substituted esters, branched esters, optionally substituted branched esters, carbonates, optionally substituted carbonates, carbamates, optionally substituted carbamates, thioesters, optionally substituted thioesters, branched thioesters, optionally substituted branched thioesters, thiocarbonates, optionally substituted thiocarbonates, S-thiocarbonate, optionally substituted S-thiocarbonate, dithiocarbonates, optionally substituted dithiocarbonates, thiocarbamates, optionally substituted thiocarbamates, oxymethoxycarbonyl, optionally substituted oxymethoxycarbonyl, oxymethoxythiocarbonyl, optionally substituted oxymethoxythiocarbonyl, oxymethylcarbonyl, optionally substituted oxymethylcarbonyl, oxymethylthiocarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, sulfenyl, optionally substituted sulfenyl, imidate, optionally substituted imidate, hydrazonate, optionally substituted hydrazonate, oximyl, optionally substituted oximyl, imidinyl, optionally substituted imidinyl, imidyl, optionally substituted imidyl, aminal, optionally substituted aminal, hemiaminal, optionally substituted hemiaminal, acetal, optionally substituted acetal, hemiacetal, optionally substituted hemiacetal, carbonimidate, optionally substituted carbonimidate, thiocarbonimidate, optionally substituted thiocarbonimidate, carbonimidyl, optionally substituted carbonimidyl, carbamimidate, optionally substituted carbamimidate, carbamimidyl, optionally substituted carbamimidyl, thioacetal, optionally substituted thioacetal, S-acyl-2-thioethyl, optionally substituted S-acyl-2-thioethyl, bis-(acyloxybenzyl)esters, optionally substituted bis-(acyloxybenzyl)esters, (acyloxybenzyl)esters, and optionally substituted (acyloxybenzyl)esters.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from an alkali agent such as sodium, potassium, calcium, magnesium, lithium, or a combination thereof. Other salts include those derived from organic compounds such as arginine, lysine, histidine, ornithine, creatine, agmatine, citrulline, or any combination thereof. Other salts can be derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Reference will now be made in detail to specific aspects of the disclosed materials, therapeutic agents, compositions, and methods, examples of which are illustrated in the accompanying Examples.

Compounds

Molecular inhibitors of pulmonary hypertension are disclosed. Particularly, small molecules that differentially affect rewired pulmonary hypertension-related gene clusters are disclosed. Piperlongumine analogs and derivatives are disclosed here as being selectively sensitive to a "hot-spot" gene cluster that is dependent upon the iron-sulfur biogenesis gene ISCU, where deficiency drives pulmonary hypertension. Piperlongumine analogs and derivatives thereof are also disclosed herein to inhibit glutathione S-transferase pi 1 (GSTP1), an enzyme that conjugates proteins and compounds with reduced glutathione. Inhibition of GSTP1 is shown to increase ISCU protein stability via preventing glutathionylation and/or protein expression, thereby increasing oxidative metabolism and decreased PAEC apoptosis.

The piperlongumine analogs or derivatives thereof can have a structure below:

Formula I

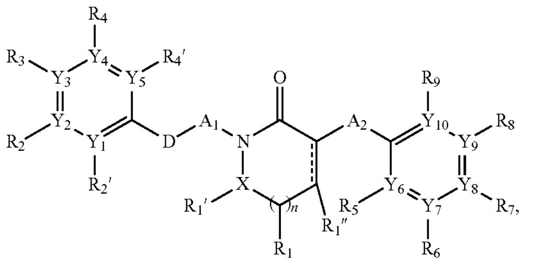

wherein $A_1$ is C(O) or $S(O)_2$;

$A_2$ is selected from —C≡C— or —C(R')═C(R")—, wherein R' and R" are independently selected from hydrogen, $C_1$-$C_6$ alkyl, $C_1$-$C_6$ alkoxy, halogen, or $C_1$-$C_6$ haloalkyl;

X is selected from CH(R'"), C(O), SO, $SO_2$, or NR'", wherein R'" is selected from hydrogen, halogen, $C_1$-$C_6$ alkyl, $C_2$-$C_6$ alkenyl, $C_1$-$C_6$ alkoxy, or $C_1$-$C_6$ haloalkyl;

$Y_1$-$Y_{10}$ are independently selected from an heteroatom or carbon;

D is selected from —C≡C— or —C(R')═C(R")—, wherein R' and R" are independently selected from hydrogen, $C_1$-$C_6$ alkyl, $C_1$-$C_6$ alkoxy, halogen, or $C_1$-$C_6$ haloalkyl;

$R_1$, $R_{1'}$, and $R_{1''}$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, or nitro, and wherein $R_1$ is optionally substituted with one or more groups;

$R_2$, $R_{2'}$, $R_3$, $R_{4'}$, and $R_4$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

$R_5$, $R_6$, $R_7$, $R_8$, and $R_9$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

n is 1 or 2; and

------- represents a bond that is present of absent;

or a pharmaceutically acceptable salt, ester, or prodrug thereof.

In some aspects of the formula disclosed herein, the piperlongumine analogs or derivatives thereof can have a structure according to Formula I:

Formula I

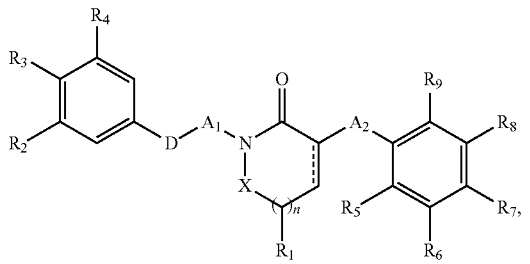

wherein $A_1$ is C(O) or $S(O)_2$;

$A_2$ is selected from —C≡C— or —C(R')═C(R")—, wherein R' and R" are independently selected from hydrogen, $C_1$-$C_6$ alkyl, $C_1$-$C_6$ alkoxy, halogen, or $C_1$-$C_6$ haloalkyl;

X is selected from CH(R'"), C(O), SO, $SO_2$, or NR'", wherein R'" is selected from hydrogen, halogen, $C_1$-$C_6$ alkyl, $C_2$-$C_6$ alkenyl, $C_1$-$C_6$ alkoxy, or $C_1$-$C_6$ haloalkyl;

D is selected from —C≡C— or —C(R')═C(R")—, wherein R' and R" are independently selected from hydrogen, $C_1$-$C_6$ alkyl, $C_1$-$C_6$ alkoxy, halogen, or $C_1$-$C_6$ haloalkyl;

$R_1$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, or nitro, and wherein $R_1$ is optionally substituted with one or more groups;

$R_2$, $R_3$, and $R_4$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

$R_5$, $R_6$, $R_7$, $R_8$, and $R_9$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

n is 1 or 2; and

------- represents a bond that is present of absent;

or a pharmaceutically acceptable salt, ester, or prodrug thereof.

In some embodiments of Formula I, the piperlongumine analog or derivative thereof can have a structure according to Formula I-A:

Formula I-A

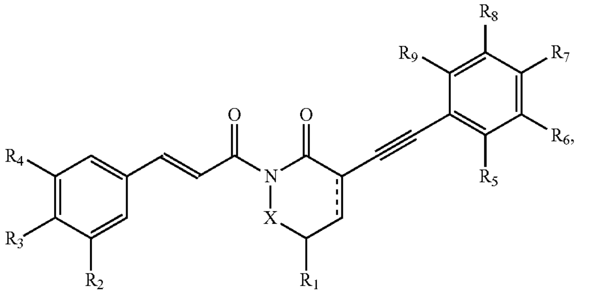

wherein

X is selected from CH(R'''), C(O), SO, $SO_2$, or NR''', wherein R''' is selected from hydrogen, halogen, $C_1$-$C_6$ alkyl, $C_2$-$C_6$ alkenyl, $C_1$-$C_6$ alkoxy, or $C_1$-$C_6$ haloalkyl;

$R_1$ is selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, or nitro, and wherein $R_1$ is optionally substituted with one or more groups;

$R_2$, $R_3$, and $R_4$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

$R_5$, $R_6$, $R_7$, $R_8$, and $R_9$ are independently selected from hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

n is 1 or 2; and

------- represents a bond that is present of absent;

or a pharmaceutically acceptable salt, ester, or prodrug thereof.

In some embodiments of the Formulas disclosed herein, $A_1$ can be C═O.

In some embodiments of the Formulas disclosed herein, $A_2$ can be —C≡C—.

In some embodiments of the Formulas disclosed herein, $A_1$ can be C═O and $A_2$ can be —C ≡C—.

In some embodiments of the Formulas disclosed herein, X can be $CH_2$.

In some embodiments of the Formulas disclosed herein, D can be —C(R')═C(R")—, and wherein R' and R" are independently selected from hydrogen or $C_1$-$C_3$ alkyl.

In some embodiments of the Formulas disclosed herein, $R_2$, $R_3$, $R_4$, and $R_7$ can all be $C_1$-$C_3$ alkoxy, preferably methoxy.

In some embodiments of the Formulas disclosed herein, $R_5$, $R_6$, $R_8$, and $R_9$ can all hydrogen.

In some examples, the piperlongumine analog can have a structure below:

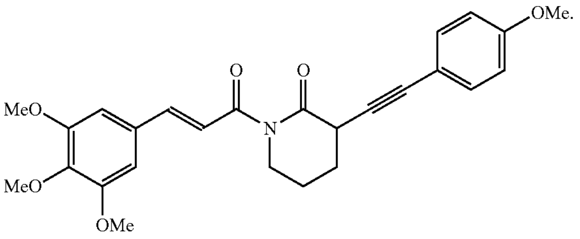 [SMILES: COc1ccc(C#CC2CCCN(C(=O)/C=C/c3cc(OC)c(OC)c(OC)c3)C2=O)cc1]

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of pulmonary hypertension, the piperlongumine analog or derivative described herein can be administered to a patient in need of treatment in combination with at least one additional agent effective to treat pulmonary hypertension. For example, piperlongumine analog or derivative described herein can be used in combination with at least one additional agents selected from one or more of phosphodiesterase inhibitors, calcium channel blockers, endothelin receptor antagonists, inotropic agents, prostacyclin pathway agonists, anti-coagulants, guanylate cyclase stimulators, PDE-5 inhibitors, or a combination thereof. In some instances, the additional agent can be a PDE-5 inhibitor, for example, avanafil, lodenafil, mirodenafil, sildenafil, tadalafil, vardenafil, udenafil, zaprinast, or icariin. Other agents include calcium channel blockers like dihydropyridines (e.g., amlodipine, nifefipine) and diltiazem; prostacyclin pathway agonists such as epoprostenol, treprostinil, iloprost, and selexipag; endothelin receptor antagonists such as bosentan, macitentan, ambrisentan, andsitaxsentan; guanylate cyclase stimulators such as riociguat; diuretics; toprimate; fusadil; or anti-coagulants like warfarin.

Methods of Use

As described herein, new pathogenic mechanisms in pulmonary hypertension have been identified and molecular inhibitors thereof are disclosed. It has been demonstrated that GSTP1 (glutathione S-transferase P1) regulates ISCU of GSSG which results in site-specific S-glutathionylation within ISCU on one or two cysteine residues. It has been shown that GSTP1 regulates ISCU stability by S-glutathionlyation. These observations indicate that GSTP1 have important role to regulate the endothelial ISCU function in pulmonary hypertension. Modulators of the GSTP1-ISCU axis in pulmonary hypertension represents a new target pathway for therapeutic development.

Piperlongumine analogs and derivatives thereof are shown as being selectively sensitive to a "hot-spot" gene cluster that is dependent upon the iron-sulfur biogenesis gene ISCU, where deficiency drives pulmonary hypertension. In vitro and in vivo models of PAH show the piperlongumine analog BRD-K34222889 inhibit glutathione S-transferase P (GSTP1), which increased ISCU protein stability via preventing glutathionylation and thereby increased oxidative metabolism and decreased PAEC apoptosis.

Disclosed herein are methods for treating pulmonary hypertension in a subject in need thereof. Pulmonary hypertension can be classified as either primary or secondary. When hypertension is not accompanied, or caused by another underlying heart or lung disease or condition, it is called primary pulmonary arterial hypertension. When hypertension is triggered by another disease state, it is designated secondary arterial pulmonary hypertension. Exemplary conditions which can cause secondary pulmonary hypertension include congenital heart defects, ventricular or atrial septal defects/holes, which are in some cases called Eisenmenger complex, as well as valve conditions such as stenosis. The methods disclosed herein include treating pulmonary arterial hypertension. Further disclosed herein are methods of treating a disorder associated with ISCU protein instability or deficiency in a subject in need thereof. Disorders associated with ISCU protein instability can include pulmonary hypertension.

In some aspects of the disclosed methods of treating pulmonary hypertension or disorder associated with ISCU protein instability, the methods can comprise administering a therapeutically effective amount of a pharmaceutical composition that inhibits glutathione S-transferase P (GSTP1). In some aspects of the disclosed methods of treating pulmonary hypertension, the methods can comprise administering a therapeutically effective amount of a pharmaceutical composition that increase iron-sulfur cluster assembly (ISCU) protein stability, increase ISCU expression, or a combination thereof. For example, the methods can include administering a therapeutically effective amount of a piperlongumine analog, such as BRD-K34222889, or a derivative thereof. The piperlongumine analog or derivative thereof can have a structure according to Formula I or I-A as described herein. In some instances, the GSTP1 inhibitor (such as piperlongumine analog) can inhibit or reduce pulmonary arterial endothelial cell (PAEC) apoptosis in the subject. In some instances, the GSTP1 inhibitor (such as piperlongumine analog) can increase iron-sulfur cluster assembly (ISCU) protein stability, increase ISCU protein expression, or a combination thereof, in the subject. In some instances, the GSTP1 inhibitor (such as piperlongumine analog) can increase oxidative metabolism and/or decreases pulmonary arterial endothelial cell (PAEC) apoptosis in the subject.

Methods for diagnosing pulmonary hypertension in a subject in need thereof are also disclosed. The method can include detecting an expression level of glutathione S-transferase P (GSTP1) in a sample obtained from the subject; comparing the level of expression of GSTP1 in the sample compared to a control sample; diagnosing the subject as having pulmonary hypertension when the level of expression of GSTP1 in the sample is higher than the level of expression in the control sample; and treating the subject for pulmonary hypertension when the quantity of GSTP1 in the sample indicates elevated levels of GSTP1 compared to the control sample. Detecting the level of expression in the sample (a) and the control sample (b) can comprises: assaying the sample or control sample using a GSTP1 antibody or isolating GSTP1 from the sample and subjecting the isolated GSTP1 to quantitative spectrometry. The GSTP1 antibody or GSTP1 can be conjugated to a fluorescent moiety or a radioactive moiety in the diagnostic methods.

Methods of assaying the efficacy of a compound for treating pulmonary hypertension are also disclosed. The method can include expressing glutathione S-transferase P (GSTP1) in a sample obtained from a subject; contacting the sample with the compound; and testing whether GSTP1 is inhibited in the sample. In some embodiments, the compound can include a piperlongumine analog or a derivative thereof.

In some instances, the compounds and compositions can be administered to a subject a single time, while in other cases compounds and compositions can be administered using an intervallic dosing regimen. For instance, compounds and compositions may be administered once, twice, or three times a day for a period of at least 1 week, for example 2 weeks, 4 weeks, 6 weeks, 8 weeks, 10 weeks, 20 weeks, 40 weeks, or 52 weeks. In some instances, compounds and compositions administration can be suspended for some period of time (e.g., 1, 2, 3, 4, 6, 8, 10, 20, 40 or 52 weeks) followed by another period of administration.

In some instances, an initial dosage (higher dose, relative to maintenance dose) and maintenance doses (lower dose, relative to initial dose) may be specified. For instance, an initial dosage may be administered over the course of 1, 3, 5, 7, 10, 14, 21 or 28 days, followed by a maintenance dosage which is administered for the duration of the treatment. In some instances, the compounds and compositions can be administered to the subject using an interval greater than a day. For instance, the compounds and compositions can be administered once every other day, once every third day, once a week, once every two weeks, once every four weeks, once a month, once every other month, once every third month, once every six months, or once a year. In some instance, injectable formulations, such as depot formulations, are suitable for dosing regimens with extended periods in between administration, however, oral formulations can also be used in such systems.

The dosage and dosage regimen may be calculated per kg body weight. The dosage regimen may vary from a day to a month. In some examples, the compositions disclosed herein may be administered at least once, twice or thrice a day in the dosing range from 0.05 mg to about 30 mg per kg per day, 0.1 mg to about 10 mg per kg per day, 0.5 mg to about 10 mg per kg per day, 0.5 mg to about 5 mg per kg per day, 1 mg to about 5 mg per kg per day, or as per the requirement of the patient to be treated.

The compounds and compositions may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the disclosure.

In some instances, the compounds and compositions can be administered by inhalation, for instance as a powder or aerosolizable formulation.

The bioavailability of the drug in a composition, depends on various attributes of the drug as well as the other inactive ingredients in the formulation. The particle size of the drug is one of such attribute that may affect the bioavailability of the drug, when administered to a patient. The particle size may thus be adjusted as per the requirements of the disclosure. In one embodiment, the compounds and compositions may be present in the form of nanoparticles which have an average particle size of less than 2000 nm, less than 1500 nm, less than 1000 nm, less than 750 nm, or less than 500 nm.

Suitable excipients may be used for formulating the dosage forms according to the present disclosure such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In some instance, injectable formulations, such as depot formulations, are suitable for dosing regimens with extended periods in between administration, however, oral formulations can also be used in such systems.

In some embodiments, pulmonary arterial hypertension can be alleviated or treated by administration of piperlongumine analogs and derivatives disclosed herein in combination with one or more other drugs either simultaneously, sequentially, or separately.

In certain embodiments, the administration of the compounds and compositions disclosed, either alone or in combination with one or more drugs selected from but not limited to phosphodiesterase inhibitors such as sildenafil, tadalafil etc., endothelin receptor antagonists such as bosentan, macitentan etc., and stimulators of soluble guanylate cyclase such as riociguat.

In certain embodiments, the compounds and compositions can be co-administered with one or more additional agents effective to lower pulmonary hypertension. In some embodiments the co-administration includes a unitary dosage form containing desipramine (or a salt thereof) and at least one more agent. In other embodiments, desipramine (or a salt thereof) is administered separately from the other agent(s). The additional agent can be a PDE-5 inhibitor, for example, avanafil, lodenafil, mirodenafil, sildenafil, tadalafil, vardenafil, udenafil, zaprinast, or icariin. Other agents include calcium channel blockers like dihydropyridines (e.g., amlodipine, nifefipine) and diltiazem; prostacyclin pathway agonists such as epoprostenol, treprostinil, iloprost, and selexipag; endothelin receptor antagonists such as bosentan, macitentan, ambrisentan, andsitaxsentan; guanylate cyclase stimulators such as riociguat; diuretics; toprimate; fusadil; or anti-coagulants like warfarin.

It may be well appreciated by a person skilled in the art that the pharmaceutical composition comprising piperlongumine analogs or derivatives disclosed herein in combination with one or more drugs may require specific dosage amounts and specific frequency of administrations specifically considering their individual established doses, the dosing frequency, patient adherence and the regimen adopted. As described herein, considering that there are various parameters to govern the dosage and administration of the combination composition as disclosed herein, it would be well acknowledged by a person skilled in the art to exercise caution with respect to the dosage, specifically, for special populations associated with other disorders.

The use of piperlongumine analogs or derivatives thereof may preferably be associated with one or more of the above referenced drugs as a combination therapy (either of the same functional class or other) depending on various factors like drug-drug compatibility, patient compliance and other such factors wherein the said combination therapy may be administered either simultaneously, sequentially, or separately for the treatment of PAH.

Piperlongumine analogs or derivatives thereof may be provided with one or more drugs in the form of a kit, wherein the kit includes piperlongumine analog or a derivative thereof and at least one other drug, and instructions for their administration to a PAH patient.

Administration

The term "administration" and variants thereof (e.g., "administering" a compound) in reference to a compound disclosed herein means introducing the compound or a derivative of the compound into the system of the animal in need of treatment. When a compound or derivative thereof is provided in combination with one or more other active agents, "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer; poly[bis(p-carboxyphenoxy) propane: sebacic acid] in a 20:80 molar ratio (as used in GLIADEL); chondroitin; chitin; and chitosan.

Compounds and compositions disclosed herein can be locally administered at one or more anatomical sites, e.g., injected or topically applied), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Kits

Kits for practicing the methods disclosed herein are further provided. By "kit" is intended any manufacture (e.g., a package or a container) comprising at least one reagent, e.g., anyone of the compounds described herein. The kit may be promoted, distributed, or sold as a unit for performing the methods disclosed herein. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1—Computational Repurposing of Therapeutic Small Molecules from Cancer to Pulmonary Hypertension ABSTRACT. Cancer therapies are being considered for treating rare non-cancerous diseases like pulmonary hypertension (PH), but effective computational screening is lacking. Via transcriptomic differential dependency analyses leveraging parallels between cancer and pulmonary hypertension, a landscape of cancer drug functions dependent upon rewiring of pulmonary hypertension gene clusters was mapped. Bromodomain and extra-terminal motif (BET) protein inhibitors were predicted to rely upon several gene clusters inclusive of galectin-8 (LGALS8). Correspondingly, LGALS8 was found to mediate the BET inhibitor-dependent control of endothelial apoptosis, an essential role for pulmonary hypertension in vivo. Separately, a piperlongumine analog's actions were predicted to depend upon the iron-sulfur biogenesis gene ISCU. Correspondingly, the analog was found to inhibit ISCU glutathionylation, rescuing oxidative metabolism, decreasing endothelial apoptosis, and improving pulmonary hypertension. Thus, crucial drug-gene axes central to endothelial dysfunction and therapeutic priorities for pulmonary hypertension were identified. These results establish a wide-ranging, network dependency platform to redefine cancer drugs for use in non-cancerous conditions.

Teaser: A network dependency platform was generated to define a landscape of cancer drug mechanisms in pulmonary hypertension.

INTRODUCTION. The repurposing of small molecules for disease therapy has gained traction, given the potential to reduce cost and time necessary for de novo drug development. Specifically, computational drug repurposing is emerging as a viable method, leveraging available large-scale clinical and molecular profiling and combining those with in silico methodologies of machine learning, network modeling, and clinical text mining to define new drug activities (Park K. *Transl Clin Pharmacol.* 2019, 27, 59-63). However, the vast majority of such strategies have depended upon identification of differentially expressed genes (DEGs) (Vanhaelen Q et al. *Drug Discov Today.* 2017, 22, 210-222), which can define some but not all key intergenic relationships. Molecular network mapping utilizing connections among genes with a tendency to be regulated together (i.e. gene regulatory dependencies) addresses some of the DEG-based analysis limitations. However, because of the large amount of data required for calculating differential dependencies across gene networks, such analytics are often not feasible across the limited -omics datasets of rare or emerging diseases.

Pulmonary hypertension (PH) represents such an enigmatic vascular disease that consists of 5 World Symposium of Pulmonary Hypertension (WSPH) groups (Simonneau G et al. *Eur Respir J* 2019, 53, 1801913). In particular, WSPH Group 1 (pulmonary arterial hypertension, PAH) and Group 3 (due to hypoxic lung disease) pulmonary hypertension subtypes are driven by shared triggers of hypoxia and inflammation, and mortality is high. Current medications primarily vasodilate, are mostly used to treat Group 1 pulmonary arterial hypertension, and are not curative. Thus, an unmet need exists for new drug discovery. In particular, endothelial pathobiology is a characteristic and pathogenic feature of pulmonary hypertension contributing to the inflammation and aberrant vascular remodeling observed in this disease (Evans C E et al. *Eur Respir J.* 2021, 2003957). However, due to complex spatio-temporal manifestations that balance critical processes such as apoptosis and proliferation during disease progression (Michelakis E D. *Circ Res.* 2006, 98, 172-175; Goldthorpe H et al. *Am J Respir Cell Mol Biol.* 2015, 53, 712-718), therapeutic targeting of endothelial dysfunction in pulmonary hypertension has been challenging. The advancing appreciation of broad molecular parallels between pulmonary hypertension and cancer in general (Pullamsetti S S et al. *Am J Respir Crit Care Med.* 2017, 195, 425-437), as well as the direct link between developing pulmonary hypertension in the setting of lung cancer specifically (Pullamsetti S S et al. *Sci Transl Med.* 2017, 9, eaai9048), have increased enthusiasm for repurposing existing small molecule inhibitors from cancer to pulmonary hypertension (Prins K W et al. *J Am Heart Assoc.* 2019, 8, e011343). This may be particularly relevant for precise therapeutic targeting of dysregulated endothelial survival—a process also crucial for hypoxic and inflammatory-driven tumorigenesis (Dudley A C. *Cold Spring Harb Perspect Med.* 2012, 2, a006536). To date, however, the broad molecular profiling existing in cancer datasets has yet to be leveraged for such pulmonary hypertension drug discovery. As such, mapping gene regulatory dependency networks relevant to pulmonary hypertension and investigating "rewiring" of these networks in connection to cancer drug activity present a unique opportunity. Here, it was hypothesized that deep analysis of the relationship between drug response and molecular rewiring in cancer cells of pathways implicated both in pulmonary hypertension and cancer will offer insight into how vascular cells in pulmonary hypertension will respond to specific drugs, and in turn support repurposing of these drugs for pulmonary hypertension.

To investigate this notion, the design of a computational strategy identifying differential dependency networks (DDNs) of genes in cancer cells associated with drug response and also overlapping with a rare disease such as pulmonary hypertension was sought. Namely, the capabilities of EDDY (Evaluation of Differential DependencY) (Jung S et al. *Nucleic Acids Res.* 2014, 42, e60), a prior-knowledge-assisted algorithm that defines differential dependency networks based on the rewiring of dependency interactions among genes in a network under different conditions, for example, cancer cell's response to drug, were applied. EDDY has been utilized in the study of human diseases (Jung S et al. *Nucleic Acids Res.* 2014, 42, e60) as well as transcriptomic analyses from human pulmonary hypertension lung tissue (Stearman R S et al. *Am J Respir Cell Mol Biol.* 2018, 60, 637-649) to identify differential dependency networks in disease. Importantly, EDDY was applied to a dataset derived from the Cancer Cell Line Encyclopedia (CCLE; encompassing a catalog of RNA sequencing data from 810 cancer cell lines (Barretina J et al. *Nature.* 2012, 483, 603-607)), and the Cancer Therapeutics Response Portal (CTRP; surveying the response of those cell lines to 368 small molecules (Seashore-Ludlow B et al. *Cancer Discov.* 2015, 5, 1210-1223; Rees M G et al. *Nat Chem Biol.* 2016, 12, 109-116)). In doing so, for each cancer drug surveyed, this EDDY-CTRP identified differential dependency networks that define drug response by virtue of their specific rewiring in sensitive vs. resistant cells (Speyer G et al. *Pac Symp Biocomput.* 2017, 22, 497-508).

Leveraging those principles, a computational platform (EDDY-CTRP-PH) was developed to predict the landscape of cancer drug functions that rely upon rewired differential dependency networks of genes common to cancer and pulmonary hypertension as well as have shared links to hypoxia and inflammation—thus exerting robust activity in controlling multiple pulmonary hypertension subtypes. Two highly ranked candidate drugs and their predicted gene network effectors were identified and experimentally tested. First, bromodomain and extra-terminal motif (BET) protein inhibitors, which target the epigenetic modifiers bromodomain containing 2/4 (Brd2/4) and are already being tested in pulmonary hypertension (Meloche J et al. *Circ Res.* 2015, 117, 525-535; Chabert C et al. *Int J Mol Sci.* 2018, 19, 2224; Van der Feen D E et al. *Am J Respir Crit Care Med.* 2019, 200, 910-920), were predicted to selectively affect a pulmonary hypertension gene cluster encompassing galectin-8 (LGALS8). LGALS8, a member of the galectin family that regulates inflammation (Cattaneo V et al. *Glycobiology.* 2014, 24, 966-973) and apoptosis (Hadari Y R et al. *J Cell Sci.* 2000, 113 (Pt 13), 2385-2397), has not been previously implicated in pulmonary hypertension nor connected to BET inhibitors. Second, an analog of the alkaloid piperlongumine, BRD-K34222889 or BRD2889 (Adams D J et al. *Proc Natl Acad Sci USA.* 2012, 109, 15115-15120), was predicted to selectively target a pulmonary hypertension cluster dependent on the iron-sulfur biogenesis gene ISCU. While deficiency of endothelial ISCU is known to drive pulmonary hypertension (White K et al. *EMBO Mol Med.* 2015, 7, 695-713), and piperlongumine and its analogs are reported to inhibit glutathione S-transferase pi 1 (GSTP1) (Harshbarger W et al. *J Biol Chem.* 2017, 292, 112-120), any functional connections among BRD2889 and GSTP1 to ISCU and to pulmonary hypertension have yet to be reported. Thus, by coupling in vitro and in vivo experimentation with in silico findings, the definition of a computational-to-empirical pipeline was sought for identifying and ranking the most robust actions of specific cancer therapeutics, revealing their disease-relevant downstream targets in an example of a rare non-cancerous disease such as pulmonary hypertension.

Results

Figure 1A:
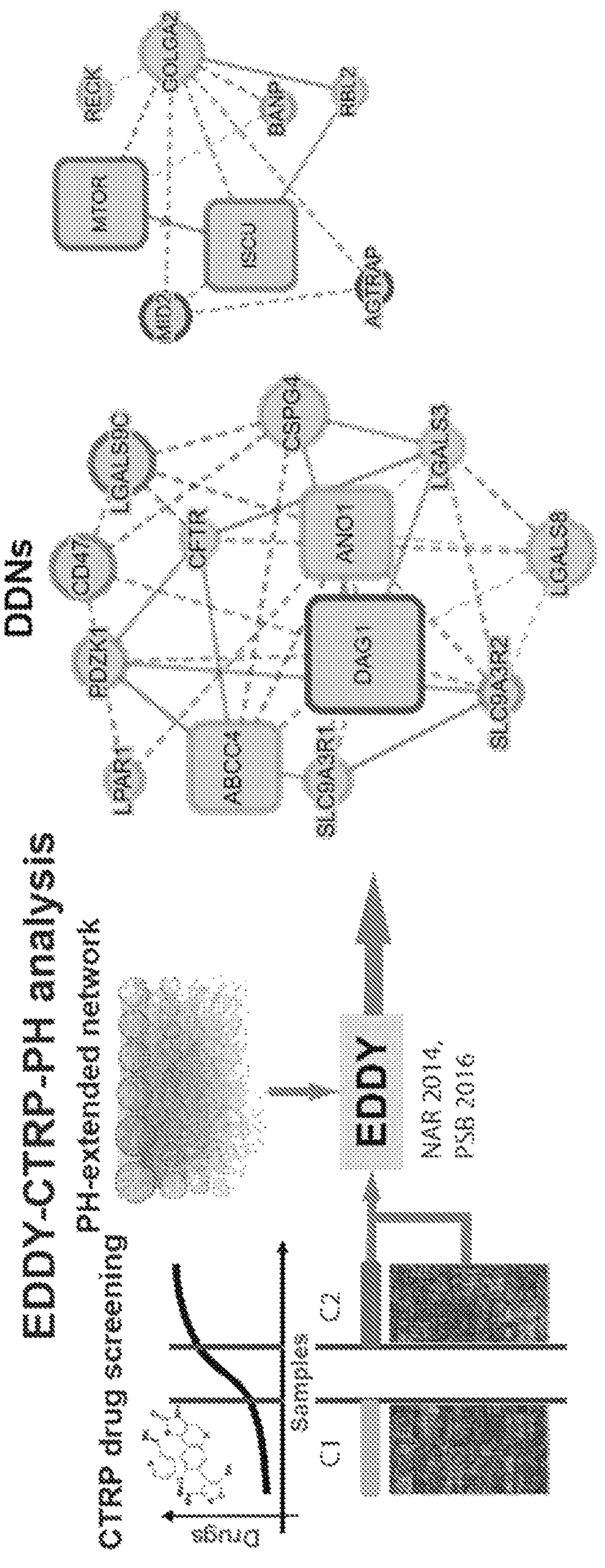

EDDY-CTRP-PH: In silico mapping of small molecules that depend upon rewired pulmonary hypertension-specific differential dependency networks for activity. To identify pulmonary hypertension-specific differential dependency networks that mediate crucial cellular responses to specific small molecules, a catalog of gene networks integral to pulmonary hypertension pathogenesis was necessary for initial input. Building upon prior methodology (Bertero T et al. *J Biol Chem.* 2014, 290, 2069-2085), 55 pulmonary hypertension-relevant gene clusters were identified (Table 1-Table 2) and analyzed by EDDY in the context of the CCLE and CTRP datasets (EDDY-CTRP-PH workflow, FIG. 1A) to discover pulmonary hypertension gene clusters strongly associated with a cancer cell's response to drugs and mediators for each pulmonary hypertension gene cluster. Namely, for each cancer drug tested, cell lines were categorized into two groups: drug-sensitive and drug-resistant, as described (Speyer G et al. *Pac Symp Biocomput.* 2017, 22, 497-508). For each drug, transcriptomic profiles were analyzed by EDDY to define pulmonary hypertension-relevant gene clusters that displayed significant rewiring of differential dependency networks between sensitive vs. resistant cell lines. Then for each differential dependency network, genes important to the network connectivity, denoted as mediators, were identified by network analysis as those that have most control over the network. Two types of mediators were defined. "Condition-specific" mediators were genes with a significant proportion of condition-specific edges (i.e., drug sensitivity vs. resistance), emphasizing their unique importance in controlling specific drug responses. "Essentiality" mediators were those genes that depended upon the betweenness centrality metric—a measure of how often network information will pass through that node. Essentiality mediators were those genes meeting a betweenness-centrality difference cutoff between the condition-specific (i.e., drug sensitivity vs. resistance) networks—thus, "essential" to differential dependency network rewiring. In total, such differential dependency network rewiring and mediator identification predicted previously unknown roles of these clusters and dependencies in mediating the actions of each drug and, consequently, the direct relevance to molecular pulmonary hypertension pathogenesis. These results are available at the following website (https://chan.vmi.pitt.edu/eddy-ctrp-ph/).

Figure 1B:
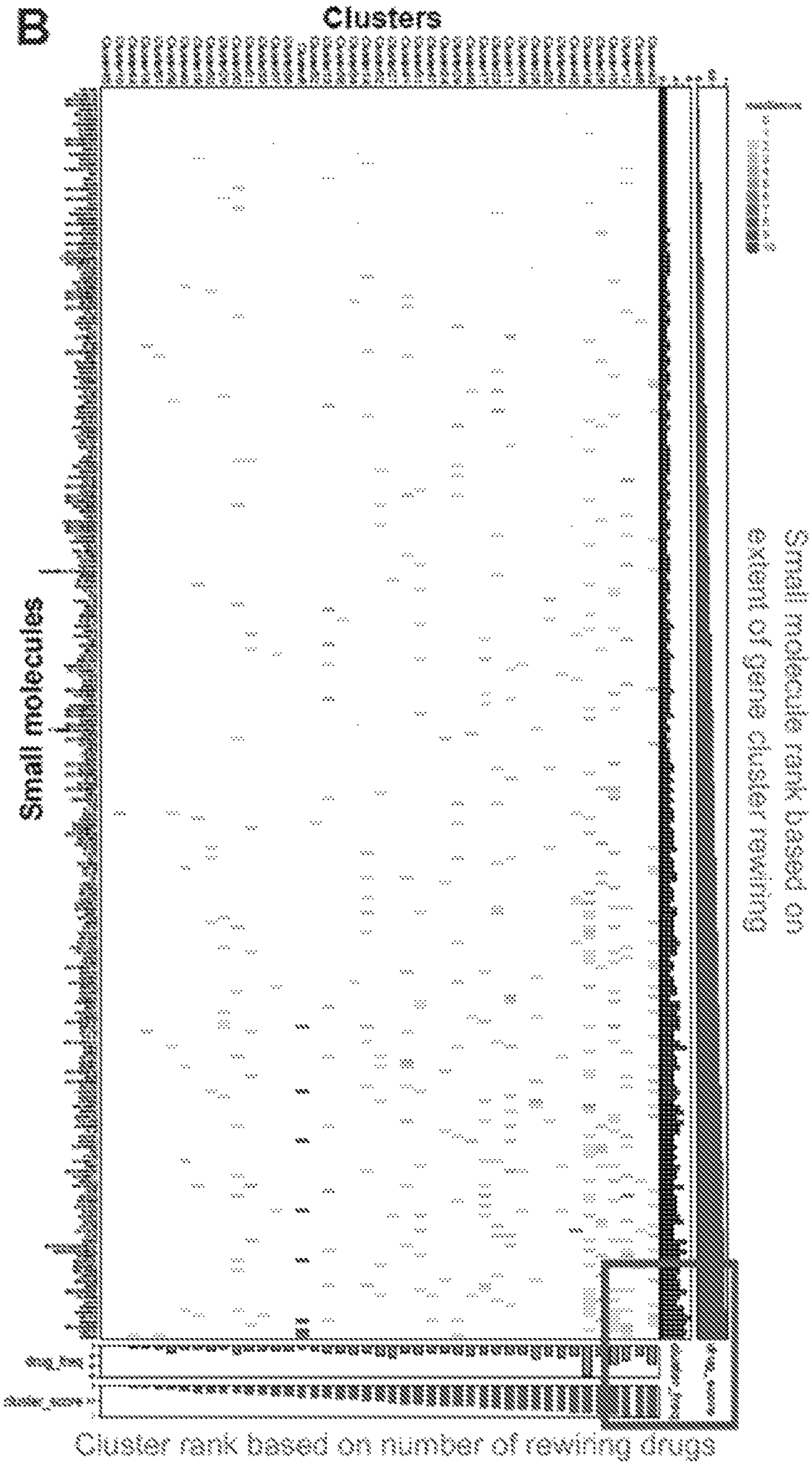

To assess the landscape of functional connections catalogued by EDDY-CTRP-PH, small molecules and clusters were sorted according to their rewiring scores as defined in Methods (FIG. 1B; Table 1-Table 3). The top 5 clusters and top 15 small molecules represented candidates for further in-depth study (FIG. 1C). These predictive outputs offered a number of wide-reaching insights. First, 60% of small molecules were predicted to be selective for rewired gene dependencies across at least two or more pulmonary hypertension clusters, indicating substantial overlap of activity of the cancer drug landscape with pulmonary hypertension pathogenic processes (full website listing under EDDY-CTRP-PH: Individual Drugs). Second, among the gene mediators identified by EDDY as essential for orchestrating pulmonary hypertension differential dependency network rewiring, 53.6% (165 out of 308 mediators identified) have not previously been linked to pulmonary hypertension pathogenesis. Third, among the gene dependencies mapped by EDDY within the pulmonary hypertension gene clusters, 72.3% represented functional connections not previously described (1230 out of 1700 wiring connections).

The EDDY-CTRP-PH platform also offered granular molecular information via either defining new pulmonary hypertension pathways targeted by known pulmonary hypertension drugs or identifying connections linking new drugs to known pulmonary hypertension pathways. As an example of the former, in addition to being selectively sensitive to a differential dependency network enriched for oxidative metabolism genes via well-established links (Cluster 23) (Ryan J J et al. *Circulation.* 2015, 131, 1691-1702), the PDK inhibitor AZD7545 was predicted to be associated with the differential dependency networks of immune response Cluster 37 (TNF signaling) and Cluster 26 (CD4 lymphocyte signaling). Similarly, while canonically PDE5 inhibitors are used clinically to treat pulmonary hypertension in the context of nitric oxide signaling and regulation of vasomotor tone, EDDY-CTRP-PH predicted sildenafil as dependent upon rewiring of pulmonary hypertension gene Cluster 28, a cluster enriched particularly with genes involved in apoptosis. Evidence of PDE5 activity in apoptosis and cell survival has more recently been reported (Yamamura A et al. *Eur J Pharmacol.* 2017, 810, 44-50), offering validation of such predictions. Moreover, differential dependency networks with new and known functions were uncovered for other drugs with already existing pulmonary hypertension connections, including the HDAC inhibitor apicidin and the carbonic anhydrase inhibitor indisulam, among others (Table 1-Table 3, full listing under EDDY-CTRP-PH: Individual Drugs). Alternatively, EDDY offered an ability to define complementary drugs that converge upon a single pulmonary hypertension pathway (full website listing under EDDY-CTRP-PH: Cluster View). For example, eight small molecules were found to converge upon Cluster 6, a network enriched for extracellular matrix (ECM) organization genes (FIG. 1D). While some of these drugs already carried known associations with ECM biology, EDDY revealed this functional connection for other drugs, such as fumonosin B1 and indisulam, that had not previously been linked to matrix organization.

EDDY-CTRP-PH identifies a functional connection between BET inhibitors and Cluster 15. Experimental validation of key predictions by EDDY-CTRP-PH, linking as-of-yet undiscovered pulmonary hypertension pathways to drugs currently under therapeutic development, was sought. An example included the epigenetic drug class of BET inhibitors being tested for pulmonary hypertension treatment (Van der Feen D E et al. *Am J Respir Crit Care Med.* 2019, 200, 910-920). Notably, BET inhibitors have mainly been studied in the context of smooth muscle cells in pulmonary hypertension (Meloche J et al. *Circ Res.* 2015, 117, 525-535; Chabert C et al. *Int J Mol Sci.* 2018, 19, 2224), with only a partial identification of BET activity in controlling endothelial processes in this disease (Van der Feen D E et al. *Am J Respir Crit Care Med.* 2019, 200, 910-920). Three BET inhibitors (JQ-1, I-BET151, and I-BET762) were included in EDDY-CTRP-PH analyses, with I-BET151 emerging as one of the top-ranked drugs (FIG. 1C). In re-calculating differential dependency networks relevant across all drugs modulating the same target (i.e., differential dependency networks shared across the same drug class), EDDY found 4 rewired pulmonary hypertension differential dependency networks associated with all three BET inhibitors (FIG. 2A, full listing under EDDY-CTRP-PH: Drug Class). The predominant actions of some of these pulmonary hypertension differential dependency networks, such as Rho GTPase (Cluster 3) (Uppal A et al. *Cell Rep.* 2019, 29, 2450-2460 e2455) and TGF-β signaling (Cluster 27) (Tang X et al. *Mol Pharmacol.,* 2013, 83, 283-293), are known to be controlled by epigenetic BET functions. Yet, EDDY also identified new functional connections of BET inhibition to previously unannotated differential dependency networks, such as Clusters 15 and 35. Cluster 15 ($C_{15}$) was further deemed a "hot-spot" gene cluster, since nearly half of the top small molecules (7 out of 15, including I-BET151) were predicted to depend upon $C_{15}$ rewiring for activity (FIG. 1C). Validation of predictions relating $C_{15}$ to BET inhibitors therefore offered the greatest opportunity for identifying new insights. Given the significant alteration in expression of a majority of $C_{15}$ genes in response to pulmonary hypertension triggers and I-BET inhibitors in endothelial cells (FIG. 11A, FIG. 11D), this cell type was focused on.

Figure 2D:
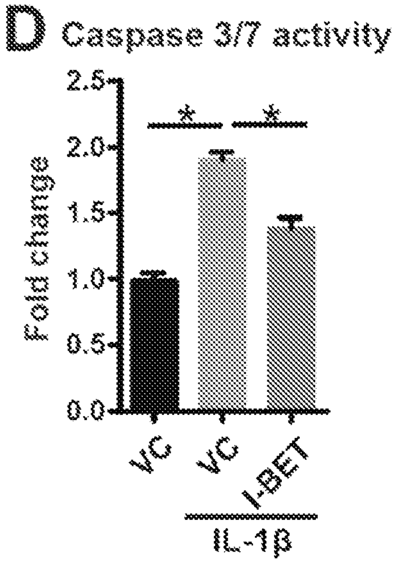
Figure 11A:
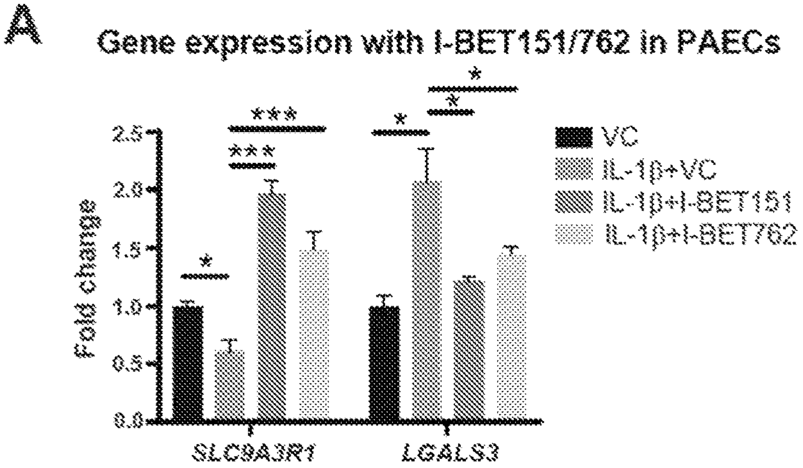
Figure 11B:
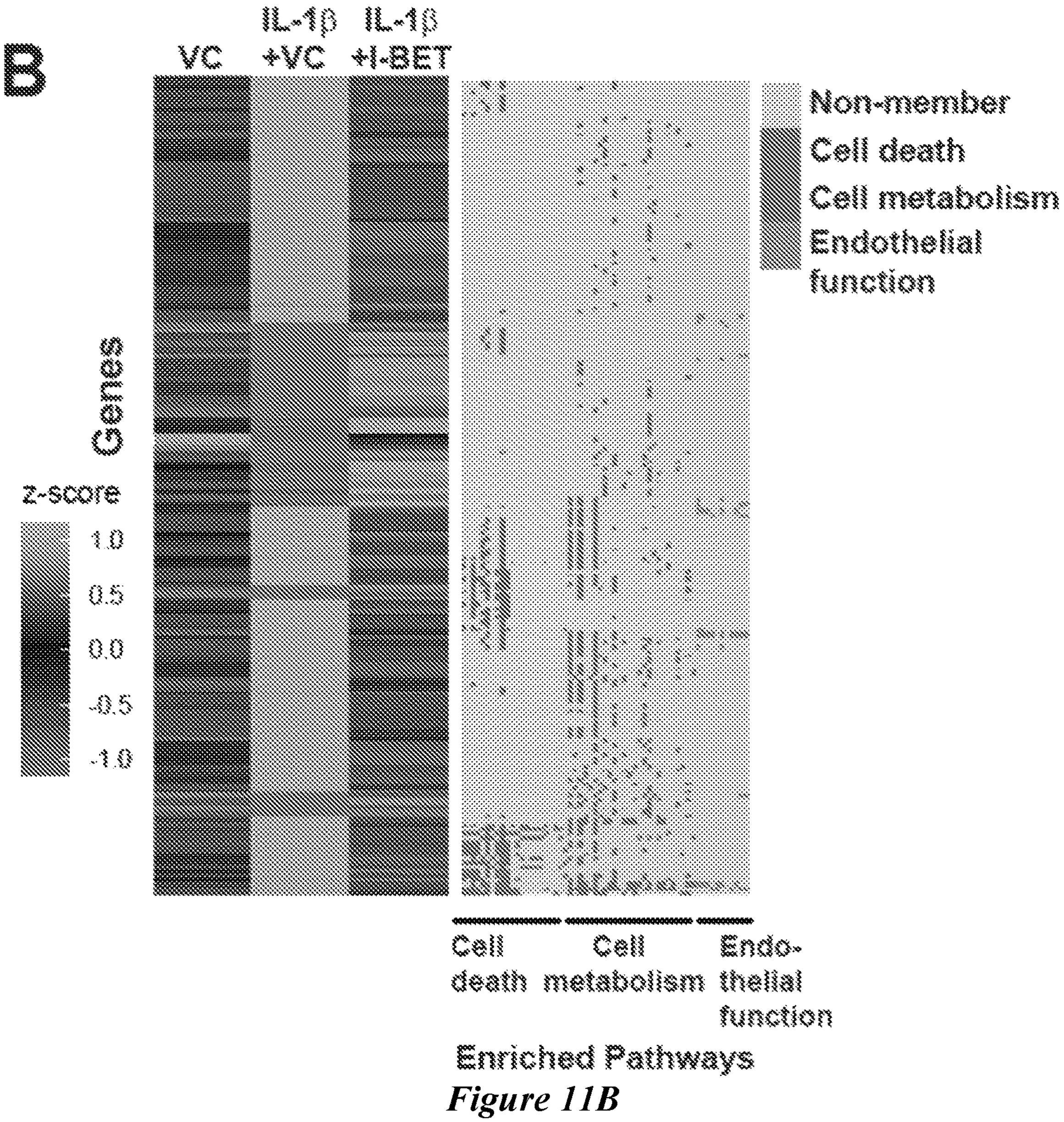
Figure 11C:
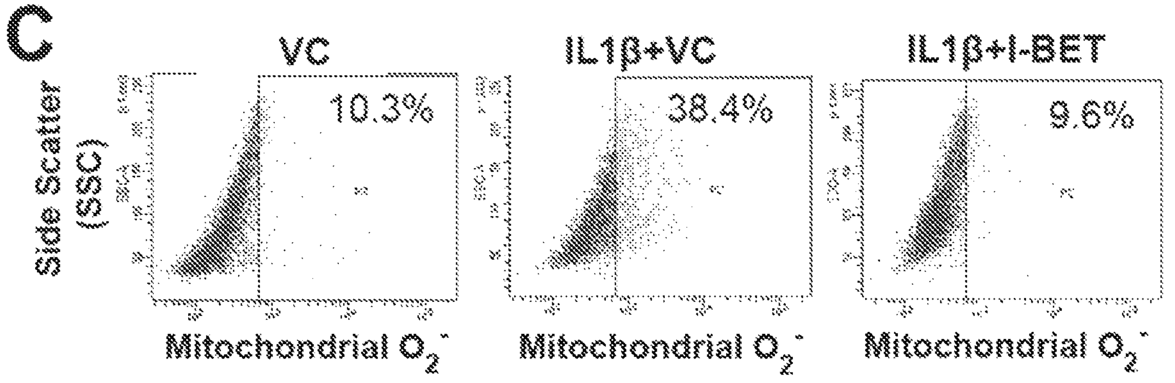

I-BET protects against apoptosis and alters $C_{15}$ gene expression in pulmonary endothelial cells (PAECs). To predict functional convergence of BET inhibition on specific $C_{15}$ genes, the $C_{15}$ differential dependency network for the collective actions of all BET inhibitors was reconstructed (FIG. 2B, full listing under EDDY-CTRP-PH: Drug Class). Using this differential dependency network as a guide, experimental definition of the novel predicted roles of these BET inhibitors was sought. Given the known mechanistic connections of BET inhibitors to interleukin-10 (IL-1β) (Khan Y M et al. *PLoS One.* 2014, 9, e95051) for modulating inflammatory phenotypes, an IL-1β-induced model of endothelial dysfunction was used to recapitulate pulmonary hypertension features in vitro (Rabinovitch M et al. *Circ Res.* 2014, 115, 165-175). I-BET762 (labeled as I-BET hereafter) was chosen to study, because I-BET762 and I-BET151 exhibited similar control of $C_{15}$ genes (FIG. 11A), and I-BET762 exhibited more favorable characteristics in clinical trials compared with either I-BET151 or JQ-1 (Mirguet O et al. *J Med Chem.* 2013, 56, 7501-7515). To determine the global transcriptomic effects of I-BET in PAECs, microarray profiling was performed after chronic exposure to IL-1β with or without I-BET (FIG. 11B). Gene set enrichment analysis of 524 differentially expressed genes revealed specific enrichment of pathways relevant to cell death, metabolism, and endothelial function, altered by IL-1β but reversed by I-BET (FIG. 11B). Consistent with these transcriptomic results and with the known importance of endothelial redox alterations and apoptosis in pulmonary hypertension (Yu Q et al. *Adv Exp Med Biol.* 2017, 967, 373-383), it was found that I-BET reduced the IL-1β-dependent increase of mitochondrial superoxide ($O_2^-$) and apoptosis in PAECs (FIG. 2C-FIG. 2D, FIG. 11C).

Figure 2E:
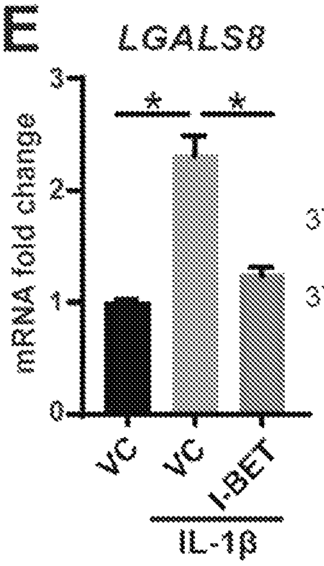
Figure 11D:
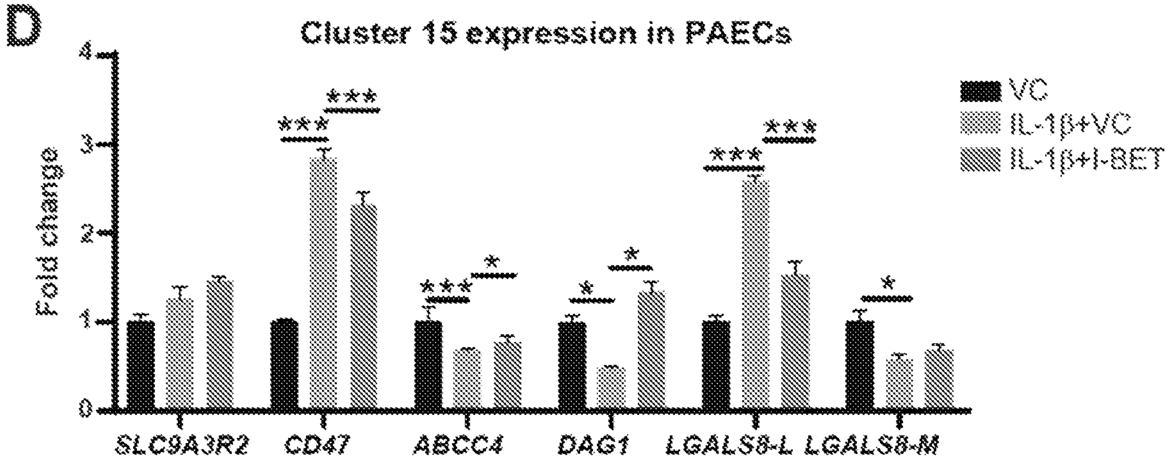
Figure 11E:
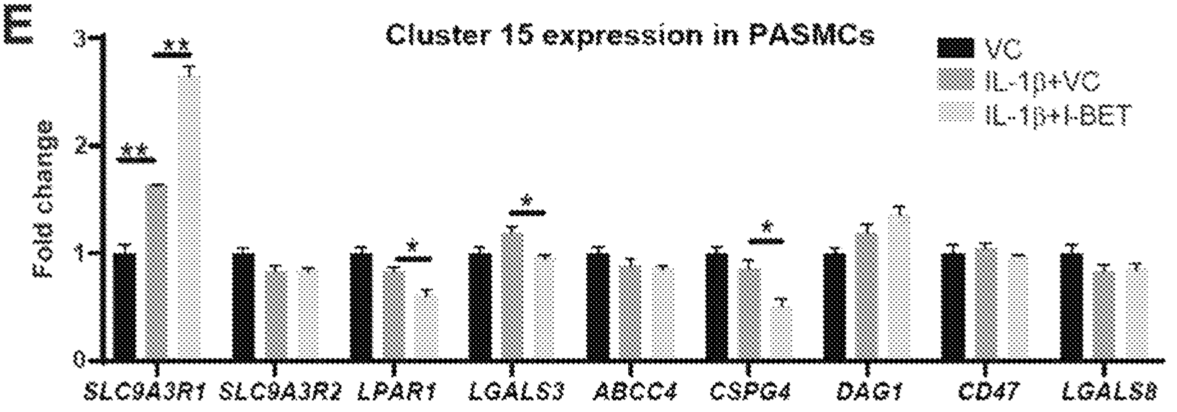

To determine the relevance of $C_{15}$ genes in such endothelial function, expression of $C_{15}$ genes was measured under the same conditions. Seven of eleven $C_{15}$ genes were expressed in human PAECs, and six of those—LGALS3, LGALS8, ABCC4, CD47, SLC9A3R1, and DAG1—were reversed by I-BET (FIG. 2E, FIG. 11A, FIG. 11D). Of those six $C_{15}$ genes, only four (LGALS3, LGALS8, DAG1, and SLC9A3R1) displayed near complete reversal by I-BET, with LGALS8 transcript (galectin-8) showing the largest fold-change alteration with IL-1β. Thus, these findings suggested an as-of-yet undescribed importance for LGALS8 in this regulatory axis which was pursued further experimentally. Interestingly, in pulmonary artery smooth muscle cells (PASMCs) in the presence of IL-1β, alterations and reversals by IL-1β and I-BET were not observed across the same $C_{15}$ genes including LGALS8 (FIG. 11E), indicating the cell-type specificity of these I-BET-$C_{15}$ connections and further guiding a focus on PAECs. Additionally, based on lung staining data from the Human Protein Atlas (https://www.proteinatlas.org), most vascular galectin-8 is localized in endothelial cells, supporting the notion of a connection between I-BET and this $C_{15}$ gene in this cell type.

Figure 2F:
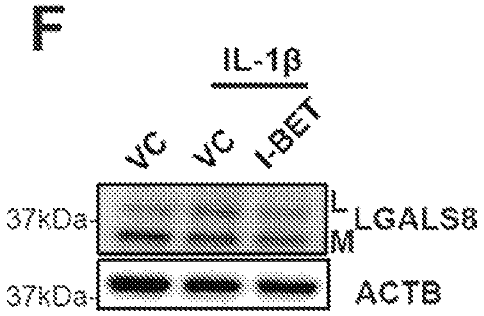
Figure 2G:
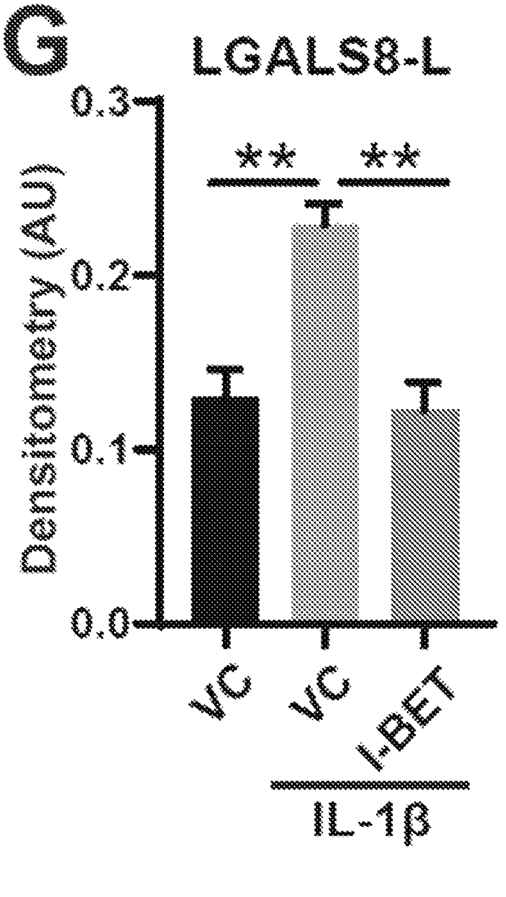
Figure 2H:
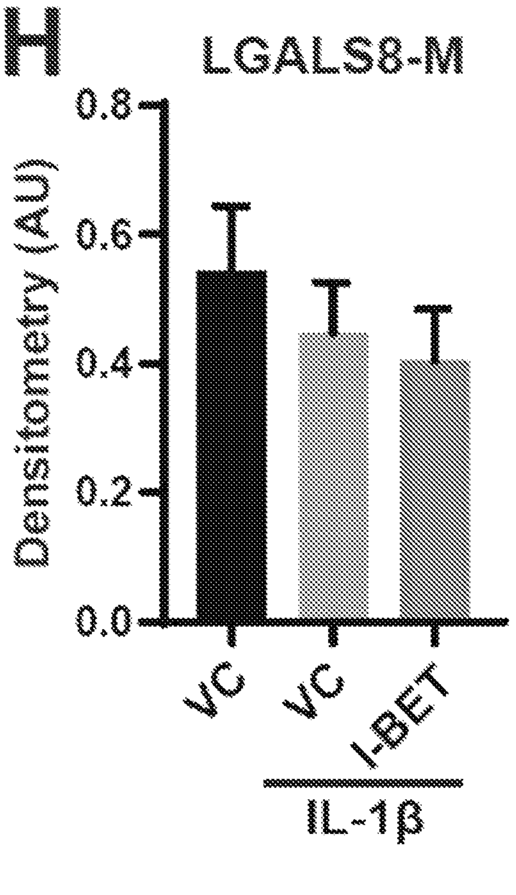

Of the two major isoforms of LGALS8, LGALS8-M and L (Cattaneo V et al. *Glycobiology.* 2014, 24, 966-973), it was found that LGALS8-L transcript in cultured PAECs was increased by IL-1β and reversed by I-BET, whereas LGALS8-M was reduced by IL-1β but not altered by I-BET (FIG. 11D). LGALS8-L protein followed its mRNA expression, but LGALS8-M showed no significant difference (FIG. 2F-FIG. 2H). Next, phenocopying I-BET, knockdown of either the canonical targets of I-BET, BRD2 or BRD4 (siRNA efficacy confirmed in FIG. 11F), blunted IL-1β-specific increases of LGALS8-L at the transcript and protein levels (FIG. 11F-FIG. 11H). Thus, I-BET depends upon Brd2/4 to regulate LGALS8 and LGALS8-L in endothelial cells.

Figure 2I:
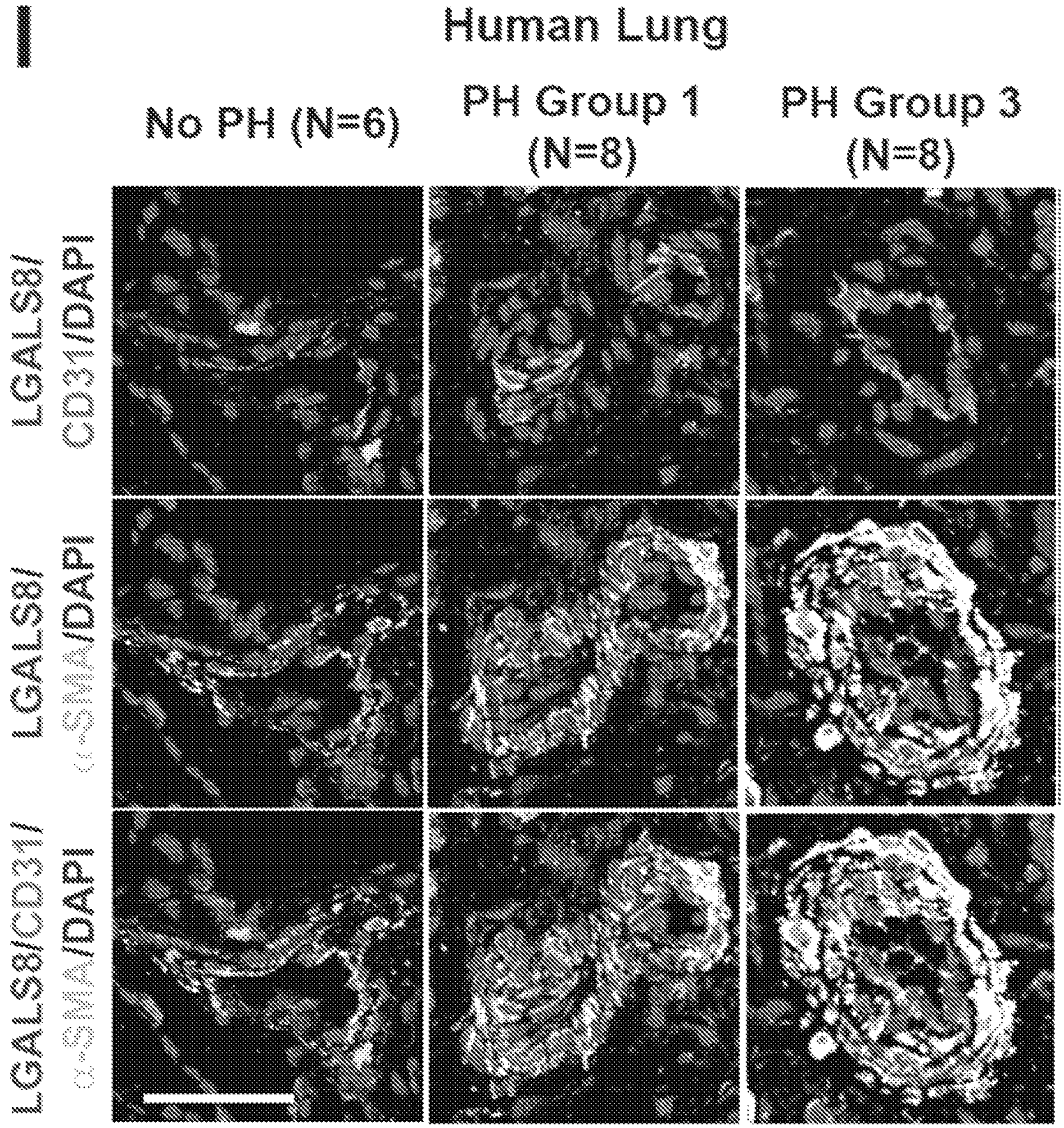
Figure 2J:
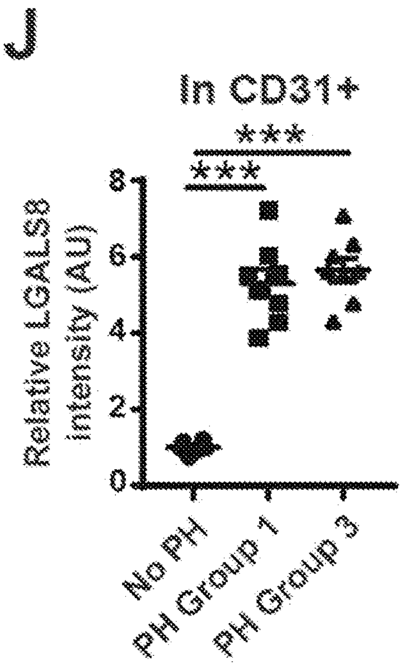
Figure 12A:
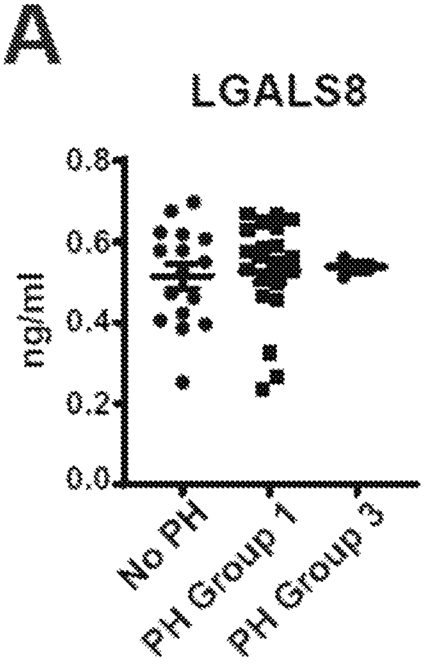
FIG. 12A-FIG. 12S. LGALS8 is upregulated in multiple animal and human examples of pulmonary hypertension.
Figure 12B:
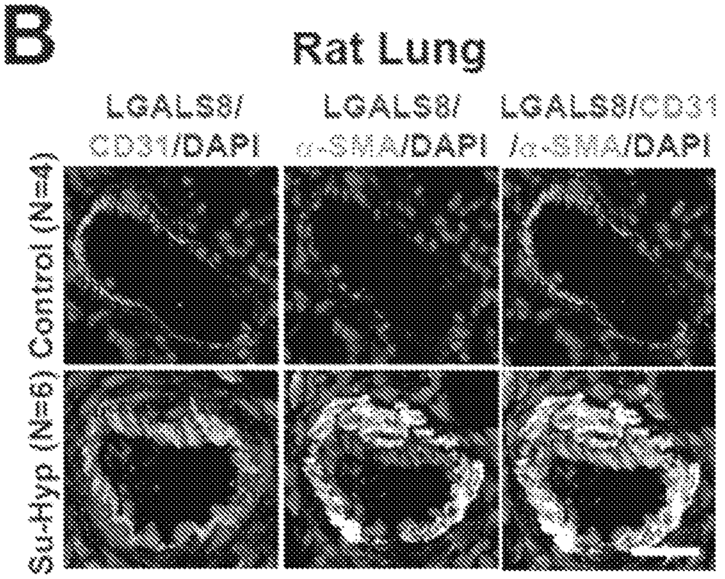
(FIG. 12B-FIG. 12E) Similarly, via immunofluorescence staining (FIG. 12B, FIG. 12D), expression of LGALS8 was upregulated in whole-vessel in CD31+ cells (FIG. 12C, FIG. 12E) in lung sections from a SU5416-hypoxia (Su-Hyp) rat model of pulmonary hypertension (n=5.
Figure 12C:
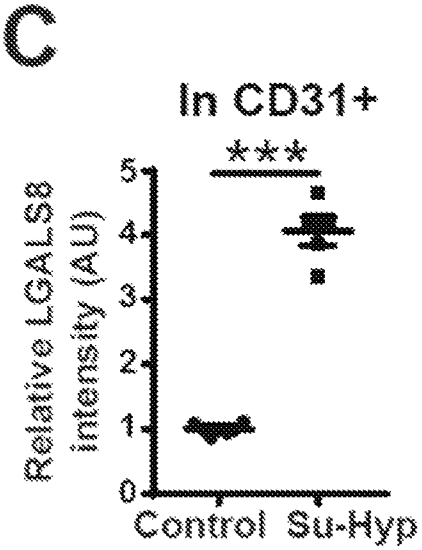
Figure 12D:
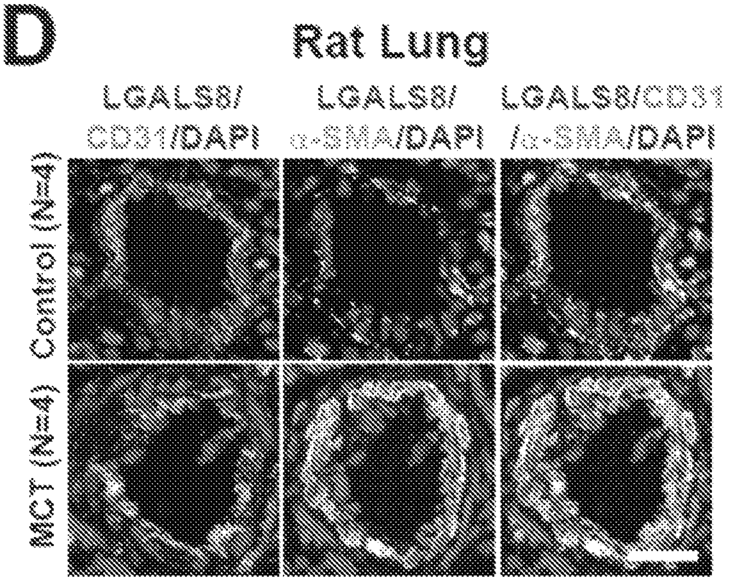
Figure 12E:
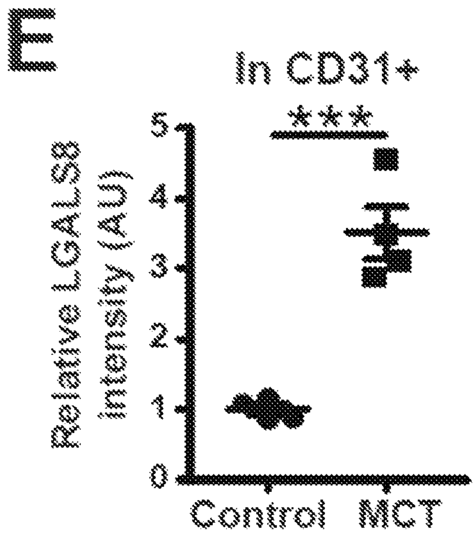
Figure 12F:
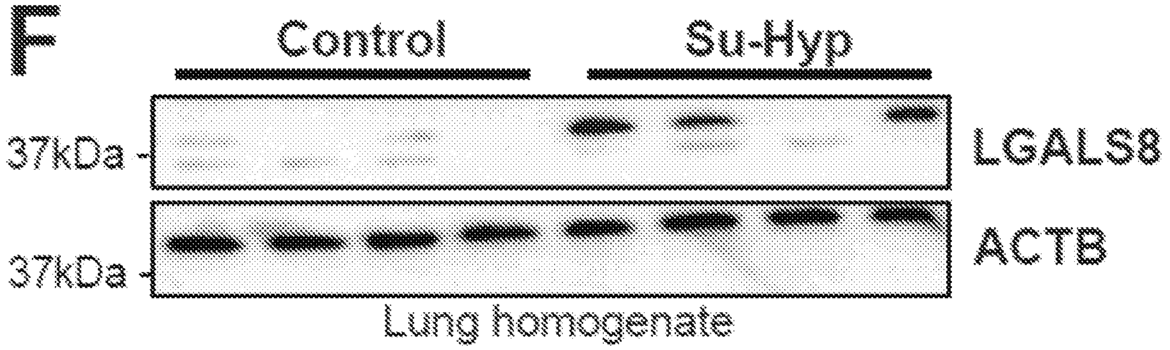
(FIG. 12F-FIG. 12I) The increase of LGALS8 was also confirmed by immunoblot and quantification in whole lung homogenate from SU5416-hypoxia (Su-Hyp; n=4-5/grp.
Figure 12G:
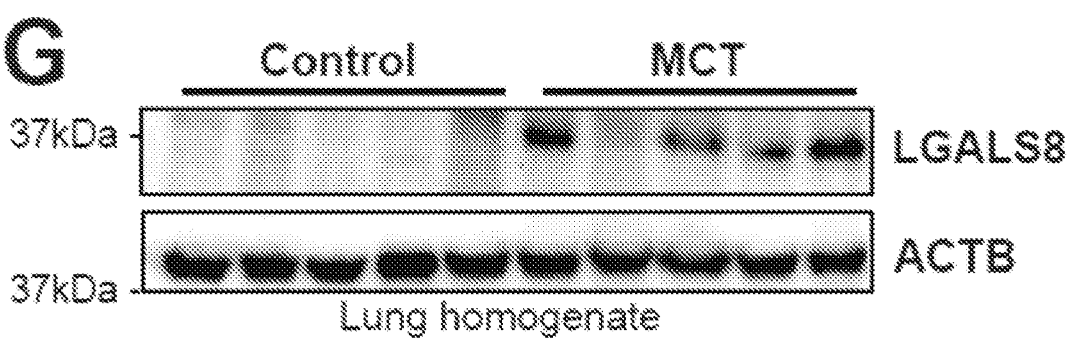
Figure 12H:
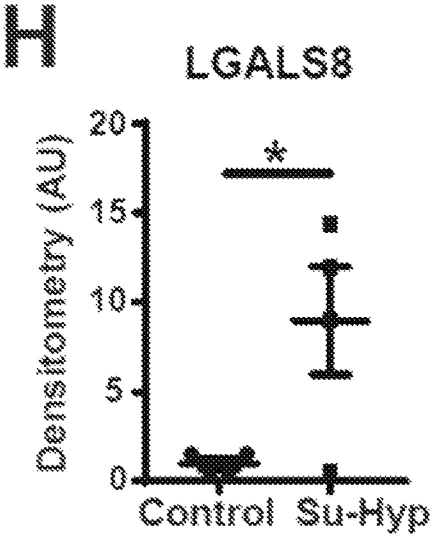
Figure 12I:
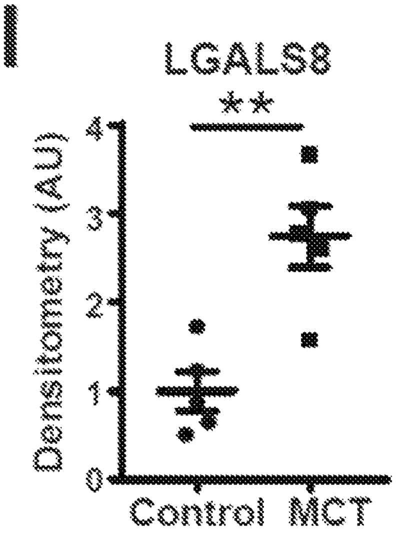
Figure 12J:
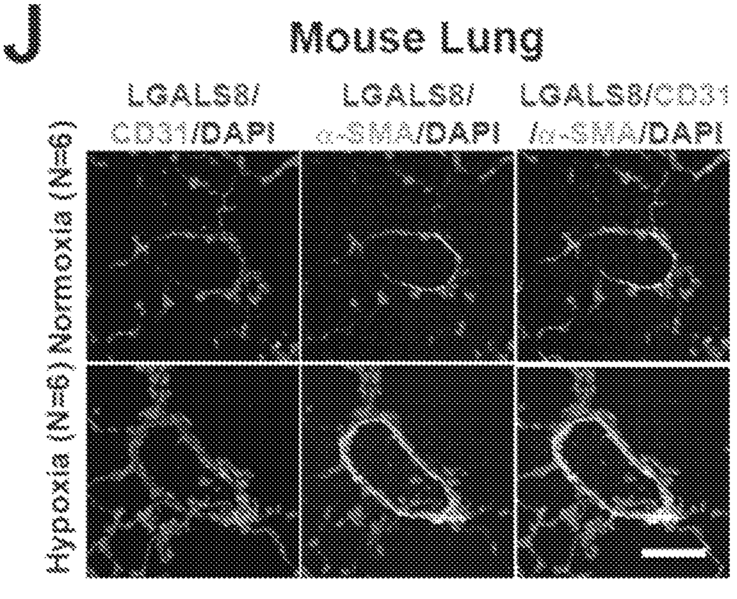
(FIG. 12J-FIG. 12K) In a chronic hypoxia mouse model of pulmonary hypertension vs. control (n=6/grp), immunofluorescence staining (FIG. 12J) demonstrated increased LGALS8 in lung CD31+ endothelial cells (FIG. 12K).
Figure 12K:
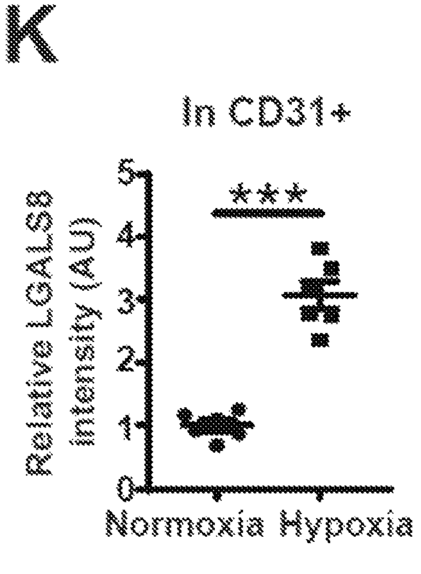
Figure 12L:
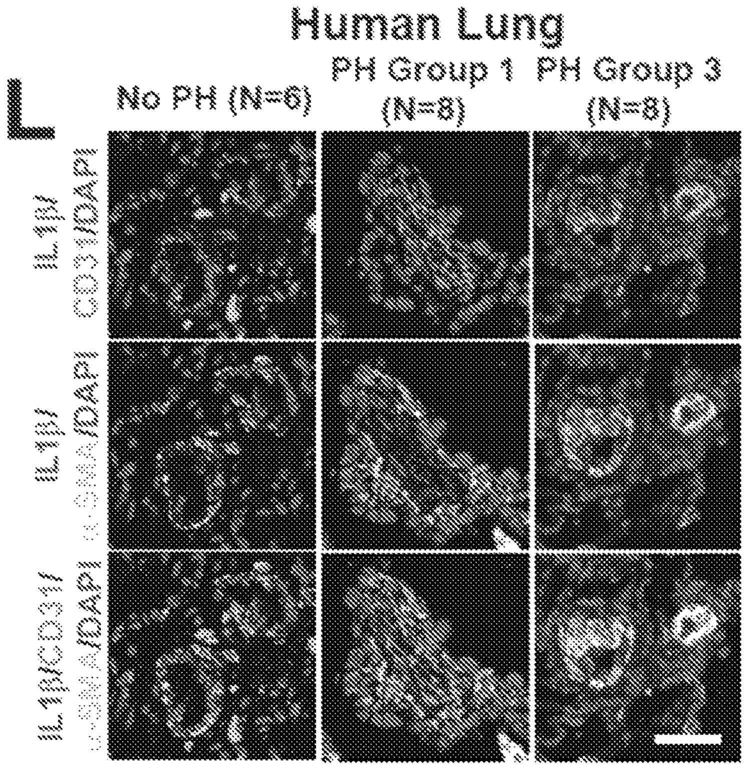
Figure 12M:
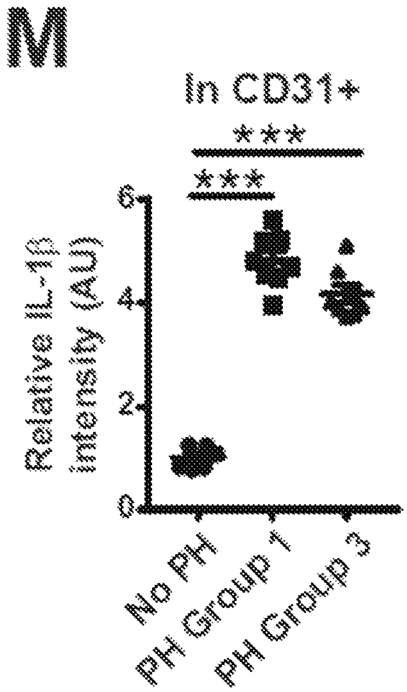
Figure 12N:
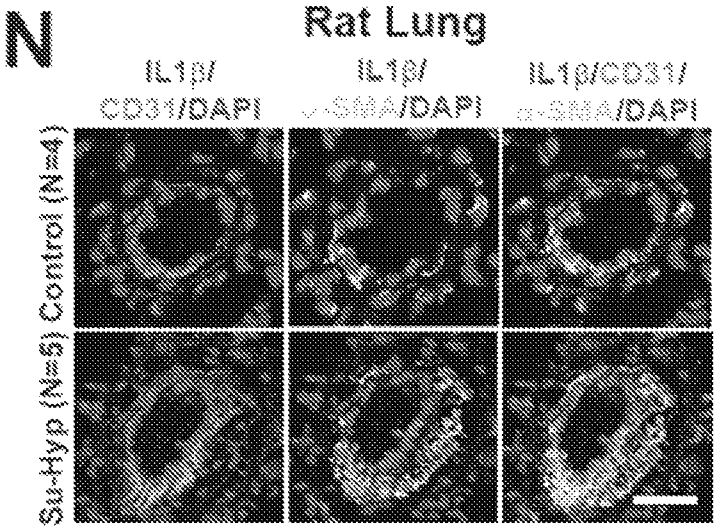
Figure 12O:
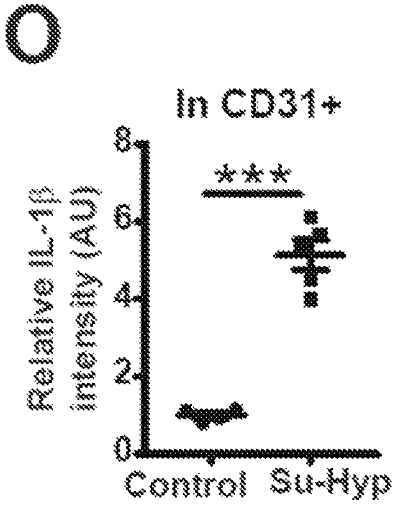
Figure 12P:
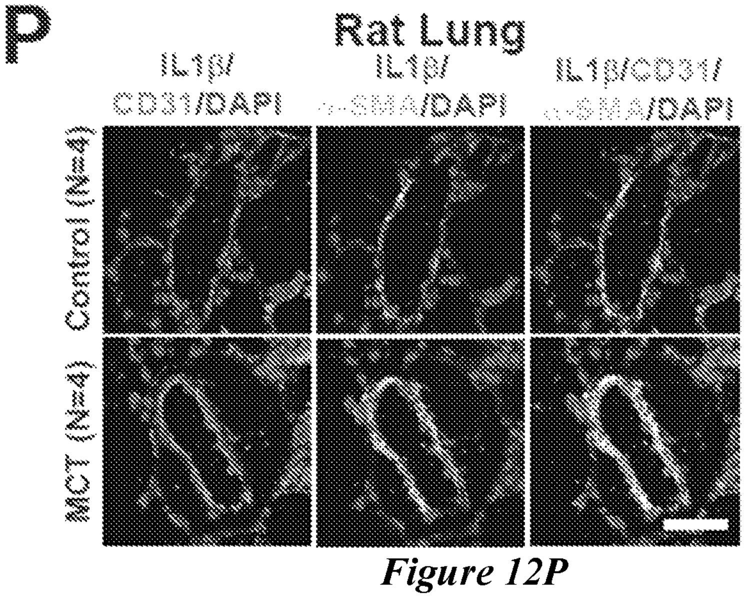
Figure 12Q:
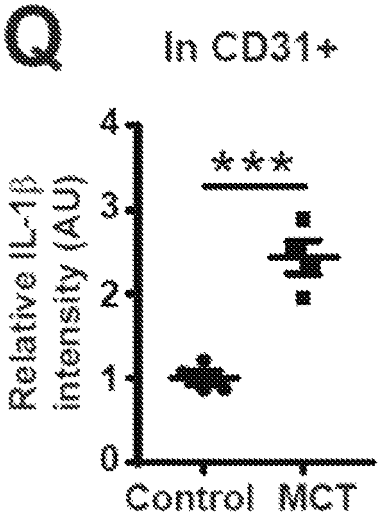
Figure 12R:
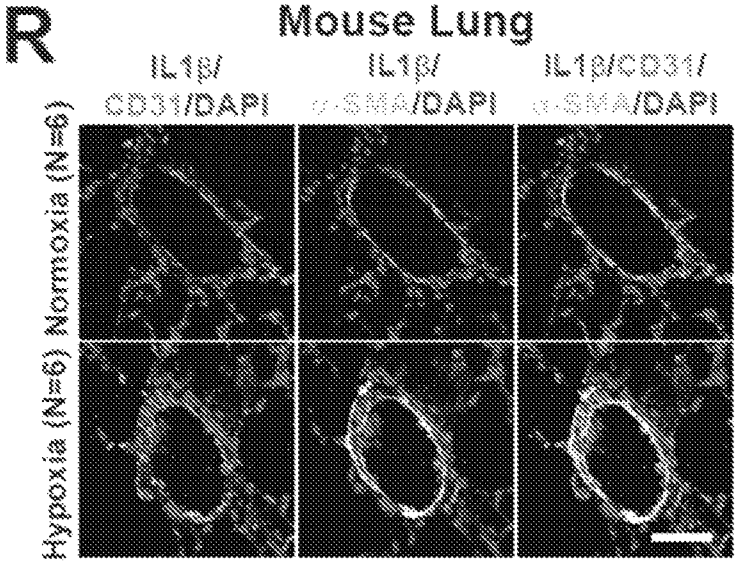
Figure 12S:
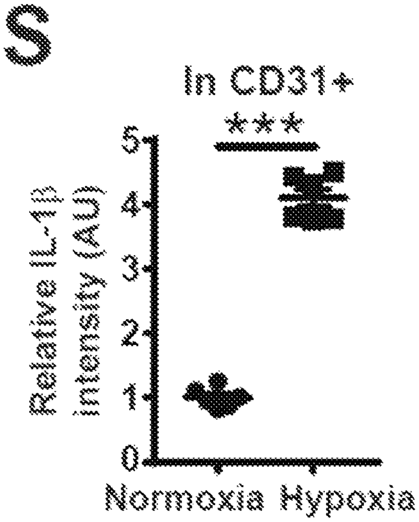

To demonstrate the translational relevance of these findings, LGALS8 was stained in pulmonary arterioles (<100 μm diameter) of two WSPH subtypes (Table 4): those with severe Group 1 pulmonary arterial hypertension and those Group 3 pulmonary hypertension due to hypoxic lung disease. LGALS8 was upregulated in the pulmonary vasculature, consistent with its known intracellular and extracellular forms and with notable increased expression CD31+ endothelial cells (FIG. 2I-FIG. 2J) but no change observed in circulating venous plasma levels (FIG. 12A). Moreover, consistent with the findings in cultured PAECs, LGALS8 was concurrently upregulated in three separate rodent models of pulmonary hypertension including chronically hypoxic mice (FIG. 12B-FIG. 12K), along with IL-1γ in both humans and rodents with pulmonary hypertension (FIG. 12L-FIG. 12S), thus emphasizing the inherent inflammatory component of pulmonary hypertension and direct relevance to LGALS8.

Figure 3L:
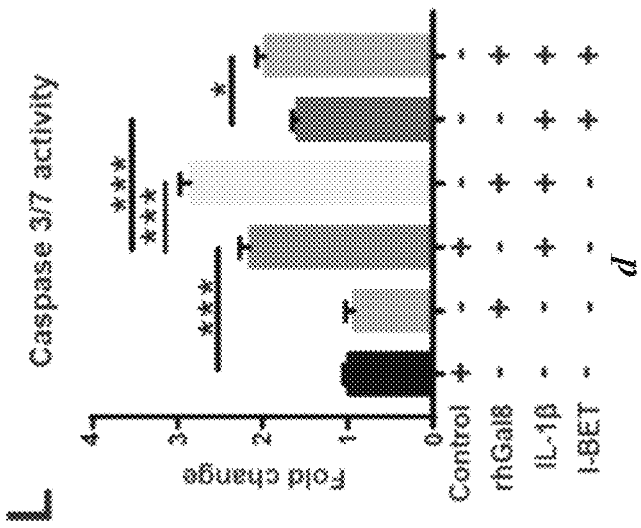
Figure 13A:
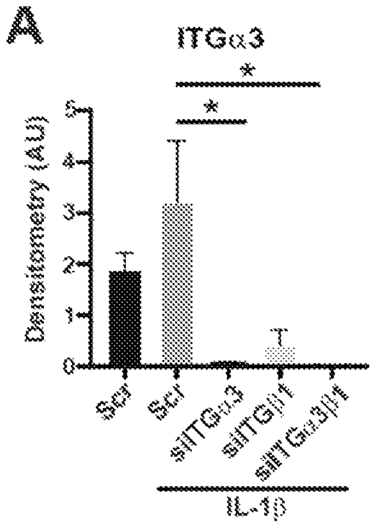
Figure 13B:
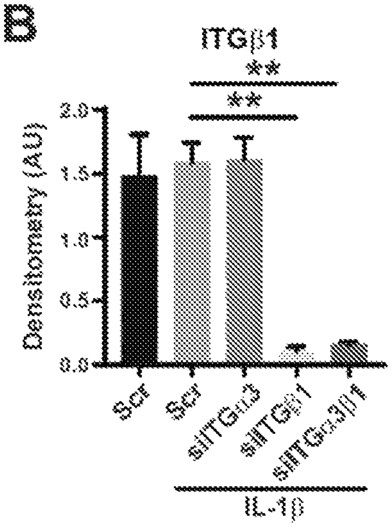
Figure 13C:
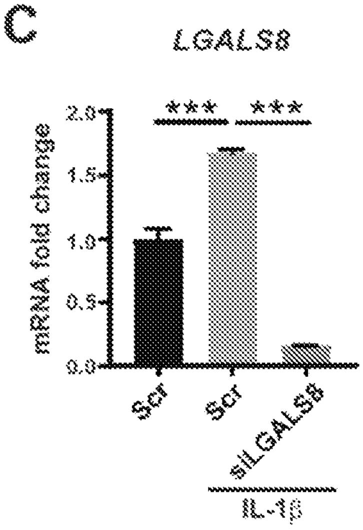
Figure 13D:
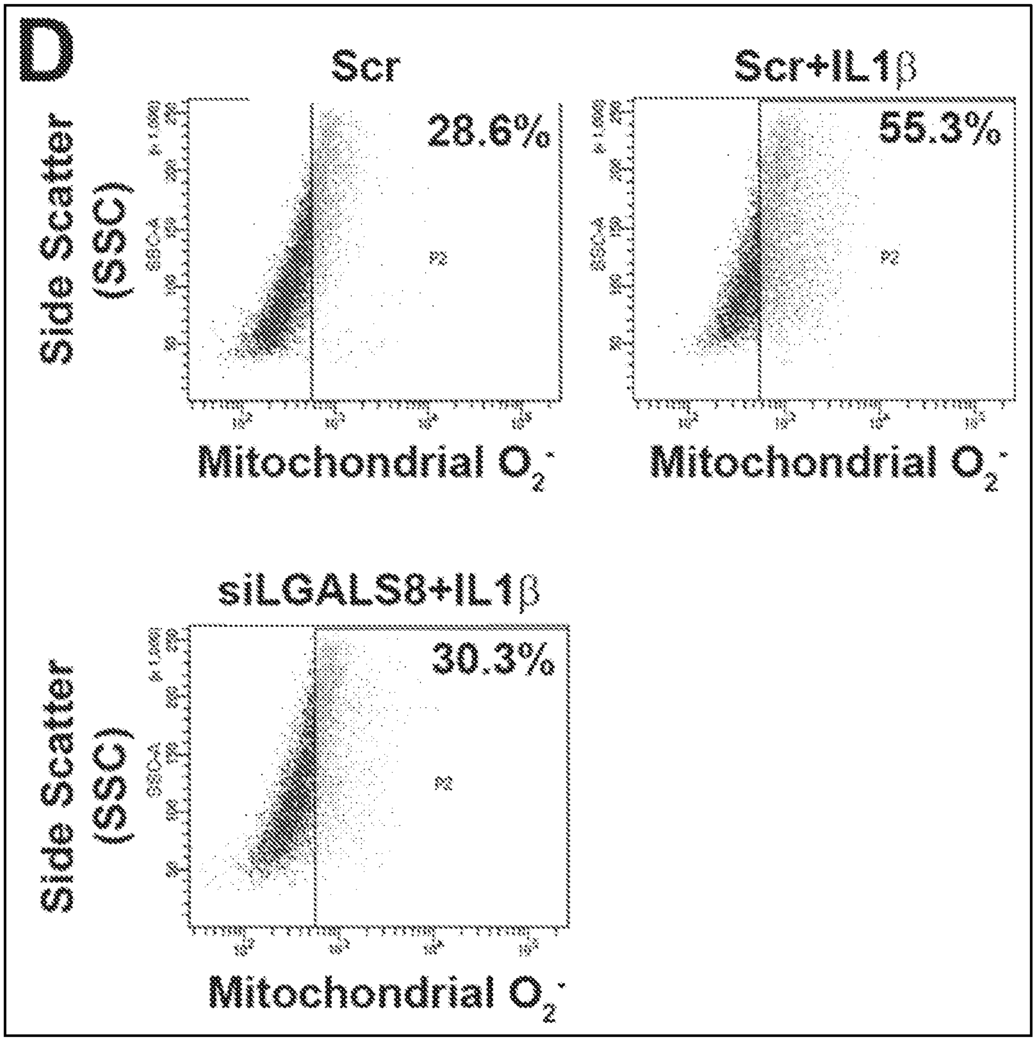

Consistent with the known binding of integrin receptor 301 to LGALS8 in other contexts (Hadari Y R et al. *J Cell Sci.* 2000, 113 (Pt 13), 2385-2397), integrin α3 (ITGα3) binding to LGALS8 in PAECs was demonstrated using a proximity ligation assay (FIG. 3A-FIG. 3B). Furthermore, given the actions of STAT1 in integrin signaling as well as its importance in generating mitochondrial ROS and apoptosis (Wang Y et al. *Int J Oncol.* 2018, 52, 305-313), its activation status was examined downstream of the LGALS8-integrin α3β1 interaction. Knockdown of integrin α3β1 (siITGα3/siITGβ1, FIG. 13A-FIG. 13B) or integrin α3 alone reduced IL-1β-induced STAT1 phosphorylation (FIG. 3C-FIG. 3E), phenocopying LGALS8 (siLGALS8, FIG. 3F-FIG. 3H, FIG. 13C). Next, revealing the role of LGALS8 in endothelial pathobiology, siLGALS8 decreased IL-1β-induced mitochondrial superoxide and apoptosis (FIG. 3I-FIG. 3J, FIG. 13D) and phenocopied the effects of I-BET. To determine whether I-BET depends critically upon LGALS8 to alter mitochondrial superoxide and apoptosis, recombinant human LGALS8 (rhGal8) was used to supplement LGALS8 function. While rhGal8 alone had no effect, its presence reduced the ability of I-BET to decrease IL-1β-specific mitochondrial superoxide (FIG. 3K, FIG. 13E) and apoptosis (FIG. 3L). Collectively, these data demonstrate the critical role of LGALS8, via integrin α3 and STAT1 activation, in mediating I-BET action on IL-1β-driven PAEC dysfunction.

Figure 4A:
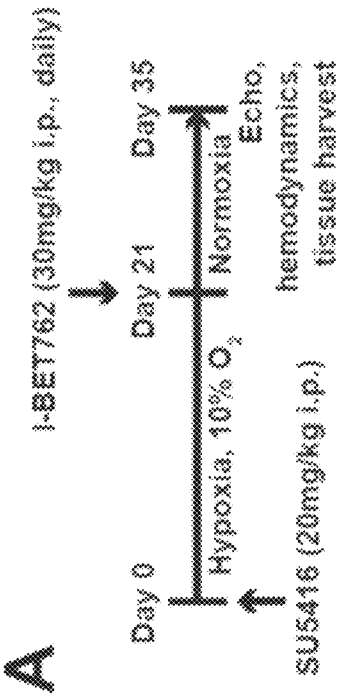
Figure 4B:
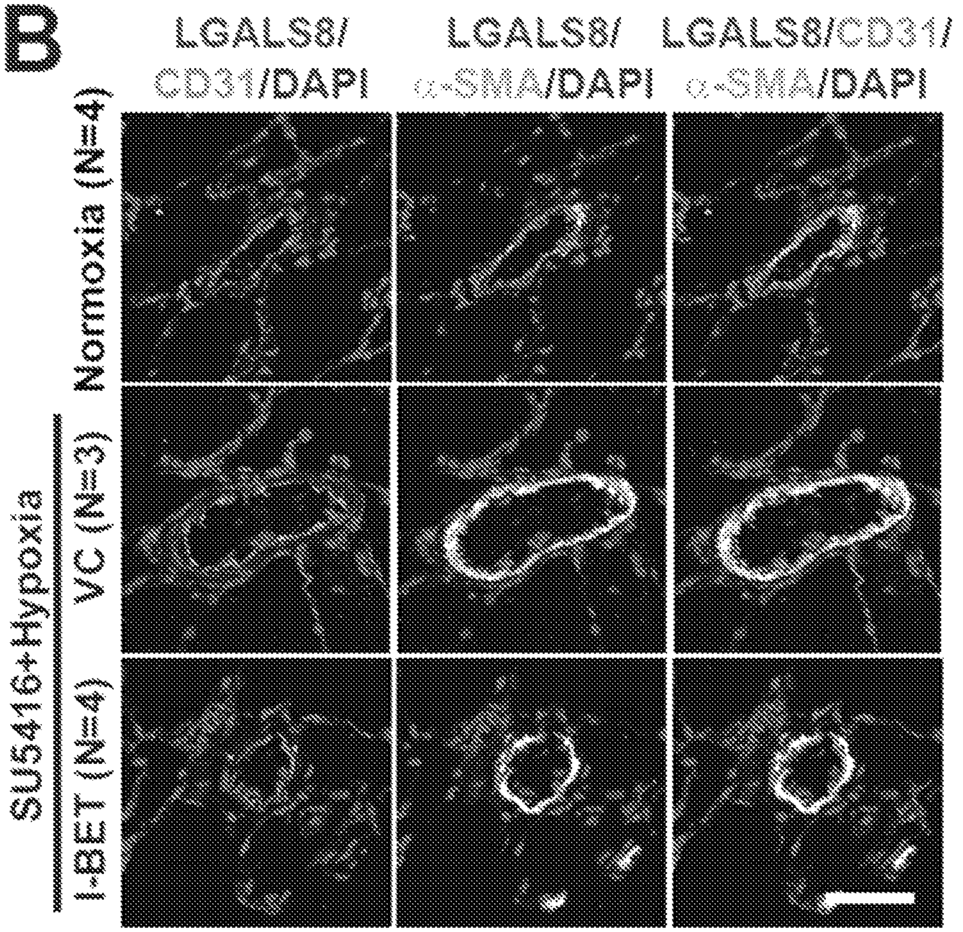
Figure 4C:
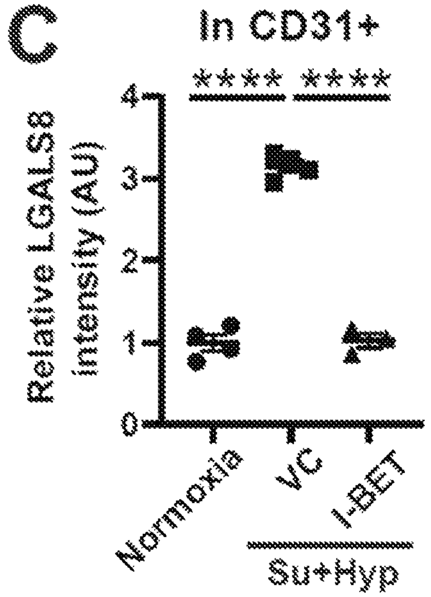
Figure 4I:
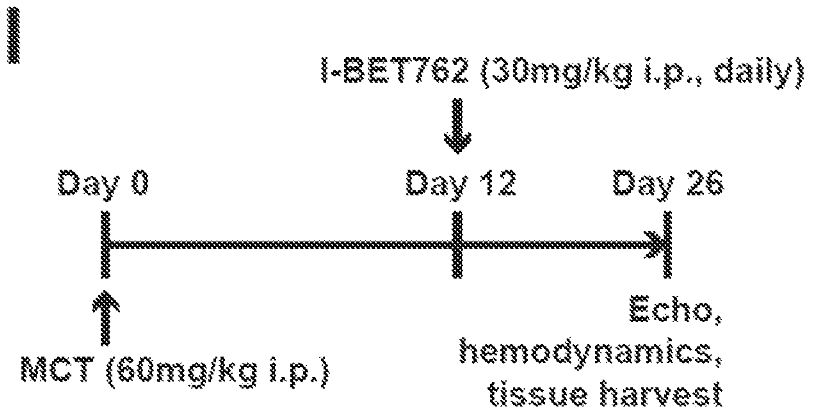
(FIG. 4I) Sprague-Dawley rats were administered monocrotaline (MCT) i.p. (60 mg/kg) to promote pulmonary arterial hypertension within 3 weeks. Rats were then treated with I-BET762 vs. vehicle control by daily i.p. injection (30 mg/kg) at Days 12-26 post-MCT injection (n=3-6/grp).
Figure 4J:
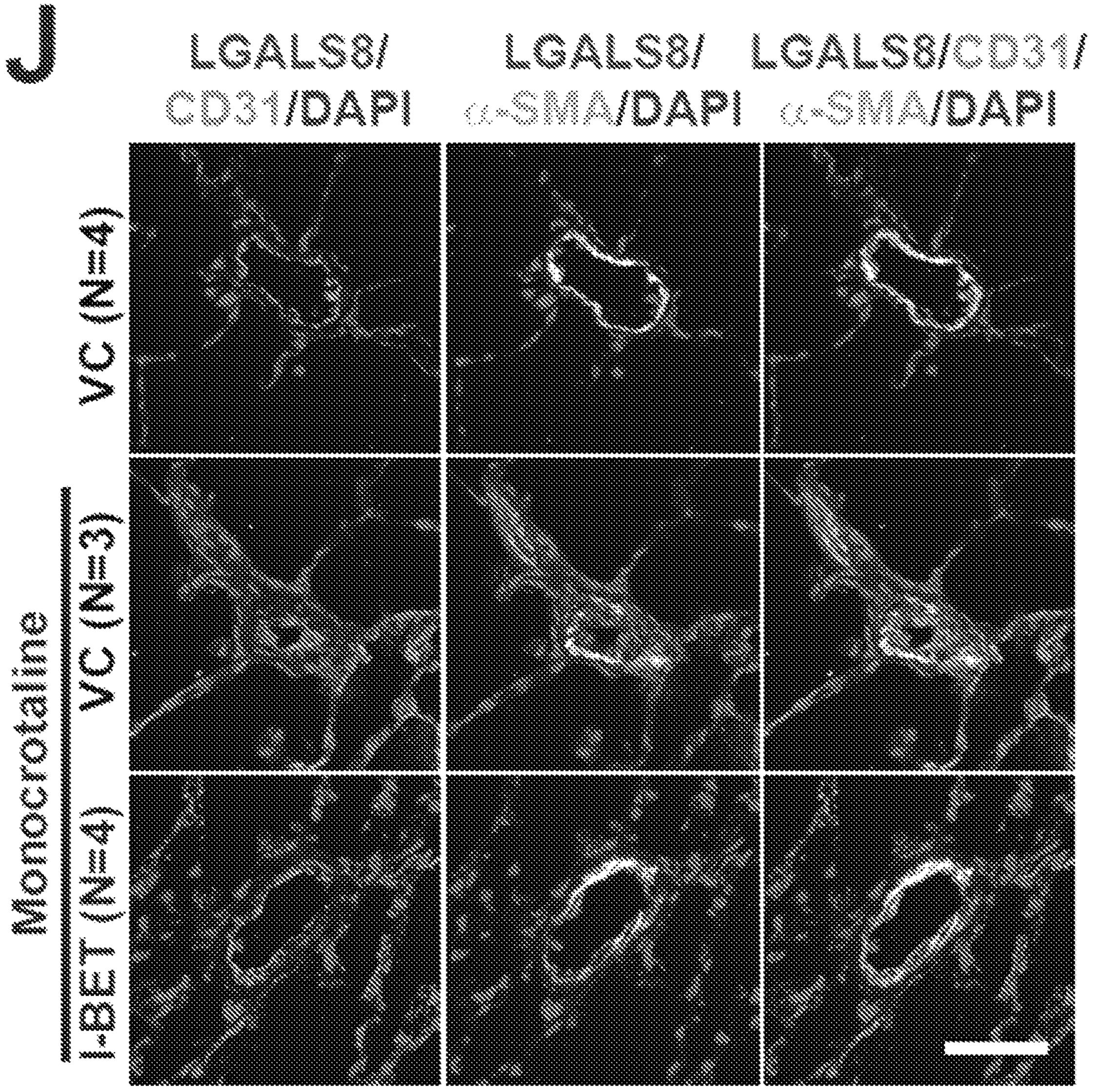
Figure 4K:
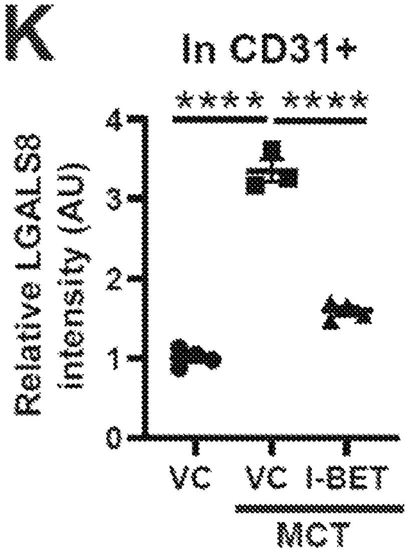
Figure 4L:
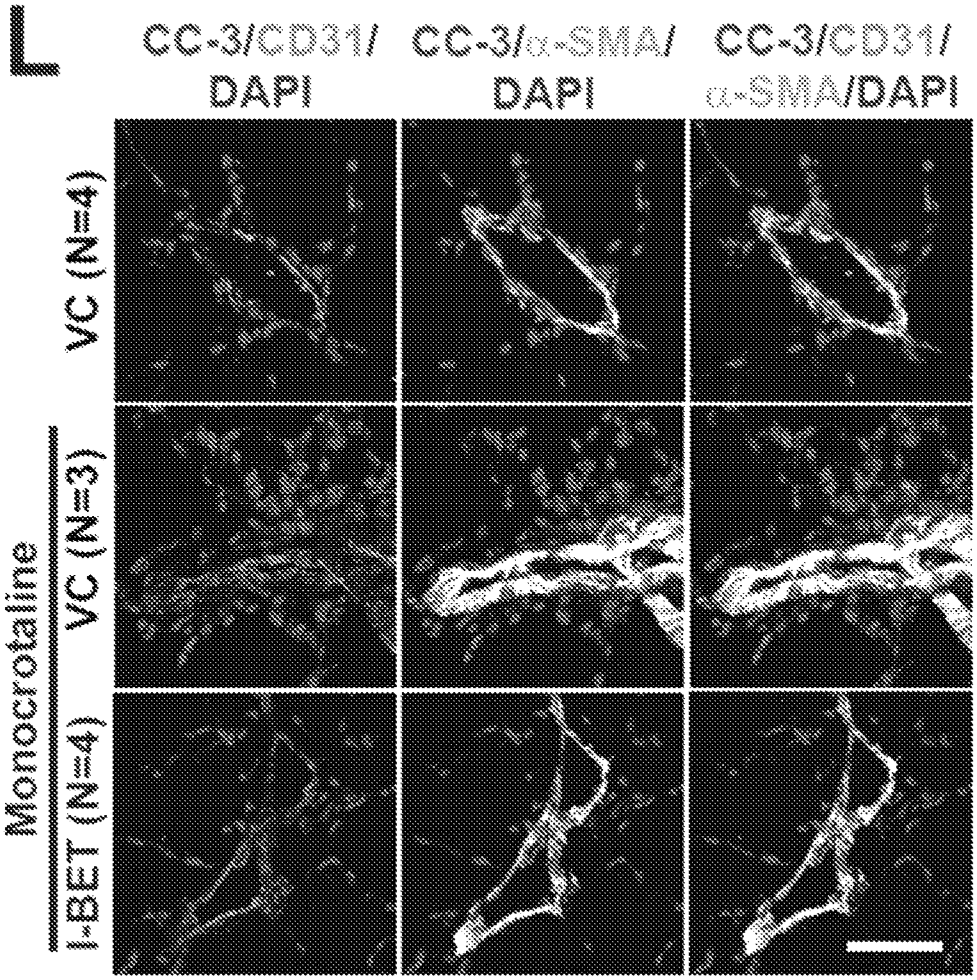

I-BET reduces endothelial LGALS8 and improves existing pulmonary arterial hypertension in rats. To investigate whether I-BET controls LGALS8 and pulmonary arterial hypertension in vivo, I-BET was administered i.p. daily in two separate models of Group 1 pulmonary arterial hypertension in rats—monocrotaline (MCT) exposure followed by 26 days in normoxia and SU5416-hypoxia exposure (3 weeks, Days 0-21) followed by 2 weeks of normoxia (Days 21-35). In both exposures, a disease-reversal protocol was utilized, whereby I-BET was administered only after disease manifested (at Days 12-26 post-MCT and at Days 21-35 after 3 weeks of SU5416-hypoxia) (FIG. 4A, FIG. 4I). Echocardiographic assessment after I-BET762 dosing in SU5415-hypoxic rats demonstrated no alteration of heart rate, left ventricular function, or aortic pressure after drug dosing (FIG. 14A-FIG. 14G). Consistent with the in vitro findings in cultured PAECs, I-BET decreased pulmonary vascular LGALS8, including in endothelial cells (FIG. 4B-FIG. 4C, FIG. 4J-FIG. 4K). Consequently, I-BET reduced downstream apoptosis, as reflected by reduced cleaved caspase-3 (FIG. 4D-FIG. 4E, FIG. 4L-FIG. 4M). As with prior studies of other BET inhibitors in pulmonary arterial hypertension rats (Van der Feen D E et al. *Am J Respir Crit Care Med.* 2019, 200, 910-920), in both rat models, a reduction of indices of disease, including reduced pulmonary vascular muscularization (via α-SMA stain), right ventricular systolic pressure (RVSP), and Fulton index (FIG. 4F-FIG. 4H, FIG. 4N-FIG. 4P), was observed.

Figure 5I:
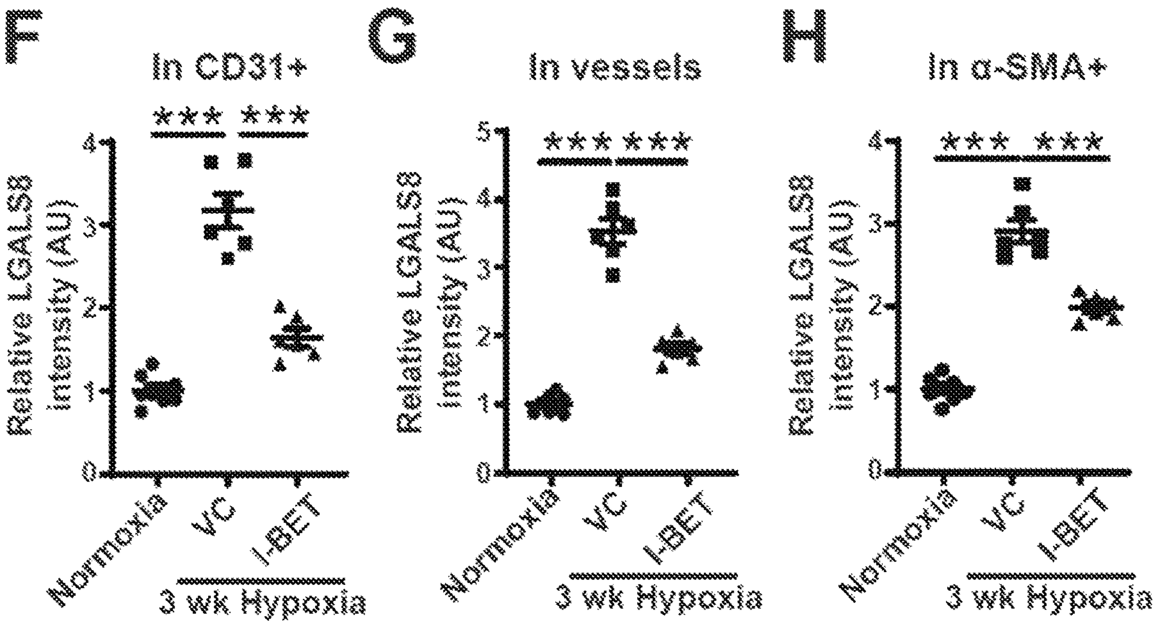
Figure 5I:
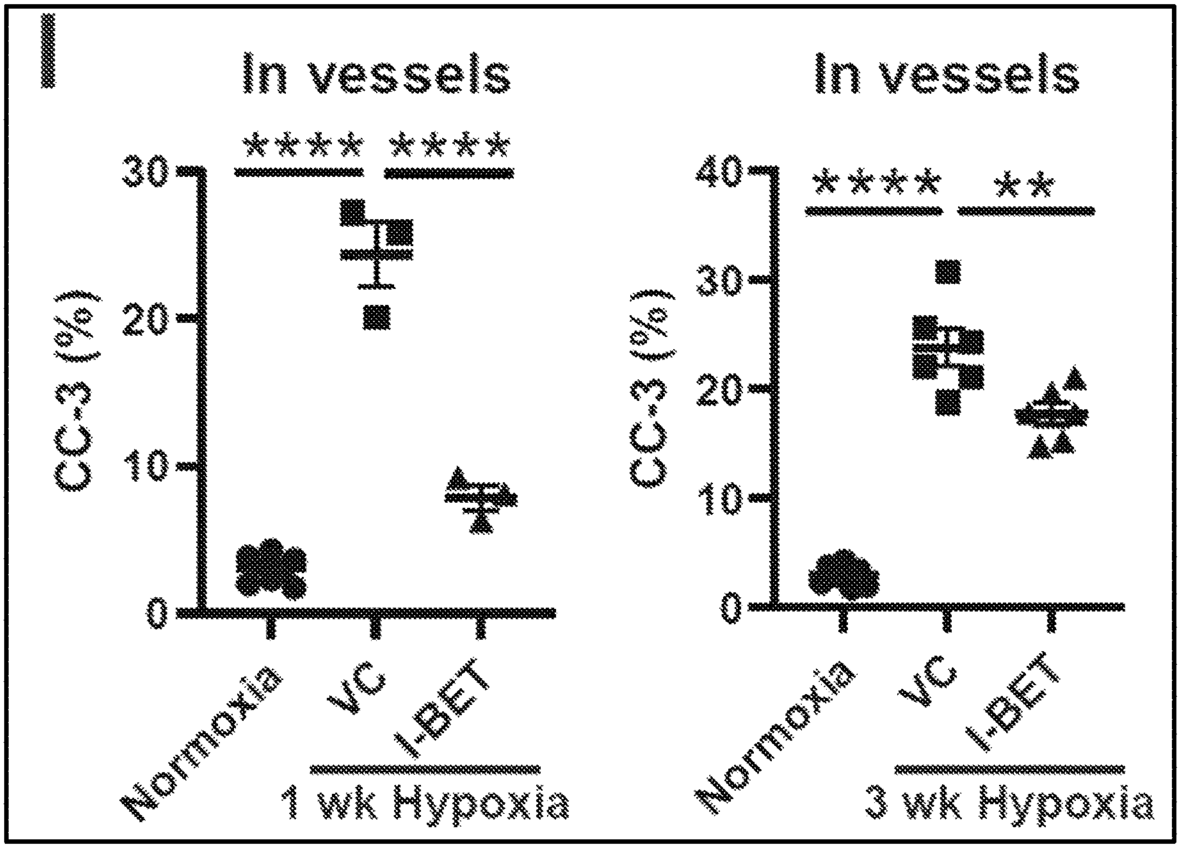
Figure 5J:
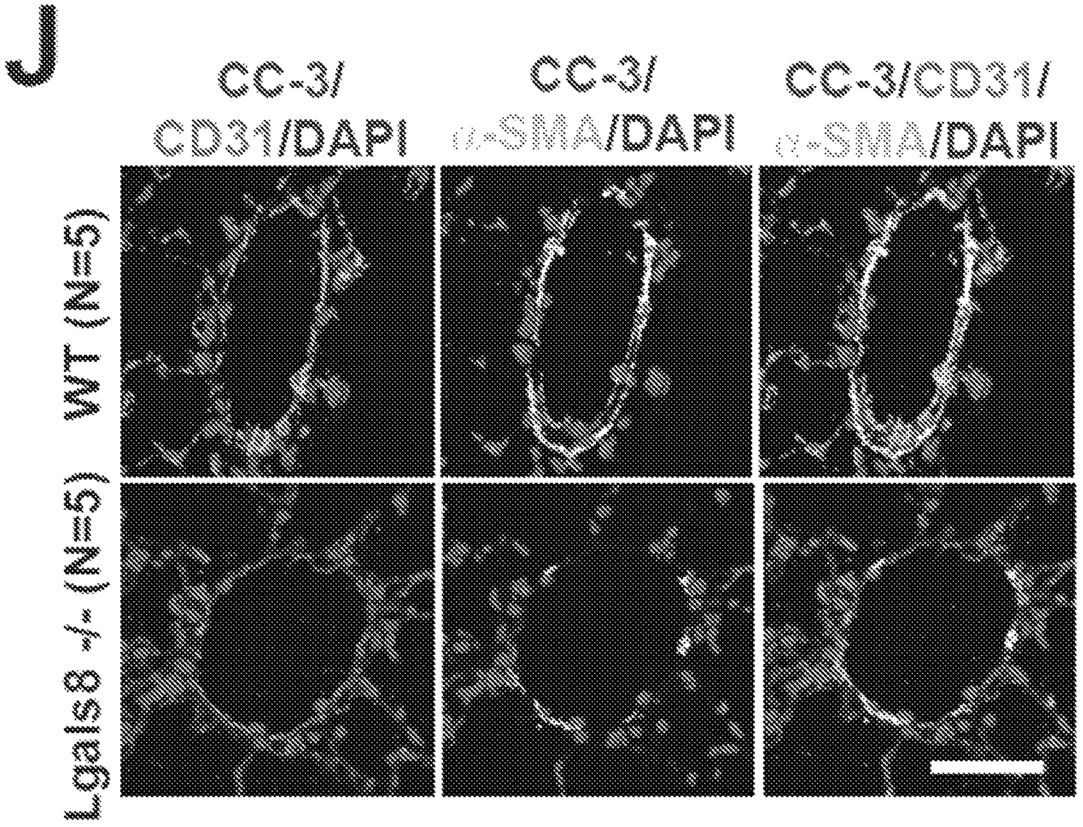
(FIG. 5J-FIG. 5N) In parallel, as compared with hypoxic wildtype (WT) mice, hypoxic Lgals8−/− mice displayed reductions in vascular cleaved caspase-3 (FIG. 5J-FIG. 5K), muscularization (FIG. 5L), RVSP (FIG. 5M), and Fulton index (FIG. 5N) (n=8-9 Lgals8−/− and 8-13 WT; black: male; red: female).
Figure 5K:
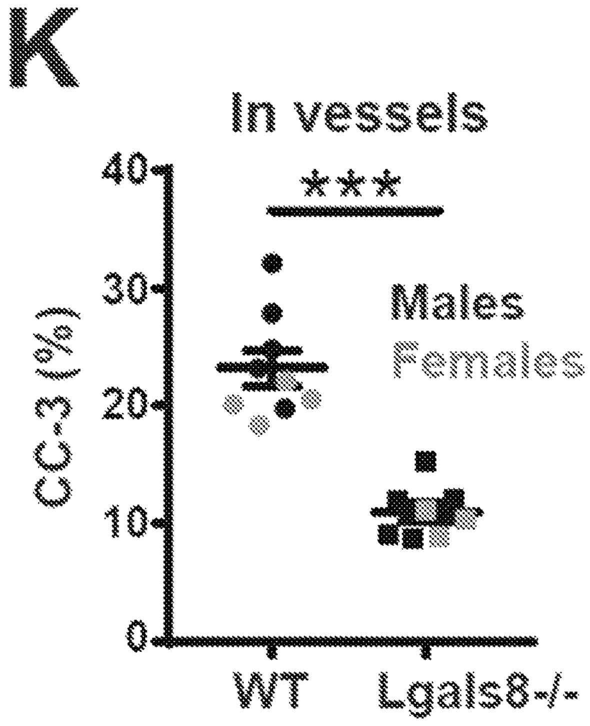
Figure 5L:
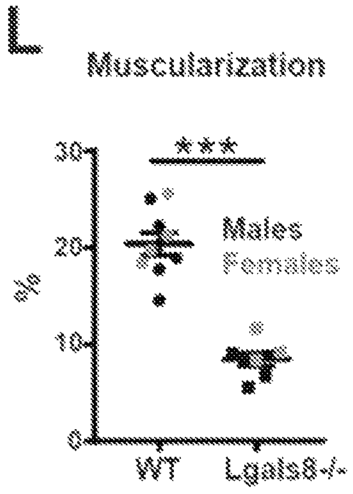
Figure 5M:
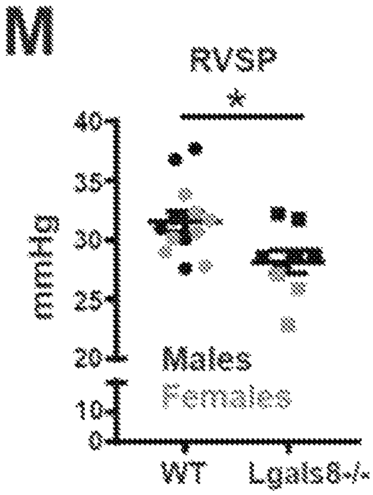
Figure 5N:
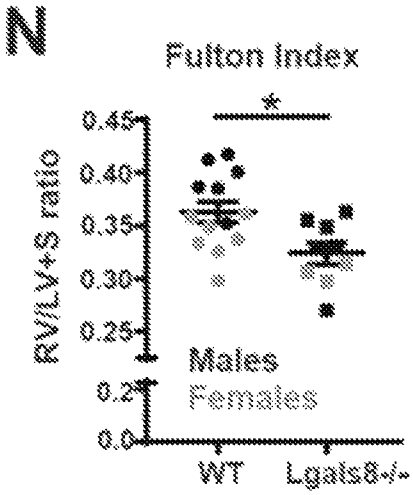
Figure 5O:
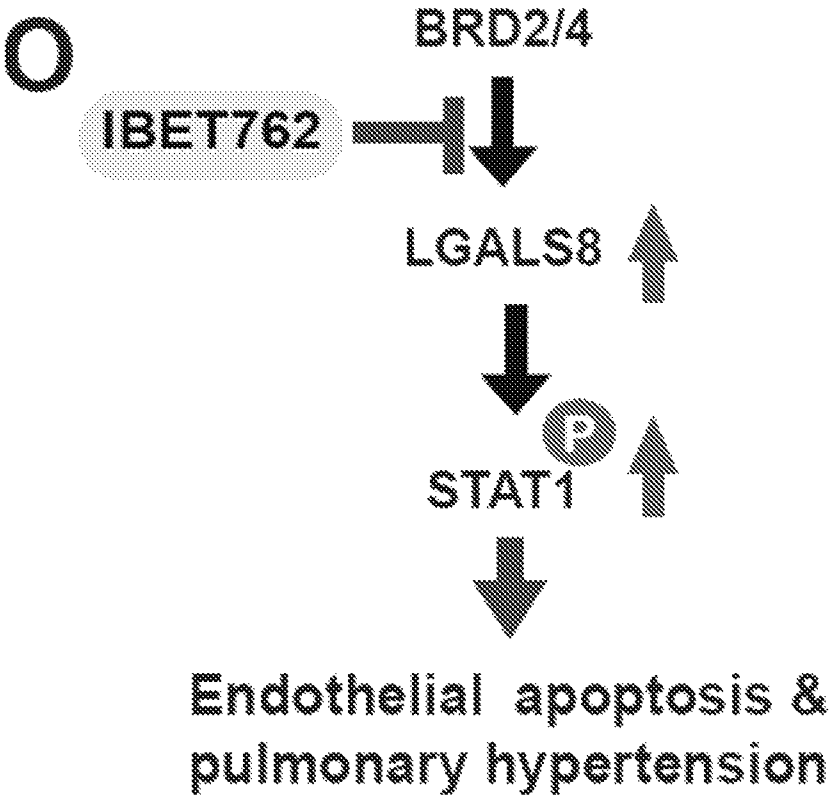

I-BET and genetic deficiency of LGALS8 protect against hypoxic pulmonary hypertension in mice. Stemming from the known link between hypoxia and inflammatory activation (Eltzschig H K et al. *N Engl J Med.* 2011, 364, 656-665), it was reasoned that IBET-762 and LGALS8 may also be relevant to inflammatory pathways activated in hypoxia and thus in Group 3 pulmonary hypertension due to hypoxic lung disease. As such, in cultured PAECs, it was found that IBET-762 and LGALS8 control inflammatory and apoptotic endothelial pathways driven by hypoxia (FIG. 15A-FIG. 15E). Correspondingly, the effects of daily and orally administered I-BET for 2 weeks in a Group 3 pulmonary hypertension model (chronically hypoxic mice) was studied. As in pulmonary arterial hypertension rats, an amelioration of pulmonary hypertension indices was observed, including reduced pulmonary vascular muscularization (via α-SMA stain; FIG. 5A-FIG. 5B) and right ventricular systolic pressure (RVSP; FIG. 5C), without significant effect on Fulton index (FIG. 5D) or heart rate (FIG. 16A). Importantly, consistent with the in vitro findings in cultured PAECs and known intracellular and extracellular forms of this protein, I-BET robustly decreased pulmonary vascular LGALS8, including in endothelial cells (FIG. 5E-FIG. 5H). Notably, similar dosing of I-BET in normoxic mice did not alter LGALS8 (1±0.02 fold change with vehicle control vs. 1.08±0.03 fold change with I-BET, mean±SEM, N=3-4/group, p=NS), consistent with the known principle that such inhibitors offer the most robust endothelial effects under inflammatory conditions (Brown J D et al. *Mol Cell.* 2014, 56, 219-231). Consequently, I-BET reduced downstream apoptosis, as reflected by reduced cleaved caspase-3 most notably seen at early stages of disease when endothelial apoptosis is highest (Evans C E et al. *Eur Respir J* 2021, 2003957) (FIG. 5A, FIG. 5I). Next, to define the role of LGALS8 in pulmonary hypertension, male and female Lgals8−/− vs. wildtype mice (FIG. 16B-FIG. 16D) were exposed to chronic hypoxia (3 weeks). Echocardiography showed no significant difference in left ventricular functional indices or heart rate (FIG. 16E-FIG. 16H) in Lgals8−/− vs. wildtype mice under hypoxia. Furthermore, Lgals8−/− mice did not display altered IL-1β expression compared with wildtype mice (FIG. 16I-FIG. 16J), indicating consistent upstream inflammatory stimulus in both groups. However, apoptosis, as quantified by cleaved caspase-3 immunoblot in whole lung lysate and by pulmonary arteriolar immunofluorescent stain, and pulmonary arteriolar muscularization were significantly reduced in Lgals8−/− mice (FIG. 5J-FIG. 5L, FIG. 16K-FIG. 16L). Importantly, Lgals8−/− mice were protected from hemodynamic manifestations of pulmonary hypertension, evidenced by lower RVSP and Fulton index vs. wildtype mice (FIG. 5M-FIG. 5N). There was no difference in RVSP between Lgals8−/− vs. wildtype mice under normoxia (18.51±0.45 mm Hg WT mice vs. 19.24±1.68 mm Hg Lgals8−/− mice, mean±SEM, N=3-4/group, p=NS). Taken together, as guided by EDDY-CTRP-PH predictions, in vitro and in vivo experimentation defined the regulation of endothelial Lgals8 and its downstream control of cellular apoptosis as a crucial mediator of I-BET's therapeutic effects of pulmonary hypertension (FIG. 5O).

Figure 6A:
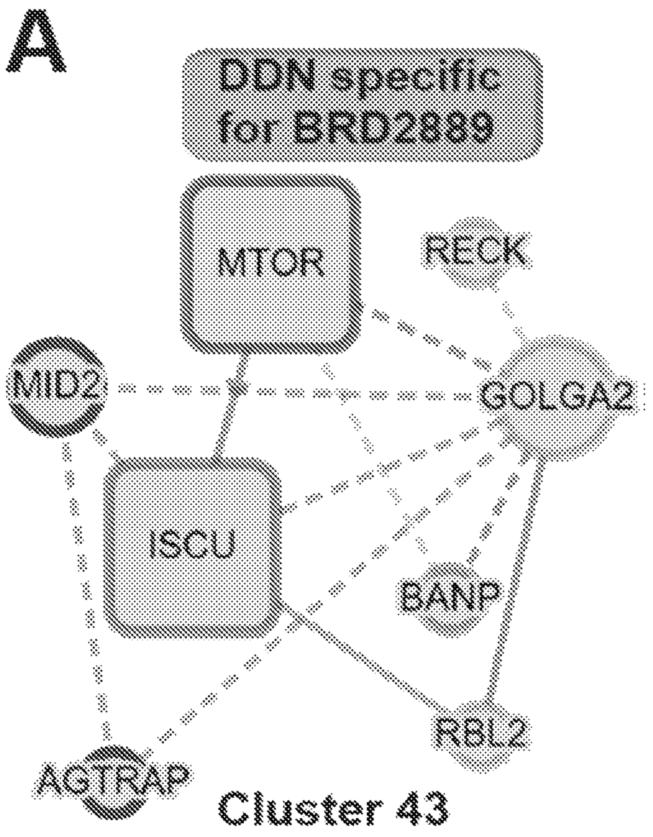
FIG. 6A-FIG. 6Q. EDDY-CTRP-PH identifies a connection among BRD2889, its target GSTP1, and Cluster 43 gene ISCU.

EDDY-CTRP-PH identifies a functional connection between BRD2889, its target GSTP1, and the Cluster 43 gene ISCU. In addition to predictions of new pathways that mediate actions of drugs already under study for pulmonary hypertension, EDDY-CTRP-PH also offered central insights into small molecules never before investigated in this disease and into their activities that have never before been connected to known pulmonary hypertension pathways. To identify the most robust and new candidate drug-pathway axes, Cluster 43 (C43), which had the highest level of rewiring across all small molecules tested (FIG. 1C), was focused on. A new analog of the anti-inflammatory and senolytic drug piperlongumine (PL), BRD2889, known to inhibit the S-glutathionylation enzyme GSTP1, was the drug with the highest rewiring score predicted to target $C_{43}$. In particular, EDDY-CTRP-PH defined the iron-sulfur (Fe—S) biogenesis gene ISCU as a specific, hypoxia-dependent mediator sensitive to this drug (FIG. 6A). Together, these predictions converge on the notion of a functional BRD2889-GSTP1-ISCU axis in hypoxia and pulmonary hypertension.

Figure 6B:
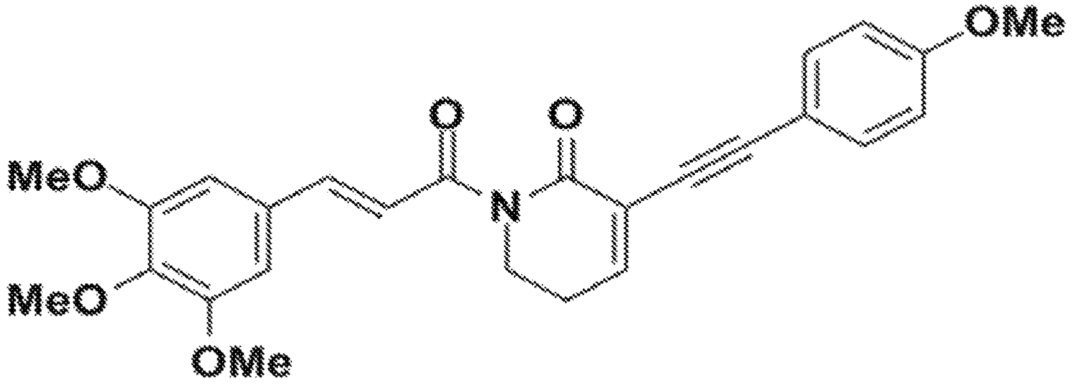
(FIG. 6B) Structure of BRD2889.
Figure 6C:
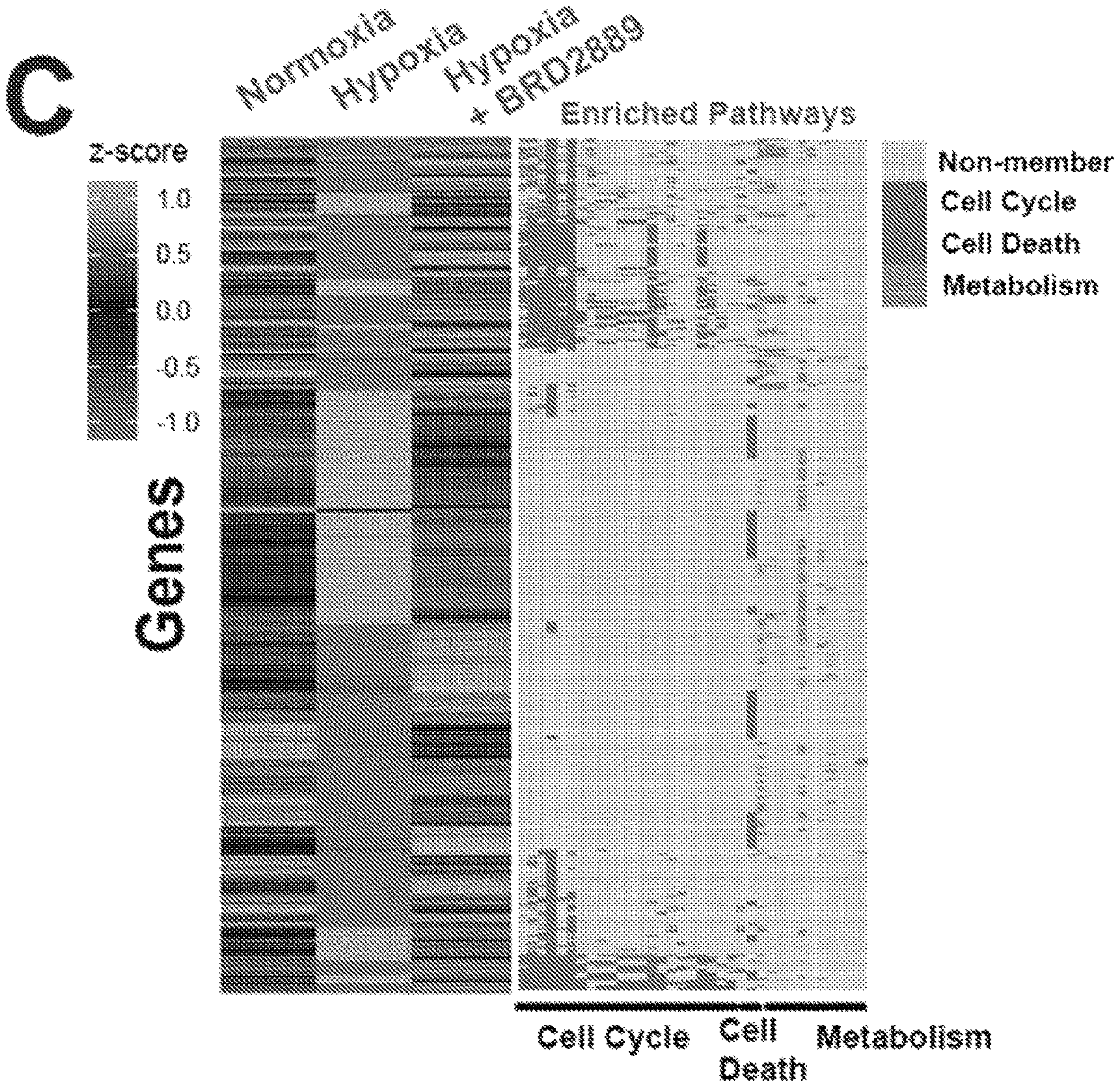
(FIG. 6C) PAEC expression array (n=3/grp) identified genes significantly altered by hypoxia but reversed by BRD2889 (left heatmap). Heatmap (right) depicts gene membership in Gene Ontology (GO) processes relevant to ISCU-related activity.
Figure 6D:
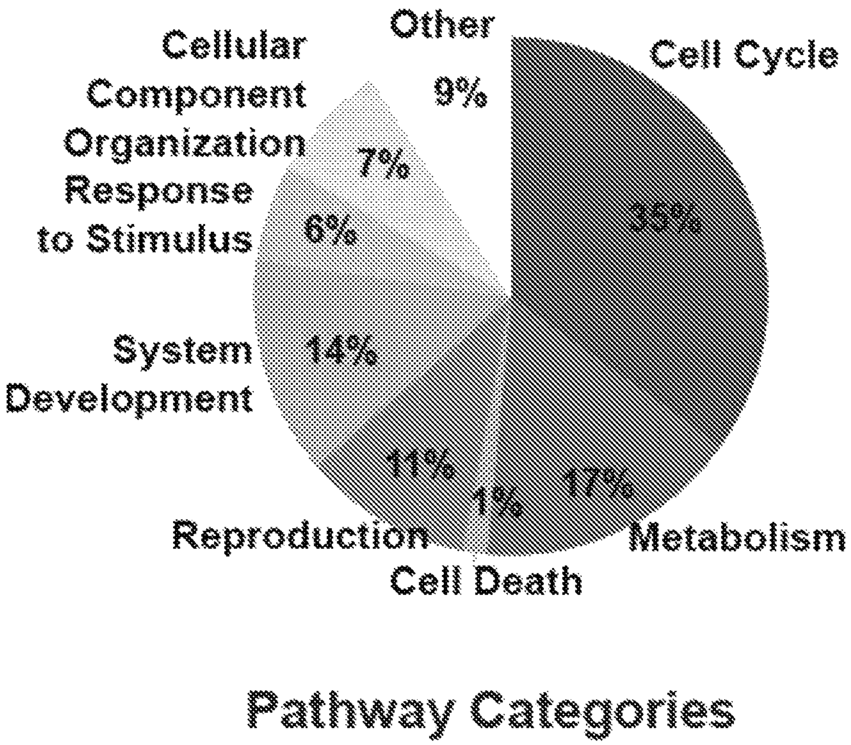
(FIG. 6D) Percentages of enriched GO terms from (FIG. 6C) with ISCU-related activity in blue.

In PAECs, it was found that BRD2889 directly altered two $C_{43}$ gene transcripts, partially reversing the decrease of mTOR and fully reversing the hypoxic decrease of ISCU (FIG. 17A). In contrast, in PASMCs, the hypoxia-induced reduction in ISCU was unaffected by BRD2889 with no change in mTOR (FIG. 17B, FIG. 17C). Because ISCU was predicted as a central mediator in $C_{43}$ rewiring by BRD2889 and prior studies have demonstrated that hypoxia-dependent endothelial ISCU deficiency promotes pulmonary hypertension via repressing iron-sulfur-dependent mitochondrial metabolism (White K et al. *EMBO Mol Med.* 2015, 7, 695-713; Chan S Y et al. *Cell Metab.* 2009, 10, 273-284), endothelial cells exposed to hypoxia were focused on to define this putative BRD2889-GSTP1-ISCU axis. To determine the landscape of activities of BRD2889 in PAECs, 3830 genes were identified by transcriptional array altered by hypoxia but reversed by BRD2889 (molecular structure of BRD2889 in FIG. 6B, heat map in FIG. 6C). By gene set enrichment analysis, a majority of these genes belonged to pathways of cell cycle, cell death, and metabolism—all relevant to ISCU biology (FIG. 6D).

Figure 6E:
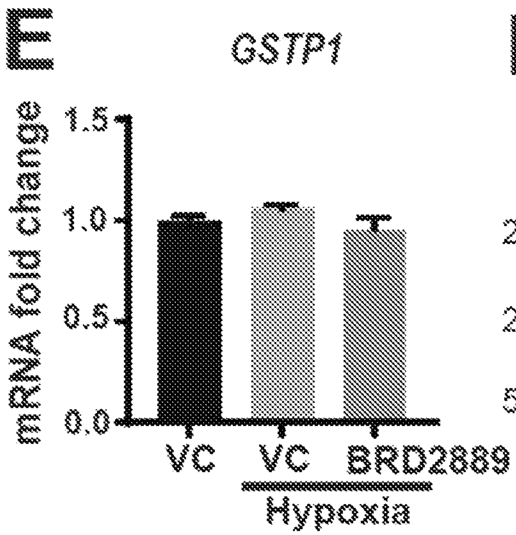
(FIG. 6E-FIG. 6H) As assessed by GSTP1 levels (FIG. 6E, FIG. 6F), glutathione S-transferase (GST) activity (FIG. 6H) and ISCU immunoblot (FIG. 6F, FIG. 6G) in hypoxic PAECs (n=3/grp), BRD2889 reversed hypoxic alterations of ISCU and GST activity (vehicle control, VC; untreated, Un).
Figure 6F:
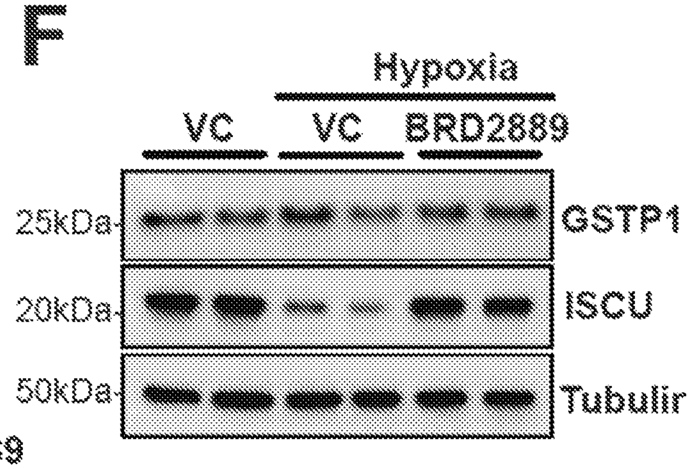
Figure 6G:
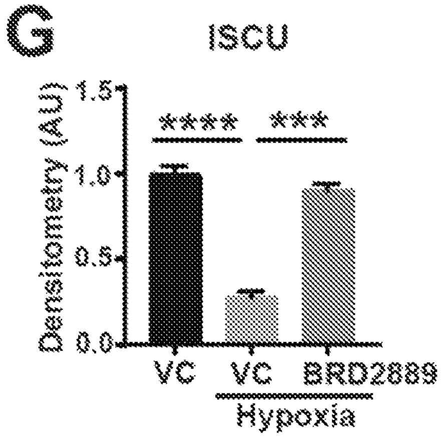
Figure 6H:
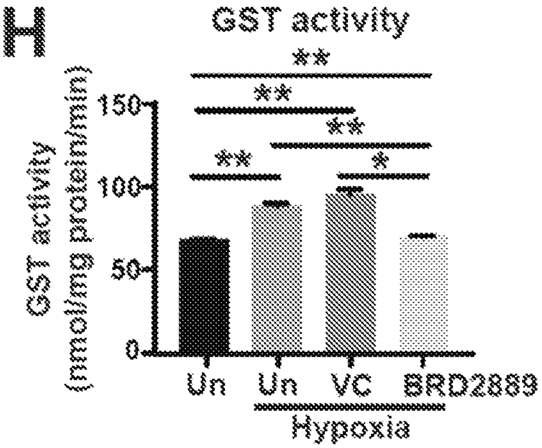
Figure 6I:
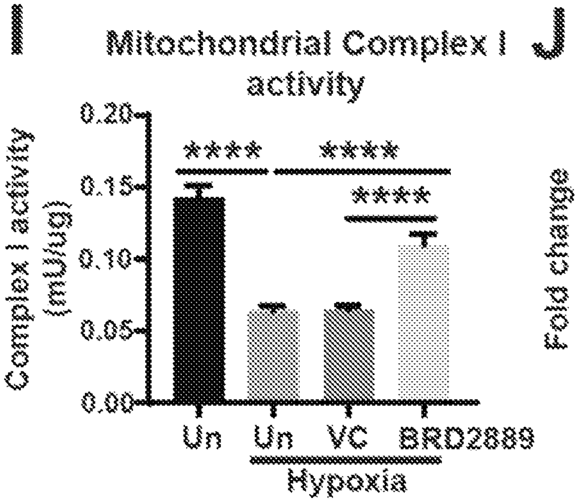
(FIG. 6I-FIG. 6K) In PAECs treated as in (FIG. 6H) (n=4/grp), BRD2889 reversed hypoxic alterations of mitochondrial Complex I activity (FIG. 6I), proliferation (via BrdU incorporation) (FIG. 6J), and apoptotic caspase 3/7 activity (FIG. 6K).
Figure 6J:
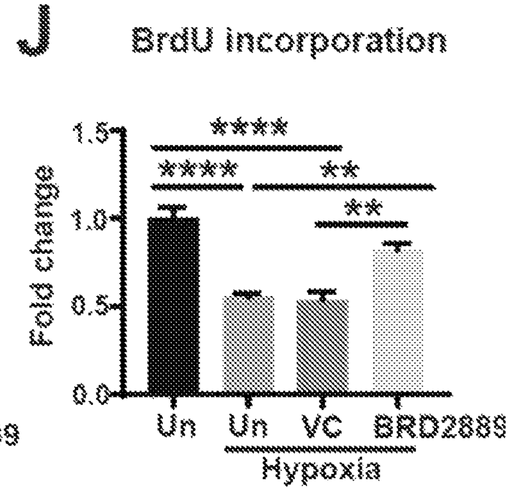
Figure 6K:
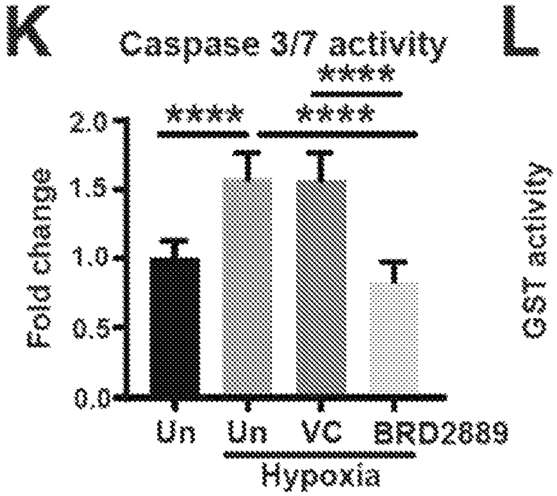
Figure 6L:
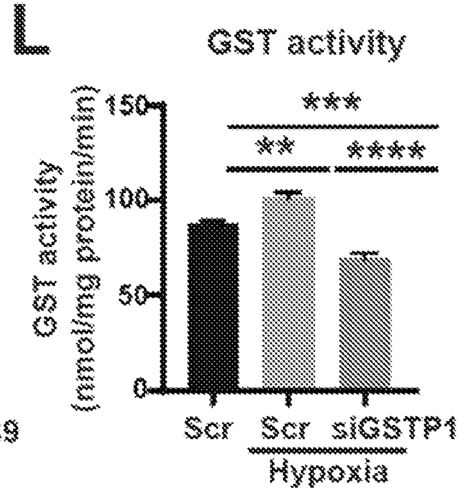
Figure 6M:
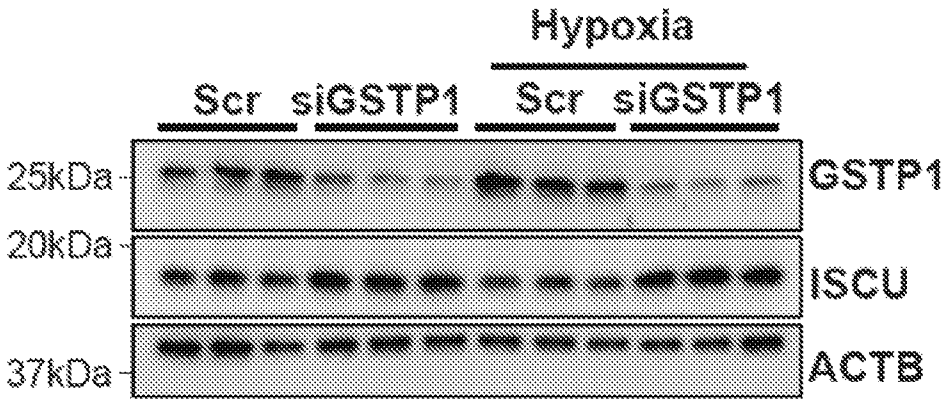
Figure 6N:
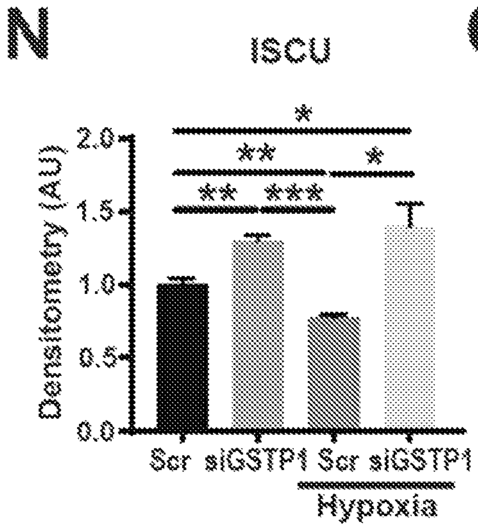
Figure 6O:
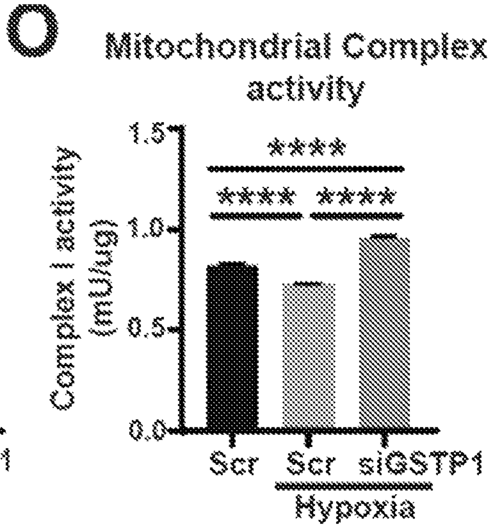
Figure 6P:
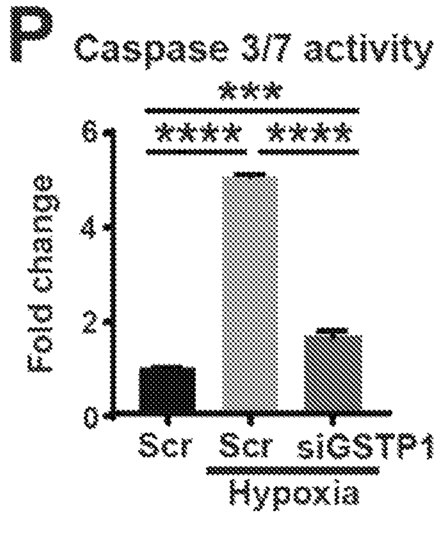
Figure 6Q:
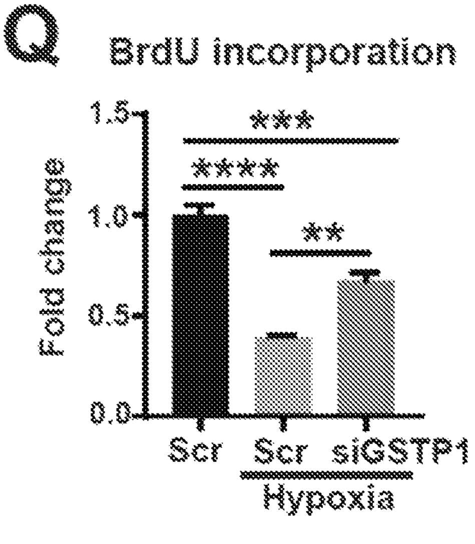

In PAECs, consistent with known inhibition of GSTP1 by piperlongumine (Adams D J et al. *Proc Natl Acad Sci USA.* 2012, 109, 15115-15120), while BRD2889 did not affect GSTP1 expression (FIG. 6E, FIG. 6F), it reduced the hypoxic increase in GST enzyme activity (FIG. 6H). In parallel, BRD2889 reversed hypoxia-dependent reduction of ISCU protein levels (FIG. 6F, FIG. 6G). Corresponding with the importance of ISCU deficiency in control of iron-sulfur dependent electron transport, endothelial redox state, and apoptosis in pulmonary hypertension (White K et al. *EMBO Mol Med.* 2015, 7, 695-713; Zhao J et al. *Circ Res.* 2020, 127, 677-692), in hypoxic PAECs, BRD2889 reversed the decrease in iron-sulfur-dependent mitochondrial Complex I activity and proliferation as well as reversed the increase in apoptosis (FIG. 6I-FIG. 6K). Similarly, GSTP1 knockdown in PAECs (FIG. 17D) decreased GST activity (FIG. 6L), increased ISCU (FIG. 6M, FIG. 6N), increased mitochondrial Complex I activity (FIG. 6O), decreased apoptosis (FIG. 6P) and increased proliferation (FIG. 6Q), reversing these parameters in hypoxia. Moreover, in normoxia, GSTP1 knockdown increased oxygen consumption rate (OCR) and mitochondrial respiration (FIG. 17E-FIG. 17F). Conversely, in PAECs, forced expression of GSTP1 (FIG. 17G-FIG. 17I) reduced ISCU (FIG. 17H, FIG. 17J), phenocopying hypoxic reduction of ISCU. Forced GSTP1 expression also increased apoptosis, reduced proliferation, and mitochondrial respiration (FIG. 17K-FIG. 17N), consistent with the increases of ISCU driven by BRD2889 (FIG. 17O-FIG. 17Q). Collectively, these observations demonstrate that pulmonary hypertension-related upregulation of GSTP1 promotes metabolic and mitochondrial endothelial dysfunction via control of ISCU, a process reversed by BRD2889-induced GSTP1 inhibition.

Figure 7A:
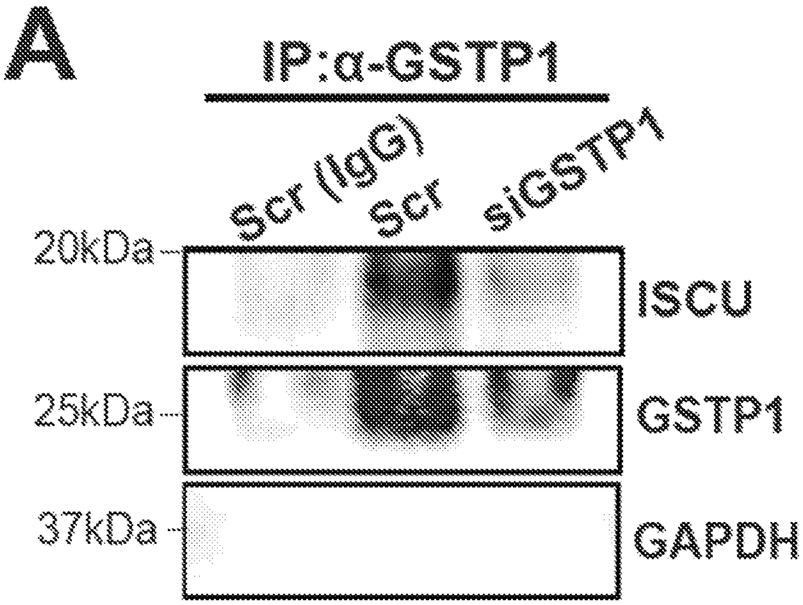
FIG. 7A-FIG. 7I. GSTP1 binds and glutathionylates ISCU to control protein stability.
Figure 7B:
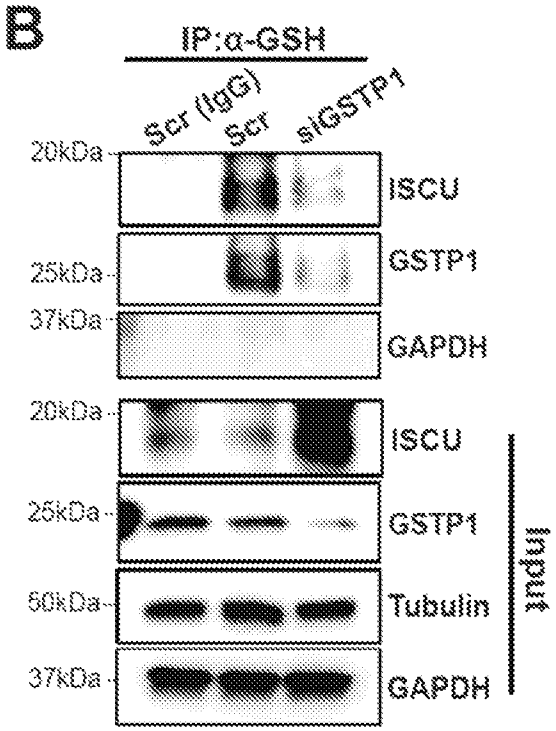
Figure 7C:
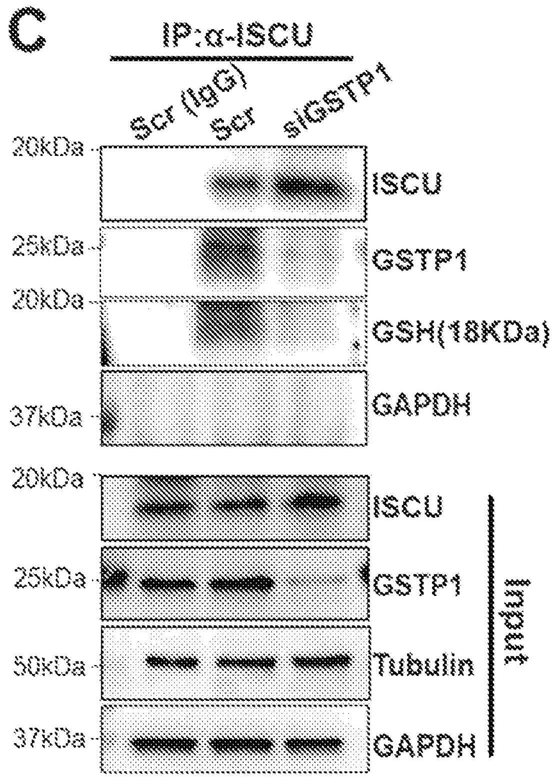

GSTP1 promotes and depends upon ISCU glutathionylation for ameliorating metabolic endothelial dysfunction. Given the connection of BRD2889 and GSTP1 to the control over ISCU and the known action of protein glutathionylation to regulate protein expression and activity (Tew K D et al. *Drug Metab Rev.* 2011, 43, 179-193), it was hypothesized that GSTP1 controls ISCU via direct protein S-glutathionylation. In PAEC lysate, α-GSTP1 immunoprecipitation revealed that ISCU was specifically pulled down with GSTP1 (FIG. 7A) demonstrating a biochemical interaction between these proteins. Similarly, ISCU and GSTP1 were detected after immunoprecipitation with an anti-glutathione antibody (α-GSH) (FIG. 7B), indicating glutathionylation of at least one of these protein partners. Importantly, knockdown of GSTP1 resulted in a decrease of co-immunoprecipitated ISCU, suggesting control of ISCU glutathionylation by GSTP1. To garner direct evidence of these interactions, α-ISCU immunoprecipitation was performed, again demonstrating specific GSTP1 pulldown with ISCU (FIG. 7C). In this case, a glutathionylated form of ISCU was prominently detected (α-GSH immunoblot after pulldown). Yet, with GSTP1 knockdown, α-ISCU immunoprecipitation revealed a concomitant reduction of GSTP1 pulldown and glutathionylated ISCU in favor of non-glutathionylated ISCU. Together, these data prove that GSTP1 interacts with ISCU in order to control its level of protein glutathionylation.

Figure 7D:
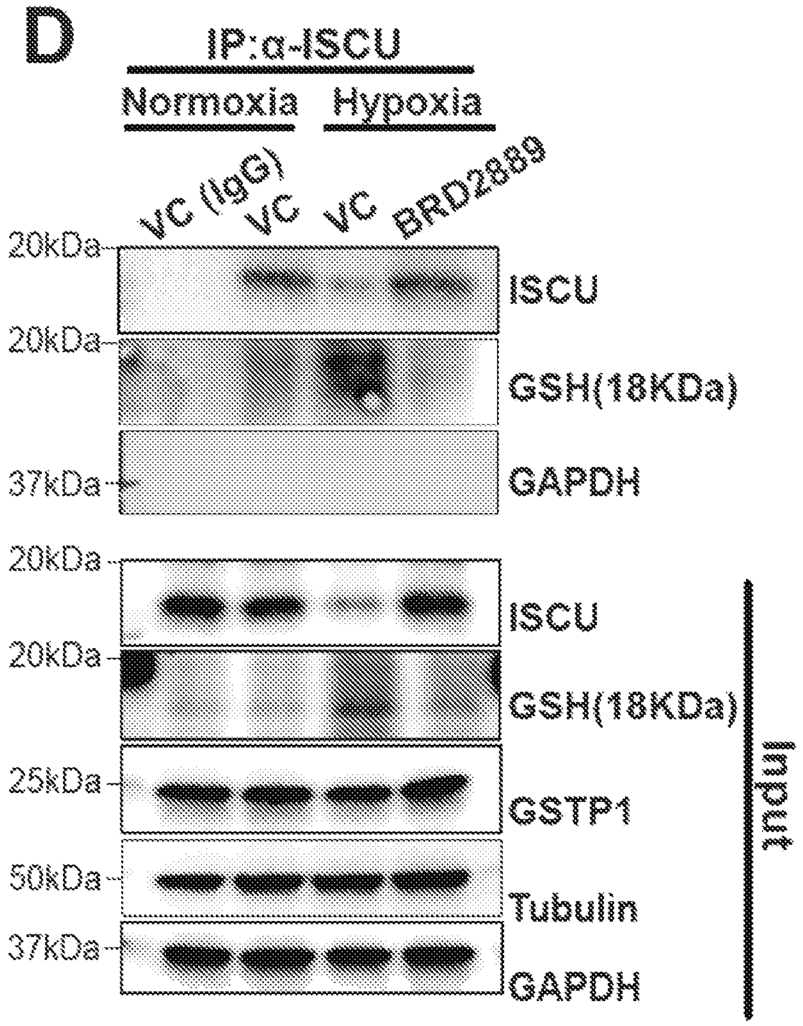
Figure 7E:
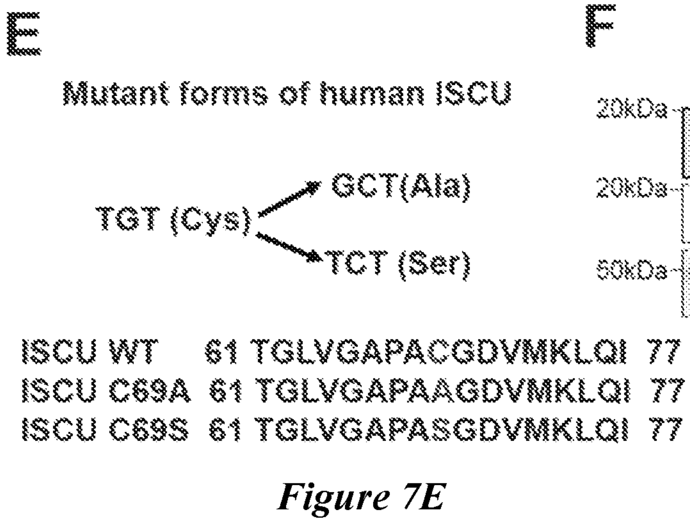
Figure 7F:
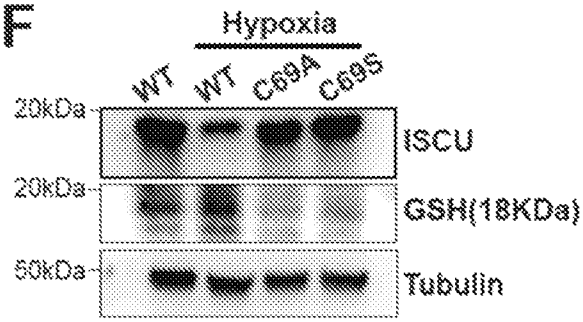
Figure 7G:
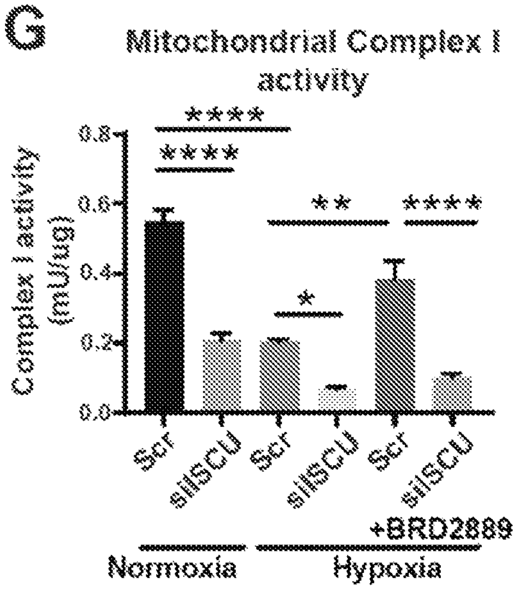
Figure 7H:
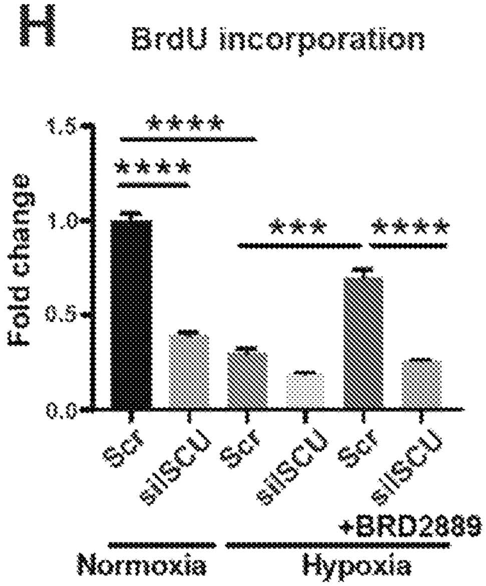
Figure 7I:
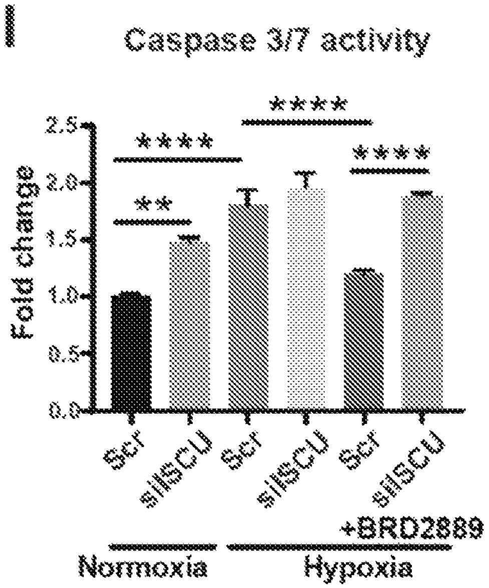

A definition of the functional role of BRD2889 on ISCU glutathionylation (FIG. 7D, FIG. 18A-FIG. 18C) was sought. In hypoxic PAECs when ISCU levels were decreased, α-ISCU immunoprecipitation revealed an increase of ISCU glutathionylation (α-GSH immunoblot after pulldown) as compared with normoxic cells (FIG. 7D). Yet, with BRD2889 treatment, ISCU levels were increased, accompanied by a converse reduction of glutathionylation, phenocopying the results of GSTP1 knockdown and indicating that glutathionylation controls ISCU expression. Inhibition of proteasomal degradation using MG132 reversed the hypoxic down-regulation of ISCU without affecting GSTP1 or glutathionylation (FIG. 18A-FIG. 18C), suggesting that ISCU degradation at least partially controls steady state levels in hypoxia and is dependent upon glutathionylation. Using the dbPTM-protein post-translational modification tool (Chen Y J et al. *PLoS One.* 2015, 10, e0118752), the cysteine residue Cys-69 in human ISCU was predicted as a specific site of S-glutathionylation. To explore the role of Cys-69 in ISCU glutathionylation, two ISCU mutants were generated converting this residue to serine (ISCU 69C/S) or alanine (ISCU 69C/A) (FIG. 7E) and thus abolish any putative glutathionylation at this site. After transfection and forced expression of either wildtype of mutant ISCU in HEK293 cells (FIG. 7F), wildtype ISCU was decreased, but ISCU glutathionylation was increased in hypoxia as compared with normoxia. Conversely, in comparison to wildtype ISCU, both mutant ISCU proteins were increased in hypoxia, while glutathionylation was decreased, thus offering direct evidence that glutathionylation at Cys-69 controls ISCU expression particularly in hypoxia. Finally, to determine if ISCU upregulation is essential for BRD2889's endothelial actions, hypoxic PAECs were treated with BRD2889 during forced siRNA knockdown of ISCU (FIG. 17O-FIG. 17Q). BRD2889 did not reverse the hypoxia-induced decrease in mitochondrial Complex I activity and proliferation and did not reverse the hypoxic increase in apoptosis (FIG. 7G-FIG. 7I). Thus, these results define the crucial role of ISCU in mediating the activity of BRD2889 in rescuing endothelial dysfunction in pulmonary hypertension.

Beyond pure hypoxic exposure alone, an appreciation is advancing of the mechanistic connections of ISCU specifically with IL-6 (Virga F et al. *Sci Adv.* 2021, 7, eabf0466), suggesting the importance of hypoxia and IL-6 together in controlling ISCU-dependent pathophenotypes. Thus, in PAECs exposed to a combination of recombinant IL-6/soluble IL-6 receptor (sIL-6R) and hypoxia, BRD2889 reversed the increase in GSTP1 activity and reversed the decrease in ISCU expression (FIG. 18D-FIG. 18F). IL-6/sIL-6R+hypoxia treatment also induced pulmonary hypertension-related inflammatory gene transcripts; BRD2889 normalized this upregulation in PAECs (FIG. 18G). Consistent with findings under hypoxia, BRD2889 also partially rescued mitochondrial Complex I activity, reduced apoptosis, and increased proliferation in IL-6/sIL-6R+hypoxia-exposed PAECs (FIG. 18H-FIG. 18J). In contrast, in IL-6/sIL-6R+hypoxia-exposed PASMCs, BRD2889 failed to rescue ISCU or alter GST activity (FIG. 18K-FIG. 18M). BRD2889 did not affect the IL-6/sIL-6R+hypoxia-induced alterations of PASMC mitochondrial Complex I activity and proliferation; and the modest alterations of PASMC apoptosis were only subtly changed by BRD2889 (FIG. 18N-FIG. 18P). Consistent with these cell type-specific differences, in PASMCs, GSTP1 knockdown (FIG. 18Q-FIG. 18R) also did not alter GST activity (FIG. 18S). Taken together, in endothelial but not smooth muscle cells, GSTP1 primarily controls GST activity and ISCU and is particularly active across inflammatory and hypoxic triggers of pulmonary hypertension.

Figure 8B:
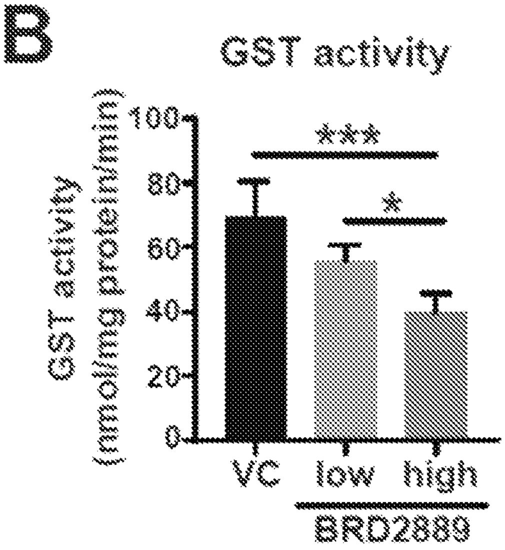
FIG. 8A-FIG. 8K. BRD2889 reverses pulmonary arterial hypertension in chronically hypoxic IL-6 Tg mice.
Figure 8A:
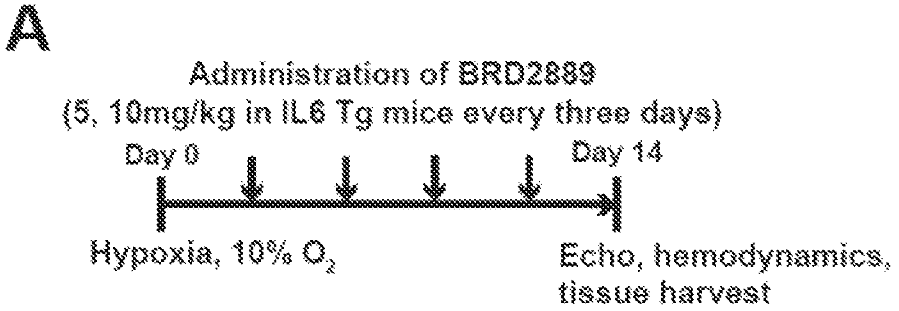
Figure 8C:
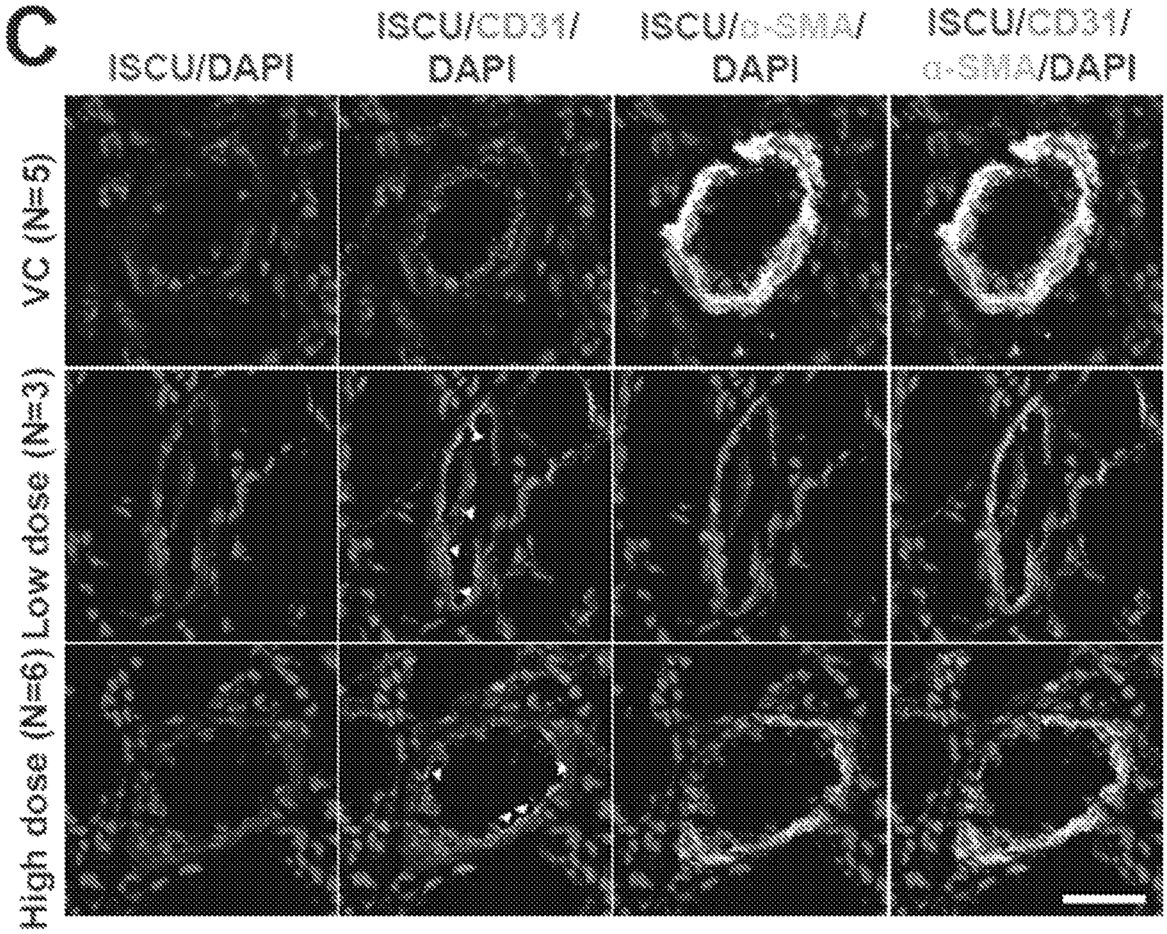
Figure 8D:
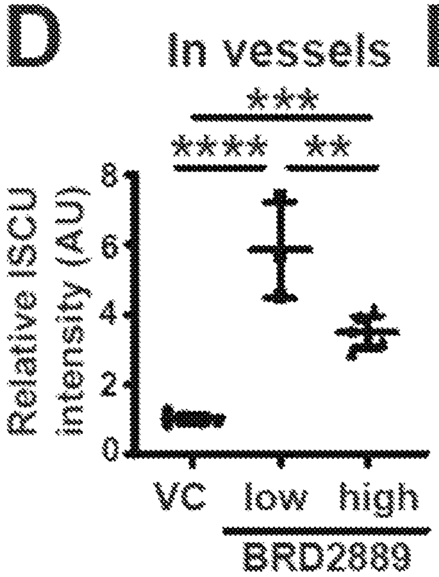
Figure 8E:
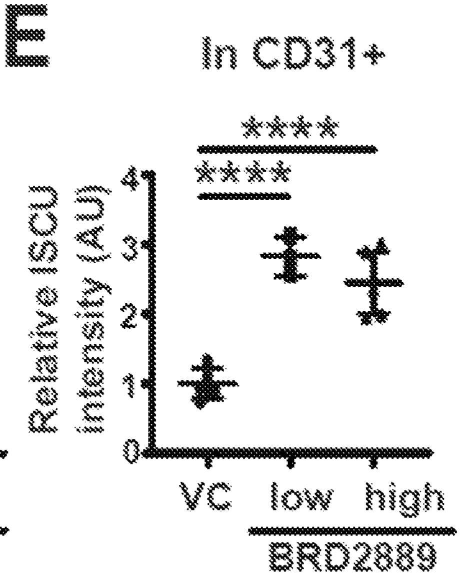
Figure 8F:
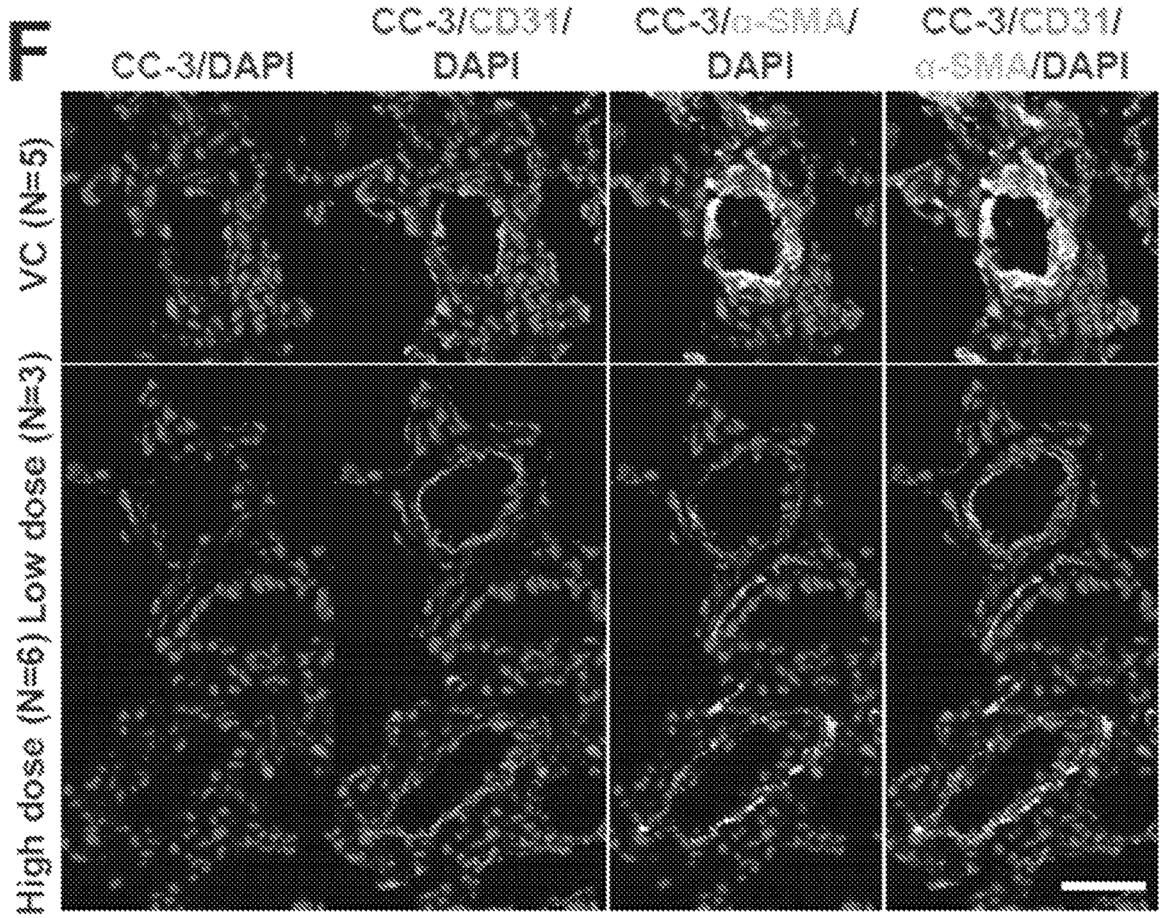
Figure 8G:
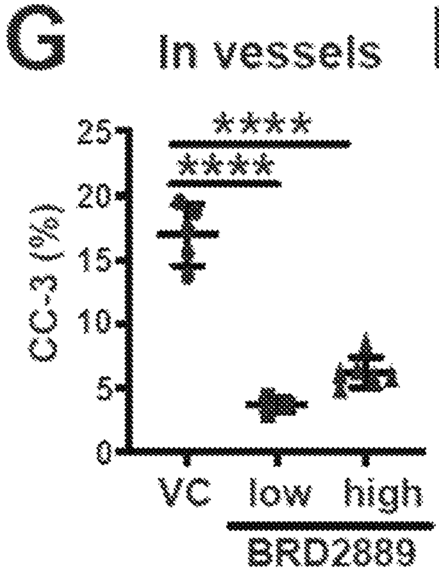
Figure 8H:
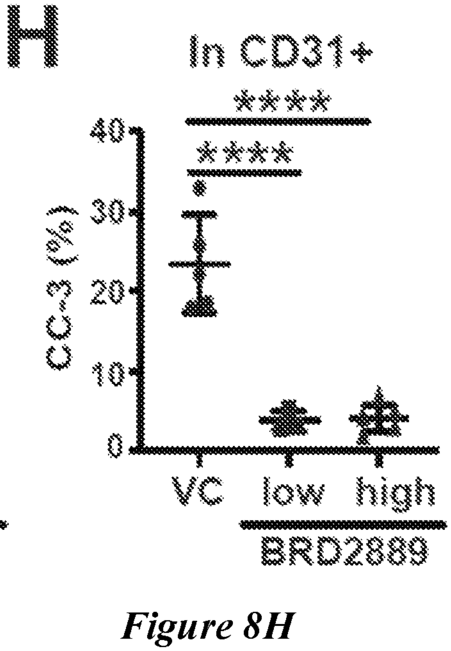
Figure 8I:
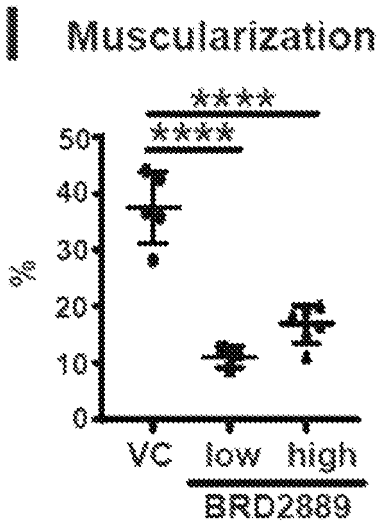
Figure 8J:
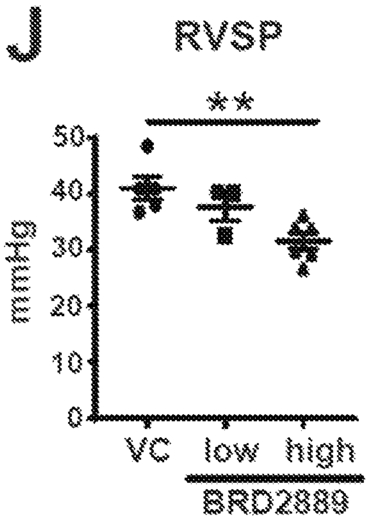
Figure 8K:
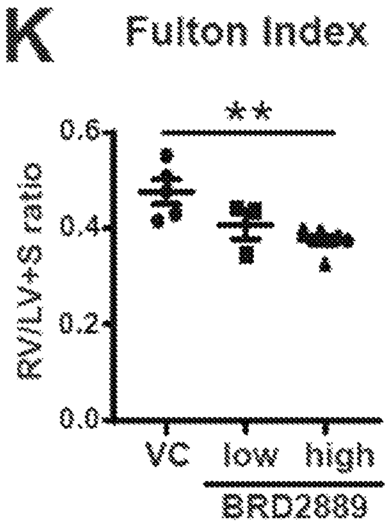
Figure 19F:
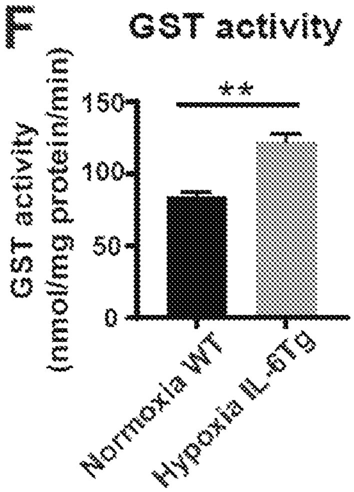
Figure 19G:
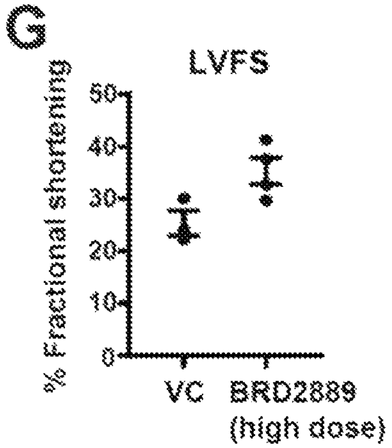
Figure 19H:
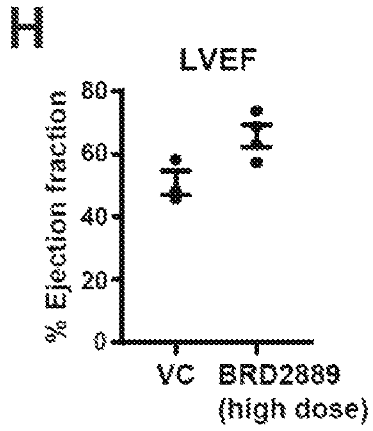
Figure 19I:
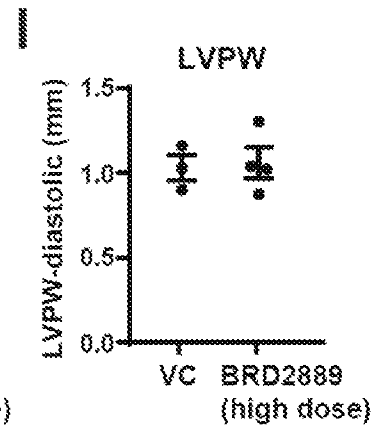
Figure 19J:
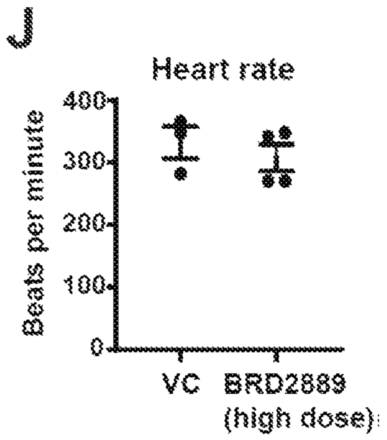

The GSTP1-ISCU axis is active in human pulmonary hypertension, and BRD2889 improves existing pulmonary arterial hypertension across multiple pulmonary arterial hypertension rodent models. To go beyond the limitations of cultured cell data and determine the relevance of the GSTP1-ISCU axis in human pulmonary hypertension, in situ staining of pulmonary arterioles of WSPH Groups 1 and 3 pulmonary hypertension patients revealed a reduction of ISCU and increase of GSTP1 in CD31+ endothelial cells compared with non-pulmonary hypertension patients (FIG. 19A-FIG. 19D; Table 4). Total GST enzyme activity from whole lung of both WSPH Group 1 and 3 pulmonary hypertension patients was also increased compared with non-pulmonary hypertension patients (FIG. 19E). To determine the effects of BRD2889 on this axis and on pulmonary hypertension in vivo, low (5 mg/kg) and high (10 mg/kg) doses of BRD were administered in a disease reversal protocol to a Group 1 pulmonary arterial hypertension mouse model (hypoxic IL-6 Tg mice), which also demonstrated increased lung GST activity with pulmonary arterial hypertension (FIG. 19F). Serial drug dosing was initiated after IL-6 Tg mice were manifesting disease but prior to hypoxic exposure (FIG. 8A). No differences in left ventricular function or heart rate (FIG. 19G-FIG. 19J) were observed in BRD2889 vs vehicle-treated mice. A dose-dependent reduction of lung total GST enzyme activity was observed across low to high BRD2889 (FIG. 8B). Via in situ staining of arterioles, both BRD2889 doses rescued ISCU, particularly in CD31+ endothelium (FIG. 8C-FIG. 8E). In response, pulmonary arterial hypertension manifestations were improved, including a reduction of downstream endothelial apoptosis (FIG. 8F-FIG. 8H), pulmonary arteriolar remodeling (FIG. 8C, FIG. 8F, FIG. 8I), and a dose-dependent reduction of RVSP and Fulton index (FIG. 8J-FIG. 8K).

Figure 9A:
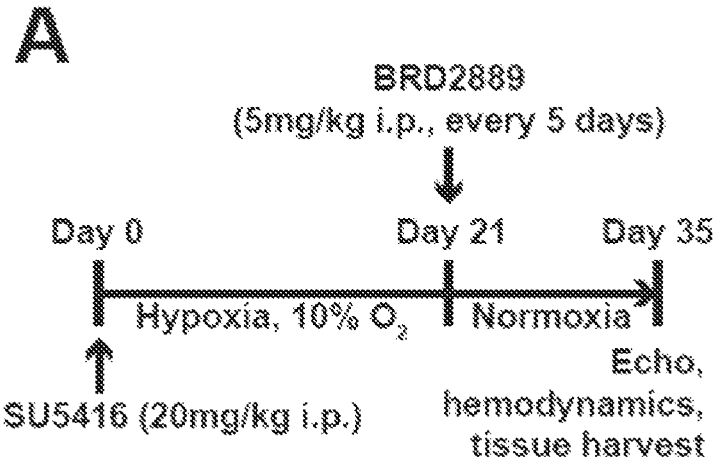
FIG. 9A-FIG. 9Q. BRD2889 increases ISCU, reduces endothelial apoptosis, and reverses pulmonary arterial hypertension in multiple pulmonary arterial hypertension rat models.
Figure 9B:
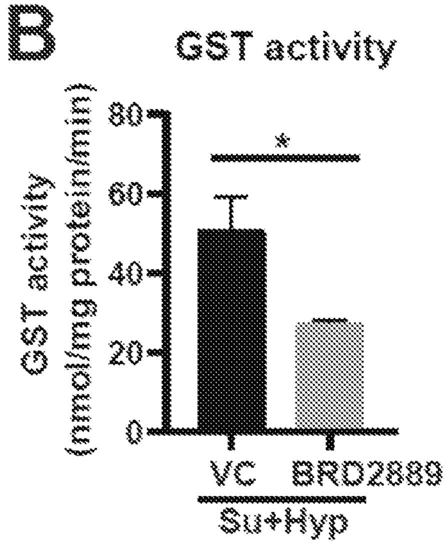
(FIG. 9B) BRD2889 decreased lung GST activity.
Figure 9K:
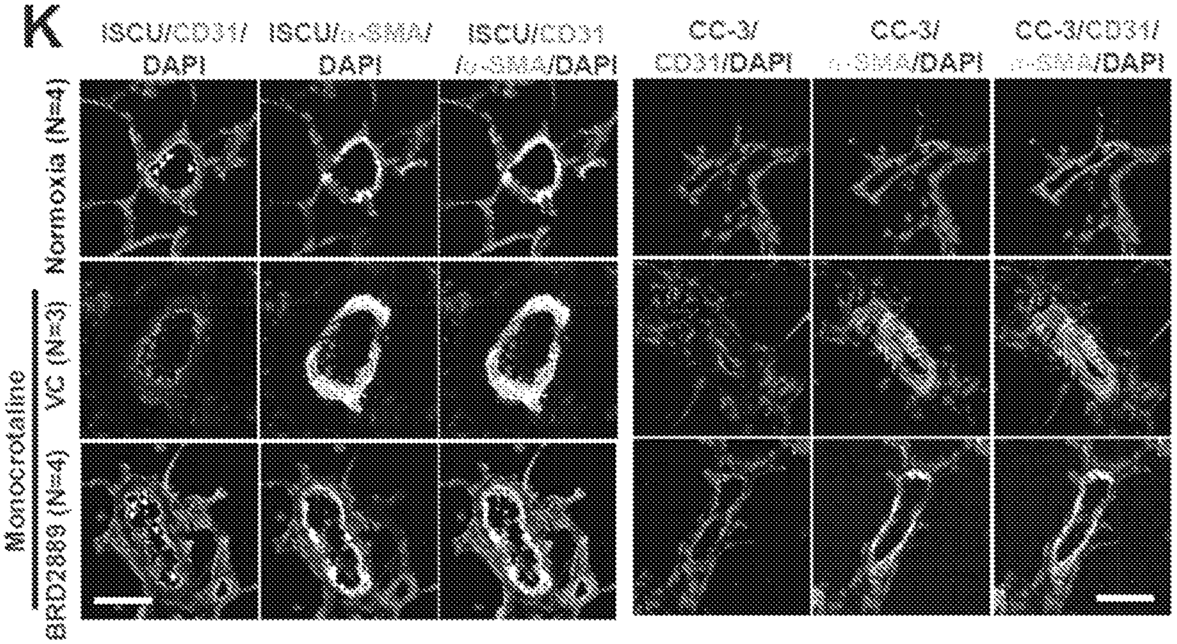
(FIG. 9K-FIG. 9M) By immunofluorescence staining and quantification of ISCU (FIG. 9K-FIG. 9L) and cleaved caspase-3 (CC-3) expression (FIG. 9K & FIG. 9M), BRD2889 increased endothelial ISCU (white arrowheads) and decreased apoptotic CC-3.
Figure 9L:
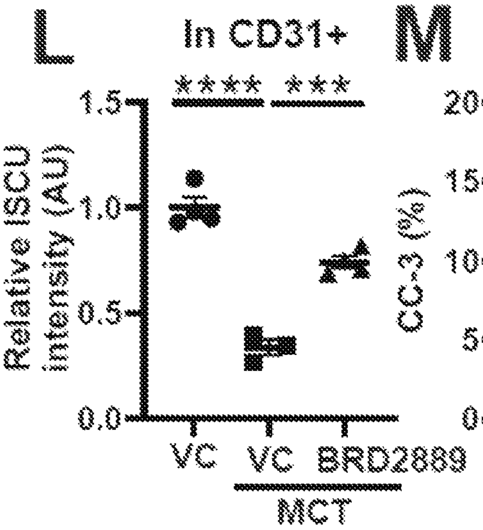
Figure 9M:
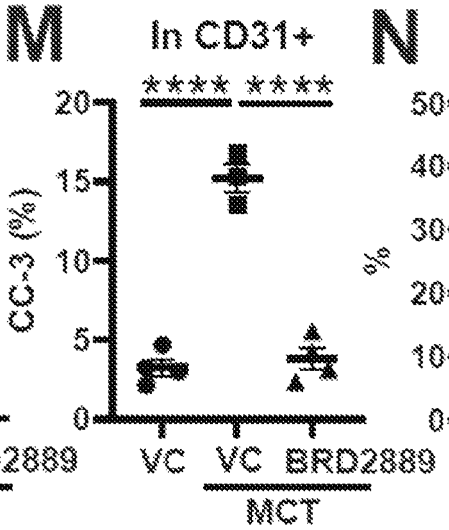
Figure 9N:
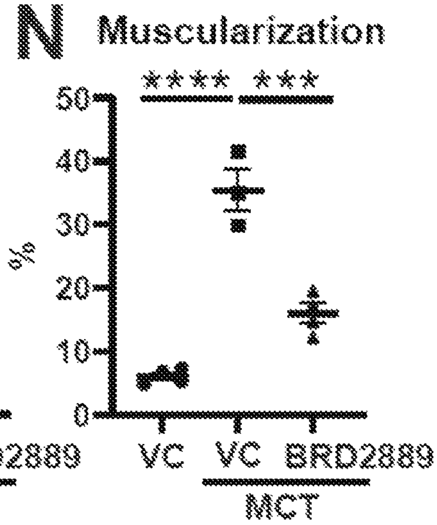
Figure 9Q:
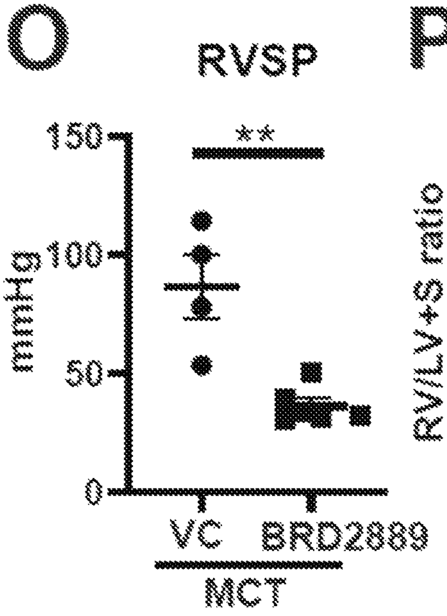
Figure 9Q:
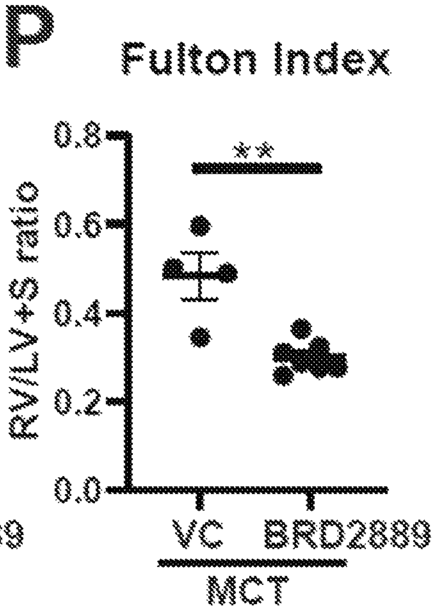
Figure 9Q:
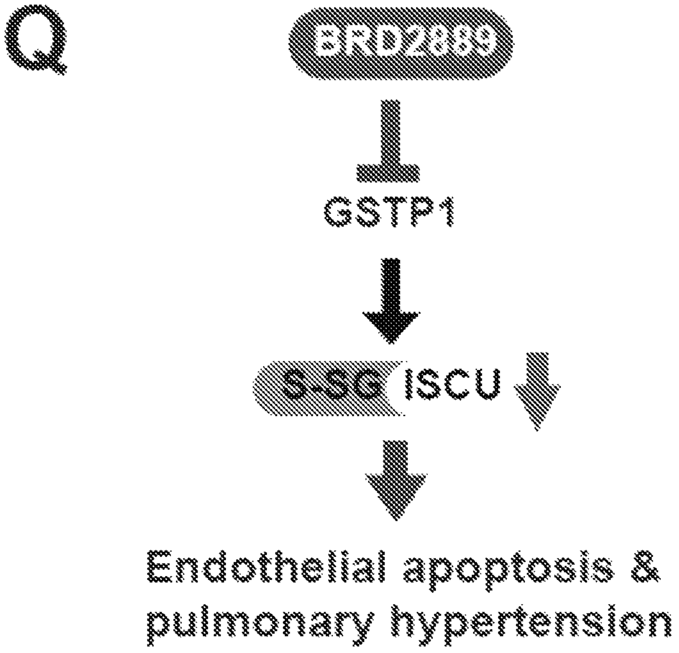

Similarly, BRD2889 was administered in a disease-reversal dosing protocol in the same two pulmonary arterial hypertension rat models tested for I-BET762-MCT and SU5416-hypoxic rats (FIG. 9A, FIG. 9I). In both rat models, such dosing reduced total lung GST enzyme activity (FIG. 9B, FIG. 9J) without significant alterations of heart rate (FIG. 20A, FIG. 20J) or aortic pressure (FIG. 20E, FIG. 20K). Echocardiographic assessment after BRD2889 dosing in SU5415-hypoxic rats demonstrated no alteration of left ventricular function after drug dosing (FIG. 20B-FIG. 20D). Of note, three SU5416-hypoxic pulmonary arterial hypertension rats treated with drug displayed accumulation of mild ascites. However, by RT-qPCR transcript screening, there was no indication of overt tissue toxicities in either model (FIG. 20F-FIG. 20I, FIG. 20L-FIG. 20P). Importantly, in both models, BRD2889 increased endothelial ISCU (FIG. 9C-FIG. 9D, FIG. 9K-FIG. 9L) while reducing endothelial apoptosis (FIG. 9C, FIG. 9E, FIG. 9K, FIG. 9M), pulmonary vascular muscularization (via α-SMA stain; FIG. 9F, FIG. 9N), right ventricular systolic pressure (RVSP; FIG. 9G, FIG. 9O), and Fulton index (FIG. 9H, FIG. 9P). Therefore, guided by EDDY-based predictions linking BRD2889 to ISCU, these findings establish BRD2889 as a potent repurposed therapy that reduces endothelial metabolic dysfunction, thus driving improvements of histologic and hemodynamic manifestations of across multiple pulmonary arterial hypertension rodent models (FIG. 9Q).

Figure 10:
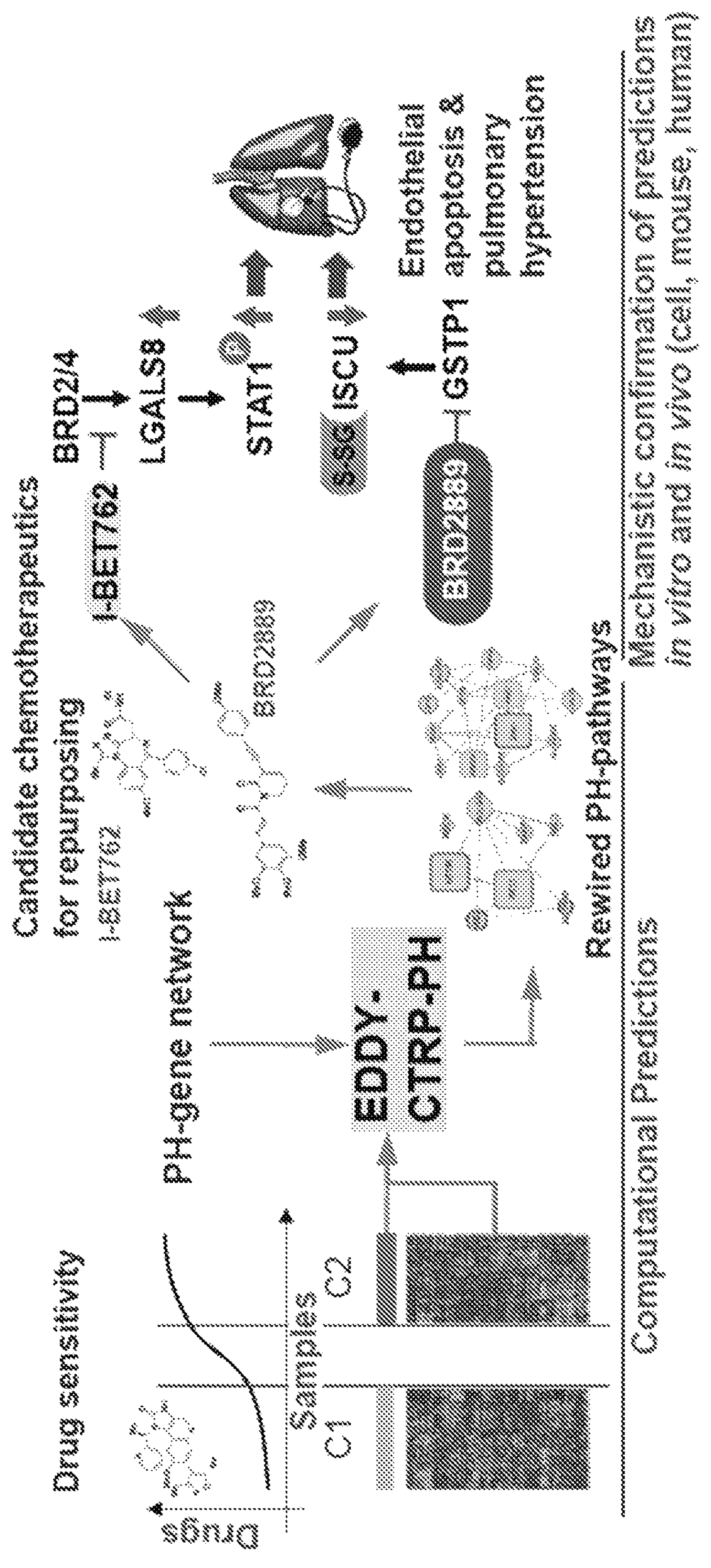
FIG. 10. EDDY-CTRP-PH: An in silico tool to map a landscape of cancer drug mechanisms in rare non-cancerous conditions such as pulmonary hypertension. Cancer therapies are considered for rare non-cancerous diseases like pulmonary hypertension (PH), but effective computational screening is lacking. Via transcriptomic differential dependency analyses leveraging parallels between cancer and pulmonary hypertension, a landscape of cancer drug functions dependent upon rewiring of pulmonary hypertension gene clusters was mapped. Experimental confirmation across independent predictions identified drug-gene axes central to endothelial dysfunction and therapeutic priorities for pulmonary hypertension. These results establish a network dependency platform to redefine cancer drugs for use in rare and emerging non-cancerous conditions such as pulmonary hypertension.

DISCUSSION In this study, the computational strengths of differential dependency analysis were leveraged to develop EDDY-CTRP-PH as a platform to predict the landscape of cancer drug functions controlling rare non-cancerous conditions such as pulmonary hypertension. BET inhibitors and BRD2889 separately were predicted and demonstrated experimentally to modulate endothelial LGALS8 and GSTP1-ISCU, respectively, under hypoxic and inflammatory conditions, thus controlling pulmonary hypertension in vivo. The results pinpoint specific compounds for future therapeutic repurposing in endothelial pathobiology across multiple pulmonary hypertension subtypes. More broadly, these findings offer wide-ranging implications for the advancement of computational network pharmacology and repurposing of drugs from cancer to other rare and often neglected conditions of health and disease (FIG. 10).

Drug repurposing has been viewed as an attractive method for reducing the cost and time of drug development, particularly for rare diseases like pulmonary hypertension where investment is lower than other prevalent diseases (Polamreddy P et al. *Drug Discov Today.* 2018, 24, 789-795). Relevant to the COVID-19 pandemic, repurposing has also been pursued for emerging diseases where prior knowledge of pathogenic target genes or pathways can be used as a linchpin for systems-wide predictions of therapeutic drug activity (Gordon D E et al. *Nature.* 2020, 583, 459-468). Here, the computational strengths in gene dependency analyses of EDDY-CTRP-PH coupled with the vast cancer cell data answer an unmet need for a rapid and systems-wide method to identify therapies for rare diseases, such as pulmonary hypertension, without a priori knowledge of the molecular drug target of interest. As deep sequencing projects mature for pulmonary hypertension and are continually applied to EDDY-CTRP-PH, broader predictions of drug-pathway interactions will be possible, extending beyond the existing pulmonary hypertension gene clusters derived from curated literature searches and the known gene interactome. This may be particularly relevant for epigenetic and pleiotropic regulators such as BET inhibitors. Given the increasing appreciation of links of lung cancer specifically to pulmonary hypertension (Prins K W et al. *J Am Heart Assoc.* 2019, 8, e011343), EDDY-CTRP-PH predictions could also be further honed by concentrating only on lung cancer cell responses to various tested compounds. Extension of advancing deep learning methods utilizing scientific literature with computational linguistics and graph theory (Gramatica R et al. *PLoS One.* 2014, 9, e84912), epidemiologic data (Shameer F et al. *AMIA Jt Summits Transl Sci Proc.* 2018, 2017, 108-117), and advanced network theory (Cheng F et al. *Nat Commun.* 2018, 9, 2691) with EDDY-CTRP-PH would be attractive. Such endeavors could offer predictions of cancer drug activity in diseases beyond pulmonary hypertension, the cell-type and context specificity of drugs, a pharmacologic differentiation of therapeutic vs. toxic drug activities across disease contexts, and the synergistic responses to specific small molecules. Moreover, with the statistical power to map differential dependency networks within a single blood or tissue sample via single cell sequencing, future applications of EDDY-CTRP-PH to precision medicine could be envisioned via identification of individuals and/or disease subtypes with specific differential dependency network profiles who are most likely to respond to repurposed cancer drugs.

The experimental validation of EDDY-CTRP-PH also advances the understanding of complex cellular pathways in pulmonary hypertension and offers guidance for translation of both I-BET762 and BRD2889 to pulmonary hypertension. First, for both drugs, their therapeutic roles emphasized the importance of endothelial pathobiology in pulmonary hypertension, with both long-term and immediate translational implications, as early human clinical trials are underway for BET inhibitors in pulmonary arterial hypertension (NCT03655704). Second, EDDY-CTRP-PH identified multiple rewiring events for these molecules, particularly in the hotspot and extensively altered clusters C15 and C43. Notably, some C15 genes were previously implicated in pulmonary hypertension supporting the accuracy of these predictions: for example, inhibition of ABCC4 improved pulmonary hypertension in mice (Hara Y et al. *J Clin Invest.* 2011, 121, 2888-2897) and identification of LGALS3 (galectin-3) as a pathogenic factor in pulmonary hypertension (Barman S A et al. *Am J Respir Crit Care Med.* 2018, 197, 1488-1492) and right ventricular fibrosis (Crnkovic S et al. *Am J Respir Crit Care Med.* 2018, 199, 1550-1560). In parallel, certain $C_{43}$ genes have also been implicated in pulmonary hypertension, namely MTOR and its control over proliferative and survival programs (Goncharova E A. *FASEB J.* 2013, 27, 1796-1807). Yet, the large majority of functional drug-pulmonary hypertension gene axes implicated here by EDDY have never been identified previously, offering a different scale of predictions and advancing understanding of the layers of interconnections among seemingly disparate mechanisms.

Separately, the computational predictions and experimental work implicate LGALS8 and GSTP1 as crucial effectors of endothelial dysfunction in pulmonary hypertension. In regard to LGALS8, prior studies characterized pro-inflammatory activities of this molecule in endothelium of other vascular beds (Cattaneo V et al. *Glycobiology.* 2014, 24, 966-973), consistent with these findings of its dependence on inflammation-relevant BRD2/4. Indeed, these findings uncovered a key undiscovered role for LGALS8 as a mediator of BRD2/4 and I-BET controlling endothelial pathophysiology in pulmonary hypertension. In delineating the connections between BET inhibitors with LGALS8, these findings specifically define a BRD-specific regulation of the LGALS8-L isoform in human PAECs, potentially reflecting the emerging role of BRD4 in splicing (Uppal A et al. *Cell Rep.* 2019, 29, 2450-2460 e2455) and with previous reports on differential regulation of different isoforms of LGALS8 under different stimuli (Cattaneo V et al. *Glycobiology.* 2014, 24, 966-973). Moreover, while the data implicated LGALS8 as essential for I-BET's control of endothelial apoptosis and pulmonary hypertension, LGALS8 did not reverse all I-BET effects (FIG. 11B). This suggests the significance of other connected genes in mediating this pleiotropic drug's actions and will be the focus of future iterations of the pipeline tailored to garner precision medicine predictions of individualized and heterogeneous responses to BET inhibitors. A putative cell type-specificity and context-specificity of BET inhibitors may be particularly relevant to these findings of an anti-apoptotic role for I-BET762—consistent with prior results in endothelial cells (Wang B et al. *EBioMedicine.* 2015, 2, 1650-1661) but distinct from the pro-apoptotic actions of other BET inhibitors in PASMCs and other pulmonary arterial hypertension models (Van der Feen D E et al. *Am J Respir Crit Care Med.* 2019, 200, 910-920). The findings regarding LGALS8 also offer therapeutic opportunities beyond I-BET. Namely, the activity of extracellular LGALS8 to modulate the effects of I-BET762 indicates the potential of therapeutic antibodies in this space. Yet, unlike LGALS3 which is increased in peripheral plasma of pulmonary arterial hypertension patients (Mazurek J A et al. *Heart Lung Circ.* 2017, 26, 1208-1215), extracellular plasma LGALS8 was poorly expressed in peripheral vascular plasma of pulmonary hypertension patients (FIG. 12A). These findings suggest the importance of paracrine, rather than endocrine, processes for LGALS8 in pulmonary hypertension and thus the need for specific delivery to the pulmonary circulation of any putative therapy. Along those lines, the data in Group 1 and 3 pulmonary hypertension rodent models coupled with two lines of investigation using hypoxia or IL-1β in cultured cells emphasize that LGALS8's role transcends the subgroup heterogeneity of pulmonary hypertension.

In parallel, the EDDY-based predictions that define GSTP1's role in regulating ISCU also advance the understanding of protein S-glutathionylation in pulmonary hypertension and the pulmonary endothelium, particularly in relation to oxidative stress (Tew K D et al. *Drug Metab Rev.* 2011, 43, 179-193). The hypoxia-dependent (Chan S Y et al. *Cell Metab.* 2009, 10, 273-284) and endocrine (Zhao J et al. *Circ Res.* 2020, 127, 677-692) activity of microRNA-210 is known to potently downregulate ISCU transcript in pulmonary hypertension (White K et al. *EMBO Mol Med.* 2015, 7, 695-713), but the findings herein reveal a more complex regulatory schema for this scaffolding protein. While S-glutathionylation has been reported in pulmonary hypertension extensively (Weise-Cross L et al. *Antioxid Redox Signal.* 2019, 31, 898-915), key regulator proteins have not been comprehensively identified. In cancer, GSTP1 has been found to be a tumor suppressor (Mian O Y et al. *Prostate.* 2016, 76, 199-206) or oncogene, depending upon the tumor of interest. Single nucleotide variants in this gene have been associated with susceptibility to hypobaric hypoxia and high altitude pulmonary edema (He Y et al. *Oncotarget.* 2017, 8, 18206-18212; Mishra A et al. *Clin Sci* (*Lond*). 2012, 122, 299-309), often thought to be driven by compromise of the endothelial barrier function. GSTP1 mutations have also been linked to chronic obstructive pulmonary disease (COPD) (Zhong L et al. *Am J Respir Crit Care Med.* 2010, 181, 763-765), a disease with clear etiologic connections to pulmonary hypertension. Interestingly, pulmonary GSTP1 is known to carry a predominant role in detoxification of toxic compounds and pollutants (Tew K D et al. *Drug Metab Rev.* 2011, 43, 179-193). While the exact relation of pollution exposure to pulmonary hypertension is emerging (Sofianopoulou E et al. *Eur Respir J.* 2019, 53, 1801429), these findings of increased GSTP1 in pulmonary hypertension may suggest a molecular mechanism for such a link.

Finally, the identification of BRD2889 as a robust modulator of the GSTP1-ISCU axis in pulmonary hypertension offers an intriguing new compound and target pathway for therapeutic development. Differences between doses of BRD2889 in mice revealed differential effects on ISCU levels likely owing to cell-specific effects of the two doses used. Dosing sensitivity protocols should clarify this issue and pave the way for clinical therapeutic development. BRD2889's parent compound piperlongumine has been tested as an anti-inflammatory and senolytic drug in select cancers (Piska K et al. *Eur J Med Chem.* 2018, 156, 13-20) but carries distinct roles in other contexts and non-transformed cells. Notably, the EDDY-based predictions found specific pulmonary hypertension pathway rewiring responsible only to BRD2889 but not the parent drug or other analogs, also indicating the context-specific activity of this drug class and potentially its interactions with its target GSTP1. Thus, even among drug analogs, these distinctions emphasize the power of EDDY-CTRP-PH via its efficiency and granular detail to map and compare downstream molecular drug responses. While the piperlongumine parent drug has minimal toxicity to normal, non-transformed cells, its derivatives have displayed low levels of reversible liver and kidney toxicity when administered systemically (Bezerra D P et al. *J Appl Toxicol.* 2008, 28, 156-163). Given the presence of ascites in some BRD2889-dosed rats, future therapeutic development of BRD2889 should assess for toxicity closely and may benefit from localized delivery to the lung, as has been described recently with PLGA microparticles (Acharya A P et al. *J Am Heart Assoc.* 2021, 10, e019091), to avoid any putative systemic side effects. Additionally, future work to integrate EDDY-CTRP-PH with a structural analytic pipeline would be appealing to define potential biophysical mechanisms by which modifications of piperlongumine can be mapped to downstream pathway rewiring. Tailored development of EDDY will be valuable to determine if the combinatorial effects of I-BET762 and BRD2889 in PAECs can be predicted and tuned.

In summary, a computational approach with experimental validation was leveraged to identify systems-level molecular relationships between pulmonary hypertension and existing cancer small molecule drugs, resulting in predictions and proof of their therapeutic potential. These results not only offer key insights into the endothelial pathobiology in pulmonary hypertension but also establish the validity of leveraging cancer-based transcriptomics for identifying the hidden activities of therapeutic small molecules in this disease. As such, this work establishes the validity for a platform of computational repositioning of cancer drugs in other rare and emerging diseases that has not yet been possible.

Materials and Methods

Experimental Design: The goal of this study was to generate a computational-to-empirical pipeline for identifying and ranking the most robust actions of specific cancer therapeutics, and revealing their disease-relevant downstream targets in an example of a rare non-cancerous disease such as pulmonary hypertension. Data sources for EDDY-CTRP-PH included CCLE (Barretina J et al. *Nature.* 2012, 483, 603-607), CTRP (Seashore-Ludlow B et al. *Cancer Discov.* 2015, 5, 1210-1223; Rees M G et al. *Nat Chem Biol.* 2016, 12, 109-116), and a specific pulmonary hypertension gene network (Table 1-Table 2).

Following identification of I-BET151/762 with convergent actions on pulmonary hypertension Gene Cluster 15 (including the gene LGALS8), gene expression, mitochondrial redox levels, and cellular apoptosis were measured in primary human pulmonary arterial endothelial cells (PAECs). To determine the effect of this drug on pulmonary hypertension in vivo, $C_{57}$BL/6 mice suffering from hypoxia-induced Group 3 pulmonary hypertension as well as two models of Sprague Dawley rats suffering from Group 1 pulmonary hypertension (monocrotaline exposure and SU5416-hypoxia) were treated with I-BET762. To determine the pathogenic actions of LGALS8 in pulmonary hypertension, male and female Lgals8−/− mice were also exposed to chronic hypoxia. Lgals8−/− mice and their littermate controls was limited on the availability by breeding. Following identification of BRD2889 with actions on pulmonary hypertension Gene Cluster 43 (including the gene ISCU), gene expression, ISCU glutathionylation, GSTP1-ISCU binding, and downstream phenotypes were measured in PAECs and PA smooth muscle cells. To determine the effect of this drug on Group 1 pulmonary hypertension in vivo, IL-6 transgenic $C_{57}$BL/6 mice exposed to hypoxia as well as monocrotaline rats and SU5416-hypoxic rats were treated with drug vs. vehicle control. Hemodynamic and histologic indices were evaluated in murine models. Sample size and statistical analyses for each experiment are described below and in the figure legends; rodent studies were performed via random assignment to various experimental groups, and hemodynamic and histologic analyses were performed in a blinded fashion. Human Group 1 and Group 3 pulmonary hypertension lung (Table 4), non-diseased lung, as well as peripheral plasma were studied (Bertero T et al. *J Cin Invest.* 2014, 124, 3514-3528). Rodent numbers were chosen to achieve 0.80 power for detecting at least a 25% difference among means with a standard deviation of 20%. The number of recruited patients was determined primarily by availability of clinically validated samples. All experimental procedures involving human tissue and blood were approved by institutional review boards at the University of Pittsburgh. Ethical approval for this study and informed consent conformed to the standards of the Declaration of Helsinki. All animal experiments were approved by the University of Pittsburgh (IACUC). Key resources are summarized in Table 5.

TABLE 5

Key Resources.

| Reagent/resource | Source | Identifier |
|---|---|---|
| PAECs | Lonza | CC-2530 |
| PASMCs | Lonza | CC-2581 |
| Endothelial cell growth media | Lonza | CC-3121, CC-4133 |
| Smooth muscle cell growth media | Lonza | CC-3182 |
| Human recombinant IL-1β | Peprotech | 200-01B |
| DMSO | Sigma | 41639 |
| I-BET151 | Selleckchem | S2780 |
| I-BET762 | Selleckchem | S7189 |
| Human recombinant galectin-8 | R&D Systems | 1305-GA-050 |
| IL-6/IL-6R alpha Protein Chimera | Millipore | 8954-SR |
| BRD2889 | Broad Institute | Adams D J et al. *Proc Natl Acad Sci USA.* 2012, 109, 15115-15120 |
| MG132 | Sigma Aldrich | 474791 |
| C57BL/6J mice | Jackson Laboratory | RRID: IMSR_JAX: 000664 |
| Lgals8—/— mice | KOMP | RRID: MGI: 5824822 |
| Sprague-Dawley rats | Charles River Laboratory | RRID: RGD_10395233 |

TABLE 5-continued

| Key Resources. | | |
|---|---|---|
| Reagent/resource | Source | Identifier |
| IL-6 transgenic mice | | Steiner M K et al. *Circ Res.* 2009, 104, 236-244, 228p following 244 |
| human LGALS8 | RnD Systems | Cat# AF1305, RRID: AB_2137229 |
| mouse/rat Lgals8 | Abcam | Cat# ab69631, RRID: AB_1268941 |
| pSTAT1 | Abcam | Cat# ab29045, RRID: AB_778096 |
| STAT1 | Abcam | Cat# ab47425, RRID: AB_882708 |
| GSTP1 | Abcam | Cat# ab153949, RRID: AB_2877700 |
| ISCU | Prointech | Cat#14812-1-AP, RRID: AB_2280362 |
| Glutathione | Abcam | Cat# ab19534, RRID: AB_880243 |
| HIF2A | Novous | Cat# NB100-122, RRID: AB_10002593 |
| α-Tubulin | Millipore sigma | Cat# CP06, RRID: AB_2617116 |
| ACTB | Santa Cruz | Cat# sc-47778, RRID: AB_2714189 |
| IL-1β | Abcam | Cat# ab9722, RRID: AB_308765 |
| cleaved caspase3 | Cell Signaling | Cat# cs-9661, RRID: AB_2341188 |
| α-SMA | Sigma | Cat# F3777, RRID: AB_476977 |
| CD31 | Abcam | Cat# ab7388, RRID: AB_305905 |
| Taqman primers | Thermo Fisher Scientific | LGALS8 (Hs01057135_m1), LGALS3 (Hs00173587_m1), NHERF1 (Hs00188594_m1), NHERF2 (Hs01033104_g1), ABCC4 (Hs00988721_m1), CD47 (Hs00179953_m1), DAG1 (Hs00189308_m1), LGALS8-L (Hs01062767_g1), VCAM1 (Hs01003372_m1), VEGF (Hs00900055_m1), CD31 (Hs00169777_m1), CDH5 (Hs00901465_m1), BRD2 (Hs01121986_g1), BRD4 (Hs04188087_m1), STAT1 (Hs01013996_m1), GSTP1 (Hs04419827_g1), ISCU (Hs00384510_m1), RECK (Hs00221638_m1), MT1G (Hs02578922_g1), MTOR (Hs00234508_m1), GOLGA2 (Hs01067737_m1), MID2 (Hs00201978_m1), KRT40 (Hs01057909_m1), BANP (Hs00215370_m1), AGTRAP (Hs01564425_m1), RBL2 (Hs00180562_m1) |

Development of EDDY-CTRP-PH: Details of pulmonary hypertension gene network and clustering and EDDY-CTRP-PH are described in below.

Data and code availability: All the microarray data have been submitted to GEO (accession no. GSE125508 and GSE160255 for I-BET and BRD2889, respectively). EDDY software is available at GitHub repository (https://github.com/dolchan/eddy-gpu). The EDDY-CTRP-PH analysis for all the clusters and small molecule is available: https://chan.vmi.pitt.edu/eddy-ctrp-ph/

Cell culture: Primary human pulmonary artery endothelial cells (PAECs) and human pulmonary artery smooth muscle cells (PASMCs) were purchased from Lonza (302-05A, CC-2581). Of note, the same two male donors were the source of all PAECs in the experiments shown. Two additional male donors were the source for all PASMCs in the experiments shown. Cells from these and any donors were characterized by flow cytometry for consistent expression of cell surface markers and by RNA (RT-qPCR) analysis of endothelial and smooth muscle gene expression. PAECs were cultured in EGM-2 media (CC-3121) along with supplements (CC-4133), and PASMCs were cultured in SmGM-2 culture media (Lonza, CC-3182) at 5% $CO_2$ in a humidified incubator.

To assess the effect of I-BET under inflammatory conditions, cells were treated with recombinant human IL-1β (10 ng/ml, Peprotech) at about 70-80% confluency for 48 h in complete media along with vehicle control (DMSO, Sigma-41639), I-BET151 (500 nM), I-BET762 (500 nM) (Selleckchem-S2780/S7189), as indicated. Human recombinant galectin-8 (1305-GA-050) was purchased from R&D Systems and was used at a working concentration of 30 nM.

For hypoxia exposure, cells were plated in 6-well cell culture plates at 1×10^5 cells/well, grown for 24 hr and placed into a normobaric hypoxia chamber (1% $O_2$) for 24 h under specific treatment conditions. Namely, for I-BET and siLGALS8 exposures, cells were either pre-treated with I-BET/vehicle control (VC) or transfected with siLgals8/Scr for 24 h. Then, they were cultured in basal media at 1% 02. After 24 h, caspase activity and mitochondrial superoxide levels were quantified. To detect activation status of pSTAT1/STAT1 by immunoblot, cells were exposed to 8 h of hypoxia.

In IL-6/sIL-6R+hypoxia experiments, a human recombinant IL-6/IL-6R alpha protein chimera (25 ng/ml, Millipore) was administered at 70-80% confluency for 48 h in complete media along with vehicle control (DMSO, Sigma-41639). BRD2889 (1 uM) vs. vehicle control were added, as indicated, and placed into a hypoxia chamber for 24 h. The hypoxia chamber (modular incubator chamber) was obtained from Billups-Rothenberg Inc. (Del Mar, Calif) and placed in regulated $CO_2$ incubator at 37° C.

Animal models: For the hypoxia-induced pulmonary hypertension mice, male $C_{57}$BL/6J mice (8 weeks old) (RRID:IMSR_JAX:000664) were purchased from Jackson laboratory and acclimatized for 3-4 days in this facility. Subsequently, mice scheduled for normoxic vs. hypoxic exposure were maintained in either normoxia or a normobaric hypoxia chamber for 1 or 3 weeks (OxyCycler, Biospherix Ltd.), where consistent exposure to 10% oxygen and control for temperature and humidity were possible. For testing the activity of I-BET in hypoxia-induced pulmonary hypertension mice, three experimental groups—normoxia+VC (vehicle control), hypoxia+VC (vehicle control), and hypoxia+I-BET were used. I-BET762 (SelleckChem, 30 mg/kg) was administered by daily oral gavage for the duration of hypoxic exposure (Wyce A et al. *Oncotarget*. 2013, 4, 2419-2429; Chaidos A et al. Blood. 2014, 123, 697-705).

Generation of the SU5416-hypoxia pulmonary hypertension rat model was described previously (Meloche J et al. *Circ Res*. 2015, 117, 525-535). Briefly, 10 week old male Sprague-Dawley rats were injected i.p. with 20 mg/kg of SU5416 (Sigma), placed in normobaric hypoxia (10% $O_2$) for 3 weeks and then transferred to normoxia for 2 weeks. During hypoxic exposure, chambers were opened twice a week for cleaning and replenishment of food and water. For I-BET762 vs vehicle control dosing, daily i.p. injections (SelleckChem, 30 mg/kg) were administered during the final two weeks of normoxia. For BRD2889 vs. vehicle control dosing, i.p. injections every 5 days (5 mg/kg) were administered during the final two weeks of normoxia. Oxygen concentrations were continuously monitored with blood gas analyzers.

For the monocrotaline (MCT) pulmonary hypertension rat model, male Sprague-Dawley rats (10-14 week old) were injected (i.p.) with 60 mg/kg monocrotaline vs. PBS and kept for 26 days in normoxia (n=4/group), as previously described (Bertero T et al. *J Clin Invest*. 2014, 124, 3514-3528). For I-BET762 vs vehicle control dosing and BRD2889 vs. vehicle control dosing experiments, dosing strategies similar to those in SU5416-chronic hypoxic rats were used from Days 12-26 post-monocrotaline injection.

I-BET was dissolved in DMSO at 100× concentration and then made into a working solution in 20% PEG400 and 80% 1×PBS. BRD2889 was made into a working solution of 2.5% DMSO.

Lgals8−/− $C_{57}$BL/6N mouse sperm was purchased from KOMP (14305A-F8) (Chen W S et al. *Nat Commun*. 2016, 7, 11302), and reconstituted in house and genotyped, as per KOMP's instructions. Male and female 8 week old Lgals8−/− mice were exposed to hypoxia for 3 weeks. Littermates were used as wildtype (WT) control when comparing with knockout mice. Prior to euthanasia, echocardiography was performed as described (Bertero T et al. J Cin Invest. 2014, 124, 3514-3528; Bertero T et al. *J Cin Invest*. 2016, 126, 3313-3335), followed by closed-chest right heart catheterization (Song Y et al. *Am J Physiol Heart Circ Physiol*. 2008, 295, H677-690) to measure right ventricular systolic pressure (RVSP) and heart rate. For rats, invasive catheterization of the abdominal aorta was performed to quantify systemic blood pressure. Following euthanasia, right ventricle/[left ventricle+septum] (RV/LV+S) mass ratio (Fulton index) was quantified, accompanied by Tissue-Tek OCT (VWR) tissue preparation for histologic staining, as described elsewhere (Bertero T et al. *J Clin Invest*. 2014, 124, 3514-3528; Bertero T et al. *J Clin Invest*. 2016, 126, 3313-3335).

Pulmonary-specific IL-6 transgenic mice ($C_{57}$BL/6 background) were described previously (Steiner M K et al. *Circ Res*. 2009, 104, 236-244, 228p following 244). These mice were bred in house, and 12 week old male transgenic mice vs. control littermates were compared. Mice were injected i.p. every 3 days with vehicle control (2.5% DMSO) vs. BRD2889 (5 mg/kg vs. 10 mg/kg), followed by exposure to normobaric hypoxia (10% $O_2$; OxyCycler chamber, Biospherix Ltd, Redfield, NY) for 14 days, as described (Steiner M K et al. *Circ Res*. 2009, 104, 236-244, 228p following 244).

Animal numbers were chosen to achieve 0.80 power for detecting >25% difference among means with a standard deviation of 20%. All animal experiments were approved by the University of Pittsburgh (IACUC). Randomization of the animals assigned to different experimental groups was achieved. Briefly, populations of animals sharing same gender, same genotype, and similar body weight were generated and placed in one container. Then, each animal was picked randomly and assigned in a logical fashion to different groups. For example, the first one is assigned to group A, second to group B, third to group A, fourth to group B, and so forth. No animals were excluded from analyses.

Human samples: Human Group 1 pulmonary hypertension (pulmonary arterial hypertension or PAH), Group 3 pulmonary hypertension, and non-diseased lung samples as well as peripheral plasma are described in Table 4 and previously described elsewhere (Bertero T et al. *J Clin Invest*. 2014, 124, 3514-3528). The number of recruited patients was determined primarily by the availability of clinical samples. Experimental procedures involving human tissue were approved by institutional review boards at the University of Pittsburgh. Ethical approval for this study and informed consent conformed to the standards of the Declaration of Helsinki.

TABLE 4

Clinical characteristics of WSPH Group 1 pulmonary arterial hypertension and Group 3 pulmonary hypertension patients used for in situ staining and plasma profiling. CHD, congenital heart disease; COPD, chronic obstructive pulmonary disease; CTD, connective tissue disease; IPAH, idiopathic pulmonary arterial hypertension; IPF, idiopathic pulmonary fibrosis; PH, pulmonary hypertension.

| Age | Gender | mPAP* (mmHg) | Diagnosis | Clinical description |
|---|---|---|---|---|
| | | PAH patients | | |
| 34 | Female | 50 | IPAH | Cardiopulmonary arrest (autopsy) |
| 64 | Female | 55 | IPAH | Cardiopulmonary arrest (autopsy) |
| 68 | Female | 44 | Scleroderma (PAH) | Bilateral lung transplant |
| 12 | Male | 53 | BMPR2 mutation (Hereditary PAH) | Bilateral lung transplant |
| 16 | Male | 62 | IPAH | Bilateral lung transplant |
| 1 | Male | 50 | Trisomy 21 (PAH) | Lung resection |
| 19 | Male | 48 | IPAH | Lung resection |
| 42 | Female | 57 | Scleroderma (PAH | Bilateral lung transplant |
| | | Group 3 PH patients | | |
| 62 | Male | 28 | IPF (Group 3 PH) | Bilateral lung transplant |
| 58 | Male | 28 | IPF (Group 3 PH) | Bilateral lung transplant |

TABLE 4-continued

Clinical characteristics of WSPH Group 1 pulmonary arterial hypertension and Group 3 pulmonary hypertension patients used for in situ staining and plasma profiling. CHD, congenital heart disease; COPD, chronic obstructive pulmonary disease; CTD, connective tissue disease; IPAH, idiopathic pulmonary arterial hypertension; IPF, idiopathic pulmonary fibrosis; PH, pulmonary hypertension.

| Age | Gender | mPAP* (mmHg) | Diagnosis | Clinical description |
|---|---|---|---|---|
| 63 | Male | 27 | IPF (Group 3 PH) | Bilateral lung transplant |
| 50 | Male | 30 | IPF (Group 3 PH) | Bilateral lung transplant |
| 61 | Male | 37 | IPF (Group 3 PH) | Bilateral lung transplant |
| 69 | Female | 29 | IPF (Group 3 PH) | Bilateral lung transplant |
| 72 | Male | 46 | IPF (Group 3 PH) | Rapid autopsy |
| 66 | Male | 34 | IPF (Group 3 PH) | Bilateral lung transplant |
| PERIPHERAL PLASMA SAMPLES | | | | |
| 46 | Female | | Control | |
| 61 | Male | | Control | |
| 59 | Female | | Control | |
| 50 | Female | | Control | |
| 65 | Female | | Control | |
| 34 | Female | | Control | |
| 49 | Female | | Control | |
| 31 | Male | | Control | |
| 52 | Female | | Control | |
| 35 | Male | | Control | |
| 43 | Male | | Control | |
| 31 | Female | | Control | |
| 51 | Female | | Control | |
| 61 | Female | | Control | |
| 54 | Female | | Control | |
| 58 | Female | 53 | IPAH | |
| 47 | Male | 52 | IPAH | |
| 43 | Female | 53 | CHD (PAH) | |
| 83 | Male | 45 | IPAH | |
| 53 | Female | 54 | IPAH | |
| 47 | Female | 32 | CTD (PAH) | |
| 73 | Female | 28 | IPAH | |
| 55 | Female | 52 | CTD (PAH) | |
| 41 | Male | 51 | IPAH | |
| 73 | Female | 41 | Scleroderma (PAH) | |
| 65 | Female | 32 | Scleroderma (PAH) | |
| 57 | Male | 53 | IPAH | |
| 26 | Female | 34 | IPAH | |
| 58 | Male | 61 | IPAH | |
| 58 | Female | 53 | CTD (PAH) | |
| 73 | Female | 32 | Scleroderma (PAH) | |
| 37 | Male | 37 | Scleroderma (PAH) | |
| 72 | Female | 27 | Scleroderma (PAH) | |
| 67 | Male | 49 | Portopulmonary hypertension (PAH) | |
| 58 | Male | 43 | CTD (PAH) | |
| 68 | Female | 25.3 | COPD (Group 3 PH) | |
| 70 | Male | 37 | COPD (Group 3 PH) | |
| 40 | Female | 29 | COPD (Group 3 PH) | |

*Mean pulmonary arterial pressure (mPAP)

BRD2889 synthesis: BRD2889 was prepared from commercially available piperlongumine via a reported 2-step procedure (ca-iodination and Sonogashira coupling) and purified by silica gel chromatography followed by recrystallization (Adams D J et al. *Proc Natl Acad Sci USA*. 2012, 109, 15115-15120).

Transfection: Human PAECs were transfected at about 70-80% confluency in OptiMEM media (Thermo Fisher Scientific) with 6.25 nM of scrambled (4390843) or Lgals8 (s8158), Brd2 (s12070), Brd4 (s23901), Jak1 (s7646), Jak2 (s7651), Stat1 (s279) silencer select siRNA (Thermo Fisher Scientific), 5 nM of non-target pool (D-001810-10-05) or 5 nM GSTP1 (J-011179-07-0010) siRNA (Dhannacon, a Horizon Discovery Group) and 5 nM JSCU (J-012837-11-0020) siRNA using Lipofectamine 2000, according to manufacturer's instructions (Thermo Fisher Scientific). After 6 hours, OptiMEM was replaced by endothelial growth media, and cells were analyzed 48 h post-transfection. Similarly, HEK293 cells (ATCC no. CRL 1573) were transfected with 0.5 μg WT-ISCU, C69S-ISCU, C69A-ISCU, or pcDNA3.1 empty vector using Lipofectamine 2000, according to the manufacturer's instructions (Thermo Fisher Scientific). After 48 hr transfection, the cells were exposed to hypoxia for 24 hr prior to harvesting for cellular lysate.

Statistical analysis: Data are represented as mean±SEM. For cell culture data, these represent 3 independent experiments performed in triplicate. The normality of data distribution was confirmed by Shapiro Wilk testing. For normally distributed data, a 2-tailed Student's t test was used for comparisons between two groups. For comparisons among groups, one-way ANOVA and post-hoc Bonferroni testing were performed. A p-value less than 0.05 was considered significant.

Detailed descriptions of other standardized and published approaches are provided in the below.

Construction of the pulmonary hypertension-extended gene network: Adapted from a prior version of the pulmonary hypertension gene network (Bertero T et al. *J Clin Invest.* 2014, 124, 3514-3528), the network was constructed with a set of 416 seed genes which were identified as related to pulmonary hypertension from a contemporaneous curated literature review. Functional interactions for the network were collected from DIP (Salwinski L et al. *Nucleic Acids Res.* 2004, 32, D449-451), BioGRID (Chatr-Aryamontri A et al. *Nucleic Acids Res.* 2015, 43, D470-478), CORUM (Ruepp A et al. *Nucleic Acids Res.* 2010, 38, D497-501), InnateDB (Breuer K et al. *Nucleic Acids Res.* 2013, 41, D1228-1233), IntAct (Orchard S et al. *Nucleic Acids Res.* 2014, 42, D358-363), MINT (Licata L et al. *Nucleic Acids Res.* 2012, 40, D857-861), and MatrixDB (Launay G et al. *Nucleic Acids Res.* 2015, 43, D321-327). The total union of interactions from all these databases was referred to as the consolidated interactome (CI).

Not all 416 seed genes were interconnected into a single largest connected component (LCC). In order to ensure inclusion of all the seed genes within a single LCC, intermediate non-seed genes were included into an expanded network. The process began by finding the LCC seeds which would form the base network. Intermediate non-seed genes were added into the network if they would connect one of the yet to be included seeds into the existing network. This process was repeated until the maximum number of possible seeds was included. It included a vast majority of the original pulmonary hypertension genes but yielded a very dense network of interactions. To decrease the network's density in order to ensure meaningful computational predictions, interactions were pruned based on the p-values assigned to each interaction computed using Monte Carlo simulation. 10,000 random networks were generated using random sets of 416 seed genes. The p-value of each interaction corresponded to its frequency of appearance in these random networks. Interactions were removed from the pulmonary hypertension network in order of descending p-value until the point where removing any additional interactions would disconnect one of the seed genes. This process generated the pulmonary hypertension (PH)-extended network, comprising 2,946 interactions among 747 genes. Finally, the pulmonary hypertension-extended network was subdivided into 55 groups of related genes (Table 1-Table 2), using the Map Equation (Bohlin L et al. Measuring Scholarly Impact. Springer, 2014, Cham. 3-34) which clusters and divides genes based on density of interactions and ready to feed into EDDY-CTRP-PH.

Development of EDDY-CTRP-PH pipeline: First, RNA expression data from the CCLE was quantified using the transcript expression quantification tool Salmon (Patro R et al. *Nat Methods.* 2017, 14, 417-419), $\log_2$-transformed, and quantized using median absolute deviation (MAD) into under-expressed, intermediate, and over-expressed levels. Second, drug sensitivity data from the CTRP was used to group sensitive, intermediate, and non-sensitive CCLE cell lines. Third, the pulmonary hypertension-related gene clusters allowed the computational interrogation of gene co-expression to be constrained to subgroups of interest. Finally, previously known interactions mined from Pathway Commons 2 (www.pathwaycommons.org) were utilized as prior knowledge in EDDY analysis with a weight of 0.5, decreasing false-discovery rate without overly reducing differential dependency detection sensitivity (Speyer G et al. *Pac Symp Biocomput.* 2016, 21, 33-44).

Once these input sources were assembled, EDDY (Jung S et al. *Nucleic Acids Res.* 2014, 42, e60) was used to construct graphs for gene dependencies in cells sensitive and resistant to a given small molecules, where edges between nodes were defined by a pairwise independence test ($c^2$ test) of gene expression, with known interactions (edges) given a priority. By repeated resampling of each group (sensitive vs. resistant cells), multiple unique networks were constructed for each group, and upon scoring, each group was characterized with a network likelihood distribution. The significance of the divergence between the two distributions was assessed via permutation test. Thus, statistically significant differential rewiring among gene networks between cells resistant and sensitive to a small molecules was catalogued. These clusters were then visualized with a differential dependency network (DDN). Across 368 compounds, 810 cell line responses presented different sensitive and non-sensitive groupings, which, in turn, yielded specific significant pulmonary hypertension cluster lists from EDDY. Of note, even when the same cluster was found to be statistically significant for two different compounds, its differential dependency network often displayed substantially different wiring. For visualization, each characteristic line in differential dependency networks indicated the identified relationship between nodes (genes): drug-sensitive (red), drug-resistant (blue), and both (gray) as well as known interactions with directionality (solid edges+/−arrow) and previously unknown statistical dependencies (dashed edges).

For each differential dependency network, genes important to the integrity of the network were identified by network analysis. Namely, the betweenness-centrality metric assessed a node's essentiality within a network (Freeman L C. *Sociometry.* 1977, 40, 35-41) and was visualized in the condition-specific network through the node size. In each differential dependency network, essentiality mediators were identified as those with the highest (top 10%) betweenness-centrality difference between the two condition-specific networks and the size of the nodes in each differential dependency network represented the betweenness-centrality difference. The condition-specific rewiring metric identified genes with a significant proportion of condition-specific edges assessed against the binomial distribution of these edges across the entire graph. In each differential dependency network, these specificity mediators were identified, highlighting particularly highly altered roles between conditions. Both essentiality and condition-specific mediators were indicated by square nodes.

Furthermore, in order to shortlist, the small molecules and clusters were ranked based on three criteria: 1) "average" p-value ($\overline{p}_{\cdot j}$ and $\overline{p}_{i\cdot}$; see the description below for detail), 2) frequency of mediator involvement, and 3) number (or frequency) of significantly rewired clusters for a given small molecule and number (or frequency) of small molecules linked to rewiring of a given cluster. Mathematically, let $C=[c_{i,j}]$, where $c_{i,j}=1$ if a pulmonary hypertension cluster $P_i$ is enriched for differentially dependencies for a drug $D_j$ with a p-value $p_{i,j}$; and $c_{i,j}=0$ otherwise. Also, let $M=[m_{ij}]$, where $m_{ij}$ is the number of mediator genes identified for a pulmonary hypertension cluster $P_i$ and a drug $D_j$. Also $m_{i\cdot}$ and $m_{\cdot j}$ are denoted as the number of unique mediator genes for a pulmonary hypertension cluster $P_i$ and the number of unique mediator genes for a drug $D_j$, respectively. For each drug $D_j$, $N_C(D_j)=\Sigma_i c_{i,j}$ denotes the number of pulmonary hypertension clusters associated with the drug $D_j$ and $\overline{p}_{\cdot j}=-1/N_C(D_j\Sigma_i \log_{10} p_{ij}$ denotes the "average" p-value for the drug $D_j$. Finally, for each pulmonary hypertension cluster $P_i$, $N_D(C_i)=$ $\Sigma_j c_{i,j}$ denotes the number of drugs the pulmonary hypertension cluster is enriched for differentially dependencies, and $$\overline{p}_{i\cdot} = -\frac{1}{N_D(C_i)}\sum_j \log_{10} p_{ij}$$

denotes the "average" p-value for the pulmonary hypertension cluster $P_i$. A drug is then ranked for $N_C(D_j)$, $m_{\cdot j}$ (both in descending order), and $\overline{p}_{\cdot j}$ (in ascending order), and denoted as $r_C(D_j)$, $r_m(D_j)$, and $r_p(D_j)$, respectively. As shown in Table 1-Table 3, ultimately, the overall rank score of a drug was the sum of these three ranks, ($r(D_j)=r_C(D_j)+r_m(D_j)+r_p(D_j)$), and a drug was ranked based on the overall rank score (ascending order), $r(D_j)$. Similarly, a pulmonary hypertension cluster was ranked for $N_D$ ($C_i$), $m_{i\cdot}$ (both in descending order), and $\overline{p}_{i\cdot}$ (in ascending order), and denoted as $r_D(C)$, $r_m(C_i)$, and $r_p(C_i)$, respectively. The overall rank score of a pulmonary hypertension cluster was the sum of these three ranks ($r(C_i)=r_D(C_i)+r_m(C_i)+r_p(C_i)$), and a pulmonary hypertension cluster was ranked based on the overall rank score (ascending order), $r(C_i)$.

TABLE 1

Genes in each cluster .

| Cluster | Genes in cluster |
|---|---|
| 1 | AAMP, CCDC8, ACO1, ACTB, MDM2, S100A7, YAP1, ALOX5, MKL1, ZC3H12A, ANK3, UBD, APP, ARG1, ARG2, ANKRD13A, DDX3Y, ATP2B1, SUMO2, ILVBL, FBXW11, NTRK1, PAPSS2, NOMO1, GUCY1A3, GUCY1B3, PARK2, WBP1, CDKN2D, DPF2, HK2, STK17B, UBC, SERPINB8, HSD17B4, VCAM1, TNC, CLIC4, FSD1, XPO1, PREP, CTGF, VHL, CALML5, ISYNA1, ZSCAN32, FBXO6, MFN2, ARIH2, LAMB2, RGS3, NAMPT, PBRM1, EGFR, ZNF197, PRMT3, CDK2, FLOT1, AK2, SMAD3 |
| 2 | GLS, MEOX2, CEBPB, CCL2, CCL3, CCL5, MMP1, MMP3, CX3CL1, CREB3, SGTA, CXCR6, AZGP1, GATA3, STAT1, STAT3, STAT4, NFATC2, KLF5, NFKB1, NFKB2, NOS2, ENTPD1, TLR4, CCRL2, SERPINE1, CD44, TNF, RELA, HGF, HMOX1, PLA2G4A, CCR1, ICAM1, TBX21, POLR2F, NOX4, ATF2, CRP, NCOR1, CCL19, SRGN, VCAN, RBPJ, IL1A, IL1B, IL1R1, IL-6, CX3CR1, IL13, CXCL10, VIP, UBQLN4, IRF4, CD82, HSD17B8, FOS, JUN, SMAD4, CTNNB1 |
| 3 | ABAT, AP2A1, AP1B1, FDPS, BCAR3, AKR1B1, MPG, ACLY, SEC31A, RHOA, RHOB, IGF1R, FOXI2, ATIC, SOD2, NUP62, SNX3, GLO1, TAGLN, NME2, DSTN, ARHGEF12, CAT, CBS, PEBP1, NME1-NME2, CFL1, CFL2, SLC25A32, HPRT1, HSPE1, CST4, CTH, PTMA, JAK1, WDR1, SLC25A41, WDYHV1, DUT, HSD17B14, LIMK1, NUTF2, RPE, ENO2 |
| 4 | MAX, YWHAB, AKT1, CAMKK1, TRIM23, ATF6, MT2A, CNDP2, GP1BA, MAP3K2, MYC, SRD5A1, PDE10A, NFU1, PRKACA, SFN, NEDD4L, TH, TPH1, PDE3A, PDK2, CYTH2, SH3BP4, UBE3A, HSPA5, HSPB1, XBP1, CPS1, YWHAZ, MAP2K5, PSMA1, TFIP11, PTPN3, KCNK3, EPM2A |
| 5 | MAP4, MAPK12, RACK1, AGTR1, ALB, APOE, SLAMF1, HSD17B6, ATP12A, ATP2B2, ATP2B3, ATP2B4, SNTA1, SNTB1, ERBIN, NOS1, NOS3, CAV1, GUCY1A2, SCN5A, PTGIS, PTGS2, LRP8, KCNA5, HTR2B, DLG1, DLG2, DLG3, DLG4, LRP2, PATJ |
| 6 | MMP2, MMP9, CXCL12, FN1, SP3, CAND1, C3, TAC1, LOXL3, CALR, TGFBI, THBS1, TIMP1, PDGFA, PDGFB, PDGFRA, PDGFRB, COL1A1, COL1A2, COL4A1, COL4A2, VWF, COL3A1, LOX, ITGAV, LRP1, ERAL1, VEGFA, KDR, ELN, EPAS1 |
| 7 | ADA, SOCS7, ANGPT4, FOXO1, ANGPT1, ANGPT2, NCKIPSD, AR, MST1, FYN, SRC, GATA2, STAT5A, SPHK1, SKAP2, TEK, ANGPTL1, PRDM14, GRB2, CCR7, LYN, SNX17, E2F4, RGS16, EFNA1, EGF, TRPV4 |
| 8 | RPL29, ESR2, ACTA2, ACTG2, PLA2G4B, DYSF, TRIM59, SEMA3F, FYTTD1, ESR1, SHBG, SNRNP70, JMJD7-PLA2G4B, SLC37A1, CASP8, PSTPIP1, SNAPIN, IL13RA2, DES, PRL |
| 9 | SNTB2, TNFSF10, APOBEC3C, NFS1, TP53, HDAC1, KLF4, PHF1, SENP1, HSD17B13, VIPR2, LLGL2, CTBP1, HDAC4, HDAC5, TSPAN10, ELAVL1 |
| 10 | GDF5, NCOA3, SMAD6, GDF2, BMP2, BMP4, BMP6, BMP7, BMPRIA, BMPRIB, BMPR2, BMP10, NOG, MIR27A, GREM1, EGR1, SMAD1, SMAD5 |
| 11 | KLHL1, ESRRB, CNDP1, CDC37, HLA-DRB1, HLA-DRB5, LOXL4, HSPA8, SMYD3, HSP90AA1, PPID, PRKG2, HSP90AB1, PKM |
| 12 | MAPK9, SLC6A4, TNFSF11, NEFH, NFATC3, MAPK14, MAPK1, MAPK8, DUSP1, DUSP7, EEF1A1, GAN, EIF2AK4 |
| 13 | EWSR1, AGT, HSD17B7, TIMM21, TERT, ZNF589, HNF4A, HSD17B2, HSD17B1, POLB, XDH, PRG2, RMND5B, ACE |
| 14 | RYR2, B2M, SRI, CACNA1C, CALM1, CALM2, CALM3, PDE1A, CRHR1, PRKAR2A, PRKAR2B, ACE2, VIPR1 |
| 15 | ABCC4, LGALS9C, PDZK1, CD47, CFTR, SLC9A3R2, LPAR1, SLC9A3R1, LGALS3, CSPG4, DAG1, ANO1, LGALS8 |
| 16 | CBL, HSD17B3, MIRLET7B, MIRLET7C, MIRLET7D, MIRLET7E, PCDH20, PRKAA2, CCND1, RYK, WNT1, CDK6, MIR21, SMAD2 |
| 17 | A2M, MAOA, APOD, ATP5A1, CYP19A1, CAPN6, EZR, CPB2, ATP6V1B2, SELP, PTX3 |
| 18 | SPRY2, TMEM17, NT5C3A, GORAB, TMEM216, EPB41L3, DYNLT1, EBAG9, NAF1, HMOX2, ZRANB2, EVC2, DVL1, DVL2, DVL3, VANGL1 |
| 19 | ERG, ACPP, NDRG1, SIAH2, SLC9A1, NEDD4, ROCK1, RGS2, ROCK2, CRMP1, EIF3E, PMEPA1 |
| 20 | CDKN2A, RGS19, MAP2K4, SH3GL2, GCH1, NOL3, MAPK10, PACSIN2, PACSIN3, CSNK2A1 |
| 21 | FHL1, CBX4, MIR424, CCNE1, CDC25A, CDKN1B, MIR503, PIM1, CCND3, ID1, MAP2K1, FOXO3, SMURF1 |
| 22 | CD209, SP1, HAS2, HTR1A, HTR1B, HTRID, S1PR1 |
| 23 | LGALS1, HLA-B, HSD17B10, ATP1B1, PDHA1, PDK3, USP4, PDK1, PTBP1, DLD |
| 24 | HEXIM1, UBE20, MIR328, HIF1A, NPPB, LYST, CSNK2B, LEP, LEPR |
| 25 | CD226, CA8, GHRL, LNX1, TBXA2R, PRKCA, PTGIR, CLDN4 |
| 26 | CD4, CD74, HLA-DPA1, HLA-DPB1, HLA-DQB1, CTSD, INS, RTN4, RFX1, RFXAP |
| 27 | ACVRL1, TGFB1, TGFBR1, TGFBR2, TGFBR3, ENG, SMAD7 |
| 28 | F2RL1, SRF, BCL2, CAPN1, CAPN2, CAPNS1, CASP9, XIAP |

TABLE 1-continued

Genes in each cluster .

| Cluster | Genes in cluster |
|---|---|
| 29 | FOXF1, PCBP4, GLI1, GLI3, PDGFRL, PFKM, CAV3, PRMT1, QKI, PCBP1 |
| 30 | MME, APBB1, EDN3, CMA1, KEL, EDN1, EDN2, EDNRA, EDNRB, TSHZ1 |
| 31 | DHDDS, HDAC11, OTUB1, AHSA1, SPINT2, NUS1, UTS2, UTS2R, HMGCR, TCTN3, HSD17B12, TCTN2 |
| 32 | NRIP1, ESRRG, ESRRA, PPARGC1A, PPARG, PPM1B, MIR130A, PDK4 |
| 33 | ACTN1, ACTN2, MEF2A, ADORA2A, ACTN4, ACTN3, CAMK2D, HIRA, CNR1 |
| 34 | IKZF1, CSNK1G1, NOTCH1, SIN3B, GZMB, MIR145, DFFA, F11R |
| 35 | MDFI, APLNR, TINAGL1, APLN, TAZ, RBPMS, CYBA, PSMA3, LOXL2 |
| 36 | NCOA2, APEH, SIRT3, SERPINA1, VKORC1, PLP2, HAX1, FGL1, DNM1L |
| 37 | BIRC2, APOA1, TNFSF13B, CD40LG, TRAF2, TNFRSF25, TNFSF4, TNFSF12, CLEC4G |
| 38 | CALCOCO2, TPD52L2, TP53RK, GDF15, CYP1B1, MRPL50, GIT2, SAE1 |
| 39 | ATP8B4, ACP5, TMEM30A, SARAF, SPP1, SRPK1, OS9, FBXO15, UBA7 |
| 40 | SSSCA1, ZPR1, KDM4A, NRAS, PLIN1, DNAJB1, PNPLA2, ABHD5, NME6, SMAD9 |
| 41 | NYX, TOPBP1, BRD4, CLK1, WNT5A, SHROOM1, AMIGO3, AMIGO2, ECE1, PTPRK |
| 42 | CEP164, NPHP3, NPHP1, AARSD1, SNX11, PRF1, IDO1, DDX24, KRT31 |
| 43 | RECK, MT1G, MTOR, GOLGA2, MID2, ISCU, KRT40, BANP, AGTRAP, RBL2 |
| 44 | FLNA, KCNIP1, CASR, KCNE4, KCND3, KCNIP2, KCND2 |
| 45 | PDE5A, TRPC1, TRPC3, TRPC6, PRKG1, TRPC4 |
| 46 | F2R, S100A4, AGER, PRMT5, NEK6, GNAT1, UNC119, ID2 |
| 47 | AP1M1, SIRT4, MLYCD, ECH1, FAM9B, ZADH2, PEX5 |
| 48 | XPO5, GSTK1, ATP2A2, PTP4A3, MIRLET7A1, PEX19, RAN, HSD17B11 |
| 49 | RTEL1, FYCO1, RAF1, ZNFX1, SS18L2 |
| 50 | NOTCH3, WWP2, POU5F1, DTYMK |
| 51 | TCTA, ATXN1, PTGDS, LOXL1 |
| 52 | KBTBD7, ATF4, FOSL2, DDIT3 |
| 53 | PRKD2, MIR17, RAE1 |
| 54 | FBXO32, EIF3F, TSC1 |
| 55 | GPER1, HES5, PTEN |

TABLE 2

Cluster information and scores. Clusters were sorted according to their rewiring scores as defined in Methods. This score considered the average p-value (mean(−log10(p))); 2) number (or frequency) of small molecules linked to rewiring of a given cluster (freq_drug); and 3) frequency of mediator involvement (freq_mediator). Rankings of clusters by these criteria individually (rank.pval, rank.freq_drug, rank.freq_mediator) as well as overall (rank.sum = sum of the ranks, rank.overall = rank based on sum.ranks) are listed.

| Cluster | mean (−log10(p)) | freq_drug | freq_mediator | rank.pval | rank.freq_drug | rank.freq_mediator | rank.sum | rank.overall |
|---|---|---|---|---|---|---|---|---|
| 6 | 1.644 | 8 | 23 | 29 | 35 | 1 | 65 | 27 |
| 10 | 1.330 | 1 | 4 | 43 | 42 | 37 | 122 | 42 |
| 11 | 1.636 | 17 | 11 | 30 | 14 | 2 | 46 | 12 |
| 12 | 1.734 | 28 | 11 | 21 | 4 | 2 | 27 | 3 |
| 13 | 1.544 | 14 | 10 | 36 | 22 | 6 | 64 | 26 |
| 14 | 1.623 | 14 | 10 | 32 | 22 | 6 | 60 | 22 |
| 15 | 1.721 | 36 | 11 | 24 | 2 | 2 | 28 | 4 |
| 16 | 2.126 | 59 | 6 | 5 | 1 | 25 | 31 | 6 |
| 17 | 1.769 | 15 | 7 | 18 | 18 | 17 | 53 | 14 |
| 18 | 1.340 | 2 | 5 | 42 | 41 | 30 | 113 | 40 |
| 19 | 1.486 | 5 | 9 | 39 | 38 | 10 | 87 | 35 |
| 20 | 1.704 | 8 | 7 | 27 | 35 | 17 | 79 | 34 |
| 21 | 1.422 | 10 | 11 | 41 | 33 | 2 | 76 | 32 |
| 23 | 1.675 | 17 | 10 | 28 | 14 | 6 | 48 | 13 |
| 24 | 1.910 | 14 | 6 | 10 | 22 | 25 | 57 | 16 |
| 25 | 1.831 | 18 | 7 | 13 | 11 | 17 | 41 | 9 |
| 26 | 1.839 | 20 | 9 | 12 | 8 | 10 | 30 | 5 |
| 27 | 1.732 | 23 | 5 | 22 | 7 | 30 | 59 | 21 |
| 28 | 1.727 | 27 | 8 | 23 | 5 | 14 | 42 | 10 |
| 29 | 1.715 | 15 | 8 | 25 | 18 | 14 | 57 | 16 |
| 30 | 1.574 | 16 | 6 | 35 | 17 | 25 | 77 | 33 |
| 31 | 1.585 | 15 | 10 | 34 | 18 | 6 | 58 | 19 |
| 32 | 2.064 | 11 | 5 | 6 | 29 | 30 | 65 | 27 |
| 33 | 1.884 | 11 | 5 | 11 | 29 | 30 | 70 | 31 |
| 34 | 2.037 | 15 | 4 | 7 | 18 | 37 | 62 | 24 |
| 35 | 1.760 | 11 | 7 | 20 | 29 | 17 | 66 | 29 |
| 36 | 1.792 | 17 | 7 | 14 | 14 | 17 | 45 | 11 |
| 37 | 1.983 | 11 | 5 | 8 | 29 | 30 | 67 | 30 |
| 38 | 1.761 | 13 | 7 | 19 | 27 | 17 | 63 | 25 |
| 39 | 1.513 | 14 | 5 | 37 | 22 | 30 | 89 | 38 |
| 40 | 1.473 | 5 | 9 | 40 | 38 | 10 | 88 | 37 |
| 41 | 1.712 | 14 | 9 | 26 | 22 | 10 | 58 | 19 |

TABLE 2-continued

Cluster information and scores. Clusters were sorted according to their rewiring scores as defined in Methods. This score considered the average p-value (mean(−log10(p))); 2) number (or frequency) of small molecules linked to rewiring of a given cluster (freq_drug); and 3) frequency of mediator involvement (freq_mediator). Rankings of clusters by these criteria individually (rank.pval, rank.freq_drug, rank.freq_mediator) as well as overall (rank.sum = sum of the ranks, rank.overall = rank based on sum.ranks) are listed.

| Cluster | mean (−log10(p)) | freq_drug | freq_mediator | rank.pval | rank.freq_drug | rank.freq_mediator | rank.sum | rank.overall |
|---|---|---|---|---|---|---|---|---|
| 42 | 2.195 | 19 | 6 | 2 | 10 | 25 | 37 | 7 |
| 43 | 2.185 | 34 | 8 | 3 | 3 | 14 | 20 | 1 |
| 44 | 1.597 | 4 | 2 | 33 | 40 | 41 | 114 | 41 |
| 45 | 1.495 | 1 | 1 | 38 | 42 | 43 | 123 | 43 |
| 46 | 2.210 | 20 | 7 | 1 | 8 | 17 | 26 | 2 |
| 47 | 2.181 | 12 | 6 | 4 | 28 | 25 | 57 | 16 |
| 48 | 1.780 | 24 | 7 | 16 | 6 | 17 | 39 | 8 |
| 49 | 1.786 | 18 | 5 | 15 | 11 | 30 | 56 | 15 |
| 50 | 1.771 | 10 | 4 | 17 | 33 | 37 | 87 | 35 |
| 51 | 1.633 | 6 | 2 | 31 | 37 | 41 | 109 | 39 |
| 52 | 1.914 | 18 | 3 | 9 | 11 | 40 | 60 | 22 |

TABLE 3

Small molecule scores. Drugs were sorted according to their rewiring scores as defined in Methods. This score considered the average p-value (mean(−1og10(p)); avg_pval); 2) number (or frequency) of rewired clusters linked to a given drug (freq_cluster); and 3) frequency of mediator involvement (freq_mediator). Rankings of clusters by these criteria individually (rank.pval, rank.freq_drug, rank.freq_mediator) as well as overall (rank.sum = sum of the ranks, rank.overall = rank based on sum.ranks) are listed.

| Drug.Name | Mean (−log10(p)) | freq_cluster | freq_mediator | rank.pval | rank.freq_cluster | rank.freq_mediator | rank.sum | rank.overall |
|---|---|---|---|---|---|---|---|---|
| AZD6482 | 2.595 | 6 | 16 | 14 | 8 | 5 | 27 | 1 |
| BRD-K34222889 | 2.303 | 6 | 11 | 24 | 8 | 15 | 47 | 2 |
| I-BET151 | 2.072 | 7 | 18 | 43 | 2 | 2 | 47 | 2 |
| indisulam | 1.971 | 7 | 22 | 57 | 2 | 1 | 60 | 4 |
| MK-1775 | 1.991 | 8 | 14 | 55 | 1 | 8 | 64 | 5 |
| momelotinib | 1.994 | 6 | 11 | 53 | 8 | 15 | 76 | 6 |
| apicidin | 2.626 | 4 | 9 | 11 | 37 | 29 | 77 | 7 |
| entinostat | 2.127 | 6 | 9 | 40 | 8 | 29 | 77 | 7 |
| TG-101348 | 2.146 | 5 | 9 | 37 | 16 | 29 | 82 | 9 |
| BRD-K11533227 | 1.917 | 7 | 12 | 69 | 2 | 12 | 83 | 10 |
| ML083 | 2.061 | 5 | 10 | 44 | 16 | 23 | 83 | 10 |
| chlorambucil | 2.027 | 5 | 9 | 49 | 16 | 29 | 94 | 12 |
| AZD7545 | 2.616 | 4 | 7 | 12 | 37 | 48 | 97 | 13 |
| VER-155008 | 2.876 | 5 | 6 | 7 | 16 | 76 | 99 | 14 |
| austocystin D | 2.164 | 5 | 7 | 36 | 16 | 48 | 100 | 15 |
| fumonisin B1 | 1.969 | 4 | 14 | 58 | 37 | 8 | 103 | 16 |
| NSC95397 | 1.899 | 5 | 11 | 75 | 16 | 15 | 106 | 17 |
| cytarabine hydrochloride | 1.819 | 7 | 12 | 94 | 2 | 12 | 108 | 18 |
| 16-beta-bromoandrosterone | 1.972 | 5 | 8 | 56 | 16 | 38 | 110 | 19 |
| crizotinib | 1.807 | 7 | 12 | 98 | 2 | 12 | 112 | 20 |
| AA-COCF3 | 2.164 | 3 | 11 | 35 | 64 | 15 | 114 | 21 |
| Ch-55 | 2.356 | 3 | 9 | 21 | 64 | 29 | 114 | 21 |
| ABT-199 | 2.912 | 3 | 7 | 6 | 64 | 48 | 118 | 23 |
| brivanib | 1.864 | 6 | 10 | 87 | 8 | 23 | 118 | 23 |
| dabrafenib | 1.859 | 5 | 11 | 88 | 16 | 15 | 119 | 25 |
| tivozanib | 1.899 | 4 | 14 | 74 | 37 | 8 | 119 | 25 |
| pevonedistat | 2.141 | 4 | 7 | 38 | 37 | 48 | 123 | 27 |
| NSC30930 | 2.132 | 4 | 7 | 39 | 37 | 48 | 124 | 28 |
| hyperforin | 1.879 | 4 | 15 | 83 | 37 | 6 | 126 | 29 |
| WAY-362450 | 1.761 | 6 | 13 | 112 | 8 | 11 | 131 | 30 |
| XL765 | 2.449 | 3 | 7 | 19 | 64 | 48 | 131 | 30 |
| mitomycin | 2.342 | 3 | 7 | 22 | 64 | 48 | 134 | 32 |
| BRD-K63431240 | 1.913 | 4 | 9 | 70 | 37 | 29 | 136 | 33 |
| necrostatin-1 | 2.002 | 4 | 7 | 51 | 37 | 48 | 136 | 33 |
| PDMP | 1.818 | 5 | 9 | 96 | 16 | 29 | 141 | 35 |
| necrostatin-7 | 2.215 | 3 | 7 | 30 | 64 | 48 | 142 | 36 |
| B02 | 2.661 | 3 | 6 | 9 | 64 | 76 | 149 | 37 |
| PIK-93 | 2.507 | 4 | 5 | 17 | 37 | 95 | 149 | 37 |
| isoevodiamine | 1.885 | 4 | 8 | 81 | 37 | 38 | 156 | 39 |
| tosedostat | 1.871 | 3 | 15 | 86 | 64 | 6 | 156 | 39 |
| PL-DI | 1.818 | 5 | 7 | 95 | 16 | 48 | 159 | 41 |
| teniposide | 2.035 | 3 | 7 | 47 | 64 | 48 | 159 | 41 |
| KU 0060648 | 1.724 | 5 | 10 | 121 | 16 | 23 | 160 | 43 |
| PLX-4720 | 1.666 | 6 | 11 | 140 | 8 | 15 | 163 | 44 |

TABLE 3-continued

Small molecule scores. Drugs were sorted according to their rewiring scores as defined in Methods. This score considered the average p-value (mean(−log10(p)); avg_pval); 2) number (or frequency) of rewired clusters linked to a given drug (freq_cluster); and 3) frequency of mediator involvement (freq_mediator). Rankings of clusters by these criteria individually (rank.pval, rank.freq_drug, rank.freq_mediator) as well as overall (rank.sum = sum of the ranks, rank.overall = rank based on sum.ranks) are listed.

| Drug.Name | Mean (−log10(p)) | freq_cluster | freq_mediator | rank.pval | rank.freq_cluster | rank.freq_mediator | rank.sum | rank.overall |
|---|---|---|---|---|---|---|---|---|
| tipifarnib-P2 | 1.886 | 4 | 7 | 80 | 37 | 48 | 165 | 45 |
| BRD1812 | 1.734 | 6 | 8 | 120 | 8 | 38 | 166 | 46 |
| CAY10594 | 1.899 | 3 | 9 | 76 | 64 | 29 | 169 | 47 |
| PHA-793887 | 1.680 | 5 | 11 | 138 | 16 | 15 | 169 | 47 |
| barasertib | 1.875 | 4 | 7 | 85 | 37 | 48 | 170 | 49 |
| sotrastaurin | 1.638 | 5 | 17 | 152 | 16 | 4 | 172 | 50 |
| SGX-523 | 1.858 | 4 | 7 | 89 | 37 | 48 | 174 | 51 |
| BRD-K80183349 | 1.953 | 3 | 7 | 64 | 64 | 48 | 176 | 52 |
| ML239 | 1.945 | 3 | 7 | 65 | 64 | 48 | 177 | 53 |
| BRD-K03536150 | 2.038 | 3 | 6 | 46 | 64 | 76 | 186 | 54 |
| UNC0321 | 1.644 | 5 | 10 | 147 | 16 | 23 | 186 | 54 |
| quizartinib | 1.783 | 4 | 7 | 102 | 37 | 48 | 187 | 56 |
| ABT-737 | 1.723 | 4 | 9 | 123 | 37 | 29 | 189 | 57 |
| ibrutinib | 1.574 | 7 | 11 | 173 | 2 | 15 | 190 | 58 |
| imatinib | 2.191 | 3 | 5 | 31 | 64 | 95 | 190 | 58 |
| GSK-3 inhibitor IX | 1.683 | 5 | 8 | 137 | 16 | 38 | 191 | 60 |
| PYR-41 | 2.721 | 3 | 4 | 8 | 64 | 123 | 195 | 61 |
| BYL-719 | 1.878 | 3 | 7 | 84 | 64 | 48 | 196 | 62 |
| NVP-231 | 1.557 | 5 | 18 | 182 | 16 | 2 | 200 | 63 |
| BRD-K02492147 | 1.642 | 5 | 8 | 150 | 16 | 38 | 204 | 64 |
| belinostat | 1.659 | 5 | 7 | 141 | 16 | 48 | 205 | 65 |
| erismodegib | 1.834 | 4 | 6 | 92 | 37 | 76 | 205 | 65 |
| ML311 | 1.637 | 5 | 8 | 153 | 16 | 38 | 207 | 67 |
| RO4929097 | 1.581 | 5 | 10 | 169 | 16 | 23 | 208 | 68 |
| vorapaxar | 2.001 | 2 | 7 | 52 | 110 | 48 | 210 | 69 |
| elocalcitol | 1.791 | 4 | 6 | 101 | 37 | 76 | 214 | 70 |
| GSK4112 | 1.658 | 4 | 8 | 142 | 37 | 38 | 217 | 71 |
| purmorphamine | 1.889 | 3 | 6 | 78 | 64 | 76 | 218 | 72 |
| canertinib | 2.187 | 3 | 4 | 32 | 64 | 123 | 219 | 73 |
| tamoxifen | 2.536 | 2 | 5 | 16 | 110 | 95 | 221 | 74 |
| BRD-K26531177 | 1.941 | 3 | 5 | 67 | 64 | 95 | 226 | 75 |
| OSI-930 | 1.845 | 3 | 6 | 91 | 64 | 76 | 231 | 76 |
| tretinoin | 3.025 | 2 | 4 | 4 | 110 | 123 | 237 | 77 |
| PF-573228 | 1.635 | 4 | 7 | 154 | 37 | 48 | 239 | 78 |
| PRIMA-1-Met | 1.710 | 4 | 6 | 127 | 37 | 76 | 240 | 79 |
| bexarotene | 1.553 | 5 | 8 | 188 | 16 | 38 | 242 | 80 |
| MK-2206 | 1.762 | 4 | 5 | 111 | 37 | 95 | 243 | 81 |
| valdecoxib | 1.778 | 3 | 6 | 107 | 64 | 76 | 247 | 82 |
| STF-31 | 1.649 | 3 | 8 | 146 | 64 | 38 | 248 | 83 |
| ML029 | 1.755 | 3 | 6 | 113 | 64 | 76 | 253 | 84 |
| SRT-1720 | 1.754 | 3 | 6 | 114 | 64 | 76 | 254 | 85 |
| ML031 | 1.524 | 4 | 10 | 196 | 37 | 23 | 256 | 86 |
| tacedinaline | 1.566 | 4 | 7 | 177 | 37 | 48 | 262 | 87 |
| pluripotin | 1.780 | 3 | 5 | 104 | 64 | 95 | 263 | 88 |
| tubastatin A | 1.890 | 2 | 6 | 77 | 110 | 76 | 263 | 88 |
| KW-2449 | 1.715 | 3 | 6 | 125 | 64 | 76 | 265 | 90 |
| ciclopirox | 1.957 | 2 | 5 | 62 | 110 | 95 | 267 | 91 |
| ruxolitinib | 1.773 | 3 | 5 | 108 | 64 | 95 | 267 | 91 |
| IU1 | 1.554 | 4 | 7 | 186 | 37 | 48 | 271 | 93 |
| CD-437 | 1.554 | 4 | 7 | 187 | 37 | 48 | 272 | 94 |
| WP1130 | 1.689 | 3 | 6 | 134 | 64 | 76 | 274 | 95 |
| NSC19630 | 1.846 | 3 | 4 | 90 | 64 | 123 | 277 | 96 |
| JQ-1 | 1.597 | 3 | 7 | 166 | 64 | 48 | 278 | 97 |
| HLI 373 | 1.824 | 2 | 6 | 93 | 110 | 76 | 279 | 98 |
| PF-750 | 1.528 | 4 | 7 | 195 | 37 | 48 | 280 | 99 |
| MGCD-265 | 1.654 | 3 | 6 | 143 | 64 | 76 | 283 | 100 |
| GDC-0879 | 1.903 | 3 | 3 | 73 | 64 | 147 | 284 | 101 |
| BRD-K27188169 | 1.714 | 3 | 5 | 126 | 64 | 95 | 285 | 102 |
| GSK2636771 | 1.700 | 3 | 5 | 129 | 64 | 95 | 288 | 103 |
| temozolomide | 1.959 | 2 | 4 | 60 | 110 | 123 | 293 | 104 |
| vorinostat | 1.616 | 3 | 6 | 156 | 64 | 76 | 296 | 105 |
| etomoxir | 1.521 | 3 | 8 | 198 | 64 | 38 | 300 | 106 |
| Ko-143 | 1.813 | 3 | 3 | 97 | 64 | 147 | 308 | 107 |
| YL54 | 1.782 | 2 | 5 | 103 | 110 | 95 | 308 | 107 |
| cytochalasin B | 1.519 | 3 | 7 | 199 | 64 | 48 | 311 | 109 |
| axitinib | 1.888 | 2 | 4 | 79 | 110 | 123 | 312 | 110 |
| BRD-K61166597 | 1.508 | 3 | 7 | 203 | 64 | 48 | 315 | 111 |
| PD 153035 | 2.450 | 2 | 2 | 18 | 110 | 187 | 315 | 111 |
| LE-135 | 1.615 | 3 | 5 | 158 | 64 | 95 | 317 | 113 |
| BRD-K37390332 | 1.954 | 2 | 3 | 63 | 110 | 147 | 320 | 114 |
| tacrolimus | 1.609 | 3 | 5 | 162 | 64 | 95 | 321 | 115 |
| BRD-K51490254 | 1.555 | 3 | 6 | 184 | 64 | 76 | 324 | 116 |

TABLE 3-continued

Small molecule scores. Drugs were sorted according to their rewiring scores as defined in Methods. This score considered the average p-value (mean(−1og10(p)); avg_pval); 2) number (or frequency) of rewired clusters linked to a given drug (freq_cluster); and 3) frequency of mediator involvement (freq_mediator). Rankings of clusters by these criteria individually (rank.pval, rank.freq_drug, rank.freq_mediator) as well as overall (rank.sum = sum of the ranks, rank.overall = rank based on sum.ranks) are listed.

| Drug.Name | Mean (−log10(p)) | freq_cluster | freq_mediator | rank.pval | rank.freq_cluster | rank.freq_mediator | rank.sum | rank.overall |
|---|---|---|---|---|---|---|---|---|
| ML203 | 2.233 | 2 | 2 | 28 | 110 | 187 | 325 | 117 |
| OSI-027 | 2.179 | 2 | 2 | 33 | 110 | 187 | 330 | 118 |
| afatinib | 2.174 | 2 | 2 | 34 | 110 | 187 | 331 | 119 |
| KH-CB19 | 4.000 | 1 | 3 | 1 | 188 | 147 | 336 | 120 |
| BRD-K13999467 | 1.696 | 2 | 5 | 132 | 110 | 95 | 337 | 121 |
| bosutinib | 3.398 | 1 | 3 | 3 | 188 | 147 | 338 | 122 |
| PF-4800567 hydrochloride | 1.883 | 2 | 3 | 82 | 110 | 147 | 339 | 123 |
| BRD-K90370028 | 2.043 | 2 | 2 | 45 | 110 | 187 | 342 | 124 |
| tamatinib | 2.602 | 1 | 3 | 13 | 188 | 147 | 348 | 125 |
| BRD-K99584050 | 1.550 | 3 | 5 | 190 | 64 | 95 | 349 | 126 |
| BRD-A94377914 | 1.735 | 2 | 4 | 118 | 110 | 123 | 351 | 127 |
| piperlongumine | 1.804 | 2 | 3 | 99 | 110 | 147 | 356 | 128 |
| foretinib | 1.581 | 2 | 6 | 171 | 110 | 76 | 357 | 129 |
| BRD-K28456706 | 1.512 | 3 | 5 | 201 | 64 | 95 | 360 | 130 |
| CHIR-99021 | 1.623 | 2 | 5 | 155 | 110 | 95 | 360 | 130 |
| masitinib | 1.706 | 2 | 4 | 128 | 110 | 123 | 361 | 132 |
| lapatinib | 1.779 | 2 | 3 | 105 | 110 | 147 | 362 | 133 |
| CAY10576 | 1.778 | 2 | 3 | 106 | 110 | 147 | 363 | 134 |
| Compound 7d-cis | 1.694 | 2 | 4 | 133 | 110 | 123 | 366 | 135 |
| PRL-3 inhibitor I | 1.772 | 2 | 3 | 109 | 110 | 147 | 366 | 135 |
| BIBR-1532 | 1.586 | 2 | 5 | 168 | 110 | 95 | 373 | 137 |
| SU11274 | 1.551 | 3 | 4 | 189 | 64 | 123 | 376 | 138 |
| JW-74 | 1.652 | 2 | 4 | 144 | 110 | 123 | 377 | 139 |
| UNC0638 | 1.943 | 1 | 4 | 66 | 188 | 123 | 377 | 139 |
| Platin | 1.644 | 2 | 4 | 148 | 110 | 123 | 381 | 141 |
| compound 1B | 1.560 | 2 | 5 | 181 | 110 | 95 | 386 | 142 |
| sunitinib | 1.614 | 2 | 4 | 160 | 110 | 123 | 393 | 143 |
| tipifarnib-P1 | 1.494 | 3 | 4 | 206 | 64 | 123 | 393 | 143 |
| IC-87114 | 1.611 | 2 | 4 | 161 | 110 | 123 | 394 | 145 |
| BRD6340 | 2.377 | 1 | 2 | 20 | 188 | 187 | 395 | 146 |
| AT7867 | 1.548 | 2 | 5 | 191 | 110 | 95 | 396 | 147 |
| ML258 | 1.959 | 1 | 3 | 61 | 188 | 147 | 396 | 147 |
| Repligen 136 | 1.602 | 2 | 4 | 164 | 110 | 123 | 397 | 149 |
| RITA | 2.337 | 1 | 2 | 23 | 188 | 187 | 398 | 150 |
| TPCA-1 | 1.594 | 2 | 4 | 167 | 110 | 123 | 400 | 151 |
| itraconazole | 1.523 | 2 | 5 | 197 | 110 | 95 | 402 | 152 |
| SB-431542 | 1.651 | 2 | 3 | 145 | 110 | 147 | 402 | 152 |
| BRD9647 | 2.229 | 1 | 2 | 29 | 188 | 187 | 404 | 154 |
| epigallocatechin-3-monogallate | 1.643 | 2 | 3 | 149 | 110 | 147 | 406 | 155 |
| fingolimod | 1.510 | 2 | 5 | 202 | 110 | 95 | 407 | 156 |
| AZD1480 | 1.738 | 2 | 2 | 117 | 110 | 187 | 414 | 157 |
| SJ-172550 | 1.615 | 2 | 3 | 157 | 110 | 147 | 414 | 157 |
| BMS-195614 | 3.699 | 1 | 1 | 2 | 188 | 225 | 415 | 159 |
| nutlin-3 | 2.092 | 1 | 2 | 41 | 188 | 187 | 416 | 160 |
| avrainvillamide | 2.076 | 1 | 2 | 42 | 188 | 187 | 417 | 161 |
| BRD-K17060750 | 3.000 | 1 | 1 | 5 | 188 | 225 | 418 | 162 |
| serdemetan | 1.555 | 2 | 4 | 185 | 110 | 123 | 418 | 162 |
| BRD-K24690302 | 1.606 | 2 | 3 | 163 | 110 | 147 | 420 | 164 |
| bardoxolone methyl | 1.601 | 2 | 3 | 165 | 110 | 147 | 422 | 165 |
| BRD8899 | 2.658 | 1 | 1 | 10 | 188 | 225 | 423 | 166 |
| nilotinib | 2.032 | 1 | 2 | 48 | 188 | 187 | 423 | 166 |
| BMS-536924 | 1.454 | 2 | 5 | 219 | 110 | 95 | 424 | 168 |
| BRD-K66532283 | 2.009 | 1 | 2 | 50 | 188 | 187 | 425 | 169 |
| AZD4547 | 1.581 | 2 | 3 | 170 | 110 | 147 | 427 | 170 |
| BRD-K71781559 | 1.451 | 2 | 5 | 222 | 110 | 95 | 427 | 170 |
| BRD-K55473186 | 2.553 | 1 | 1 | 15 | 188 | 225 | 428 | 172 |
| pyrazolanthrone | 1.991 | 1 | 2 | 54 | 188 | 187 | 429 | 173 |
| RG-108 | 1.438 | 2 | 5 | 224 | 110 | 95 | 429 | 173 |
| MLN2480 | 1.573 | 2 | 3 | 174 | 110 | 147 | 431 | 175 |
| BMS-270394 | 1.567 | 2 | 3 | 175 | 110 | 147 | 432 | 176 |
| decitabine | 1.518 | 2 | 4 | 200 | 110 | 123 | 433 | 177 |
| neratinib | 1.685 | 2 | 2 | 136 | 110 | 187 | 433 | 177 |
| MI-2 | 1.565 | 2 | 3 | 178 | 110 | 147 | 435 | 179 |
| tigecycline | 1.564 | 2 | 3 | 179 | 110 | 147 | 436 | 180 |
| CBB-1007 | 2.284 | 1 | 1 | 25 | 188 | 225 | 438 | 181 |
| ETP-46464 | 2.284 | 1 | 1 | 25 | 188 | 225 | 438 | 181 |
| AC55649 | 2.237 | 1 | 1 | 27 | 188 | 225 | 440 | 183 |
| semagacestat | 1.381 | 2 | 5 | 236 | 110 | 95 | 441 | 184 |
| dasatinib | 1.921 | 1 | 2 | 68 | 188 | 187 | 443 | 185 |
| cabozantinib | 1.482 | 2 | 4 | 212 | 110 | 123 | 445 | 186 |

TABLE 3-continued

Small molecule scores. Drugs were sorted according to their rewiring scores as defined in Methods. This score considered the average p-value (mean(−log10(p)); avg_pval); 2) number (or frequency) of rewired clusters linked to a given drug (freq_cluster); and 3) frequency of mediator involvement (freq_mediator). Rankings of clusters by these criteria individually (rank.pval, rank.freq_drug, rank.freq_mediator) as well as overall (rank.sum = sum of the ranks, rank.overall = rank based on sum.ranks) are listed.

| Drug.Name | Mean (−log10(p)) | freq_cluster | freq_mediator | rank.pval | rank.freq_cluster | rank.freq_mediator | rank.sum | rank.overall |
|---|---|---|---|---|---|---|---|---|
| fluorouracil | 1.364 | 2 | 5 | 240 | 110 | 95 | 445 | 186 |
| pifithrin-mu | 1.764 | 1 | 3 | 110 | 188 | 147 | 445 | 186 |
| gefitinib | 1.910 | 1 | 2 | 71 | 188 | 187 | 446 | 189 |
| BIRB-796 | 1.541 | 2 | 3 | 192 | 110 | 147 | 449 | 190 |
| PF-543 | 1.338 | 2 | 5 | 245 | 110 | 95 | 450 | 191 |
| skepinone-L | 1.724 | 1 | 3 | 122 | 188 | 147 | 457 | 192 |
| AZD8055 | 1.507 | 2 | 3 | 204 | 110 | 147 | 461 | 193 |
| tanespimycin | 1.492 | 2 | 3 | 208 | 110 | 147 | 465 | 194 |
| nintedanib | 1.473 | 2 | 3 | 214 | 110 | 147 | 471 | 195 |
| thalidomide | 1.967 | 1 | 1 | 59 | 188 | 225 | 472 | 196 |
| istradefylline | 1.463 | 2 | 3 | 216 | 110 | 147 | 473 | 197 |
| Ki8751 | 1.364 | 2 | 4 | 241 | 110 | 123 | 474 | 198 |
| BRD-K07442505 | 1.796 | 1 | 2 | 100 | 188 | 187 | 475 | 199 |
| PF-184 | 1.334 | 2 | 4 | 246 | 110 | 123 | 479 | 200 |
| CCT036477 | 1.575 | 1 | 4 | 172 | 188 | 123 | 483 | 201 |
| pitstop2 | 1.429 | 2 | 3 | 226 | 110 | 147 | 483 | 201 |
| CIL41 | 1.907 | 1 | 1 | 72 | 188 | 225 | 485 | 203 |
| spautin-1 | 1.638 | 1 | 3 | 151 | 188 | 147 | 486 | 204 |
| pandacostat | 1.418 | 2 | 3 | 230 | 110 | 147 | 487 | 205 |
| carboplatin | 1.415 | 2 | 3 | 231 | 110 | 147 | 488 | 206 |
| BRD-K92856060 | 1.391 | 2 | 3 | 233 | 110 | 147 | 490 | 207 |
| COL-3 | 1.745 | 1 | 2 | 115 | 188 | 187 | 490 | 207 |
| MK-0752 | 1.387 | 2 | 3 | 235 | 110 | 147 | 492 | 209 |
| BRD-K50799972 | 1.735 | 1 | 2 | 119 | 188 | 187 | 494 | 210 |
| BRD-K33199242 | 1.375 | 2 | 3 | 238 | 110 | 147 | 495 | 211 |
| SB-525334 | 1.717 | 1 | 2 | 124 | 188 | 187 | 499 | 212 |
| NVP-BEZ235 | 1.699 | 1 | 2 | 130 | 188 | 187 | 505 | 213 |
| lenvatinib | 1.567 | 1 | 3 | 176 | 188 | 147 | 511 | 214 |
| myricetin | 1.469 | 2 | 2 | 215 | 110 | 187 | 512 | 215 |
| BIX-01294 | 1.454 | 2 | 2 | 220 | 110 | 187 | 517 | 216 |
| BRD-K88742110 | 1.454 | 2 | 2 | 221 | 110 | 187 | 518 | 217 |
| O-6-benzylguanine | 1.447 | 2 | 2 | 223 | 110 | 187 | 520 | 218 |
| BRD-A71883111 | 1.421 | 2 | 2 | 229 | 110 | 187 | 526 | 219 |
| saracatinib | 1.745 | 1 | 1 | 115 | 188 | 225 | 528 | 220 |
| BRD-K09587429 | 1.407 | 2 | 2 | 232 | 110 | 187 | 529 | 221 |
| EX-527 | 1.697 | 1 | 1 | 131 | 188 | 225 | 544 | 222 |
| BRD-K16147474 | 1.484 | 1 | 3 | 211 | 188 | 147 | 546 | 223 |
| BRD-K99006945 | 1.688 | 1 | 1 | 135 | 188 | 225 | 548 | 224 |
| sildenafil | 1.310 | 2 | 2 | 251 | 110 | 187 | 548 | 224 |
| simvastatin | 1.680 | 1 | 1 | 139 | 188 | 225 | 552 | 226 |
| marinopyrrole A | 1.556 | 1 | 2 | 183 | 188 | 187 | 558 | 227 |
| VU0155056 | 1.431 | 1 | 3 | 225 | 188 | 147 | 560 | 228 |
| ISOX | 1.539 | 1 | 2 | 193 | 188 | 187 | 568 | 229 |
| BRD-A02303741 | 1.538 | 1 | 2 | 194 | 188 | 187 | 569 | 230 |
| CIL55 | 1.614 | 1 | 1 | 159 | 188 | 225 | 572 | 231 |
| BRD-K14844214 | 1.343 | 1 | 3 | 243 | 188 | 147 | 578 | 232 |
| alisertib | 1.474 | 1 | 2 | 213 | 188 | 187 | 588 | 233 |
| Mdivi-1 | 1.457 | 1 | 2 | 217 | 188 | 187 | 592 | 234 |
| BEC | 1.562 | 1 | 1 | 180 | 188 | 225 | 593 | 235 |
| Compound 1541A | 1.381 | 1 | 2 | 237 | 188 | 187 | 612 | 236 |
| nelarabine | 1.374 | 1 | 2 | 239 | 188 | 187 | 614 | 237 |
| ciclosporin | 1.355 | 1 | 2 | 242 | 188 | 187 | 617 | 238 |
| dexamethasone | 1.499 | 1 | 1 | 205 | 188 | 225 | 618 | 239 |
| linsitinib | 1.493 | 1 | 1 | 207 | 188 | 225 | 620 | 240 |
| BRD-K03911514 | 1.491 | 1 | 1 | 209 | 188 | 225 | 622 | 241 |
| BRD-K29313308 | 1.485 | 1 | 1 | 210 | 188 | 225 | 623 | 242 |
| trametinib | 1.306 | 1 | 2 | 252 | 188 | 187 | 627 | 243 |
| azacitidine | 1.456 | 1 | 1 | 218 | 188 | 225 | 631 | 244 |
| GSK1059615 | 1.426 | 1 | 1 | 227 | 188 | 225 | 640 | 245 |
| A-804598 | 1.425 | 1 | 1 | 228 | 188 | 225 | 641 | 246 |
| BCL-LZH-4 | 1.390 | 1 | 1 | 234 | 188 | 225 | 647 | 247 |
| vandetanib | 1.341 | 1 | 1 | 244 | 188 | 225 | 657 | 248 |
| BRD-K79669418 | 1.334 | 1 | 1 | 247 | 188 | 225 | 660 | 249 |
| BRD-K48477130 | 1.320 | 1 | 1 | 248 | 188 | 225 | 661 | 250 |
| TG-100-115 | 1.313 | 1 | 1 | 249 | 188 | 225 | 662 | 251 |
| VAF-347 | 1.312 | 1 | 1 | 250 | 188 | 225 | 663 | 252 |

Gene set enrichment analysis: Gene set enrichment analysis (GSEA) was performed using fgsea (Sergushichev A A. *bioRxiv.* 2016, 060012), adapted from the original description (Subramanian A et al. *Proc Natl Acad Sci USA.* 2005, 102, 15545-15550). Gene Ontology (Ashburner M et al. *Nat Genet.* 2000, 25, 25-29; The Gene Ontology Consortium.

*Nucleic Acids Res.* 2017, 45, D331-D338) biological processes were retrieved from the molecular signatures database (MSigDB) (Liberzon A et al. *Bioinformatics.* 2011, 27, 1739-1740; Subramanian A et al. *Proc Natl Acad Sci USA.* 2005, 102, 15545-15550).

Global transcriptome analysis: Total RNA isolated from PAECs treated with IL-1β and vehicle or I-BET762 using RNeasy kit (Qiagen) according to manufacturer's instruction and were analyzed to determine global transcriptome expression using Affymetrix Clariom S array. The gene expression was normalized with Robust Multiarray Analysis (RMA). For BRD2889, the same approach was employed using Affymetrix Clariom S array on RNA isolated from PAECs treated with BRD2889 or vehicle and subjected to either hypoxia or normoxia. Differentially expressed genes were defined as any gene for which the FDR adjusted p-value was below 0.05 (n=3/grp). Reversed genes were further defined as those genes that were differentially expressed in both (hypoxia versus normoxia) and in (hypoxia+BRD2889 versus hypoxia)+vehicle as well as were regulated in opposite directions. Similarly, for I-BET that were differentially expressed in IL-1β+VC versus control and IL-1β+I-BET versus IL-1β+VC and were regulated in opposite directions. The data for both I-BET and BRD2889 have been submitted to the NCBI Gene Expression Omnibus with accession numbers GSE125508 and GSE160255, respectively.

RT-qPCR analysis: Cells were lysis in 1 ml of QiaZol reagent (Qiagen). Total RNA content was extracted using the RNeasy kit (Qiagen), according to the manufacturer's instructions. Total RNA concentration was determined using a BioTek Synergy multimode plate reader. Messenger RNAs were reverse transcribed to generate cDNA using the Multiscript RT kit (Thermo Fisher Scientific). cDNA for specific gene targets was amplified and quantified via fluorescently-labeled Taqman primer sets and Taqman fast advanced master mix (Thermo Fisher Scientific) using an Applied Biosystems QuantStudio 6 Flex Real-Time PCR System. Taqman primers used for RT-qPCR are listed in Table 5.

Protein stability assay: The proteasome inhibitor MG132 (M7449, Sigma) was stored at −20° C. at a concentration of 10 mM diluted in dimethyl sulfoxide (DMSO). PAECs were exposed to MG132 (5 mM) vs. DMSO vehicle control for 2 hr under hypoxia, prior to harvesting of cellular lysate for immunoblotting.

Proximity ligation assay: A Duolink PLA assay was developed according to the manufacturer's instructions (Sigma Aldrich, DUO96020). Briefly, PAECs were grown on coverslips, and then blocked for 1 hr with Duolink Blocking Solution. Samples were then stained with the indicated antibodies (anti-Integrin 3 (E-8), Santa Cruz Biotechnology, sc-393298; anti-Galectin 8/Gal-8 antibody, Abcam, ab109519; and normal Goat IgG Control, R&D Systems, AB-108-C) overnight at 4° C., diluted 1:100 in Duolink Antibody Diluent. PLUS and MINUS secondary PLA probes against rabbit and mouse IgG in Duolink® Antibody Diluent were added, and the cells were incubated at 37° C. for 1 h with, followed by incubation with ligation mix for 30 min at 37° C. Amplification mix was then applied for 100 min at 37° C. The coverslips were mounted on microscope slides with Duolink Mounting Medium with Dapi, and the cells photographed under a fluorescence microscope.

Mitochondrial function assays: Baseline mitochondrial function and mitochondrial stress response were measured by oxygen consumption rate (OCR) using the Cell Mito Stress Kit with a XF24 extracellular flux analyzer (SeaHorse Bioscience, North Billerica, MA) following manufacturer's instructions. Briefly, 30,000 cells per well were grown overnight and, for OCR measurements, washed with XF assay medium (SeaHorse Bioscience) containing 10 mM Glucose, 1 mM Sodium-Pyruvate and 2 mM L-Glutamine set to pH=7.40. OCR was measured over time at baseline and following consecutive injections of 1 μM Oligomycin, 1 μM FCCP and a mix of 1 μM Rotenone+1 μM Antimycin A. Following the manufacturer's instructions, maximal mitochondrial respiration was determined as OCR following FCCP (Carbonylcyan ideptrifluoromethoxyphenylhydrazone) injection. Spare respiratory capacity was defined as ΔOCRFCCP-baseline and mitochondrial ATP production as ΔOCR Baseline-Oligomycin. For extracellular acidification rate (ECAR) measurements cells were washed in glucose-free XF base medium (Seahorse Bioscience) containing 2 mM L-Glutamine at pH 7.35. ECAR was determined after serial injections with 10 mM D-Glucose, 1 μM Oligomycin, and 100 mM 2-Deoxyglucose.

Mitochondria isolation: Mitochondrial fraction from cultured PAECs with drug and siGSTP1 using the Mammalian Mitochondria Isolation Kit for Tissue & Cultured Cells (Biovision, Inc.) according to the manufacturer's instructions.

Measurement of mitochondrial complex activities: Complex I activity of isolated mitochondria were measured using Complex I Enzyme Activity Microplate assay kit (Abcam, ab109721) according to the manufacturer's protocol. These enzymes were captured within the wells of the microplate coated by the corresponding complex enzyme antibody, and activities were detected colorimetrically.

Flow cytometry detection of mitochondrial superoxide: For measuring mitochondrial superoxide, cells were incubated with 5 μM of MitoSOX Red mitochondrial superoxide indicator (Thermo Fisher Scientific) for 10 min in 37° C. $CO_2$ incubator. Next, cells were washed with 1×PBS, trypsinized, and fluorescence (488 nm/580 nm) was measured on flow analyzer (BD LSR FORTESSA or BD LSRII) using BD FACSDIVA software.

Cellular apoptosis: Caspase-3/7 activity was quantified using the Caspase-Glo 3/7 Assay (Promega), according to manufacturer's instructions. Caspase-3/7 activity was normalized to total protein content determined by BCA method (Thermo Fisher Scientific).

BrdU growth assay: Cell proliferation was assayed relative to day 0 using a BrdU Cell Proliferation Assay Kit (#6813, Cell Signaling) according to the manufacturer's protocol after incubation for 2 h with BrdU.

Lentivirus production: HEK293 cells were transfected using Lipofectamine 2000 (Invitrogen) with indicated lentiviral plasmids along with packaging plasmids (pPACK, System Biosciences), according to the manufacturer's instructions. Virus was harvested, sterile filtered (0.22 μm), titered via serial dilution and visualization of GFP expression, and utilized for subsequent infection of PAECs for gene transduction.

Immunoblot and densitometry: Cells were lysed in RIPA buffer (Sigma) along with 1× protease inhibitor cocktail (Sigma). Protein lysate was resolved by gradient 4%-15% SDS-PAGE gels and transferred onto a 0.2 μm PVDF membrane (Bio-Rad). Membranes were blocked in 5% non-fat milk in 1×PBST buffer for one hour at room temperature. Later, they were incubated in the presence of the primary antibody overnight at 4° C. and then appropriate HRP-conjugated secondary antibodies (Life Technologies). The following antibodies were used: human LGALS8 (AF1305, RnD Systems), mouse/rat Lgals8 (ab69631, Abcam), pSTAT1 (ab29045, Abcam) and STAT1 (ab47425, Abcam), GSTP1 (ab153949, Abcam), ISCU (14812-1-AP, Prointech), Glutathione (ab19534, Abcam), HIF2A (NB100-122, Novous), α-Tubulin (CP06, Millipore sigma), and ACTB (sc-47778, Santa Cruz). The immunoreactive bands were visualized with the Chemidoc XRS+system (Bio-Rad) using SuperSignal West Femto chemiluminescent substrates (Thermo Fisher Scientific). The images were later quantified using AlphaEaseFC software (Alpha Innotech).

Plasmids: To construct a lentiviral plasmid carrying a GSTP1 transgene, oligonucleotides were synthesized by Integrated DNA Technologies. The primer sequences were as follows: forward, CGGGATCCCATGCCGCCCTA-CACCGTGGTG (SEQ ID NO: 1) and reverse, AGTT-TAGCGGCCGCGTCAGTGGTGGTGGTGGTGGTGCT-GTTTCCCGTT (SEQ ID NO: 2). The GSTP1 PCR products were amplified from a purchased plasmid (RG2030086, OriGene Technologies) and cloned into the vector pCDH-CMV (CD511B-1, System Biosciences) at the BamHI (underlined)/NotI (underlined) sites. Appropriate GSTP1 sequence was confirmed in comparison to sequence reference GenBank: NM_000852.4. The control lentiviral vector expressing GFP was used as a negative control.

Site-directed mutagenesis: The full-length human ISCU sequence (NCBI accession number BC061903) was used as the reference sequence for wildtype (WT) ISCU and cloned using the primers: forward, CCGGAATTCGACTACAAA-GACGATGACGACAAGATGGCGGCGGCTGGG-GCTTTC (SEQ ID NO: 3); and reverse, CGGGATCCCGT-CATTTCTTCTCTGCCTCTCCTTTTTTGGGTTCTTG (SEQ ID NO: 4).

Via the QuikChange Primer Design tool (Agilent Technologies), mutagenesis forward primers and their reverse complement were then designed to replace the 69th cysteine residue position of ISCU to serine (5'-CATTACGTCAC-CACTTGCTGGAGCCCCCA-3') (SEQ ID NO: 5) or alanine (5'-TGCCGTCGACCCCATTGACGGCAGCACGCT-GATGAGCAAG-3') (SEQ ID NO: 6). Specifically, the codon TGT for Cys69 was replaced by TCT for serine and by GCT for alanine. Site directed mutagenesis was carried out using the QuikChange Lightning Site-Directed Mutagenesis kit (Agilent Technologies, Santa Clara, CA). XL10-Gold Ultracompetent Cells were transformed with the PCR products. The cells were plated on LB agar containing ampicillin (100 μg/mL) and kept at 37° C. overnight. Plasmids were extracted and transformed into BL21 (DE3) competent cells for protein expression and purification. Mutagenesis was confirmed by sequencing and cloned into the vector pCDH-CMV-GFP (CD511B-1, System Biosciences) at the EcoRI (underlined)/BamHI (underlined) sites.

LGALS8 (Galectin-8) ELISA: Human LGALS8 ELISA quantification was performed using a kit (Sigma-Aldrich, RAB1050) according to the manufacturer's instructions.

Measurement of GST activity: The GST activity from lung tissue and PAECs was assayed using GST assay kit (Cayman, MI, USA) per the manufacturer's instructions.

Rodent echocardiography: Echocardiography was performed using a 15-45 MHz transthoracic transducer and a Visual Sonics Vevo 3100 system (Fujifilm). Inhaled isoflurane anesthesia was used at 2% in 100% $O_2$ during positioning and hair removal and then decreased to isoflurane 0.8% during imaging. Digital echocardiograms were analyzed off-line for quantitative analysis as previously described (Bertero T et al. *J Clin Invest.* 2014, 124, 3514-3528).

Immunoprecipitation: PAECs were transfected with the indicated combinations of siRNAs by Lipofectamine 2000 (Thermo Fisher Scientific) according to the manufacturer's instructions and/or treated with BRD2889 (1 mM, 24 h). Whole cell extract (200 μg) of cells were immunoprecipitated with IgG control (1 mg, Abcam), anti-GTSP1 Ab (1 mg, Abcam), anti-GSH Ab (1 mg, Abcam), or anti-ISCU (1 mg, Abcam) and the immune complexes were pulled down with protein A/G agarose beads (Santa Cruz, sc-2003). After extensive washing, the immunoprecipitated proteins were analyzed by immunoblotting with the indicated antibodies.

Immunofluorescent staining: Cryostat sections were cut from OCT-embedded lung tissues at 5-10 μm and mounted on gelatin-coated histological slides. Slides were thawed at room temperature for 10-20 min and rehydrated in wash buffer for 10 minutes. All sections were blocked in 10% donkey serum and exposed to primary antibody and Alexa 488, 568 and 647-conjugated secondary antibodies (Thermo Fisher Scientific). The following primary antibodies were used: Lgals8 (Ab69631, Abcam; 1/200), IL-1β (ab9722, Abcam; 1/200), GSTP1 (ab153949, Abcam; 1:100), ISCU (14812-1-AP, Proteintech; 1:100), cleaved caspase 3 (cs-9661, Cell Signaling; 1/400), α-SMA (F3777, Sigma; 1/200) and CD31 (ab7388, Abcam; 1/200). Images were obtained using Nikon A1 confocal microscope with 40× objective. Small pulmonary vessels (10 vessels/section) that were not associated with bronchial airways were selected for analysis. Intensity of staining was quantified using ImageJ software (NIH). Degree of pulmonary arteriolar muscularization was assessed in OCT lung sections stained for α-SMA by calculation of the proportion of fully and partially muscularized peripheral (<100 μm diameter) pulmonary arteriole to total peripheral pulmonary arterioles (Bertero T et al. *J Clin Invest.* 2014, 124, 3514-3528).

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:

1. A method of treating pulmonary hypertension in a subject in need thereof, the method comprising:

administering a therapeutically effective amount of a pharmaceutical composition to the subject;

wherein the pharmaceutical composition comprises piperlongumine analog BRD-K34222889 or a derivative thereof; and wherein the piperlongumine analog BRD-K34222889 or a derivative thereof has a structure according to Formula I:

Formula I

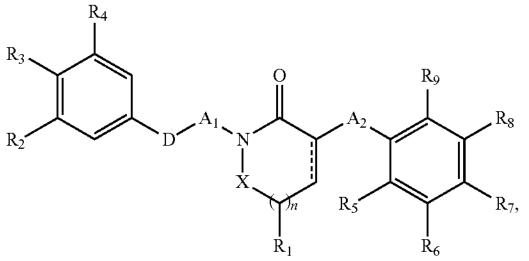

wherein $A_1$ is C(O) or $S(O)_2$;

$A_2$ is —C≡C— or —C(R')═C (R")—, wherein R' and R" are independently hydrogen, $C_1$-$C_6$ alkyl, $C_1$-$C_6$ alkoxy, halogen, or $C_1$-$C_6$ haloalkyl;

X is CH(R"), C(O), SO, $SO_2$, or NR"', wherein R"' is hydrogen, halogen, $C_1$-$C_6$ alkyl, $C_2$-$C_6$ alkenyl, $C_1$-$C_6$ alkoxy, or $C_1$-$C_6$ haloalkyl;

D is —C≡C— or —C(R')═C (R")—, wherein R' and R" are independently selected from hydrogen, $C_1$-$C_6$ alkyl, $C_1$-$C_6$ alkoxy, halogen, or $C_1$-$C_6$ haloalkyl;

$R_1$ is hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, or nitro, and wherein $R_1$ is optionally substituted with one or more groups;

$R_2$, $R_3$, and $R_4$ are independently hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

$R_5$, $R_6$, $R_7$, $R_8$, and $R_9$ are independently hydrogen, halogen, alkyl, haloalkyl, heteroalkyl, alkenyl, haloalkenyl, alkynyl, haloalkynyl, alkoxy, haloalkoxy, amine, alkylamine, amide, alkylamide, hydroxyl, cycloalkyl, heterocycloalkyl, cyano, nitro, carboxyl, ester, hydroxylamine, carbonyl substituted hydroxylamine, or thiol;

n is 1 or 2; and

------- represents a bond that is present or absent;

or a pharmaceutically acceptable salt, ester, or prodrug thereof.

2. The method of claim 1, wherein the pulmonary hypertension is pulmonary arterial hypertension.

3. The method of claim 1, wherein the pharmaceutical composition inhibits or reduces pulmonary arterial endothelial cell (PAEC) apoptosis in a subject in need thereof.

4. The method of claim 1, wherein $A_1$ is C(O) and $A_2$ is —C≡C—.

5. The method of claim 1, wherein X is $CH_2$.

6. The method of claim 1, wherein D is —C(R')═C (R")—, and wherein R' and R" are independently hydrogen or $C_1$-$C_3$ alkyl.

7. The method of claim 1, wherein $R_2$, $R_3$, $R_4$, and $R_7$ are all $C_1$-$C_3$ alkoxy.

8. The method of claim 1, wherein $R_5$, $R_6$, $R_8$, and $R_9$ are all hydrogen.

9. The method of claim 1, further comprising administering at least one additional agent effective to treat pulmonary hypertension.

10. The method of claim 9, wherein the at least one additional agent comprises one or more of phosphodiesterase inhibitors, calcium channel blockers, endothelin receptor antagonists, inotropic agents, prostacyclin pathway agonists, anti-coagulants, guanylate cyclase stimulators, or a combination thereof.

11. The method of claim 1, wherein $R_2$, $R_3$, $R_4$, and $R_7$ are all methoxy.

* * * * *

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
```

-continued

<223> OTHER INFORMATION: Synthetic construct

<400> SEQUENCE: 1
cgggatccca tgccgcccta caccgtggtg                                    30

<210> SEQ ID NO 2
<211> LENGTH: 48
<212> TYPE: DNA
<213> ORGANISM: Artificial Sequence
<220> FEATURE:
<223> OTHER INFORMATION: Synthetic construct

<400> SEQUENCE: 2
agtttagcgg ccgcgtcagt ggtggtggtg gtggtgctgt ttcccgtt                48

<210> SEQ ID NO 3
<211> LENGTH: 54
<212> TYPE: DNA
<213> ORGANISM: Artificial Sequence
<220> FEATURE:
<223> OTHER INFORMATION: Synthetic construct

<400> SEQUENCE: 3
ccggaattcg actacaaaga cgatgacgac aagatggcgg cggctggggc tttc          54

<210> SEQ ID NO 4
<211> LENGTH: 46
<212> TYPE: DNA
<213> ORGANISM: Artificial Sequence
<220> FEATURE:
<223> OTHER INFORMATION: Synthetic construct

<400> SEQUENCE: 4
cgggatcccg tcatttcttc tctgcctctc cttttttggg ttcttg                  46

<210> SEQ ID NO 5
<211> LENGTH: 29
<212> TYPE: DNA
<213> ORGANISM: Artificial Sequence
<220> FEATURE:
<223> OTHER INFORMATION: Synthetic construct

<400> SEQUENCE: 5
cattacgtca ccacttgctg gagccccca                                     29

<210> SEQ ID NO 6
<211> LENGTH: 40
<212> TYPE: DNA
<213> ORGANISM: Artificial Sequence
<220> FEATURE:
<223> OTHER INFORMATION: Synthetic construct

<400> SEQUENCE: 6
tgccgtcgac cccattgacg gcagcacgct gatgagcaag                         40